US012779012B2

(12) United States Patent
Gianneschi et al.

(10) Patent No.: US 12,779,012 B2

(45) Date of Patent: Nov. 3, 2026

(54) KEAP1/NRF2 PROTEIN-LIKE POLYMERS

(71) Applicant: Northwestern University, Evanston, IL (US)

(72) Inventors: Nathan C. Gianneschi, Wilmette, IL (US); Kendal Paige Carrow, Evanston, IL (US)

(73) Assignee: Northwestern University, Evanston, IL (US)

( * ) Notice: Subject to any disclaimer, the term of this patent is extended or adjusted under 35 U.S.C. 154(b) by 425 days.

(21) Appl. No.: 18/283,749

(22) PCT Filed: Apr. 4, 2022

(86) PCT No.: PCT/US2022/023274

§ 371 (c)(1),
(2) Date: Sep. 22, 2023

(87) PCT Pub. No.: WO2022/216588

PCT Pub. Date: Oct. 13, 2022

(65) Prior Publication Data

US 2024/0189385 A1 Jun. 13, 2024

Related U.S. Application Data

(60) Provisional application No. 63/170,830, filed on Apr. 5, 2021.

(51) Int. Cl.

| | |
|---|---|
| ***A61K 38/16*** | (2006.01) |
| ***C07K 7/06*** | (2006.01) |
| ***C07K 7/08*** | (2006.01) |
| ***C07K 14/00*** | (2006.01) |

(52) U.S. Cl.

CPC ................ *A61K 38/16* (2013.01); *C07K 7/06* (2013.01); *C07K 7/08* (2013.01); *C07K 14/001* (2013.01)

(58) Field of Classification Search

None

See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,034,506 | A | 7/1991 | Summerton et al. |
| 5,212,162 | A | 5/1993 | Missel et al. |
| 5,235,033 | A | 8/1993 | Summerton et al. |
| 5,403,841 | A | 4/1995 | Lang et al. |
| 5,830,658 | A | 11/1998 | Gryaznov |
| 6,306,993 | B1 | 10/2001 | Rothbard et al. |
| 8,232,360 | B2 | 7/2012 | Sampson et al. |
| 9,040,626 | B2 | 5/2015 | Chien et al. |
| 9,737,525 | B2 | 8/2017 | Kazantsev et al. |
| 10,980,744 | B2 | 4/2021 | Blum et al. |
| 11,072,681 | B2 | 7/2021 | Rush et al. |
| 2003/0113740 | A1 | 6/2003 | Mirkin et al. |
| 2011/0166063 | A1 | 7/2011 | Bossard et al. |
| 2011/0251363 | A1 | 10/2011 | Sampson et al. |
| 2012/0149843 | A1 | 6/2012 | Chien et al. |
| 2014/0105896 | A1 | 4/2014 | Cload et al. |
| 2014/0256767 | A1 | 9/2014 | Hu et al. |
| 2018/0042843 | A1 | 2/2018 | Blum et al. |
| 2018/0092845 | A1 | 4/2018 | Gianneschi et al. |
| 2018/0303945 | A1 | 10/2018 | Adams et al. |
| 2019/0070251 | A1 | 3/2019 | Bossard et al. |
| 2021/0283054 | A1 | 9/2021 | Blum et al. |
| 2021/0301078 | A1 | 9/2021 | Rush et al. |
| 2022/0280625 | A1 | 9/2022 | Gianneschi et al. |
| 2022/0372200 | A1 | 11/2022 | Gianneschi et al. |

FOREIGN PATENT DOCUMENTS

| | | |
|---|---|---|
| WO | WO 2016/018917 | 2/2016 |
| WO | WO 2016/023036 | 2/2016 |
| WO | WO 2018/156617 | 8/2018 |
| WO | WO 2019/198075 | 10/2019 |
| WO | WO 2021/030326 | 2/2021 |
| WO | WO 2021/222523 | 11/2021 |
| WO | WO 2022/006387 | 1/2022 |

(Continued)

OTHER PUBLICATIONS

Abderrazak et al. (2015) "NLRP3 inflammasome: from a danger signal sensor to a regulatory node of oxidative stress and inflammatory diseases," Redox Biol, 4, 296-307.

Abed et al. (2015) "Discovery of direct inhibitors of Keap1—Nrf2 protein—protein interaction as potential therapeutic and preventive agents," Acta Pharmaceutica Sinica B; 5(4): 285-299.

Adamiak et al. (2017) "Peptide Brush Polymers and Nanoparticles with Enzyme-Regulated Structure and Charge for Inducing or Evading Macrophage Cell Uptake," ACS Nano, 11(10): 9877-9888. https://doi.org/10.1021/acsnano.7b03686.

Aigner et al. (2018) "Biomedical Applications of Recombinant Silk-Based Materials," Adv. Mater. 30 (19), 1704636. https://doi.org/10.1002/ADMA.201704636.

Allegrezza et al. (2016) "Trametinib drives T cell-dependent control of k-Ras-mutated tumors by inhibiting pathological myelopoiesis," Cancer Res. 76: 6253-6265. PMC5094194.

Al-Muhammed et al. (1996) "In-vivo studies on dexamethasone sodium phosphate liposomes," J. Microencapsul. 13(3): 293-306.

Alzheimer's Association (2021) "Alzheimer's Disease Facts and Figures," Alzheimers Dementia;17(3). 327-406.

(Continued)

*Primary Examiner* — Christina Bradley

(74) *Attorney, Agent, or Firm* — Leydig, Voit & Mayer, Ltd.

(57) ABSTRACT

In an aspect, the invention provides therapeutic agents comprising brush polymers that address challenges associated with conventional administration of free therapeutic peptides. In an embodiment, for example, the invention provides brush polymers incorporating one or more therapeutic peptides comprising a sequence having 75% or greater sequence identity of SEQ ID NO: 1 (LDEETGEFL) as side chain moieties. Therapeutic agents of the invention comprising brush polymers include high-density brush polymers including cross-linked brush polymers, brush block copolymers, and brush random copolymers. In an embodiment, brush polymers of the invention exhibit proteolysis-resistant characteristics and maintain their biological function during formulation and administration. The invention also includes methods of making and using therapeutic agents comprising brush polymers.

15 Claims, 92 Drawing Sheets

Specification includes a Sequence Listing.

(56) References Cited

FOREIGN PATENT DOCUMENTS

| | | |
|---|---|---|
| WO | WO 2022/216588 | 10/2022 |
| WO | WO 2023/086949 | 5/2023 |
| WO | WO 2023/178074 | 9/2023 |
| WO | WO 2023/196769 | 10/2023 |

OTHER PUBLICATIONS

Arcidiacono et al. (1998) "Purification and Characterization of Recombinant Spider Silk Expressed in *Escherichia Coli*," Appl. Microbiol. Biotechnol. 49 (1), 31-38. https://doi.org/10.1007/s002530051133.

Arunachalam et al. (2000) "Enzymatic reduction of disulfide bonds in lysosomes: characterization of a gamma-interferon-inducible lysosomal thiol reductase (GILT)," Proc Natl AcadSci U S A, 97 (2), 745-50.

Ayyoub et al. (1998) "Analysis of the degradation mechanisms of MHC class I-presented tumor antigenic peptides by high performance liquid chromatography/electrospray ionization mass spectrometry: application to the design of peptidase-resistant analogs," Rapid Commun Mass Spectrom, 12 (9), 557-64.

Barbieri et al. (2013) "Peptide Receptor Targeting in Cancer: The Somatostatin Paradigm," Int. J. Pept. 2013, 926295: 20 pp.

Battistella et al. (Dec. 2019) "Delivery of Immunotherapeutic Nanoparticles to Tumors via Enzyme-Directed Assembly," Adv Healthc Mater, 8 (23), e1901105.

Belitsky et al. (2002) "Cellular uptake of N-methylpyrrole/N-methylimidazole polyamide-dye conjugates," Bioorg. Med. Chem. 10(10): 3313-3318.

Berge et al. (1977) "Pharmaceutical Salts," Journal of Pharmaceutical Science 66(1): 1-19.

Berger et al. (Mar. 2022) "Mussel Adhesive-Inspired Proteomimetic Polymer," J. Am. Chem. Soc. 144, 10, 4383-4392.

Bertin et al. (2005) "High-density doxorubicin-conjugated polymeric nanoparticles via ring-opening metathesis polymerization," Chem. Commun., issue 30: 3793-3795.

Biron et al. (2008) "Improving Oral Bioavailability of Peptides by Multiple N-Methylation: Somatostatin Analogues," Angew. Chem., Int. Ed. 47(14): 2595-2599.

Bitler et al. (2015) "Targeting EZH2 methyltransferase activity in ARID1A mutated cells as a synthetic lethal therapeutic strategy," Nature Med.; 21: 231-238. PMC4352133.

Blackwell et al. (1998) "Highly Efficient Synthesis of Covalently Cross-Linked Peptide Helices by Ring-Closing Metathesis," Angew. Chem., Int. Ed. 37(23): 3281-3284.

Blanchet et al. (2001) "A new generation of Melan-A/MART-1 peptides that fulfill both increased immunogenicity and high resistance to biodegradation: implication for molecular anti-melanoma immunotherapy," J Immunol, 167 (10), 5852-61.

Blum et al. (2014) "Peptides Displayed as High Density Brush Polymers Resist Proteolysis and Retain Bioactivity," J. Am. Chem. Soc. 136 (43), 15422-15437. https://doi.org/10.1021/ja5088216.

Blum et al. (2016) "Activating Peptides for Cellular Uptake via Polymerization into High Density Brushes," Chem. Sci. 7 (2), 989-994. https://doi.org/10.1039/c5sc03417e.

Blum et al. (Jan. 2022) "Stimuli Induced Uptake of Protein-Like Peptide Brush Polymers," Chem. Eur. J. 28, e202103438.

Blum et al. (Oct. 2019) "Peptide Brush Polymers for Efficient Delivery of a Gene Editing Protein to Stem Cells," Angew. Chem. Int. Ed. 58: 15646-15649.

Bolli et al. (1994) "α-Bicyclo-DNA: Synthesis, Characterization, and Pairing Properties of α-DNA-Analogues with Restricted Conformational Flexibility in the Sugar—Phosphate Backbone," Chapter 7 in Carbohydrate Modifications in Antisense Research, Sanghvi and Cook, eds. pp. 100-117.

Brinckerhoff et al. (1999) "Terminal modifications inhibit proteolytic degradation of an immunogenic mart-127-35 peptide: Implications for peptide vaccines," Int. J. Cancer 83(3): 326-334.

Broos et al. (2010) "Immunomodulatory nanoparticles as adjuvants and allergen-delivery system to human dendritic cells: Implications for specific immunotherapy," Vaccine, 28 (31), 5075-5085.

Bulte et al. (2004) "Iron oxide MR contrast agents for molecular and cellular imaging," NMR Biomed. 17(7): 484-499.

Burke et al. (2010) "Synthesis and Characterization of Biodegradable HPMA-Oligolysine Copolymers for Improved Gene Delivery," Bioconjugate Chem. 21(1): 140-150.

Busseron et al. (May 2013) "Supramolecular self-assemblies as functional nanomaterials," Nanoscale 5: 7098-7140.

Cai et al. (2019) "Brusatol, an NRF2 inhibitor for future cancer therapeutic," Cell Biosci 9, 45. https://doi.org/10.1186/s13578-019-0309-8.

Callmann et al. (2015) "Therapeutic Enzyme-Responsive Nanoparticles for Targeted Delivery and Accumulation in Tumors," Adv Mater., 27(31):4611-4615. PMCID: PMC4699560.

Callmann et al. (Jan. 2020) "Poly(peptide): Synthesis, Structure, and Functionof Peptide-Polymer Amphiphiles and Protein-like Polymers," Accounts Chem Res, 53 (2), 400-413.

Callmann et al. (Jul. 2019) "Antitumor Activity of 1, 18-Octadecanedioic Acid-Paclitaxel Complexed with Human Serum Albumin," J Am Chem Soc., 141(30):11765-1769. DOI: 10.1021/jacs.9b04272. PMCID: PMC6676409.

Canning et al. (2015) "Structural basis of Keap1 interactions with Nrf2," Free Radic Biol Med, 88, part B, 101-107.

Carbone et al. (2017) "First-line nivolumab in stage IV or recurrent non-small-cell lung cancer," New England Journal of Medicine, 376(25), 2415-2426. PMCID: PMC6487310.

Cardarelli (2011) "Quantitative Analysis of Tat Peptide Binding to Import Carriers Reveals Unconventional Nuclear Transport Properties," The Journal of Biological Chemistry 286(14): 12292-12299.

Carreno et al. (2015) "A dendritic cell vaccine increases the breadth and diversity of melanoma neoantigen-specific T cells," Science, 348 (6236), 803-8.

Carrington et al. (2015) "Mussels as a Model System for Integrative Ecomechanics," Ann. Rev. Mar. Sci. 7, 443-469. https://doi.org/10.1146/ANNUREV-MARINE-010213-135049.

Cartier et al. (2002) "Utilization of synthetic peptides containing nuclear localization signals for nonviral gene transfer systems," Gene Ther. 9: 157-167.

Chang et al. (2015) "Blocking of the PD-1/PD-L1 Interaction by a D-Peptide Antagonist for Cancer Immunotherapy," Angew Chem Int Ed Engl, 54 (40), 11760-4.

Chartoumpekis et al. (2015) "Keap1/Nrf2 pathway in the frontiers of cancer and non-cancer cell metabolism," Biochem Soc Trans;43:639-44. https://doi.org/10.1042/BST20150049.

Chatterjee et al. (2008) "N-Methylation of Peptides: A New Perspective in Medicinal Chemistry," Acc. Chem. Res. 41(10): 1331-1342.

Chen et al. (2017) "Camptothecin suppresses NRF2-ARE activity and sensitises hepatocellular carcinoma cells to anticancer drugs," Br J Cancer, 117:1495-506. https://doi.org/10.1038/bjc.2017.317.

Chen et al. (Jun. 2021) "High-Throughput Screening Test for Adhesion in Soft Materials Using Centrifugation," ACS Cent. Sci. acscentsci.1c00414. https://doi.org/10.1021/ACSCENTSCI.1C00414.

Chiappori et al. (Dec. 2018) "Randomized-controlled phase II trial of salvage chemotherapy after immunization with a TP53-transfected dendritic cell-based vaccine (Ad.p53-DC) in patients with recurrent small cell lung cancer," Cancer Immunol Immunother. PMID: 30591959.

Chien et al. (2012) "Fluorogenic enzyme-responsive micellar nanoparticles," Chem. Sci. 3(9): 2690-2694.

Chien et al. (Dec. 2013) "Enzyme-Directed Assembly of Nanoparticles in Tumors Monitored by in Vivo Whole Animal Imaging and ex Vivo Super-Resolution Fluorescence Imaging," J. Am. Chem. Soc. 135(50): 18710-18713.

Chien et al. (publicly available May 2013) "Enzyme-Directed Assembly of a Nanoparticle Probe in Tumor Tissue," Adv. Mater. (Jul. 2013), 25(26): 3599-3604.

Choi et al. (2003) "Controlled living ring-opening-metathesis polymerization by a fast-initiating ruthenium catalyst," Angew Chem Int Ed Engl, 42 (15), 1743-6.

(56) References Cited

OTHER PUBLICATIONS

Choi et al. (2014) "Highly Purified Mussel Adhesive Protein to Secure Biosafety for in Vivo Applications," Microb. Cell Fact. 13 (1), 1-12. https://doi.org/10.1186/1475-2859-13-52.
Chonn et al. (1995) "Recent advances in liposomal drug-delivery systems," Curr. Opin. Biotechnol. 6:698-708.
Chu et al. (2012) "Cathepsin B-sensitive polymers for compartment-specific degradation and nucleic acid release," J. Controlled Release 157(3): 445-454.
Clarke et al. (2000) "Characterization ofthe ovalbumin-specific TCR transgenic line OT-I: MHC elements for positive and negative selection," ImmunolCell Biol, 78 (2), 110-7.
Cogan et al. (2017) "Topical Delivery of Anti-VEGF Drugs to the Ocular Posterior Segment Using Cell-Penetrating Peptides," IVOS., 58, 2578-2590.
Colarusso et al. (Nov. 2020) "Optimization of linear and cyclic peptide inhibitors of KEAP1-NRF2 protein-protein interaction," Bioorganic & Medicinal Chemistry. Vol. 28, No. 21; DOI: 10.1016/j.bmc.2020.115738.
Conejo-Garcia et al. (2004) "Tumor infiltrating dendritic cell precursors recruited by a b-defensin contribute to vasculogenesis under the influence of Vegf-A," Nat Med; 10:950-958.
Congdon et al. (2018) "Tau-targeting therapies for Alzheimer disease," Nat Rev Neurol 14, 399-415.
Conlon et al. (2013) "Mouse, but not human STING, binds and signals in response to the vascular disrupting agent 5,6-dimethylxanthenone-4-acetic acid," J Immunol, 190(10), 5216-25.
Conrad et al. (2009) "Tunable, Temperature-Responsive Polynorbornenes with Side Chains Based on an Elastin Peptide Sequence," Angew. Chem. Int. Edit. 48(44): 8328-8330.
Corrales et al. (2015) "Direct Activation of STING in the Tumor Microenvironment Leads to Potent and Systemic Tumor Regression and Immunity," CellRep, 11 (7), 1018-30.
Cottet et al. (2008) "Separation of Synthetic (Co)Polymers by Capillary Electrophoresis Techniques," Methods Mol. Biol. 384, 541-567. https://doi.org/10.1007/978-1-59745-376-9_21.
Craik et al. (publicly available Dec. 2012) "The Future of Peptide-based Drugs," Chem. Biol. Drug Des. (Jan. 2013), 81(1): 136-147.
Creelan et al. (2015) "Safety and tolerability results from a phase I study of MEDI4736, a human IgG1 anti-programmed cell death-ligand-1 (PD-L1) antibody, combined with gefitinib in patients with non-small-cell lung cancer," Journal of Clinical Oncology 33, 15S: 3047.
Creelan et al. (Aug. 2013) "Phase II trial of a GM-CSF-producing and CD40L expressing bystander cell line combined with an allogeneic tumor cell-based vaccine for refractory lung adenocarcinoma." Journal of Immunotherapy. 36(8); 442-450. PMCID: PMC3846277.
Creelan et al. (Aug. 2017) "Safety, pharmacokinetics, and pharmacodynamics of oral omaveloxolone, a synthetic triterpenoid, in a first-in-human trial of patients with advanced solid tumors," Onco Targets Ther. 10:4239-50. PMCID: PMC5587199.
Creelan et al. (Aug. 2020) "Abstract CT056: Durable complete responses to adoptive cell transfer using tumor infiltrating lymphocytes (TIL) in nonsmall cell lung cancer (NSCLC): a phase I trial," AACR Annual meeting. Late Breaking and Clinical Trials. Cancer Res (2020) 80 (16_Supplement): CT056.
Creelan et al. (Mar. 2013) "Indoleamine 2,3-dioxygenase activity and clinical outcome following induction chemotherapy and concurrent chemoradiation in stage III non-small cell lung cancer," Oncolmmunology . 1;2(3). PMCID: PMC3661168.
Creelan et al. (May 2017) "Two phase I/II open label clinical trials evaluating the safety and efficacy of autologous T cells expressing enhanced TCRs specific for NY-ESO-1 or MAGE-A10 in subjects with stage IIIb or stage IV non-small cell lung cancer (NCT02588612/NCT02592577)," TPS3096 Journal of Clinical Oncology 35, No. 15_suppl.
Creelan et al. (Sep. 2018) "OA05. 03 Safety and Clinical Activity of Adoptive Cell Transfer Using Tumor Infiltrating Lymphocytes (TIL) Combined with Nivolumab in NSCLC," Journal of Thoracic Oncology, 13(10), pp. S330-S331.
Croy et al. (2004) "Biophysical characterization of the free IκBα ankyrin repeat domain in solution," Protein Science, 13, 1767.
Cuadrado et al. (2019) "Therapeutic targeting of the NRF2 and KEAP1 partnership in chronic diseases," Nat Rev Drug Discov, 295-317. https://doi.org/10.1038/s41573-018-0008-x.
Cubillos-Ruiz et al. (2009) "Polyethylenimine-based siRNA nanocomplexes reprogram tumor-associated dendritic cells via TLR5 to elicit therapeutic antitumor immunity," J Clin Invest; 119:2231-2244. PMC2719935.
Cubillos-Ruiz et al. (2015) "ER Stress Sensor XBP1 Controls Anti-tumor Immunity by Disrupting Dendritic Cell Homeostasis," Cell: 1527-1538. PMC4580135.
Curiel et al. (2004) "Specific recruitment of regulatory T cells in ovarian carcinoma fosters immune privilege and predicts reduced survival," Nat Med; 10:942-949.
Dalsin et al. (2003) "Mussel Adhesive Protein Mimetic Polymers for the Preparatioono of Nonfouling Surfaces," J. Am. Chem. Soc. 125 (14), 4253-4258.
Darden et al. (1993) "Particle mesh Ewald: An N.log(N) method for Ewald sums in large systems," J. Chem. Phys. 98(12): 10089-10092.
De Gregorio et al. (2009) "Immunology of TLR-independent vaccine adjuvants," Curr OpinImmunol, 21 (3), 339-45.
De Jong et al. (2016) "Martini straight: Boosting performance using a shorter cutoff and GPUs," Comput. Phys. Commun. 199, 1-7.
Debelle et al. (1999) "Elastin: Molecular Description and Function," International Journal of Biochemistry and Cell Biology. Pergamon, pp. 261-272. https://doi.org/10.1016/S1357-2725(98)00098-3.
Demaria et al. (2015) "STING activation of tumorendothelial cells initiates spontaneous and therapeutic antitumor immunity," Proc Natl Acad Sci U S A, 112(50), 15408-13.
Deming (1993) "Mussel Byssus and Biomolecular Materials," Curr. Opin. Chem. Biol. 3 (1), 100-105. https://doi.org/10.1016/S1367-5931(99)80018-0.
Dinkova-Kostova et al. (2018) "The role of Nrf2 signaling in counteracting neurodegenerative diseases," FEBS J. 3576-3590.
Doherty et al. (2009) "Mechanisms of Endocytosis," Annu. Rev. Biochem. 78: 31.1-31.46 and Supplementary Information (69 pp. total).
Dominguez et al. (2017) "Exogenous IL-33 Restores Dendritic Cell Activation and Maturation in Established Cancer," J Immunol, 198 (3), 1365-1375.
Elices et al. (2011) "Bioinspired Fibers Follow the Track of Natural Spider Silk," Macromolecules, 44 (5), 1166-1176. https://doi.org/10.1021/ma102291m.
Engelhardt et al. (2000) "Capillary Electrophoresis in Polymer Analysis," Adv. Polym. Sci. 150, 189-217. https://doi.org/10.1007/3-540-48764-6_3.
Escriou et al. (2003) "NLS bioconjugates for targeting therapeutic genes to the nucleus," Adv. Drug Delivery Rev. 55(2): 295-306.
Essmann et al. (1995) "A smooth particle mesh Ewald method," J. Chem. Phys. 103(19): 8577-8593.
Evans et al. (Jul. 2018) "Seeded Growth of Single-Crystal Two-Dimensional Covalent Organic Frameworks," Science, 361(6397):52-57. PMID: 29930093. DOI: 10.1126/science.aar7883.
Evans et al. (Mar. 2022) "Protein complex prediction with AlphaFold-Multimer," bioRxiv, 2021.10.04.463034.
Eyles et al. (1997) "Oral Delivery and Fate of Poly(lactic acid) Microsphere-encapsulated Interferon in Rats," J. Pharm. Pharmacol. 49: 669-674.
Fahnestock et al. (1997) "Production of Synthetic Spider Dragline Silk Protein in Pichia Pastoris," Appl. Microbiol. Biotechnol. 47 (1), 33-39. https://doi.org/10.1007/s002530050884.
Falciani et al. (2007) "Molecular Basis of Branched Peptides Resistance to Enzyme Proteolysis," Chem. Biol. Drug Des. 69(3): 216-221.
Falo et al. (1992) "Serum proteases alter the antigenicity of peptides presented by class I major histocompatibility complex molecules," Proc Natl Acad Sci U S A, 89(17), 8347-50.
Ferrara et al. (2016) "Ten years of anti-vascular endothelial growth factor therapy," Nat Rev Drug Discov. 15(6), 385-403.

(56) References Cited

OTHER PUBLICATIONS

Fichman et al. (2014) "Seamless Metallic Coating and Surface Adhesion of Self-Assembled Bioinspired Nanostructures Based on Di-(3,4-Dihydroxy- I -Phenylalanine) Peptide Motif," ACS Nano, 8 (7), 7220-7228. https://doi.org/10.1021/nn502240r.
Figenschau et al. (Aug. 2018) "ICAM1 Expression is Induced by Proinflammatory Cytokines and Associated with TLS Formation in Aggressive Breast Cancer Subtypes," Sci Rep 8, 11720.
Foret et al. (2019) "Effect of antioxidant supplements on lipid peroxidation levels in primary cortical neuron cultures," Free Radical Biology and Medicine, vol. 130, 471-477.
Frankel et al. (1988) "Cellular uptake of the tat protein from human immunodeficiency virus," Cell 55(6): 1189-1193.
Fu et al. (2015) "STING agonist formulated cancer vaccines can cure established tumors resistant to PD-1 blockade," Sci Transl Med, 7 (283), 283ra52.
Fukutomi et al. (2014) "Kinetic, Thermodynamic, and Structural Characterizations of the Association between Nrf2-DLGex Degron and Keap1," Mol. Cell. Biol., 34(5): 832-846.
Futaki et al. (2001) "Arginine-rich Peptides: An Abundant Source of Membrane-Permeable Peptides Having Potential as Carriers for Intracellular Protein Delivery," J. Biol. Chem. 276(8): 5836-5840.
Gameiro et al. (2017) "Discovery of the first dual GSK3β inhibitor/Nrf2 inducer. A new multitarget therapeutic strategy for Alzheimer's disease," Scientific Reports vol. 7, Article No. 45701.
Gao et al. (1995) "Controlled Release of a Contraceptive Steroid from Biodegradable and Injectable Gel Formulations: In Vitro Evaluation," Pharm. Res. 12(6): 857-863.
Gaudet (2008) "A primer on ankyrin repeat function in TRP channels and beyond," Mol. BioSyst., 4, 372.
Georgakopoulos et al. (2018) "Modified Peptide Inhibitors of the Keap1—Nrf2 Protein-Protein Interaction Incorporating Unnatural Amino Acids," ChemBioChem, 19, 1810-1816.
Gordon et al. (2001) "Inhibition of β-Amyloid(40) Fibrillogenesis and Disassembly of β-Amyloid(40) Fibrils by Short β-Amyloid Congeners Containing N-Methyl Amino Acids at Alternate Residues," Biochemistry 40(28): 8237-8245.
Gray et al. (Sep. 2018) "A phase I/randomized phase II study of GM.CD40L vaccine in combination with CCL21 in patients with advanced lung adenocarcinoma," Cancer Immunol Immunother. 67:1853-1862.
Green et al. (1988) "Autonomous functional domains of chemically synthesized human immunodeficiency virus tat trans-activator protein," Cell 55(6): 1179-1188.
Gubin et al. (2014) "Checkpoint blockade cancer immunotherapy targets tumour-specific mutant antigens," Nature, 515 (7528), 577-81.
Guo et al. (2013) "Therapeutic cancer vaccines: past, present, and future," Adv Cancer Res, 119, 421-75.
Guo et al. (Jul. 2018) Neoantigen Vaccine Delivery for Personalized Anticancer Immunotherapy, Front Immunol. 9:1499.
Hahn et al. (Apr. 2013) "Polymerization of a peptide-based enzyme substrate," Chem Commun (Camb) 49(28): 2873-2875 (8 pp.).
Hamamoto et al. (2002) "Antimicrobial Activity and Stability to Proteolysis of Small Linear Cationic Peptides with D-Amino Acid Substitutions," Microbiol. Immunol. 46(11): 741-749.
Hanahan et al. (2011) "Hallmarks of cancer: the next generation," Cell, 144(5), 646-674.
Hancock et al. (2012) "Peptide inhibitors of the Keap1—Nrf2 protein—protein interaction," Free Radical Biology & Medicine 52, 444-451.
Hancock et al. (2013) "Peptide inhibitors of the Keap1—Nrf2 protein—protein interaction with improved binding and cellular activity," Org. Biomol. Chem., 11, 3553.
Hanover et al. (1984) "Kinetics of transit of transferrin and epidermal growth factor through clathrin-coated membranes," Cell 39(2): 283-293.
Hastings et al. (2011) "Disulfide reduction in the endocytic pathway: immunological functions of gamma-interferon-inducible lysosomal thiol reductase," Antioxid Redox Signal, 15 (3), 657-68.
Heidebrecht et al. (2013) "Recombinant Production of Spider Silk Proteins," in Advances in Applied Microbiology; Academic Press Inc., vol. 82, pp. 115-153. https://doi.org/10.1016/B978-0-12-407679-2.00004-1.
Heitz et al. (2009) "Twenty years of cell-penetrating peptides: from molecular mechanisms to therapeutics," Br. J. Pharmacol. 157(2): 195-206.
Hellmann et al. (2014) "Smoking History and Response to Nivolumab in Patients with Advanced NSCLC," Annals of Oncology 25, S4 426-70, 1229PD.
Hellmann et al. (Apr. 2018) "Genomic Features of Response to Combination Immunotherapy in Patients with Advanced Non-Small-Cell Lung Cancer," Cancer Cell. pii: S1535-6108(18)30123-5. PMCID: PMC5953836.
Henikoff et al. (1992) "Amino acid substitution matrices from protein blocks," Proc. Nat'l Acad. Sci. USA 89(22):10915-10919.
Henninot et al. (Feb. 2018) "The Current State of Peptide Drug Discovery: Back to the Future?," J. Med. Chem. 61, 1382-1414.
Herdewijn et al. (1994) "Hexopyranosyl-Like Oligonucleotides," Chapter 6 in Carbohydrate Modifications in Antisense Research, Sanghvi and Cook, eds. pp. 80-99.
Hess et al. (2008) "GROMACS 4: Algorithms for Highly Efficient, Load Balanced, and Scalable Molecular Simulation," J. Chem. Theory Comput. 4, 435-447.
Horsch et al. (2018) "Polymerizing Like Mussels Do: Toward Synthetic Mussel Foot Proteins and Resistant Glues," Angew. Chemie, 130 (48), 15954-15958. https://doi.org/10.1002/ange.201809587.
Huang et al. (Jan. 2017) "CHARMM36m: An Improved Force Field for Folded and Intrinsically Disordered Proteins," Nat. Meth. 14 (1), 71-73.
Huang et al. (May 2017) "Mimicking Melanosomes: Polydopamine Nanoparticles as Artificial Microparasols," ACS Cent Sci., 3(6):564-569. https://doi.org/10.1021/acscentsci.6b00230.
Huemmerich et al. (2004) "Novel Assembly Properties of Recombinant Spider Dragline Silk Proteins," Curr. Biol. 14 (22), 2070-2074. https://doi.org/10.1016/j.cub.2004.11.005.
Huh et al. (2005) "In Vivo Magnetic Resonance Detection of Cancer by Using Multifunctional Magnetic Nanocrystals," J. Am. Chem. Soc. 127(35): 12387-12391.
Humphrey et al. (1996) "VMD: Visual Molecular Dynamics," J. Malec. Graphics 14: 33-38.
Hundal et al. (2016) "pVAC-Seq: A genome-guided in silico approach to identifying tumor neoantigens," Genome Med, 8 (1), 11.
Hwang et al. (2007) "Practical Recombinant Hybrid Mussel Bioadhesive Fp-151," Biomaterials, 28 (24), 3560-3568. https://doi.org/10.1016/j.biomaterials.2007.04.039.
International Search Report and Written Opinion, dated Sep. 8, 2022, corresponding to International Application No. PCT/US2022/023274, 18 pp.
Isenberg et al. (2007) "Thrombospondin-1 Inhibits Nitric Oxide Signaling via CD36 by Inhibiting Myristic Acid Uptake," J. Bio. Chem. 282(21), 15404-15415.
Jacobs et al. (1998) "Structure of an IκBα/NF-κB Complex," Cell, 95, 749.
Jakalian et al. (2000) "Fast, efficient generation of high-quality atomic charges. AM1-BCC model: I. Method," J. Comput. Chem. 21(2): 132-146.
Jakalian et al. (2002) "Fast, efficient generation of high-quality atomic charges. AM1-BCC model: II. Parameterization and validation," J. Comput. Chem. 23(16): 1623-1641.
James et al. (Jul. 2014) "Poly(oligonucleotides)," Journal of the American Chemical Society 136: 11216-11219.
Jernigan et al. (2015) "Tandem-Repeat Protein Domains across the Tree of Life," PeerJ, 3e732. https://doi.org/10.7717/peerj.732.
Jiang et al. (2018) "Identification of a novel small-molecule Keap1—Nrf2 PPI inhibitor with cytoprotective effects on LPS-induced cardiomyopathy," Journal of Enzyme Inhibition and Medicinal Chemistry, 33:1, 833-841, DOI: 10.1080/14756366.2018.1461856.
Jiang et al. (Jan. 2020) "Single-chain heteropolymers transport protons selectively and rapidly," Nature, 577 (7789), 216-220.

(56) References Cited

OTHER PUBLICATIONS

Johnson et al. (2010) "Drug-Loaded, Bivalent-Bottle-Brush Polymers by Graft- through ROMP," Macromolecules 43(24): 10326-10335.
Johnson et al. (2010) "Synthesis of Statistical Copolymers Containing Multiple Functional Peptides for Nucleic Acid Delivery," Biomacromolecules 11(11): 3007-3013.
Johnson et al. (2011) "Core-Clickable PEG-Branch-Azide Bivalent-Bottle-Brush Polymers by ROMP: Grafting-Through and Clicking-To," J. Am. Chem. Soc. 133(3): 559-566.
Johnson et al. (2015) "Nrf2—a therapeutic target for the treatment of neurodegenerative diseases," Free Radical Biology and Medicine 88, 253-267.
Jun et al. (2005) "Nanoscale Size Effect of Magnetic Nanocrystals and Their Utilization for Cancer Diagnosis via Magnetic Resonance Imaging," J. Am. Chem. Soc. 127(16): 5732-5733.
Kajava (2012) "Tandem repeats in proteins: From sequence to structure," J. Struct. Bio, 179, 279-288.
Kammeyer et al. (2013) "Polymerization of protecting-group-free peptides via ROMP," Polymer Chemistry 4(14): 3929-3933.
Kansanen et al. (2013) "The Keap1-Nrf2 pathway: Mechanisms of activation and dysregulation in cancer," Redox Biol:45-9. https://doi.org/10.1016/j.redox.2012.10.001.
Kaplan et al. (2005) "Cationic TAT peptide transduction domain enters cells by macropinocytosis," J. Controlled Release 102(1): 247-253.
Karttunen et al. (2018) "Prediction of Binding Energy of Keap1 Interaction Motifs in the Nrf2 Antioxidant Pathway and Design of Potential High-Affinity Peptides," J. Phys. Chem. B, 122, 5851-5859.
Kaspar et al. (Sep. 2013) "Future directions for peptide therapeutics development," Drug Discovery Today 18(17-18): 807-817.
Kaur et al. (2018) "Direct Observation of the Interplay of Catechol Binding and Polymer Hydrophobicity in a Mussel-Inspired Elastomeric Adhesive," ACS Cent. Sci. 4, 10, 1420-1429. https://doi.org/10.1021/acscentsci.8b00526.
Kawai et al. (2010) "The role of pattern-recognition receptors in innate immunity: update on Toll-like receptors," Nature Immunology, 11 (5), 373-384.
Kebriaei et al. (Jun. 2018) "A phase 1 multicenter study evaluating the safety and efficacy of MHC class II-restricted MAGE-A3/A6 T-cell receptor engineered T cells (KITE-718) in patients with advanced cancer," Journal of Clinical Oncology 2018 36:15_suppl, TPS3104.
Keskin et al. (Jan. 2019) "Neoantigen vaccine generates intratumoral T cell responsesin phase Ib glioblastoma trial," Nature, 565 (7738), 234-239.
Khalil et al. (2016) "The future of cancer treatment:immunomodulation, CARs and combination immunotherapy," Nat Rev Clin Oncol, 13(5): 273-290.
Khan et al. (2013) "Readily Accessible and Easily Modifiable Ru-Based Catalysts for Efficient and Z-Selective Ring-Opening Metathesis Polymerization and Ring-Opening/Cross-Metathesis," J. Am. Chem. Soc., 135 (28), 10258-10261.
Kim et al. (2011) "Synthesis of all-hydrocarbon stapled α-helical peptides by ring-closing olefin metathesis," Nat. Protoc. 6(6): 761-771.
Kim et al. (2013) "Mussel Adhesive Protein-Based Whole Cell Array Biosensor for Detection of Organophosphorus Compounds," Biosens. Bioelectron. 41 (1), 199-204. https://doi.org/10.1016/j.bios.2012.08.022.
Kinkead et al. (Oct. 2018) "Combining STING-based neoantigen-targeted vaccine with checkpoint modulators enhances antitumorimmunity in murine pancreatic cancer," Jci Insight, 3 (20).
Kirkin et al. (1999) "Establishment of gp100 and MART-1/Melan-A-specific cytotoxic T lymphocyte clones using in vitro immunization against preselected highly immunogenic melanoma cell clones," Cancer Immunol Immunother, 48 (5), 239-46.
Knutson et al. (2005) "Tumor antigen-specific T helper cells in cancer immunity and immunotherapy," Cancer Immunol Immunother. 54(8):721-8.
Kolonko et al. (2008) "A Polymeric Domain That Promotes Cellular Internalization," J. Am. Chem. Soc. 130(17): 5626-5627.
Kolonko et al. (2009) "General Synthetic Route to Cell-Permeable Block Copolymers via Romp," J. Am. Chem. Soc. 131(21): 7327-7333.
Kord Forooshani et al. (2017) "Recent Approaches in Designing Bioadhesive Materials Inspired by Mussel Adhesive Protein," Journal of Polymer Science, Part A: Polymer Chemistry. John Wiley and Sons Inc. pp 9-33. https://doi.org/10.1002/pola.28368.
Koren et al. (2012) "Cell-penetrating peptides: breaking through to the other side," Trends Mol. Med. 18(7): 385-393.
Kraft et al. (2004) "Nuclear Factor E2-Related Factor 2-Dependent Antioxidant Response Element Activation by tert-Butylhydroquinone and Sulforaphane Occurring Preferentially in Astrocytes Conditions Neurons against Oxidative Insult," The Journal of Neuroscience, 24(5):1101-1112.
Kreiter et al. (2015) "Mutant MHC class II epitopes drive therapeutic immune responses to cancer," Nature, 520 (7549), 692-U269.
Ku et al. (2011) "Controlling and Switching the Morphology of Micellar Nanoparticles with Enzymes," J. Am. Chem. Soc. 133: 8392-8395.
Kuykendall et al. (2015) "Distribution of Immune Markers and Their Association with Overall Survival and Time to Progression in Non-Small-Cell Lung Cancer," Journal of Thoracic Oncology. 10, S2, 9, S268, Mini oral session, Sep. 7, 2015, Abstract.
Lam et al. (Oct. 2018) "LBA38 Safety and anti-tumor effects of MAGE-A10c796 TCR T-cells in two clinical trials," Annals of Oncology, vol. 29, Issue suppl_8, 1.
Lange et al. (2007) "Classical Nuclear Localization Signals: Definition, Function, and Interaction with Importin α," J. Biol. Chem. 282(8): 5101-5105.
Lee et al. (2001) "Nrf2-Dependent Activation of the Antioxidant Responsive Element by tert-Butylhydroquinone Is Independent of Oxidative Stress in IMR-32 Human Neuroblastoma Cells," Biochemical and Biophysical Research Communications 280, 286-292.
Lee et al. (2003) "N-Terminal Site-Specific Mono-PEGylation of Epidermal Growth Factor," Pharm. Res. 20(5): 818-825.
Lee et al. (2007) "Mussel-Inspired Surface Chemistry for Multifunctional Coatings," Science, 318 (5849), 426-430. https://doi.org/10.1126/science.1147241.
Lee et al. (2011) "Inspired Adhesives and Coatings," Annu. Rev. Mater. Res. 41 (1), 99-132. https://doi.org/10.1146/annurev-matsci-062910-100429.
Lee et al. (2016) "CHARMM-GUI Input Generator for NAMD, GROMACS, AMBER, OpenMM, and CHARMM/OpenMM Simulations Using the CHARMM36 Additive Force Field," J. Chem. Theory Comput. 12 (1), 405-413.
Lee et al. (Apr. 2020) "Nrf2 activation through the inhibition of Keap1—Nrf2 protein—protein interaction," Medicinal Chemistry Research, 29:846-867.
Lei et al. (1995) "Structure-Function Analysis of Human Glucose-6-phosphatase, the Enzyme Deficient in Glycogen Storage Disease Type 1a," J. Biol. Chem. 270(20): 11882-11886.
Leicher et al. (1998) "Coexpression of the KCNA3B Gene Product with Kv1.5 Leads to a Novel A-type Potassium Channel," J. Biol. Chem. 273(52):35095-35101.
Lewis et al. (2010) "Nrf2, a Guardian of Healthspan and Gatekeeper of Species Longevity," pp. 829-843. Integrative and Comparative Biology. vol. 50, No. 5; DOI: 10.1093/icb/icq034.
Li et al. (2002) "Preparation and characterization of PEGylated adducts of recombinant human tumor necrosis factor-α from *Escherichia coli*," Biotechnol. 92(3): 251-258.
Li et al. (2006) "Ankyrin Repeat: A Unique Motif Mediating Protein—Protein Interactions," Biochemistry, 45, 15168.
Li et al. (2016) "Structure and Function of Iron-Loaded Synthetic Melanin," ACS Nano, 10(11):10186-10194. PMCID: PMC5295137.
Li et al. (2017) "CD54-NOTCH1 Axis Controls Tumor Initiation and Cancer Stem Cell Functions in Human Prostate Cancer," Theranostics. 7(1):67-8.

(56) References Cited

OTHER PUBLICATIONS

Li et al. (Jun. 2018) "A facile approach to enhance antigen response for personalized cancer vaccination," Nat Mater, 17 (6), 528-534.
Lindorff-Larsen et al. (2010) "Improved side-chain torsion potentials for the Amber ff99SB protein force field," Proteins 78(8): 1950-1958.
Liu et al. (Oct. 2019) "Discovery of low-molecular weight anti-PD-L1 peptides for cancer immunotherapy," J Immunother Cancer, 7 (1), 270.
Livant et al. (2000) "The PHSRN sequence induces extracellular matrix invasion and accelerates wound healing in obese diabetic mice," J. Clin. Invest. 105(11):1537-1545.
Lopez et al. (2011) "Molecular Mechanism of Cyclodextrin Mediated Cholesterol Extraction," PLoS Comp. Biol. 7(3): e1002020, pp. 1-11.
Lu et al. (2009) "One-Pot Synthesis of Brush-Like Polymers via Integrated Ring-Opening Metathesis Polymerization and Polymerization of Amino Acid N-Carboxyanhydrides," JACS 131(38): 13582-13583.
Lu et al. (2015) "Binding thermodynamics and kinetics guided optimization of potent Keap1—Nrf2 peptide inhibitors," RSC Advances, 5:85983-7.
Lu et al. (2018) "Discovery of a head-to-tail cyclic peptide as the Keap1—Nrf2 protein—protein interaction inhibitor with high cell potency," European Journal of Medicinal Chemistry, 143, 1578-1589.
Lu et al. (Dec. 2020) "Discovery of 2-oxy-2-phenylacetic acid substituted naphthalene sulfonamide derivatives as potent KEAP1—NRF2 protein—protein interaction inhibitors for inflammatory conditions," European Journal of Medicinal Chemistry, 207, 112734.
Lynn et al. (Mar. 2020) "Peptide-TLR-7/8a conjugate vaccines chemically programmed for nanoparticle self-assembly enhanceCD8 T-cell immunity to tumor antigens," Nat Biotechnol, 38 (3), 320-332.
Lytle et al. (Nov. 2018) "Stem cell fate in cancer growth, progression and therapy resistance," Nat Rev Cancer. Nov. 2018;18(11):669-680.
Mackerell et al. (1998) "All-Atom Empirical Potential for Molecular Modeling and Dynamics Studies of Proteins," J. Phys. Chem. B, 102 (18), 3586-3616.
Macri et al. (2016) "Targeting dendritic cells: a promising strategy to improve vaccine effectiveness," Clin Transl Immunology, 5 (3), e66.
Madden et al. (Jul. 2020) "Structural and mechanistic insights into the Keap1—Nrf2 system as a route to drug discovery," BBA—Proteins and Proteomics 1868, 140405.
Maier et al. (2015) "Adaptive Synergy between Catechol and Lysine Promotes Wet Adhesion by Surface Salt Displacement," Science (80-. ). 349 (6248), 628-632. https://doi.org/10.1126/science.aab0556.
Main et al. (2003) "The folding and design of repeat proteins: reaching a consensus," Curr. Opinion in Struct. Bio,13, 482.
Marrink et al. (2007) "The MARTINI Force Field: Coarse Grained Model for Biomolecular Simulations," J. Phys. Chem. B, 111 (27), 7812-7824. 19.
Marrink et al. (2013) "Perspective on the Martini model," Chem. Soc. Rev. 42 (16), 6801-6822.
Martinez Rodriguez et al. (2015) "Mussel Adhesive Protein Provides Cohesive Matrix for Collagen Type-1α," Biomaterials, 51, 51-57. https://doi.org/10.1016/J.BIOMATERIALS.2015.01.033.
Matson et al. (2010) "Monotelechelic Poly(oxa)norbornenes by Ring-Opening Metathesis Polymerization using Direct End-Capping and Cross Metathesis," Macromolecules 43(1): 213-221.
Maynard et al. (2000) "Synthesis of Norbornenyl Polymers with Bioactive Oligopeptides by Ring-Opening Metathesis Polymerization," Macromolecules 33(17):6239-6248.
Maynard et al. (2001) "Inhibition of Cell Adhesion to Fibronectin by Oligopeptide-Substituted Polynorbornenes," J. Am. Chem. Soc. 123, 1275-1279.
Mcgregor (2008) "Discovering and improving novel peptide therapeutics," Curr. Opin. Pharmacol. 8(5): 616-619.
Meeth et al. (2016) "The YUMM lines: a series of congenic mouse melanoma cell lines with defined genetic alterations," Pigm Cell Melanoma R, 29 (5), 590-597.
Mellman et al. (2011) Cancer immunotherapy comes of age. Nature, 480 (7378),480-9.
Merrifield (1963) "Solid Phase Peptide Synthesis. I. The Synthesis of a Tetrapeptide," J. Am. Chem. Soc. 85 (14), 2149-2154. https://doi.org/10.1021/ja00897a025.
Millar et al. (Apr. 2020) "Antibody-mediated delivery of viral epitopes to tumors harnesses CMV-specific T cells for cancer therapy," Nat Biotechnol. 38(4):420-425.
Miller et al. (1994) "Proteolytic studies of homologous peptide and N-substituted glycine peptoid oligomers," Bioorg. Med. Chem. Lett. 4(22): 2657-2662.
Mitchell et al. (2000) "Polyarginine enters cells more efficiently than other polycationic homopolymers," J. Pept. Res. 56(5): 318-325.
Miyamoto et al. (1992) "SETTLE: An Analytical Version of the SHAKE and RATTLE Algorithm for Rigid Water Models," J. Comput. Chem. 13, 952-962.
Monfardini et al. (1995) "A Branched Monomethoxypoly(ethylene glycol) for Protein Modification," Bioconjugate Chem. 6(1): 62-69.
Mosavi et al (2002) "Consensus-derived structural determinants of the ankyrin repeat motif," PNAS, 99, 16029.
Mou et al. (Sep. 2020) "Recent progress in Keap1—Nrf2 protein—protein interaction inhibitors," European Journal of Medicinal Chemistry 202, 112532.
Mougel et al. (Mar. 2019) "Therapeutic Cancer Vaccine and Combinations With Antiangiogenic Therapies and Immune Checkpoint Blockade," Front Immunol, 10.
Moynihan et al. (Sep. 2018) "Enhancement of Peptide Vaccine Immunogenicity by Increasing Lymphatic Drainage and Boosting Serum Stability," Cancer Immunol Res, 6 (9), 1025-1038.
Murata et al. (1997) "Syntheses and Radical Polymerization Behavior of Methacrylamides Having Peptide Moieties: Effect of the Methylene Chain Introduced between the Methacrylamide and Peptide Moieties on the Polymerizability and Polymer Structure," Macromolecules 30(10): 2902-2906.
Naing et al. (Jul. 2018) "Epacadostat plus durvalumab in patients with advanced solid tumors: preliminary results of the ongoing, open-label, phase I/II ECHO-203 study," AACR; Cancer Res 2018 Abstract CT177.
Nakase et al. (2004) "Cellular Uptake of Arginine-Rich Peptides: Roles for Macropinocytosis and Actin Rearrangement," Mol. Ther. 10(6): 1011-1022.
Needleman et al. (1970) "A general method applicable to the search for similarities in the amino acid sequence of two proteins," J. Mol. Biol. 48: 443-453.
Newberg et al. (1996) "Importance of MHC class 1 alpha2 and alpha3 domains in the recognition of self and non-self MHC molecules," J Immunol, 156 (7), 2473-80.
Nguyen et al. (2015) "Enzyme-responsive Nanoparticles for Targeted Accumulation and Prolonged Scaffold Retention in Heart Tissue After Myocardial Infarction," Adv Mater., 27(37):5547-5552. PMID: PMC4699559.
Nicklisch et al. (2012) "Mini-Review: The Role of Redox in Dopa-Mediated Marine Adhesion," Biofouling, 28 (8), 865-877. https://doi.org/10.1080/08927014.2012.719023.
Nischan et al. (publicly available Aug. 2013) "Stabilization of Peptides for Intracellular Applications by Phosphoramidate-Linked Polyethylene Glycol Chains," Angew. Chem., Int. Ed. (Nov. 2013), 52(45): 11920-11924.
Nomura et al. (2010) "Precise Synthesis of Polymers Containing Functional End Groups by Living Ring-Opening Metathesis Polymerization (ROMP): Efficient Tools for Synthesis of Block/Graft Copolymers," Polymer, 51 (9), 1861-1881. https://doi.org/10.1016/J.POLYMER.2010.02.028.
North et al. (2017) "High Strength Underwater Bonding with Polymer Mimics of Mussel Adhesive Proteins," ACS Appl. Mater. Interfaces, 9 (8), 7866-7872. https://doi.org/10.1021/acsami.7b00270.

(56) References Cited

OTHER PUBLICATIONS

O'Brien-Simpson et al. (1997) "Polymerization of Unprotected Synthetic Peptides: A View toward Synthetic Peptide Vaccines," J. Am. Chem. Soc. 119(6): 1183-1188.
Ontoria et al. (Apr. 2020) "Combined Peptide and Small-Molecule Approach towards Nonacidic THIQ Inhibitors of the KEAP1/NRF2 Interaction," ACS Med. Chem. Lett. 11, 5, 740-746.
Osapay et al. (1997) "Lanthionine-somatostatin analogs: synthesis, characterization, biological activity, and enzymatic stability studies," J. Med. Chem. 40(14): 2241-2251.
Ostankovitch et al. (1998) "A partially modified retro-inverso pseudopeptide modulates the cytokine profile ofCTL specific for an influenza virus epitope," J Immunol, 161 (1), 200-8.
Ostro (1989) "Use of liposomes as injectable-drug delivery systems ," Am. J. Hosp. Pharm.46:1576-1587.
Ott et al. (2017) "An immunogenic personal neoantigen vaccine for patients with melanoma," Nature, 547 (7662), 217-221.
Ouyang et al. (2010) "Simultaneous Visualization of Protumorigenic Src and MT1-MMP Activities with Fluorescence Resonance Energy Transfer," Cancer Res. 70(6): 2204-2212.
Overwijk et al. (1998) "gp100/pmel 17 is a murine tumor rejection antigen: induction of "self"-reactive, tumoricidal T cells using high-affinity, altered peptide ligand," J Exp Med, 188 (2), 277-86.
Panganiban et al. (2018) "Random Heteropolymers Preserve Protein Function in Foreign Environments," Science, 359 (6381), 1239-1243.
Panieri et al. (2019) "Potential applications of NRF2 inhibitors in cancer therapy," Oxid Med Cell Longev, vol. 2019, 8592348, https://doi.org/10.1155/2019/8592348.
Parent et al. (Oct. 2018) "Hierarchical Spidroin Micellar Nanoparticles as the Fundamental Precursors of Spider Silks," Proc Nat Acad Sci U S A, 115(45):11507-11512. PMCID: PMC6233143.
Patel et al. (2007) "Cell Penetrating Peptides: Intracellular Pathways and Pharmaceutical Perspectives," Pharm. Res. 24(11): 1977-1992.
Patel et al. (2012) "Synthesis and Cell Adhesive Properties of Linear and Cyclic RGD Functionalized Polynorbornene Thin Films," Biomacromolecules 13(8): 2546-2553.
Patterson et al. (2015) "Observing the Growth of Metal-Organic Frameworks by In Situ Liquid Cell Tem," J Am Chem Soc., 137(23):7322-7328. https://doi.org/10.1021/jacs.5b00817.
Payne et al. (Aug. 2020) "BTN3A1 governs antitumor responses by coordinating ab and gd T cells," Science 369, 942-949.
Pazos et al. (2009) "Peptide-based fluorescent biosensors," Chem. Soc. Rev. 38(12): 3348-3359.
Pearson et al. (1988) "Improved tools for biological sequence comparison," Proc. Nat'l. Acad. Sci. USA 85(8):2444-2448.
Pena-Francesch et al. (2019) "Squid-Inspired Tandem Repeat Proteins: Functional Fibers and Films," Frontiers in Chemistry. Frontiers Media S.A. 7, 69. https://doi.org/10.3389/fchem.2019.00069.
Peng et al. (2006) "Characterization of HLA-A2-restricted HPV-16 E7-specific CD8(+) T-cell immune responses induced by DNA vaccines in HLA-A2 transgenic mice," Gene Ther, 13 (1), 67-77.
Perales-Puchalt et al. (2016) "Follicle-stimulating hormone receptor is expressed by most ovarian cancer subtypes and is a safe and effective immunotherapeutic target," Clin. Cancer Res. 23:441-53. PMC5241180.
Periole et al. (2009) "Combining an Elastic Network With a Coarse-Grained Molecular Force Field: Structure, Dynamics, and Intermolecular Recognition," J. Chem. Theory Comput. 5 (9), 2531-2543.
Peters et al. (2017) "Impact of tumor mutation burden on the efficacy of first-line nivolumab in stage iv or recurrent non-small cell lung cancer: An exploratory analysis ofCheckMate 026," Cancer Res;77(13 Suppl): Abstract nr CT082.
Phillips et al. (2005) "Scalable molecular dynamics with NAMD," Journal of Computational Chemistry 26(16): 1781- 1802.
Pini et al. (2008) "Branched Peptides as Therapeutics," Curr. Protein Pept. Sci. 9(5): 468-477.
Plückthun (2015) "Designed Ankyrin Repeat Proteins (DARPins): Binding Proteins for Research, Diagnostics, and Therapy," Annu. Rev. Pharmacol. Toxicol. 55, 489.
Poropatich et al. (2017) "Comprehensive T-cell immunophenotyping and next-generation sequencing of human papillomavirus (HPV)-positive and HPV-negative head and neck squamous cell carcinomas," J Pathol, 243 (3), 354-365.
Powell et al. (1993) "Peptide Stability in Drug Development. II. Effect of Single Amino Acid Substitution and Glycosylation on Peptide Reactivity in Human Serum," Pharm. Res. 10(9): 1268-1273.
Price et al. (2004) "A modified TIP3P water potential for simulation with Ewald summation," J. Chem. Phys. 121(20): 10096-10103.
Proetto et al. (2016) "Cellular Delivery of Nanoparticles Revealed with Combined Optical and Isotopic Nanoscopy," ACS Nano, 10 (4),4046-54.
Pronk et al. (publicly available Feb. 2013) "GROMACS 4.5: a high-throughput and highly parallel open source molecular simulation toolkit," Bioinformatics (Apr. 2013) 29(7): 845-854.
Puglisi et al. (1995) "Solution Structure of a Bovine Immunodeficiency Virus Tat-TAR Peptide-RNA Complex," Science 270(5239): 1200-1203, (Machine Generated Copy).
Qiao et al. (2019) "Water Follows Polar and Nonpolar Protein Surface Domains," Proc. Natl. Acad. Sci. U. S. A. 116, 19274-19281.
Qiao et al. (Apr. 2019) ""Mirror"-Like Protein Dimers Stabilized by Local Heterogeneity at Protein Surfaces," J. Phys. Chem. B, 123 (18), 3907-3915.
Qiao et al. (Aug. 2020) "Enhanced Binding of SARS-CoV-2 Spike Protein to Receptor by Distal Polybasic Cleavage Sites," ACS Nano, 14, 10616-10623.
Ramon et al. (2005) "PEGylated Interferon-α2b: A Branched 40K Polyethylene Glycol Derivative," Pharm. Res. 22(8): 1374-1386.
Ramsey et al. (2007) "Expression of Nrf2 in Neurodegenerative Diseases," J Neuropathol Exp Neurol;66:75-85. https://doi.org/10.1097/nen.0b013e31802d6da9.
Ramshaw et al. (2014) "Bioengineered Collagens," Bioengineered, 5 (4), 227-233. https://doi.org/10.4161/BIOE.28791.
Rankin et al. (2007) "The controlled homogeneous organic solution polymerization of new hydrophilic cationic exo-7-oxanorbornenes via ROMP with RuCl2(PCy3)2CHPh in a novel 2,2,2-trifluoroethanol/methylenechloride solvent mixture," J. Polym. Sci. A Polym. Chem. 45(11): 2113-2128.
Rao (1995) "Recent developments of collagen-based materials for medical applications and drug delivery systems," Biomater Sci. Polym. Ed. 7:623-645.
Rao et al. (2012) "Norbornene Derived Doxorubicin Copolymers as Drug Carriers with pH Responsive Hydrazone Linker," Biomacromolecules 13(1): 221-230.
Regenbrecht et al. (2008) "Stemming cancer: functional genomics of cancer stem cells in solid tumors," Stem Cell Rev. 4(4):319-28.
Reissmann et al. (2000) "The LHRH antagonist Cetrorelix: a review," Human Reproduction Update 6(4): 322-331.
Richard et al. (2003) "Cell-penetrating Peptides: A Reevaluation of the Mechanism of Cellular Uptake," J. Biol. Chem. 278(1): 585-590.
Rodal et al. (1999) "Extraction of Cholesterol with Methyl-β-Cyclodextrin Perturbs Formation of Clathrin-coated Endocytic Vesicles," Mol. Biol. Cell 10(4): 961-974.
Roloff et al. (2017) "Micellar Thrombin-Binding Aptamers: Reversible Nanoscale Anticoagulants," J Am Chem Soc., 139(46):16442-16445. PMID: 29135251. DOI: 10.1021/jacs.7b07799.
Roloff et al. (Jan. 2018) "Self-Transfecting Micellar RNA: Modulating Nanoparticle Cell Interactions via High Density Display of Small Molecule Ligands on Micelle Coronas," Bioconjug Chem., 29(1):126-135. PMCID: PMC5993044.
Rosemalen et al. (2017) "Tuning the Flexibility of Glycine, Serine Linkers to Allow Rational Design of Multidomain Proteins," pp. 6565-6574. Biochemistry. vol. 56, No. 50; DOI: 10.1021/acs.biochem.7b00902.
Rouse et al. (2010) "A Review of Keratin-Based Biomaterials for Biomedical Applications," Materials (Basel). 3 (2), 999-1014. https://doi.org/10.3390/ma3020999.

(56) References Cited

OTHER PUBLICATIONS

Rozek et al. (2003) "Structure-Based Design of an Indolicidin Peptide Analogue with Increased Protease Stability," Biochemistry 42(48): 14130-14138.
Ruijtenbeek et al. (2001) "Peptoid—Peptide Hybrids That Bind Syk SH2 Domains Involved in Signal Transduction," ChemBioChem 2(3): 171-179.
Rush et al. (2013) "Nuclease-resistant DNA via High Density Packing in Polymeric Micellar Nanoparticle Coronas," ACS Nano, 7(2):1379-1387. PMCID: PMC3608424.
Rush et al. (May 2014) "Intracellular mRNA Regulation with Self-Assembled Locked Nucleic Acid Polymer Nanoparticles," J. Am. Chem. Soc. 136: 7615-7618.
Rutkowski et al. (2015) "Microbially driven TLR-dependent signalling governs distal malignant progression through tumor-promoting inflammation," Cancer Cell; 27: 27-40. PMC4293269.
Ruttekolk et al. (2011) "Coupling to Polymeric Scaffolds Stabilizes Biofunctional Peptides for Intracellular Applications," Mol. Pharmacol. 79(4): 692-700.
Sahin et al. (Mar. 2018) "Personalized vaccines for cancer immunotherapy," Science. 359. 1355-1360.
Salim et al. (Feb. 2020) "Development of a Cell-Permeable Cyclic Peptidyl Inhibitor against the Keap1—Nrf2 Interaction," J. Org. Chem. 85, 1416-1424.
Samarajeewa et al. (publicly available Dec. 2013) "Programmed hydrolysis of nanoassemblies by electrostatic interaction-mediated enzymatic-degradation," Chem. Commun. (Jan. 2014), 50(8): 968-970.
Sánchez-Paulete et al. (Dec. 2017) "Antigen cross-presentation and T-cell cross-priming in cancer immunology and immunotherapy," Ann Oncol. 28(suppl_12):xii44-xii55.
Sanford et al. (2001) "A Versatile Precursor for the Synthesis of New Ruthenium Olefin Metathesis Catalysts," Organometallics 20(25): 5314-5318.
Scarlett et al. (2012) "Ovarian cancer progression is controlled by phenotypic changes in dendritic cells," J Exp Med; 209:495-506. PMC3302234.
Schabath et al. (2016) "Differential association of STK11 and TP53 with KRAS mutation-associated gene expression, proliferation and immune surveillance in lung adenocarcinoma," Oncogene 35(24): 3209-3216, PMCID: PMC4837098.
Schafmeister et al. (2000) "An All-Hydrocarbon Cross-Linking System for Enhancing the Helicity and Metabolic Stability of Peptides," J. Am. Chem. Soc. 122(24): 5891-5892.
Scheller et al. (2001) "Production of Spider Silk Proteins in Tobacco and Potato," Nat. Biotechnol. 19 (6), 573-577. https://doi.org/10.1038/89335.
Schellinger et al. (Jul. 2013) "Block Copolymers Containing a Hydrophobic Domain of Membrane-Lytic Peptides Form Micellar Structures and Are Effective Gene Delivery Agents," ACS Macro Lett. 2(8): 725-730.
Schmidlin et al. (2019) "Redox regulation by NRF2 in aging and disease," Free Radic Biol Med:702-7. https://doi.org/10.1016/j.freeradbiomed.2019.01.016.
Scholl et al. (1999) "Synthesis and Activity of a New Generation of Ruthenium-Based Olefin Metathesis Catalysts Coordinated with 1,3-Dimesityl-4,5-dihydroimidazol-2-ylidene Ligands," Org. Lett. 1(6): 953-956.
Schuster et al. (1997) "Neoglycopolymers produced by aqueous ring-opening metathesis polymerization: decreasing saccharide density increases activity," J. Mol. Catal. 116(1-2): 209-216.
Search Report and Written Opinion, dated Jan. 21, 2021, corresponding to International Application No. PCT/US2020/045729, 15 pp.
Shae et al. (Mar. 2019) "Endosomolytic polymersomes increase the activity of cyclic dinucleotide STING agonists to enhance cancer immunotherapy," Nat Nanotechnol, 14 (3), 269-278.
Shannon et al. (2001) "Novel cyclic peptide inhibits intercellular adhesion molecule-1-mediated cell aggregation," J Pept Res. 58(2):140-50.
Sharp et al. (2009) "Uptake of particulate vaccine adjuvants by dendritic cells activates the NALP3 inflammasome," P Natl Acad Sci USA, 106 (3), 870-875.
Shi et al. (Oct. 2013) "Engineering biodegradable and multifunctional peptide-based polymers for gene delivery," J. Biol. Eng. 7: 25, pp. 1-10.
Silverman et al. (2007) "Understanding Marine Mussel Adhesion," Marine Biotechnology. Springer, pp. 661-681. https://doi.org/10.1007/s10126-007-9053-x.
Simov et al. (Nov. 2021) "Discovery and characterization of novel peptide inhibitors of the NRF2/MAFG/DNA ternary complex for the treatment of cancer," European Journal of Medicinal Chemistry, 224, 113686.
Singh et al. (2016) "Small Molecule Inhibitor of NRF2 Selectively Intervenes Therapeutic Resistance in KEAP1-Deficient NSCLC Tumors," ACS Chem Biol; 11:3214-25. https://doi.org/10.1021/ACSCHEMBIO.6B00651.
Sionkowska et al. (2017) "The Review of Versatile Application of Collagen," Polym. Adv. Technol. 28 (1), 4-9. https://doi.org/10.1002/pat.3842.
Sivick et al. (Dec. 2018) "Magnitude of Therapeutic STING Activation Determines CD8(+) T Cell-Mediated Anti-tumor Immunity," Cell Rep, 25 (11), 3074-3085 e5.
Smirnova et al. (2011) "Development of Neh2-luci-ferase reporter and its application for high throughput screening and real-time monitoring of Nrf2 Activators," Chemistry & Biology, 18, 752-765.
Smith et al. (1981) "Comparison of Biosequences," Adv. Appl. Math. 2:482-489.
Smith et al. (2017) "MET:GRB2 Signaling-Associated Complexes Correlate with Oncogenic MET Signaling and Sensitivity to MET kinase inhibitors," Clin Cancer Res. PMCID: PMC5833309.
Smyth et al. (2016) "Combination cancer immunotherapies tailored to the tumour microenvironment," Nat Rev Clin Oncol, 13 (3), 143-58.
Som et al. (2011) "Self-Activation in De Novo Designed Mimics of Cell-Penetrating Peptides," Angew. Chem., Int. Ed. 123: 6271-6274.
Song et al. (Oct. 2018) "IRE1α—XBP1 controls T cell function in ovarian cancer by regulating mitochondrial activity," Nature. 562:423-8. PMC6237282.
Spring et al. (publicly available May 2014) "The preparation of well-controlled poly(N-cyclohexyl-exo-norbornene-5, 6-dicarboximide) polymers," Polymer Journal (Sep. 2014) 46: 576-583.
Steel et al. (2012) "Anti-inflammatory Effect of a Cell-Penetrating Peptide Targeting the Nrf2/Keap1 Interaction," ACS Med. Chem. Lett. 3, 407-410.
Steer et al. (2002) "β-Amino Acids: Versatile Peptidomimetics," Curr. Med. Chem. 9(8): 811-822.
Stephen et al. (2014) "Transforming Growth Factor-beta-Mediated Suppression of Antitumor T Cells Requires FoxP1 Transcription Factor Expression," Immunity; 41:427-39. PMC4174366.
Stephen et al. (2017) "SATB1 expression governs epigenetic repression of PD-1 in tumor-reactive T cells," Immunity; 46: 51-64. PMC5336605.
Stickle et al. (1992) "Hydrogen bonding in globular proteins," J. Mol. Biol. 226(4): 1143-1159.
Su et al. (1991) "In Vitro Stability of Growth Hormone Releasing Factor (GRF) Analogs in Porcine Plasma," Horm. Metab. Res. 23(1): 15-21.
Su et al. (2014) "Resilin: Protein-Based Elastomeric Biomaterials," Acta Biomaterialia. Elsevier BV, pp. 1601-1611. https://doi.org/10.1016/j.actbio.2013.06.038.
Sun et al. (2012) "A novel mouse CD133 binding-peptide screened by phage display inhibits cancer cell motility in vitro," Clin Exp Metastasis, 29, 185-196.
Sun et al. (Dec. 2021) "Origin of Proteolytic Stability of Peptide-Brush Polymers as Globular Proteomimetics," ACS Cent. Sci. 7 (12), 2063-2072.
Sun et al. (Nov. 2019) "Bioactive Peptide Brush Polymers via Photoinduced Reversible-Deactivation Radical Polymerization," Angewandte Chemie International Edition in English. vol. 58, No. 48; pp. 17359-17364; DOI: 10.1002/anie.201908634.

(56) References Cited

OTHER PUBLICATIONS

Sun et al. (Oct. 2020) "Direct inhibition of Keap1—Nrf2 Protein-Protein interaction as a potential therapeutic strategy for Alzheimer's disease," Bioorg Chem;103:104172. https://doi.org/10.1016/j.bioorg.2020.104172.
Sutthasupa et al. (2010) "Recent advances in ring-opening metathesis polymerization, and application to synthesis of functional materials," Polymer Journal 42: 905-915.
Svoronos et al. (2017) "Tumor cell-independent estrogen signaling drives malignant progression through MDSC mobilization," Cancer Discovery. 7: 72-85. PMC5222699.
Tang et al. (2011) "Luteolin inhibits Nrf2 leading to negative regulation of the Nrf2/ARE pathway and sensitization of human lung carcinoma A549 cells to therapeutic drugs," Free Radic Biol Med;50:1599-1609. https://doi.org/10.1016/J.FREERADBIOMED.2011.03.008.
Tanji et al. (2013) "Keap1 Is Localized in Neuronal and Glial Cytoplasmic Inclusions in Various Neurodegenerative Diseases," J Neuropathol Exp Neurol; 72:18-28. https://doi.org/10.1097/NEN.0b013e31827b5713.
Tesone et al. (2016) "Satb1 Overexpression Drives Tumor-Promoting Activities in Cancer-Associated Dendritic Cells," Cell Reports.14: 1774-1786. PMC4767618.
Thompson et al. (publicly available Dec. 2013) "Labelling Polymers and Micellar Nanoparticles via Initiation, Propagation and Termination with ROMP," Polym Chem, Mar. 2014 5(6):1954-1964.
Thundimadathil (Dec. 2012) "Cancer Treatment Using Peptides: Current Therapies and Future Prospects," Journal of Amino Acids 2012(967347): 1-13.
Tijssen (1993) "Overview of principles of hybridization and the strategy of nucleic acid probe assays," in Techniques in Biochemistry and Molecular Biology—Hybridization with Nucleic Probes, 19-78.
Tomita (2011) "Transgenic Silkworms That Weave Recombinant Proteins into Silk Cocoons," Biotechnology Letters. Springer, pp. 645-654. https://doi.org/10.1007/s10529-010-0498-z.
Toti et al. (2010) "Interfacial Activity Assisted Surface Functionalization: A Novel Approach to Incorporate Maleimide Functional Groups and cRGD Peptide on Polymeric Nanoparticles for Targeted Drug Delivery," Mol Pharm. 7(4): 1108-1117.
Touve et al. (Apr. 2018) "Polymerization-Induced Self-Assembly of Micelles Observed by Liquid Cell Transmission Electron Microscopy," ACS Central Sci. 4, 543-547.
Trabulo et al. (2010) "Cell-Penetrating Peptides—Mechanisms of Cellular Uptake and Generation of Delivery Systems," Pharmaceuticals 3(4): 961-993.
Tran et al. (2019) "A Comparative Assessment Study of Known Small-Molecule Keap1-Nrf2 Protein-Protein Interaction Inhibitors: Chemical Synthesis, Binding Properties, and Cellular Activity," J. Med. Chem. 62, 17, 8028-8052.
Trnka et al. (2001) "The Development of L2X2RuCHR Olefin Metathesis Catalysts: An Organometallic Success Story," Acc. Chem. Res. 34(1): 18-29.
Tsai et al. (2015) "ICAM1 Is a Potenital Cancer Stem Cell Marker of Esophageal Squamous Cell Carcinoma," PLOS ONE 10(11): e0142834.
Turbant et al. (2009) "Cynomolgus macaques immunized with two HIV-1 Tat stabilized proteins raise strong and long-lasting immune responses with a pattern of Th1/Th2response differing from that in mice," Vaccine, 27 (39), 5349-56.
Tymoczko ed. (2010) Biochemistry: A Short Course, 2nd ed., W.H. Freeman and Company: 13-15.
Ungerleider et al. (2017) "Enzyme-Targeted Nanoparticles for Delivery to Ischemic Skeletal Muscle," Polym Chem., 8(34):5212-5219. PMCID: PMC5662209.
Uto et al. (2009) "Modulation of innate and adaptive immunity by biodegradable nanoparticles," Immunol Lett, 125 (1), 46-52.
Van Der Burg et al. (2016) "Vaccines for established cancer: overcoming the challenges posed by immune evasion," Nat Rev Cancer. 16(4):219-33.
Vanommeslaeghe et al. (2010) "CHARMM general force field: A force field for drug-like molecules compatible with the CHARMM all-atom additive biological force fields," J. Comput. Chem. 31(4): 671-690.
Vanommeslaeghe et al. (2012) "Automation of the CHARMM General Force Field (CGenFF) I: Bond Perception and Atom Typing," J. Chem. Inf. Model. 52(12): 3144-3154.
Vanommeslaeghe et al. (2012) "Automation of the CHARMM General Force Field (CGenFF) II: Assignment of Bonded Parameters and Partial Atomic Charges," J. Chem. Inf Model. 52(12): 3155-3168.
Verdine et al. (2012) "Chapter one—Stapled Peptides for Intracellular Drug Targets, " Methods Enzymol. 503: 3-33.
Vlieghe et al. (2010) "Synthetic therapeutic peptides: science and market," Drug Discovery Today 15(1-2): 40-56.
Vonderheit et al. (2005) "Rab7 Associates with Early Endosomes to Mediate Sorting and Transport of Semliki Forest Virus to Late Endosomes," PLoS Biol. 3(7): 1225-1238.
Waite (2017) "Mussel Adhesion—Essential Footwork," Journal of Experimental Biology. Company of Biologists Ltd, pp. 517-530. https://doi.org/10.1242/jeb.134056.
Wang et al. (1999) "Phase I trial of a MART-1 peptide vaccine with incomplete Freund's adjuvant for resected high-risk melanoma," ClinCancer Res, 5 (10), 2756-65.
Wang et al. (2004) "Development and testing of a general amber force field," J. Comput. Chem. 25(9): 1157-1174.
Wang et al. (2014) "Recent progress of cell-penetrating peptides as new carriers for intracellular cargo delivery," J. Controlled Release (Jan. 2014) 174: 126-136.
Wang et al. (May 2019) "Rational vaccinology with spherical nucleic acids," Proc Natl Acad Sci U S A, 116(21), 10473-10481.
Warren et al. (2000) "APC Stimulated by CpG Oligodeoxynucleotide Enhance Activation of MHC Class I-Restricted T Cells," J. Immunol. 165 (11), 6244-6251. https://doi.org/10.4049/JIMMUNOL. 165.11.6244.
Weinstock et al. (2012) "Protease-resistant peptide design—empowering nature's fragile warriors against HIV," Pept. Sci. 98(5): 431-442.
Weiss et al. (2017) "The STING agonist DMXAA triggers a cooperation between T lymphocytes and myeloid cells that leads to tumor regression," Oncoimmunology, 6 (10), e1346765.
Wender et al. (2000) "The design, synthesis, and evaluation of molecules that enable or enhance cellular uptake: Peptoid molecular transporters," Proc. Natl. Acad. Sci. U. S. A. 97(24): 13003-13008.
Widmann et al. (1991) "Differential stability of antigenic MHC class I restricted synthetic peptides," J Immunol, 147 (11), 3745-51.
Willaert (2018) "Cell Immobilization and Its Applications in Biotechnology: Current Trends and Future Prospects," Ferment. Microbiol. Biotechnol. Fourth Ed. 323-358. https://doi.org/10.1201/9780429506987-17.
Williamson et al. (2012) "Discovery of Potent, Novel Nrf2 Inducers Via Quantum Modeling, Virtual Screening, and In Vitro Experimental Validation," Chem Biol Drug Des; 80: 810-820.
Wolchok et al. (2007) "Safety and immunogenicity of tyrosinase DNA vaccines in patients with melanoma," Mol Ther, 15 (11), 2044-50.
Woodley (1994) "Enzymatic barriers for GI peptide and protein delivery," Crit. Rev. Ther. Drug Carrier Syst. 11(2-3): 61-95.
Xiao et al. (2015) "Bioinspired Structural Colors Produced via Self-Assembly of Synthetic Melanin Nanoparticles," ACS Nano, 9(5):5454-5460. https://doi.org/10.1021/acsnano.5b01298.
Xiao et al. (2017) "Bio-Inspired Bright Non-Iridescent Photonic Melanin Supraballs," Science Advances, 3(9):e1701151. DOI: 10.1126/sciadv.1701151.
Xu et al. (2007) "Construct Synthetic Gene Encoding Artificial Spider Dragline Silk Protein and Its Expression in Milk of Transgenic Mice," Anim. Biotechnol. 18 (1), 1-12. https://doi.org/10.1080/10495390601091024.

(56) References Cited

OTHER PUBLICATIONS

Xu et al. (2013) "Cytomegalovirus-based cancer vaccines expressing TRP2 induce rejection of melanoma in mice," Biochem Biophys Res Commun, 437 (2), 287-91.

Xu et al. (2017) "Mussel-Inspired Polyesters with Aliphatic Pendant Groups Demonstrate the Importance of Hydrophobicity in Underwater Adhesion," Adv. Mater. Interfaces, 4 (22), 1700506. https://doi.org/10.1002/admi.201700506.

Xu et al. (Feb. 2021) "Injectable and Biocompatible Mussel-Inspired Adhesive for Enhanced Reendothelialization of Injured Artery," Adv. Mater. Interfaces, 8 (7), 2001955. https://doi.org/10.1002/ADMI.202001955.

Yadav et al. (2014) "Predicting immunogenic tumour mutations by combining mass spectrometry and exome sequencing," Nature, 515(7528), 572-6.

Yamaguchi et al. (2003) "Effect of α,α-Dialkyl Amino Acids on the Protease Resistance of Peptides," Biosci., Biotechnol., Biochem. 67(10): 2269-2272.

Zhang et al. (2003) "Intratumoral T cells, recurrence and survival in epithelial ovarian cancer," N Engl J Med; 348:201-211.

Zhang et al. (2007) "Thrombospondin-based antiangiogenic therapy," Microvasc Res. 74(2-3), 90-99.

Zhang et al. (2015) "Polyelectrolyte Multilayers Assembled Entirely from Immune Signals on Gold Nanoparticle Templates Promote Antigen-Specific T Cell Response," ACS Nano, 9 (6), 6465-77.

Zhang et al. (Apr. 2020) "Emerging Substrate Proteins of Kelch-like ECH Associated Protein 1 (Keap1) and Potential Challenges for the Development of Small-Molecule Inhibitors of the Keap1-Nuclear Factor Erythroid 2-Related Factor 2 (Nrf2) Protein—Protein Interaction," J. Med. Chem. 63, 7986-8002.

Zhao et al. (2016) "Prognostic value of the expression of cancer stem cell-related markers CD133 and CD44 in hepatocellular carcinoma: From patients to patient-derived tumor xenograft models," Oncotarget. 7(30):47431-47443.

Zhao et al. (publicly available Aug. 2013) "Mimicry of High-Density Lipoprotein: Functional Peptide—Lipid Nanoparticles Based on Multivalent Peptide Constructs," J. Am. Chem. Soc. (Sep. 2013) 135(36): 13414-13424.

Zhou et al. (2015) "Adhesion Properties of Catechol-Based Biodegradable Amino Acid-Based Poly(Ester Urea) Copolymers Inspired from Mussel Proteins," Biomacromolecules, 16 (1), 266-274. https://doi.org/10.1021/bm501456g.

Zidovetzki et al. (2007) "Use of cyclodextrins to manipulate plasma membrane cholesterol content: Evidence, misconceptions and control strategies," Biochim. Biophys. Acta 1768(6): 1311-1324.

Zielińska et al. (2020) "Polymeric Nanoparticles: Production, Characterization, Toxicology and Ecotoxicology," Molecules, 25: 3731.

Peptide Sequence: LDPETGEFLRRRR

Peptide Sequence: LDPETGEFLRRRR

Peptide Sequence: DERLERPLTRGFR

Peptide Sequence: DERLERPLTRGFR

Peptide Sequence: DELEPLTGFRRRR

Peptide Sequence: DELEPLTGFRRRR

Peptide Sequences: LDPETGEFL, YGRKKRRQRRR

| | ProPep PLP | ProPep Peptide | ProPepR PLP | ProPepR Peptide |
|---|---|---|---|---|
| AbsoluteIC50 | 0.1095 | 0.3139 | 0.05385 | 1.866 |

Cell membrane (green); Cell nucleus (blue); PLP (red)

Cell membrane (green); Cell nucleus (blue); PLP (red)

Cell membrane (green); Cell nucleus (blue); PLP (red)

Cell membrane (green); Cell nucleus (blue); PLP (red)

Cell membrane (green); Cell nucleus (blue); PLP (red)

Cell membrane (green); Cell nucleus (blue); PLP (red)

KEAP1/NRF2 PROTEIN-LIKE POLYMERS

CROSS-REFERENCE TO RELATED APPLICATIONS

This application is a U.S. National Stage Application under 35 U.S.C. § 371 of International Application No. PCT/US2022/023274, filed Apr. 4, 2022, which claims the benefit of priority to U.S. Provisional Patent Application No. 63/170,830, filed Apr. 5, 2021, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 32,200 Byte ASCII (Text) file named "339168_14-21_WO_ST25.TXT," created on Mar. 3, 2022.

BACKGROUND OF INVENTION

The use of protein and peptide therapeutics continues to increase dramatically for diverse clinical applications. However, inefficiencies in cellular uptake and rapid digestion by proteases are two problems that have limited the clinical adoption of peptide-based therapeutics. Accordingly, many peptide therapeutics are incompatible with systemic administration and, therefore, must be administered by injection at the site of action due to poor in vivo stability. This can result in poor patient compliance and, as such, many peptide therapies only are used clinically as salvage treatments.

One particular area of interest is in developing therapeutics targeting the protein-protein interaction between Nuclear factor (erythroid-derived 2)-like 2 (Nrf2) and Kelch-like ECH-Associating protein 1 (Keap1). The Keap1/Nrf2 interaction is important in a number of conditions including, for example, neurodegenerative diseases such as Alzheimer's and Parkinson's disease as well as heart and skin diseases among others. A therapeutic that successfully inhibits Keap1/Nrf2 binding can enhance the antioxidant and anti-inflammatory response to provide cytoprotective and neuroprotective effects for a number of disease states.

In this regard, Colarusso et al. (*Bioorganic Med. Chem.*, 28; 1-12 (2020)) discloses the optimization of linear and cyclic peptide inhibitors of Keap1/Nrf2 protein-protein interaction. More particularly, Colarusso et al. generates a library of linear peptides based on the Nrf2-binding motif SEQ ID NO: 1 (LDEETGEFL). However, the linear and cyclic peptide inhibitors of Keap1/Nrf2, disclosed by Colarusso et al. suffer from substantial lack of cell permeability and were inactive. Thus, there remains a need for therapeutics targeting the protein-protein interaction between Nuclear factor (erythroid-derived 2)-like 2 (Nrf2) and Kelch-like ECH-Associating protein 1 (Keap1), which are cell permeable and enhance cellular Nrf2 activity.

Once the inefficiencies of cellular uptake are addressed, there remains the issue of digestion by proteases. Several approaches for producing peptides protected from proteolysis involve chemical modification of the amino acid sequence, which generally necessitates multiple rounds of structure-function studies to confirm that the activity of the peptide is not altered. Other approaches not using chemical modification of the amino acid sequence involve conjugation of the peptide to a pre-formed higher molecular weight structure, such as a polymer or nanomaterial. The downside of these approaches includes requiring additional conjugation and purification steps, as well as the formation of, and release from, the high molecular weight carrier.

Despite these challenges, there remaining significant interest in developing improved delivery systems to enhance clinical applicability and overall efficacy for therapies involving therapeutic peptides. Thus, there remains a need for delivery systems and methods for therapeutic peptides, such as those targeting the protein-protein interaction between Nuclear factor (erythroid-derived 2)-like 2 (Nrf2) and Kelch-like ECH-Associating protein 1 (Keap1), which provide improved pharmacokinetic properties, administration routes and overall efficacies.

SUMMARY OF THE INVENTION

In an aspect, the invention provides a peptide having from 11 to 16 amino acid residues comprising a sequence having 85% or greater (e.g., 90% or greater, 95% or greater, or 100%) sequence identity of SEQ ID NO: 1 (LDEETGEFL), wherein the peptide further comprises a charge modulating domain having from 2 to 7 amino acid residues. In some embodiments, the sequence having 85% or greater (e.g., 90% or greater, 95% or greater, or 100%) sequence identity of SEQ ID NO: 1 (LDEETGEFL) is SEQ ID NO: 1 (LDEETGEFL). In other embodiments, the sequence having 85% or greater sequence identity of SEQ ID NO: 1 (LDEETGEFL) is SEQ ID NO: 2 (LDPETGEFL). Typically, the charge modulating domain is a glycine-serine domain, a cationic residue domain, or a combination thereof.

In some aspects, the present invention further provides a peptide comprising a sequence having 75% or greater (e.g., 80% or greater, 85% or greater, 90% or greater, 95% or greater, or 100%) sequence identity of SEQ ID NO: 1-SEQ ID: 138, SEQ ID: 140, or SEQ ID: 141. In certain aspects, the present invention provides a peptide selected from: SEQ ID NO: 3 (LDEETGEFLRR), SEQ ID NO: 4 (LDEETGEFLRRR), SEQ ID NO: 5 (LDEETGEFLRRRR), SEQ ID NO: 6 (LDEETGEFLRRRRR), SEQ ID NO: 7 (RRLDEETGEFL), SEQ ID NO: 8 (RRRLDEETGEFL), SEQ ID NO: 9 (RRRRLDEETGEFL), SEQ ID NO: 10 (RRRRRLDEETGEFL), SEQ ID NO: 11 (RRLDEETGEFLRR), SEQ ID NO: 12 (RRRLDEETGEFLRRR), SEQ ID NO: 13 (RLDEETGEFLR), SEQ ID NO: 14 (RLDEETGEFLRR), SEQ ID NO: 15 (RRLDEETGEFLR), SEQ ID NO: 16 (RLDEETGEFLRRR), SEQ ID NO: 17 (RRRLDEETGEFLR), SEQ ID NO: 18 (RLDEETGEFLRRRR), SEQ ID NO: 19 (RRLDEETGEFLRRR), SEQ ID NO: 20 (RRRLDEETGEFLRR), SEQ ID NO: 21 (RRRRLDEETGEFLR), SEQ ID NO: 22 (RLDEETGEFLRRRRR), SEQ ID NO: 23 (RRLDEETGEFLRRRR), SEQ ID NO: 24 (RRRRLDEETGEFLRR), SEQ ID NO: 25 (RRRRRLDEETGEFLR), SEQ ID NO: 26 (LDEETGEFLKK), SEQ ID NO: 27 (LDEETGEFLKKK), SEQ ID NO: 28 (LDEETGEFLKKKK), SEQ ID NO: 29 (LDEETGEFLKKKKK), SEQ ID NO: 30 (KKLDEETGEFL), SEQ ID NO: 31 (KKKLDEETGEFL), SEQ ID NO: 32 (KKKKLDEETGEFL), SEQ ID NO: 33 (KKKKKLDEETGEFL), SEQ ID NO: 34 (KKLDEETGEFLKK), SEQ ID NO: 35 (KKKLDEETGEFLKKK), SEQ ID NO: 36 (KLDEETGEFLK), SEQ ID NO: 37 (KLDEETGEFLKK), SEQ ID NO: 38 (KKLDEETGEFLK), SEQ ID NO: 39 (KLDEETGEFLKKK), SEQ ID NO: 40 (KKKLDEETGEFLK), SEQ ID NO: 41 (KLDEETGEFLKKKK), SEQ ID NO: 42 (KKLDEETGEFLKKK), SEQ ID NO: 43 (KKKLDEETGEFLKK), SEQ ID NO: 44 (KKKKLDEETGEFLK), SEQ ID NO: 45 (KLDEETGEFLKKKKK), SEQ ID NO: 46 (KKLDEETGEFLKKKK), SEQ ID NO: 47 (KKKKLDEETGEFLKK), SEQ ID NO: 48 (KKKKKLDEETGEFLK), SEQ ID NO: 49 (LDEETGEFLKRKR), SEQ ID NO: 50 (KRKRLDEETGEFL), SEQ ID NO: 51 (RKRKLDEETGEFL), SEQ ID NO: 52 (LDEETGEFLRKRK), SEQ ID NO: 53 (KKLDEETGEFLRR), SEQ ID NO: 54 (RRLDEETGEFLKK), SEQ ID NO: 55 (KLDEETGEFLRRR), SEQ ID NO: 56 (KKKLDEETGEFLR), SEQ ID NO: 57 (RRRLDEETGEFLK), SEQ ID NO: 58 (KRLDEETGEFLKR), SEQ ID NO: 59 (RKLDEETGEFLRK), SEQ ID NO: 60 (RKLDEETGEFLKR), SEQ ID NO: 61 (KRLDEETGEFLRK), SEQ ID NO: 62 (LDEETGEFLKKRR), SEQ ID NO: 63 (LDEETGEFLRRKK), SEQ ID NO: 64 (KKRRLDEETGEFL), SEQ ID NO: 65 (RRKKLDEETGEFL), SEQ ID NO: 66 (LDEETGEFLGSGSGRR), SEQ ID NO: 67 (GSGSGRRLDEETGEFL), SEQ ID NO: 68 (LDEETGEFLGSGSGKK), SEQ ID NO: 69 (GSGSGKKLDEETGEFL), SEQ ID NO: 70 (LDPETGEFLRR), SEQ ID NO: 71 (LDPETGEFLRRR), SEQ ID NO: 72 (LDPETGEFLRRRR), SEQ ID NO: 73 (LDPETGEFLRRRRR), SEQ ID NO: 74 (RRLDPETGEFL), SEQ ID NO: 75 (RRRLDPETGEFL), SEQ ID NO: 76 (RRRRLDPETGEFL), SEQ ID NO: 77 (RRRRRLDPETGEFL), SEQ ID NO: 78 (RRLDPETGEFLRR), SEQ ID NO: 79 (RRRLDPETGEFLRRR), SEQ ID NO: 80 (RLDPETGEFLR), SEQ ID NO: 81 (RLDPETGEFLRR), SEQ ID NO: 82 (RRLDPETGEFLR), SEQ ID NO: 83 (RLDPETGEFLRRR), SEQ ID NO: 84 (RRRLDPETGEFLR), SEQ ID NO: 85 (RLDPETGEFLRRRR), SEQ ID NO: 86 (RRLDPETGEFLRRR), SEQ ID NO: 87 (RRRLDPETGEFLRR), SEQ ID NO: 88 (RRRRLDPETGEFLR), SEQ ID NO: 89 (RLDPETGEFLRRRRR), SEQ ID NO: 90 (RRLDPETGEFLRRRR), SEQ ID NO: 91 (RRRRLDPETGEFLRR), SEQ ID NO: 92 (RRRRRLDPETGEFLR), SEQ ID NO: 93 (LDPETGEFLKK), SEQ ID NO: 94 (LDPETGEFLKKK), SEQ ID NO: 95 (LDPETGEFLKKKK), SEQ ID NO: 96 (LDPETGEFLKKKKK), SEQ ID NO: 97 (KKLDPETGEFL), SEQ ID NO: 98 (KKKLDPETGEFL), SEQ ID NO: 99 (KKKKLDPETGEFL), SEQ ID NO: 100 (KKKKKLDPETGEFL), SEQ ID NO: 101 (KKLDPETGEFLKK), SEQ ID NO: 102 (KKKLDPETGEFLKKK), SEQ ID NO: 103 (KLDPETGEFLK), SEQ ID NO: 104 (KLDPETGEFLKK), SEQ ID NO: 105 (KKLDPETGEFLK), SEQ ID NO: 106 (KLDPETGEFLKKK), SEQ ID NO: 107 (KKKLDPETGEFLK), SEQ ID NO: 108 (KLDPETGEFLKKKK), SEQ ID NO: 109 (KKLDPETGEFLKKK), SEQ ID NO: 110 (KKKLDPETGEFLKK), SEQ ID NO: 111 (KKKKLDPETGEFLK), SEQ ID NO: 112 (KLDPETGEFLKKKKK), SEQ ID NO: 113 (KKLDPETGEFLKKKK), SEQ ID NO: 114 (KKKKLDPETGEFLKK), SEQ ID NO: 115 (KKKKKLDPETGEFLK), SEQ ID NO: 116 (LDPETGEFLKRKR), SEQ ID NO: 117 (KRKRLDPETGEFL), SEQ ID NO: 118 (RKRKLDPETGEFL), SEQ ID NO: 119 (LDPETGEFLRKRK), SEQ ID NO: 120 (KKLDPETGEFLRR), SEQ ID NO: 121 (RRLDPETGEFLKK), SEQ ID NO: 122 (KLDPETGEFLRRR), SEQ ID NO: 123 (KKKLDPETGEFLR), SEQ ID NO: 124 (RRRLDPETGEFLK), SEQ ID NO: 125 (KRLDPETGEFLKR), SEQ ID NO: 126 (RKLDPETGEFLRK), SEQ ID NO: 127 (RKLDPETGEFLKR), SEQ ID NO: 128 (KRLDPETGEFLRK), SEQ ID NO: 129 (LDPETGEFLKKRR), SEQ ID NO: 130 (LDPETGEFLRRKK), SEQ ID NO: 131 (KKRRLDPETGEFL), SEQ ID NO: 132 (RRKKLDPETGEFL), SEQ ID NO: 133 (LDPETGEFLGSGSGRR), SEQ ID NO: 134 (GSGSGRRLDPETGEFL), SEQ ID NO: 135 (LDPETGEFLGSGSGKK), SEQ ID NO: 136 (GSGSGKKLDPETGEFL), SEQ ID NO: 140 (YGRKKRRLDPETGEFL), and SEQ ID NO: 141 (LDPETGEFLYGRKKRR).

The present invention further includes brush polymer therapeutic agents comprising a peptide comprising a sequence having 75% or greater (e.g., 80% or greater, 85% or greater, 90% or greater, 95% or greater, or 100%) sequence identity of SEQ ID NO: 1 (LDEETGEFL), including drugs and prodrugs thereof, which address challenges associated with conventional administration of such a therapeutic peptide.

In an embodiment, for example, the invention provides brush polymers (e.g., therapeutic polymers or therapeutic agents) incorporating one or more peptides comprising a sequence having 75% or greater (e.g., 80% or greater, 85% or greater, 90% or greater, 95% or greater, or 100%) sequence identity of SEQ ID NO: 1 (LDEETGEFL) as side chain moieties. Brush polymers of some embodiments are characterized by high brush densities, including optionally cross-linked brush polymers, brush block copolymers, or brush random copolymers. Brush polymers of the invention include brush polymers having polymer side chains characterized by one or more degradable linker, such as an in vivo degradable linker or triggerable linker.

In an embodiment, brush polymers of the invention exhibit proteolysis-resistant characteristics and maintain their biological function during formulation and in vivo administration to a subject. In some embodiments, conjugation of the therapeutic peptide to the brush polymer backbone renders it more resistant to in vivo degradation by proteolytic enzymes as compared to a free therapeutic peptide. Moreover, the higher molecular weight of the brush polymer, relative to its free therapeutic peptide analogue, confers longer circulation time than the free therapeutic peptide. As a result, the therapeutic polymers can be administered less frequently and in smaller doses than the free peptide therapeutics used in the clinic. Further, the enhanced stability and resistance to degradation of the present brush polymer therapeutic agents allows for more versatility with respect to administration route and conditions, including in injection at the site of action and systemic administration. Alternatively, or in addition to, the brush polymers of the invention may exhibit stronger binding affinity than the free peptide The invention also includes methods of using brush polymers for a range of clinical applications including, by way of example, for treatment or management of conditions associated with an inflammatory state, increased oxidative stress, autoimmune pathophysiology, chemo-preventative measures, neurodegeneration, or a combination thereof. More particularly, the brush polymers described herein can be used for treatment or management of autoimmune disease, respiratory disease, gastrointestinal disease, cardiovascular disease, or neurodegenerative disease.

The invention also includes methods for making therapeutic agents comprising brush polymers, for example, via "grafting from" methods, "grafting onto" methods and "grafting through" methods. In some methods, a ring opening metathesis polymerization (ROMP) synthetic approach is used to make therapeutic agents comprising brush polymers, for example, having high graft densities and low polydispersity. The present methods of making therapeutic agents comprising brush polymers include other non-ROMP synthetic pathways such as, by way of example, reversible addition fragmentation chain transfer (RAFT) polymerization, stable free radical mediated polymerization and atom transfer radical polymerization (ATRP).

In an embodiment, the invention provides a polymer comprising a polymer comprising a first polymer segment comprising at least 2 first repeating units and optionally 2-30, 5-30, 10-30, 15-30, or 20-30 first repeating units; wherein each of the first repeating units of the first polymer segment comprises a first polymer backbone group directly or indirectly covalently linked to a first polymer side chain group comprising a peptide; wherein the peptide comprises a sequence having 75% or greater (e.g., 80% or greater, 85% or greater, 90% or greater, 95% or greater, or 100%) sequence identity of SEQ ID NO: 1 (LDEETGEFL), optionally wherein the peptide comprises SEQ ID NO: 1 (LDEETGEFL) or SEQ ID NO: 2 (LDPETGEFL). In certain embodiments, the peptide further comprises a charge modulating domain having from 2 to 7 amino acid residues and/or has a total of from 11 to 16 amino acid residues. In certain embodiments, the peptide is SEQ ID NO: 72 (LDPETGEFLRRRR).

In an aspect, a polymer is provided, the polymer is characterized by the formula (FX2a), (FX2b), or (FX2c):

(FX2a)

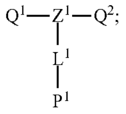

(FX2b)

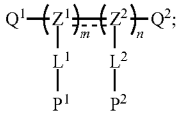 or (FX2c)

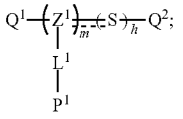

wherein each $Z^1$ is independently a first polymer backbone group and each $Z^2$ is independently a second polymer backbone group; each S is independently a repeating unit having a composition different from the first repeating unit; $Q^1$ is a first backbone terminating group and $Q^2$ is a second backbone terminating group; each $L^1$ is independently a first linking group, each $L^2$ is independently a second linking group; each $P^1$ is the peptide; wherein each $P^2$ is a polymer side chain having a composition different from that of $P^1$; each m is independently an integer selected from the range of 2 to 1000; each n is independently an integer selected from the range of 0 to 1000; and each h is independently an integer selected from the range of 0 to 1000, wherein $P^1$ comprises a sequence having 75% or greater (e.g., 80% or greater, 85% or greater, 90% or greater, 95% or greater, or 100%) sequence identity of SEQ ID NO: 1 (LDEETGEFL), optionally wherein $P^1$ comprises SEQ ID NO: 1 (LDEETGEFL) or SEQ ID NO: 2 (LDPETGEFL). In certain embodiments, $P^1$ further comprises a charge modulating domain having from 2 to 7 amino acid residues and/or $P^1$ has a total of from 11 to 16 amino acid residues.

In an aspect, a polymer is provided comprising: a first polymer segment comprising at least 2 first repeating units; wherein each of the first repeating units of the first polymer segment comprises a first polymer backbone group directly or indirectly covalently linked to a first polymer side chain group comprising a peptide; wherein the peptide interrupts the protein-protein interaction between Nuclear factor (erythroid-derived 2)-like 2 (Nrf2) and Kelch-like ECH-Associating protein 1 (Keap1) (e.g., by inhibiting binding to the ETGE motif of Nrf2); and wherein the polymer exhibits efficacy for treatment or management of a condition associated with an inflammatory state, increased oxidative stress, autoimmune pathophysiology, chemo-preventative measures, neurodegeneration, or a combination thereof. In an embodiment of this aspect, the peptide comprises a sequence having 75% or greater sequence identity, optionally 80% or greater, 85% or greater, 90% or greater, 95% or greater, or 100%, of SEQ ID NO: 1 (LDEETGEFL) or the peptide comprises a sequence having 75% or greater sequence identity, optionally 80% or greater, 85% or greater, 90% or greater, 95% or greater, or 100%, with the full length of SEQ ID NO: 2 (LDPETGEFL). In an embodiment of this aspect, the peptide comprises SEQ ID NO: 1 (LDEETGEFL) or SEQ ID NO: 2 (LDPETGEFL). In certain embodiments, the peptide is SEQ ID NO: 72 (LDPETGEFLRRRR).

In an aspect, a polymer is provided comprising: a first polymer segment comprising at least 2 first repeating units; wherein each of the first repeating units of the first polymer segment comprises a first polymer backbone group directly or indirectly covalently linked to a first polymer side chain group comprising a peptide; wherein the peptide is selected from SEQ ID NO: 1-SEQ ID NO: 136, SEQ ID NO: 140, and SEQ ID NO: 141. In an embodiment of this aspect, the peptide interrupts the protein-protein interaction between Nuclear factor (erythroid-derived 2)-like 2 (Nrf2) and Kelch-like ECH-Associating protein 1 (Keap1) (e.g., by inhibiting binding to the ETGE motif of Nrf2), optionally for the treatment or management of a condition associated with an inflammatory state, increased oxidative stress, autoimmune pathophysiology, chemo-preventative measures, neurodegeneration, or a combination thereof.

In an embodiment, the polymer is a homopolymer or a copolymer. In an embodiment, the polymer is a brush polymer, optionally a brush block copolymer or a brush random copolymer. In an embodiment, the first polymer segment of the polymer comprises at least 5 first repeating units, optionally 5-30 first repeating units. In an embodiment, the polymer is characterized by a degree of polymerization of 2 to 1000. In an embodiment, the polymer is characterized by a polydispersity index less than 1.75.

In an embodiment, the peptide has from 11 to 16 amino acid residues, optionally from 11 to 15 amino acid residues or from 12 to 14 amino acid residues. In an embodiment, the peptide is a branched peptide, a linear peptide, cyclic peptide, or a cross-linked peptide. In an embodiment, the polymer is characterized by a structure wherein at least a portion of the peptide is linked to the polymer backbone group via an enzymatically degradable linker, such a matrix metalloproteinase (MMP) cleavage sequence, cathepsin B cleavage sequence, ester bond, reductive sensitive bond-disulfide bond, pH sensitive bond-imine bond or any combinations of these. In an embodiment, the polymer is characterized by a structure wherein at least a portion of the peptide side-chain is linked to the polymer backbone or consists of a degradable or triggerable linker. In some embodiments, the peptide and/or polymer further comprises a tag for imaging and/or analysis. For example, the peptide and/or polymer can further comprise a dye, radiolabeling, an imaging agent, tritiation, and the like.

In an embodiment, the polymer is characterized by the formula (FX1a), (FX1b), (FX1c), (FX1d); (FX1e); (FX1f); or (FX1g):

$$Q^1\text{-T-}Q^2 \qquad \text{(FX1a);}$$

$Q^1$-T-$[S]_h$-$Q^2$ (FX1b);

$Q^1$-$[S]_h$-T-$Q^2$ (FX1c);

$Q^1$-$[S]_i$-T-$[S]_h$-$Q^2$ (FX1d);

$Q^1$-$[S]_i$-T-$[S]_h$-T-$Q^2$ (FX1e);

$Q^1$-T-$[S]_i$-T-$[S]_h$-$Q^2$ (FX1f); or $Q^1$-T-$[S]_i$-T-$[S]_h$-T-$Q^2$ (FX1g);

wherein each T is independently the first polymer segment comprising the first repeating units and each S is independently an additional polymer segment; $Q^1$ is a first backbone terminating group; $Q^2$ is a second backbone terminating group; and wherein h is zero or an integer selected over the range of 1 to 1000 and i is zero or an integer selected over the range of 1 to 1000. In an embodiment, the polymer is characterized by any of formulas (FX1a)-(FX1g), wherein each -T- is independently —$[Y^1]_m$—; wherein each $Y^1$ is independently the first repeating unit of the first polymer segment; and each m is independently an integer selected from the range 0 to 1000, provided that at least one m is an integer selected from the range 1 to 1000.

In an embodiment, the polymer is characterized by the formula (FX2a), (FX2b), or (FX2c):

(FX2a)

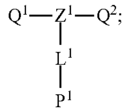

(FX2b)

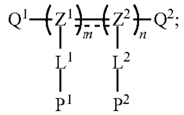

or (FX2c)

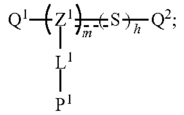

wherein each $Z^1$ is independently a first polymer backbone group and each $Z^2$ is independently a second polymer backbone group; wherein each S is independently a repeating unit having a composition different from the first repeating unit; the wherein $Q^1$ is a first backbone terminating group and $Q^2$ is a second backbone terminating group; wherein each $L^1$ is independently a first linking group, each $L^2$ is independently a second linking group; wherein each $P^1$ is the polymer side chain comprising the peptide; wherein each $P^2$ is a polymer side chain having a composition different from that of $P^1$; and wherein each m is independently an integer selected from the range of 2 to 1000 (e.g., 2 to 500, 2 to 250, or 2 to 100); wherein each n is each independently an integer selected from the range of 0 to 1000 (e.g., 0 to 500, 0 to 250, or 0 to 100); and wherein h are each independently an integer selected from the range of 0 to 1000 (e.g., 0 to 500, 0 to 250, or 0 to 100). In certain embodiments, each of the first polymer backbone group and/or the second polymer backbone group is a substituted or unsubstituted polymerized norbornene, olefin, cyclic olefin, norbornene anhydride, cyclooctene, cyclopentadiene, styrene, acrylamide, or acrylate.

In an embodiment, the polymer is characterized by any of formulas (FX2a)-(FX2c), wherein each $Z^1$ connected to $L^1$, and $P^1$ or a combination thereof is independently characterized by the formula (FX3a) or (FX3b):

(FX3a)

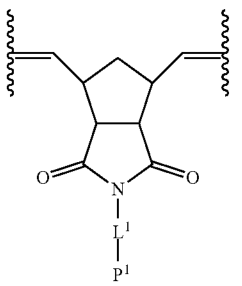

or (FX3b)

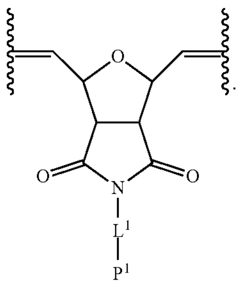

and wherein each $Z^2$ connected to $L^2$, and $P^2$ or a combination thereof is independently characterized by the formula (FX4a) or (FX4b)

(FX4a)

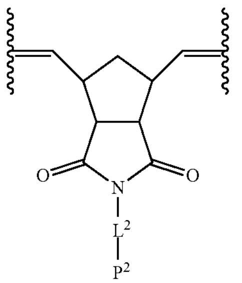

or (FX4b)

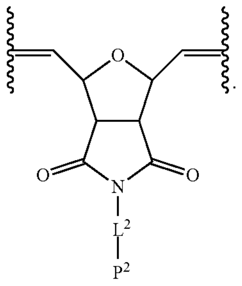

In an embodiment, the polymer is characterized by any of formulas (FX2a)-(FX2c), wherein each of $Z^1$ and $Z^2$ is independently a substituted or unsubstituted norbornene, oxanorbornene, olefin, cyclic olefin, cyclooctene, or cyclopentadiene. In an embodiment, the polymer is characterized by any of formulas (FX2a)-(FX2c), wherein each of $Q^1$ and $Q^2$ is independently selected from a hydrogen, $C_1$-$C_{30}$ alkyl, $C_3$-$C_{30}$ cycloalkyl, $C_5$-$C_{30}$ aryl, $C_5$-$C_{30}$ heteroaryl, $C_1$-$C_{30}$ acyl, $C_1$-$C_{30}$ hydroxyl, $C_1$-$C_{30}$ alkoxy, $C_2$-$C_{30}$ alkenyl, $C_2$-$C_{30}$ alkynyl, $C_5$-$C_{30}$alkylaryl, —$CO_2R^3$, —$CONR^4R^5$, —$COR^6$, —$SOR^7$, —$OSR^8$, —$SO_2R^9$, —$OR_{10}$, —$SR^{11}$, —$NR^{12}R^{13}$, —$NR^{14}COR^{15}$, $C_1$-$C_{30}$ alkyl halide, phosphonate, phosphonic acid, silane, siloxane, silsesquioxane, $C_2$-$C_{30}$ halocarbon chain, $C_2$-$C_{30}$ perfluorocarbon, $C_2$-$C_{30}$ polyethylene glycol, a metal, or a metal complex, wherein each of $R^3$-$R^{15}$ is independently H, $C_5$-$C_{10}$ aryl or $C_1$-$C_{10}$ alkyl. In an embodiment, the polymer is characterized by any of formulas (FX2a)-(FX2c), wherein each of $L^1$ and $L^2$ is independently selected from a single bond, an oxygen, and groups having an alkyl group, an alkenylene group, an arylene group, an alkoxy group, an acyl group, a triazole group, a diazole group, a pyrazole group, and combinations thereof. In an embodiment, the polymer is characterized by any of formulas (FX2a)-(FX2c), wherein each of $L^1$ and $L^2$ is independently selected from a single bond, —O—, $C_1$-$C_{10}$ alkyl, $C_2$-$C_{10}$ alkenylene, $C_3$-$C_{10}$ arylene, $C_1$-$C_{10}$ alkoxy, $C_1$-$C_{10}$ acyl and combinations thereof.

In an embodiment, the polymer is characterized by any of formulas (FX2a)-(FX2c), wherein $P^1$ comprises a sequence having 75% or greater sequence identity, optionally 80% or greater, 85% or greater, 90% or greater, 95% or greater, or 100%, of SEQ ID NO: 1 (LDEETGEFL) or $P^1$ comprises a sequence having 75% or greater sequence identity, optionally 80% or greater, 85% or greater, 90% or greater, 95% or greater, or 100%, with the full length of SEQ ID NO: 2 (LDPETGEFL). In certain embodiments, the polymer is characterized by any of formulas (FX2a)-(FX2c), wherein $P^1$ comprises SEQ ID NO: 1 (LDEETGEFL) or SEQ ID NO: 2 (LDPETGEFL). In certain embodiments, the peptide is SEQ ID NO: 72 (LDPETGEFLRRRR).

In an embodiment, the polymer is characterized by any of formulas (FX2a)-(FX2c), wherein $P^1$ is selected from SEQ ID NO: 1-SEQ ID NO: 136, SEQ ID NO: 140, and SEQ ID NO: 141, optionally wherein $P^1$ is selected from SEQ ID NO: 3-SEQ ID NO: 136.

In an aspect, provided are methods of treatment comprising administering to a subject an effective amount of any of the polymers disclosed herein.

In an aspect, provided are methods of treating or managing a condition in a subject comprising: administering to a subject an effective amount of a polymer comprising: a first polymer segment comprising at least 2 first repeating units; wherein each of the first repeating units of the first polymer segment comprises a first polymer backbone group directly or indirectly covalently linked to a first polymer side chain group comprising a peptide; wherein the peptide interrupts the protein-protein interaction between Nuclear factor (erythroid-derived 2)-like 2 (Nrf2) and Kelch-like ECH-Associating protein 1 (Keap1) (e.g., by inhibiting binding to the ETGE motif of Nrf2); wherein the condition is associated with an inflammatory state, increased oxidative stress, autoimmune pathophysiology, chemo-preventative measures, neurodegeneration, or a combination thereof.

In an aspect, provided are methods of treating or managing a condition in a subject comprising: administering to a subject an effective amount of a polymer comprising: a first polymer segment comprising at least 2 first repeating units; wherein each of the first repeating units of the first polymer segment comprises a first polymer backbone group directly or indirectly covalently linked to a first polymer side chain group comprising a peptide; wherein the peptide interrupts the protein-protein interaction between Nuclear factor (erythroid-derived 2)-like 2 (Nrf2) and Kelch-like ECH-Associating protein 1 (Keap1) (e.g., by inhibiting binding to the ETGE motif of Nrf2); wherein the condition is an autoimmune disease (e.g., multiple sclerosis, systemic lupus erythematous, Sjogren syndrome, rheumatoid arthritis, vitiligo, or psoriasis), a respiratory disease (e.g., COPD, emphysema, potential treatment for smokers, idiopathic pulmonary fibrosis, chronic sarcoidosis, or hypersensitivity pneumonitis), a gastrointestinal disease (e.g., ulcerative colitis, ulcers, prevent acetaminophen toxicity, non-alcoholic steatohepatitis, primary biliary cholangitis, cirrhosis, type 2 diabetes, or diabetic nephropathy), a cardiovascular disease (e.g., cardiac ischemia-reperfusion injury, heart failure, or atherosclerosis), or a neurodegenerative disease (e.g., Alzheimer's disease, Parkinson's disease, amyotrophic lateral sclerosis (ALS), Huntington's disease, Friedreich ataxia, or frontotemporal lobar degeneration).

In an embodiment, any of the present methods further comprise contacting a target tissue of the subject with the polymer or a metabolite or product thereof. In an embodiment, any of the present methods further comprise contacting a target cell of the subject with the polymer or a metabolite or product thereof. In an embodiment, any of the present methods further comprise contacting a target receptor of the subject with the polymer or a metabolite or product thereof. In preferred embodiments of the methods described herein, the polymer passes through the cell membrane and contacts an intracellular target.

In some embodiments a polymer, a method, or a formulation disclosed herein, each of the first polymer backbone group and/or the second polymer backbone group is a polymerized acrylamide (e.g., acrylamide or methacrylamide) monomer. In certain embodiments of a polymer, a method, or a formulation disclosed herein, each of the first polymer backbone group and the second polymer backbone group is a polymerized acrylamide (e.g., acrylamide or methacrylamide) monomer. For example, for any of the polymers, methods, or formulations disclosed herein, each of the first polymer backbone group is a polymerized acrylamide (e.g., acrylamide or methacrylamide) monomer. Alternatively, or additionally, for any of the polymers, methods, or formulations disclosed herein, each of the second polymer backbone group of the polymer is a polymerized acrylamide (e.g., acrylamide or methacrylamide) monomer. Optionally in any embodiment of a polymer, a method, or a formulation disclosed herein, each of the first polymer backbone group and/or the second polymer backbone group comprises a polymerized acrylamide (e.g., acrylamide or methacrylamide) monomer. Optionally in any embodiment of a polymer, a method, or a formulation disclosed herein, each of the first polymer backbone group and the second polymer backbone group comprises a polymerized acrylamide (e.g., acrylamide or methacrylamide) monomer. Optionally in any embodiment of a polymer, a method, or a formulation disclosed herein, each of the first polymer backbone group comprises a polymerized acrylamide (e.g., acrylamide or methacrylamide) monomer. Optionally in any embodiment of a polymer, a method, or a formulation disclosed herein, each polymer backbone group of the polymer comprises a polymerized acrylamide (e.g., acrylamide or methacrylamide) monomer.

Preferably in any embodiment of a polymer, a method, or a formulation disclosed herein, each of the first polymer backbone group and/or the second polymer backbone group is a polymerized norbornene dicarboxyimide monomer. Preferably in any embodiment of a polymer, a method, or a formulation disclosed herein, each of the first polymer backbone group and the second polymer backbone group is a polymerized norbornene dicarboxyimide monomer. Preferably in any embodiment of a polymer, a method, or a formulation disclosed herein, each of the first polymer backbone group is a polymerized norbornene dicarboxyimide monomer. Preferably in any embodiment of a polymer, a method, or a formulation disclosed herein, each polymer backbone group of the polymer is a polymerized norbornene dicarboxyimide monomer. Optionally in any embodiment of a polymer, a method, or a formulation disclosed herein, each of the first polymer backbone group and/or the second polymer backbone group comprises a polymerized norbornene dicarboxyimide monomer. Optionally in any embodiment of a polymer, a method, or a formulation disclosed herein, each of the first polymer backbone group and the second polymer backbone group comprises a polymerized norbornene dicarboxyimide monomer. Optionally in any embodiment of a polymer, a method, or a formulation disclosed herein, each of the first polymer backbone group comprises a polymerized norbornene dicarboxyimide monomer. Optionally in any embodiment of a polymer, a method, or a formulation disclosed herein, each polymer backbone group of the polymer comprises a polymerized norbornene dicarboxyimide monomer.

Preferably in any embodiment of a polymer, a method, or a formulation disclosed herein, the polymer is stable against enzymatic digestion. Optionally in any embodiment of a polymer, a method, or a formulation disclosed herein, the polymer is stable against enzymatic digestion by a metalloproteinase. Optionally in any embodiment of a polymer, a method, or a formulation disclosed herein, the polymer is stable against enzymatic digestion by matrix metalloproteinases and thermolysin. Preferably in any embodiment of a polymer, a method, or a formulation disclosed herein, the polymer is stable against enzymatic digestion for at least 450 minutes. Optionally in any embodiment of a polymer, a method, or a formulation disclosed herein, the polymer is stable against enzymatic digestion by thermolysin such that less than 20% of thermolysin-cleavable sites are cleaved by thermolysin after at least 450 minutes of the polymer's exposure to thermolysin. Optionally in any embodiment of a polymer, a method, or a formulation disclosed herein, each polymer individually solvated by water when a plurality of said polymers is dispersed in water.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 8A shows the overall binding structure of the Kelch domain and ProPepR, FIG. 8B shows that the 1st Arg residue (red) forms a hydrogen bond with Asn382 (pink), and FIG. 8C shows that the 3rd Arg residue (red) forms salt bridge with $Asp_{385}$ (pink).

FIG. 21G), about 17mer (t=24 hours; FIG. 21H), and about 16mer (t=6 hours FIG. 21I) of the (meth)acrylamide-based brush polymer (i.e., SEQ ID NO: 72 (LDPETGEFLRRRR)), prepared in Example 17.

FIG. 41 (Bottom) shows the superimposed structures of ProPepR peptide (i.e., SEQ ID NO: 72 (LDPETGEFLRRRR)) of the PLP at 0 ρs and 3 ρs (Teal—Kelch, Pink—PLP, Orange—docked peptide at 0 μs, Red—peptide at 3 μs).

FIG. 43A shows that ProPepR PLP with DP=15 cannot simultaneously bind to both Kelch domains due to limited polymer length. However, FIGS. 43B and 43C show that the ProPepR PLP with DP=20 and 25, respectively, are docked into both Kelch domains.

STATEMENTS REGARDING CHEMICAL COMPOUNDS AND NOMENCLATURE

Figure 1:
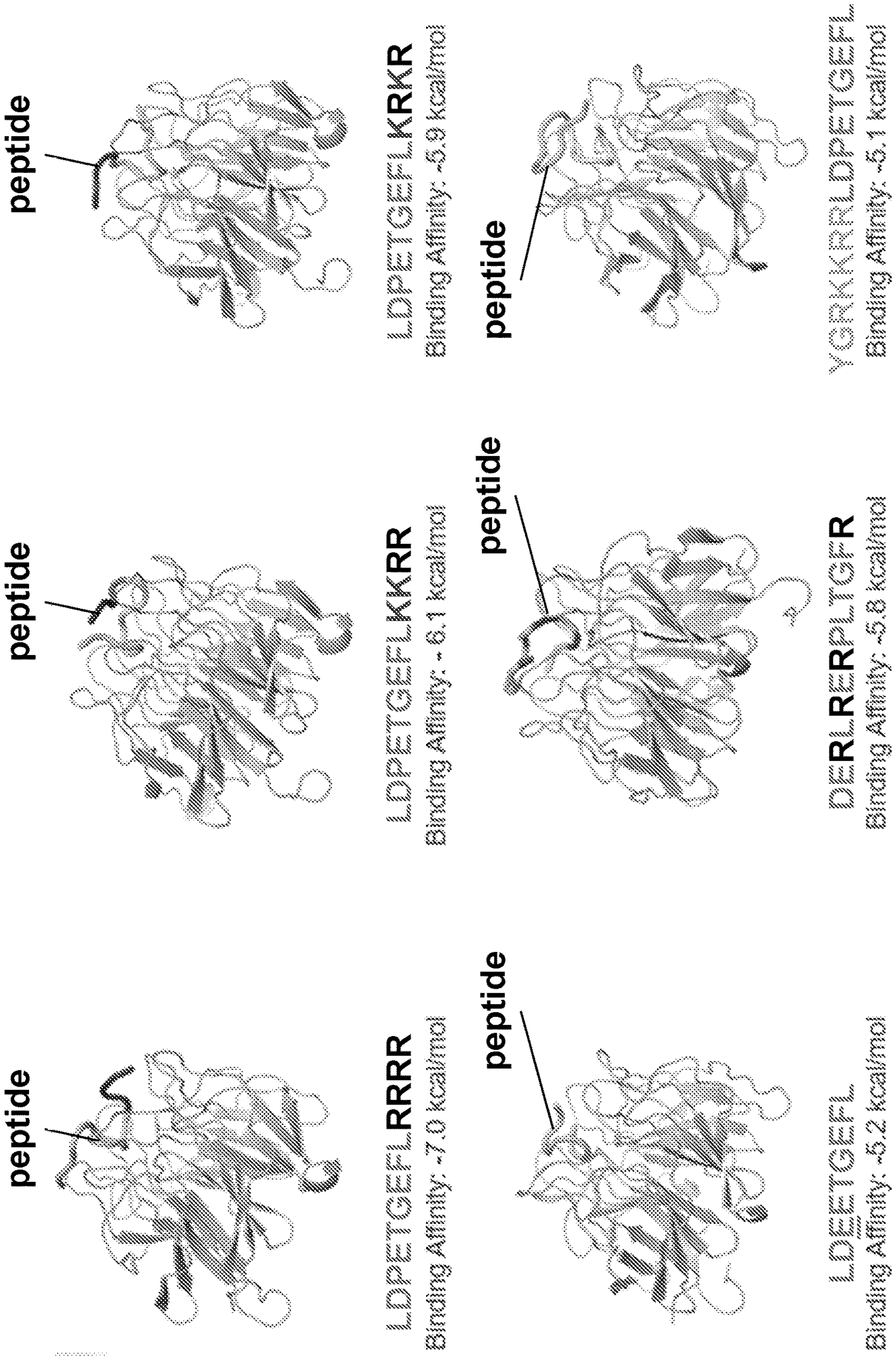
FIG. 1 depicts six different peptide sequences, namely, SEQ ID NO: 72 (LDPETGEFLRRRR), SEQ ID NO: 129 (LDPETGEFLKKRR), SEQ ID NO: 116 (LDPETGEFLKRKR), SEQ ID NO: 1 (LDEETGEFL), SEQ ID NO: 139 (DERLRERPLTGFR), and SEQ ID NO: 140 (YGRKKRRLDPETGEFL), and their calculated binding affinity for the Kelch domain of Keap1, as described in Example 1.

The following abbreviations are used herein: Keap1 refers to Kelch-like ECH-associated protein 1; Nrf2 refers to Nuclear factor-erythroid factor 2-related factor 2; BBB refers to blood brain barrier; CNS refers to central nervous system; SPPS refers to solid phase peptide synthesis; ROMP refers to ring-opening metathesis polymerization; RAFT refers to reversible addition fragmentation chain transfer polymerization; DMF refers to dimethylformamide; TFA refers to trifluoroacetic acid; TIPS refers to triisopropyl silane; DTT refers to dithiothreitol; LJ refers to Lennard-Jones; RP-HPLC refers to reverse-phase high performance liquid chromatography; ESI-MS refers to electrospray ionization mass spectrometry; NMR refers to nuclear magnetic resonance spectrometry; MALDI-MS refers to matrix-assisted laser desorption/ionization mass spectrometry; SEC-MALS refers to size-exclusion chromatography coupled with multiangle light scattering; GPC refers to gel permeation chromatography; SDS-PAGE refers to sodium dodecyl sulfate-polyacrylamide gel electrophoresis; CD refers to circular dichroism; SAXS refers to Small-angle X-ray scattering; ARE refers to antioxidant response element; BSA refers to bovine serum albumin; tBHQ refers to tert-Butylhydroquinone; PLP refers to protein-like polymer; PDI refers to polydispersity index; MW refers to molecular weight; and DP refers to degree of polymerization.

In an embodiment, a peptide, a polymer, or a composition (e.g., formulation) of the invention is isolated or purified. In an embodiment, an isolated or purified peptide, polymer, or composition (e.g., formulation) is at least partially isolated or purified as would be understood in the art. In an embodiment, the peptide, polymer, or composition (e.g., formulation) of the invention has a chemical purity of at least 95%, optionally for some applications at least 99%, optionally for some applications at least 99.9%, optionally for some applications at least 99.99%, and optionally for some applications at least 99.999% pure. The invention includes isolated and purified compositions of any of the brush polymers (e.g., brush homopolymers and peptide brush copolymers) described herein including the brush block polymers or brush random polymers having one or more side chains comprising the peptide analogues, derivative, variants or fragments.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 5 repeating units, in some embodiments greater or equal to 10 repeating units) and a high molecular weight (e.g., greater than or equal to 1 kDa, in some embodiments greater than or equal to 5 kDa or greater than or equal to 50 kDa). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits (e.g., 3 or more monomer subunits, 4 or more monomer subunits, 5 or more monomer subunits, or 6 or more monomer subunits), and include random, block, brush, brush block, alternating, segmented, grafted, tapered and other architectures. In some embodiments, copolymers of the invention comprise from 2 to 10 different monomer subunits. Useful polymers include organic polymers that may be in amorphous, semi-amorphous, crystalline or semi-crystalline states. Cross linked polymers having linked monomer chains are useful for some applications, for example linked by one or more disulfide linkages. The invention provides polymers comprising therapeutic agents, such as brush polymers having at least a portion of the repeating units comprising polymer side chains such as peptide side chains.

As used herein, the term "polymer segment" (e.g., first polymer segment, second polymer segment, etc.) refers to a section (e.g., portion) of the polymer comprising a particular monomer or arrangement of monomers. A polymer segment can be a homopolymer or a copolymer. In embodiments where a polymer segment is a copolymer, the copolymer can exist in any suitable arrangement of monomers (e.g., random, block, brush, brush block, alternating, segmented, grafted, tapered, statistical and other architectures). In some embodiments, the polymer segments are homopolymers, random copolymers, statistical copolymers or block copolymers. Any polymer (e.g., brush polymer) described herein can have a single polymer segment or multiple polymer segments. In embodiments where the polymer has multiple polymer segments, the polymer segments can exist in any suitable arrangement (random, block, brush, brush block, alternating, segmented, grafted, tapered, statistical, and other architectures).

An "oligomer" refers to a molecule composed of repeating structural units connected by covalent chemical bonds often characterized by a number of repeating units less than that of a polymer (e.g., equal to or less than 3 repeating units) and a lower molecular weights (e.g., less than or equal to 1,000 Da) than polymers. Oligomers may be the polymerization product of one or more monomer precursors.

A "peptide" or "oligopeptide" herein are used interchangeably and refer to a polymer of repeating structural units connected by a peptide bond. Typically, the repeating structural units of the peptide are amino acids including naturally occurring amino acids, non-naturally occurring amino acids, analogues of amino acids or any combination of these. The number of repeating structural units of a peptide, as understood in the art, are typically less than a "protein", and thus the peptide often has a lower molecular weight than a protein.

"Block copolymers" are a type of copolymer comprising blocks or spatially segregated domains, wherein different domains comprise different polymerized monomers, for example, including at least two chemically distinguishable blocks. Block copolymers may further comprise one or more other structural domains, such as hydrophobic groups, hydrophilic groups, etc. In a block copolymer, adjacent blocks are constitutionally different, i.e., adjacent blocks comprise constitutional units derived from different species of monomer or from the same species of monomer but with a different composition or sequence distribution of constitutional units. Different blocks (or domains) of a block copolymer may reside on different ends or the interior of a polymer (e.g., [A][B]), or may be provided in a selected sequence ([A][B][A][B]). "Diblock copolymer" refers to block copolymer having two different polymer blocks. "Triblock copolymer" refers to a block copolymer having three different polymer blocks, including compositions in which two non-adjacent blocks are the same or similar. "Pentablock" copolymer refers to a copolymer having five different polymer including compositions in which two or more non-adjacent blocks are the same or similar.

"Random copolymers" are a type of copolymer comprising spatially randomized units, wherein at least two chemically distinguishable polymerized monomers are randomly distributed throughout the polymer.

"Polymer backbone group" refers to groups that are covalently linked to make up a backbone of a polymer, such as a block copolymer or a random copolymer. Polymer backbone groups may be linked to side chain groups, such as polymer side chain groups. Some polymer backbone groups useful in the present compositions are derived from polymerization of a monomer selected from the group consisting of a substituted or unsubstituted norbornene, olefin, cyclic olefin, norbornene anhydride, cyclooctene, cyclopentadiene, styrene, acrylamide, and acrylate. Some polymer backbone groups useful in the present compositions are obtained from a ring opening metathesis polymerization (ROMP) reaction. Polymer backbones may terminate in a range of backbone terminating groups including hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, $—CO_2R^{30}$, $—CONR^{31}R^{32}$, $—COR^{33}$, $—SOR^{34}$, $—OSR^{35}$, $—SO_2R^{36}$, $—OR^{37}$, $—SR^{38}$, $—NR^{39}R^{40}$, $—NR^{41}COR^{42}$, $C_1$-$C_{10}$ alkyl halide, phosphonate, phosphonic acid, silane, siloxane, acrylamide, acrylate, or catechol; wherein each of $R^{30}$-$R^{42}$ is independently hydrogen, $C_1$-$C_{10}$ alkyl or $C_5$-$C_{10}$ aryl.

"Polymer side chain group" refers to a group covalently linked (directly or indirectly) to a polymer backbone group that comprises a polymer side chain, optionally imparting steric properties to the polymer. In an embodiment, for example, a polymer side chain group is characterized by a plurality of repeating units having the same, or similar, chemical composition. A polymer side chain group may be directly or indirectly linked to the polymer back bone groups. In some embodiments, polymer side chain groups provide steric bulk and/or interactions that result in an extended polymer backbone and/or a rigid polymer backbone. Some polymer side chain groups useful in the present compositions include unsubstituted or substituted peptide groups. Some polymer side chain groups useful in the present compositions comprise repeating units obtained via anionic polymerization, cationic polymerization, free radical polymerization, group transfer polymerization, or ring-opening polymerization. A polymer side chain may terminate in a wide range of polymer side chain terminating groups including hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, $—CO_2R^{30}$, $—CONR^{31}R^{32}$, $—COR^{33}$, $—SOR^{34}$, $—OSR^{35}$, $—SO_2R^{36}$, $—OR^{37}$, $—SR^{38}$, $—NR^{39}R^{40}$, $—NR^{41}COR^{42}$, $C_1$-$C_{10}$ alkyl halide, phosphonate, phosphonic acid, silane, siloxane, acrylamide, acrylate, or catechol; wherein each of $R^{30}$-$R^{42}$ is independently hydrogen or $C_1$-$C_5$ alkyl.

As used herein, the term "degree of polymerization" refers to the average number of monomer units per polymer chain. For example, for certain polymers described herein, comprising $Z^1$, $Z^2$, and/or S monomer units, the degree of polymerization would be represented by the sum total of $Z^1$, $Z^2$, and S monomer units. Since the degree of polymerization can vary from polymer to polymer, the degree of polymerization is generally represented by an average.

As used herein, the term "brush polymer" refers to a polymer comprising repeating units each independently comprising a polymer backbone group covalently linked to at least one polymer side chain group. A brush polymer may be characterized by brush density which refers to the percentage of the repeating units comprising polymer side chain groups. Brush polymers of certain aspects are characterized by a brush density greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Brush polymers of certain aspects are characterized by a brush density selected from the range 50% to 100%, optionally some embodiments a density selected from the range of 75% to 100%, or optionally for some embodiments a density selected from the range of 90% to 100%.

As used herein, the term "peptide density" refers to the percentage of monomer units in the polymer chain which have a peptide covalently linked thereto. The percentage is based on the overall sum of monomer units in the polymer chain. For example, for certain polymers described herein, each $P^1$ is the polymer side chain comprising the peptide, each $P^2$ is a polymer side chain having a composition different from that of $P^1$, and each S is independently a repeating unit having a composition different from $P^1$ and $P^2$. Thus, the peptide density, or percentage of monomer units comprising the peptide (i.e., $P^1$ for this particular example) would be represented by the formula:

$$\frac{P^1}{P^1+P^2+S}\times 100,$$

where each variable refers to the number of monomer units of that type in the polymer chain. Polymers of certain aspects are characterized by a peptide density greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Polymers of certain aspects are characterized by a peptide density selected from the range 50% to 100%, optionally some embodiments a density selected from the range of 75% to 100%, or optionally for some embodiments a density selected from the range of 90% to 100%. In some embodiments, the brush density is equal to the peptide density.

In an aspect, the polymer side chain groups can have any suitable spacing on the polymer backbone. Typically, the space between adjacent polymer side chain groups is from 3 angstroms to 30 angstroms, and optionally 5 to 20 angstroms and optionally 5 to 10 angstroms. By way of illustration, in certain embodiments having a brush density of 100%, the polymer side chain groups typically are spaced 6±5 angstroms apart on the polymer backbone. In some embodiments the brush polymer has a high a brush density (e.g., greater than 70%), wherein the polymer side chain groups are spaced 5 to 20 angstroms apart on the polymer backbone.

The term "sequence homology" or "sequence identity" means the proportion of amino acid matches between two amino acid sequences. When sequence homology is expressed as a percentage, e.g., 50%, the percentage denotes the fraction of matches over the length of sequence that is compared to some other sequence. Gaps (in either of the two sequences) are permitted to maximize matching; for example, wherein gap lengths of 5 amino acids or less, optionally 3 amino acids or less, are usually used. In other words, a sequence having 75% or greater sequence identity of SEQ ID NO: 1 (LDEETGEFL) or SEQ ID NO: 2 (LDPETGEFL) can indicate that the foregoing sequences can have one or two point mutations (i.e., amino acid change), one or two amino acid deletions, one or two amino acid additions, one point mutation and one amino acid deletion, or one point mutation and one amino acid addition. Similarly, a sequence having 85% or greater sequence identity of SEQ ID NO: 1 (LDEETGEFL) or SEQ ID NO: 2 (LDPETGEFL) indicates that the foregoing sequences can have one point mutation (i.e., amino acid change), one amino acid deletion, or one amino acid addition.

The term "fragment" refers to a portion, but not all of, a composition or material, such as a peptide composition or material. In an embodiment, a fragment of a peptide refers to 50% or more of the sequence of amino acids, optionally 70% or more of the sequence of amino acids and optionally 90% or more of the sequence of amino acids.

As used herein, the phrase "charge modulating domain" refers to one or more amino acids added to the peptide sequences described herein to modulate the charge of the peptide. For example, the charge modulating domain can be a TAT sequence, a glycine-serine domain, a cationic residue domain, or a combination thereof, or optionally a glycine-serine domain, a cationic residue domain, or a combination thereof. In certain embodiments, the charge modulating domain has from 2 to 7 amino acid residues. The 2 to 7 amino acids can be added in a single block containing from 2 to 7 amino acid residues or more than one block containing from 1 to 6 amino acid residues. In preferred embodiments, the charge modulating domain is a cationic residue domain having from 2 to 7 amino acid residues selected from lysine, arginine, histidine, or a combination thereof. Generally, the charge modulating domain modulates the charge of the peptide to have a net positive charge. Without wishing to be bound by any particular theory, it is believed that the net positive charge increases the cellular uptake of the peptide or polymer comprising the peptide. The overall charge of the peptide or polymer comprising the peptide can be determined by any suitable means. For example, the overall charge can be determined by (i) structural analysis of the functional residues on the peptide sequence and their respective pKa, (ii) physical characterization by measuring the zeta potential, and/or (iii) by virtue of the material moving towards a negative pole in an electrophoresis polymer gel. In certain embodiments, the overall charge of the peptide or polymer comprising the peptide is determined by measuring the zeta potential.

"Polymer blend" refers to a mixture comprising at least one polymer, such as a brush polymer, e.g., brush block copolymer or brush random copolymer, and at least one additional component, and optionally more than one additional component. In some embodiments, for example, a polymer blend of the invention comprises a first brush copolymer and one or more addition brush polymers having a composition different than the first brush copolymer. In some embodiments, for example, a polymer blend of the invention further comprises one or more additional brush block copolymers, brush random copolymers, homopolymers, copolymers, block copolymers, random copolymers, brush block copolymers, oligomers, solvent, small molecules (e.g., molecular weight less than 500 Da, optionally less than 100 Da), or any combination of these. Polymer blends useful for some applications comprise a first brush polymer, and one or more additional components comprising polymers, block copolymers, brush polymers, linear block copolymers, random copolymers, homopolymers, or any combinations of these. Polymer blends of the invention include mixture of two, three, four, five and more polymer components.

As used herein, the term "compound" can be used to refer to any of the peptides or polymers described herein. Alternatively, or additionally, the term compound can refer to any of the synthetic precursors, reagents, additives, excipients, etc. used in preparation of or formulation with the peptides or polymers described herein.

As used herein, the term “group” may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term “substituted” refers to a compound wherein a hydrogen is replaced by another functional group.

Unless otherwise specified, the term “average molecular weight,” refers to number average molecular weight. Number average molecular weight is the defined as the total weight of a sample volume divided by the number of molecules within the sample. As is customary and well known in the art, peak average molecular weight and weight average molecular weight may also be used to characterize the molecular weight of the distribution of polymers within a sample.

As is customary and well known in the art, hydrogen atoms in formulas (FX1a)-(FX6b) are not always explicitly shown, for example, hydrogen atoms bonded to the carbon atoms of aromatic, heteroaromatic, and alicyclic rings are not always explicitly shown in formulas ((FX1a)-(FX6b). The structures provided herein, for example in the context of the description of formulas (FX1a)-(FX6b) and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms “alkylene” and “alkylene group” are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g., $L^1$-$L^2$).

As used herein, the terms “cycloalkylene” and “cycloalkylene group” are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups (e.g., $L^1$-$L^2$).

As used herein, the terms “arylene” and “arylene group” are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g., $L^1$-$L^2$).

As used herein, the terms “heteroarylene” and “heteroarylene group” are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g., $L^1$-$L^2$).

As used herein, the terms “alkenylene” and “alkenylene group” are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g., $L^1$-$L^2$).

As used herein, the terms “cycloalkenylene” and “cycloalkenylene group” are used synonymously and refer to a divalent group derived from a cycloalkenyl group as defined herein. The invention includes compounds having one or more cycloalkenylene groups. Cycloalkenylene groups in some compounds function as linking and/or spacer groups. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups, for example, as one or more linking groups (e.g., $L^1$-$L^2$).

As used herein, the terms “alkynylene” and “alkynylene group” are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g., $L^1$-$L^2$).

As used herein, the term “halo” refers to a halogen group such as a fluoro (—F), chloro (—Cl), bromo (—Br), iodo (—I) or astato (—At).

The term “heterocyclic” refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term “carbocyclic” refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides are comprised of two or more amino acids connected via peptide bonds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON$(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON$(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N$(R)_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—$SO_2N(R)_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, which is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or D- or L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms. Isomers include structural isomers and stereoisomers such as enantiomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "〰" denotes the point of attachment of a chemical moiety to the remainder of a molecule or chemical formula.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to a subject, such as a patient in need of treatment; slowing in the rate of degeneration or decline; making the final point of degeneration less debilitating; improving a subject's physical or mental well-being. The treatment or amelioration of symptoms can be based on objective or subjective parameters; including the results of a physical examination, neuropsychiatric exams, and/or a psychiatric evaluation.

An "effective amount" is an amount sufficient to accomplish a stated purpose (e.g., achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g., transcription factor) relative to the absence of the antagonist. An "activity increasing amount," as used herein, refers to an amount of agonist (activator) required to increase the activity of an enzyme or protein (e.g., transcription factor) relative to the absence of the agonist. A "function disrupting amount," as used herein, refers to the amount of antagonist (inhibitor) required to disrupt the function of an enzyme or protein (e.g., transcription factor) relative to the absence of the antagonist. A "function increasing amount," as used herein, refers to the amount of agonist (activator) required to increase the function of an enzyme or protein (e.g., transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g., agonist) interaction means positively affecting (e.g., increasing) the activity or function of the protein.

The term "modulator" refers to a composition that increases or decreases the level of a target molecule or the function of a target molecule.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym*. Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der waal's bond(s)/interactions, hydrogen bond (s), polar bond(s), or combinations or mixtures thereof).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

DETAILED DESCRIPTION OF THE INVENTION

In the following description, numerous specific details of the compounds, compositions components and methods of the present invention are set forth in order to provide a thorough explanation of the precise nature of the invention. It will be apparent, however, to those of skill in the art that the invention can be practiced without these specific details.

In an aspect, the invention provides a peptide having from 11 to 16 amino acid residues (e.g., 11 amino acid residues, 12 amino acid residues, 13 amino acid residues, 14 amino acid residues, 15 amino acid residues, or 16 amino acid residues) comprising a sequence having 85% or greater sequence identity of SEQ ID NO: 1 (LDEETGEFL), wherein the peptide further comprises a charge modulating domain having from 2 to 7 amino acid residues. In some embodiments, the peptide has 11 to 15 amino acid residues or the peptide has 12 to 14 amino acid residues.

As used herein, a sequence having 85% or greater sequence identity of SEQ ID NO: 1 (LDEETGEFL) indicates that the foregoing sequence can have one point mutation (i.e., amino acid change), one amino acid deletion, or one amino acid addition. In certain embodiments, the sequence having 85% or greater sequence identity of SEQ ID NO: 1 (LDEETGEFL) has a point mutation to comprise a proline residue. For example, any one of the glutamate residues can be changed to a proline residue. In some embodiments, the sequence having 85% or greater sequence identity of SEQ ID NO: 1 (LDEETGEFL) is SEQ ID NO: 1 (LDEETGEFL). In other embodiments, the sequence having 85% or greater sequence identity of SEQ ID NO: 1 (LDEETGEFL) is SEQ ID NO: 2 (LDPETGEFL).

In this aspect of the invention, the peptide comprises a charge modulating domain having from 2 to 7 amino acid residues. Typically, the charge modulating domain is a glycine-serine domain, a cationic residue domain, or a combination thereof. In certain embodiments, the charge modulating domain is a cationic residue domain having from 2 to 7 amino acid residues selected from lysine, arginine, histidine, and a combination thereof. In preferred embodiments, the charge modulating domain modulates the peptide to have a net positive charge. Without wishing to be bound by any particular theory, it is believed that the net positive charge increases the cellular uptake of the peptide or polymer comprising the peptide. Additionally, the addition of residues to form a net positive charge may enhance the aqueous solubility of the compound to facilitate therapeutic use.

In some embodiments, the peptide having from 11 to 16 amino acid residues comprises a sequence having 75% or greater (e.g., 80% or greater, 85% or greater, 90% or greater, 95% or greater, or 100%) sequence identity of SEQ ID NO: 1-SEQ ID: 138, SEQ ID: 140, or SEQ ID: 141. In some embodiments, the peptide having from 11 to 16 amino acid residues is selected from SEQ ID NO: 3-SEQ ID NO: 136, SEQ ID NO: 140, and SEQ ID NO: 141. In certain embodiments, the peptide having from 11 to 16 amino acid residues is selected from SEQ ID NO: 3-SEQ ID NO: 136.

In another aspect, the invention provides a polymer comprising a first polymer segment comprising at least 2 first repeating units; wherein each of the first repeating units of the first polymer s comprises a first polymer backbone group directly or indirectly covalently linked to a first polymer side chain group comprising a peptide; wherein the peptide comprises a sequence having 75% or greater (e.g., 80% or greater, 85% or greater, 90% or greater, 95% or greater, or 100%) sequence identity of SEQ ID NO: 1 (LDEETGEFL). The inventive polymer can be any suitable polymer type described herein and can comprise, or be derived from, any suitable number of monomers. For example, in some embodiments, the polymer is a homopolymer (i.e., derived from one type of monomer). Alternatively, in some embodiments, the polymer can be a copolymer comprising (e.g., derived from) more than one type of monomer (e.g., from 2 to 10 types of monomers). It will be understood that the inventive polymer, along with the linked polymer side chains, can have any suitable configuration. For example, in some embodiments wherein the polymer is a homopolymer, the polymer can be a brush polymer. In other embodiments wherein the polymer is a copolymer, the polymer can be a brush block copolymer or brush random copolymer.

The polymer comprises a first polymer segment comprising at least 2 first repeating units, and optionally at least 5 first repeating units (e.g., 2-30, 5-30, 10-30, 15-30, or 20-30 first repeating units); wherein each of the first repeating units of the first polymer segment comprises a first polymer backbone group directly or indirectly covalently linked to a first polymer side chain group comprising a peptide (e.g., a therapeutic peptide) comprising a sequence having 75% or greater sequence (e.g., 80% or greater, 85% or greater, 90% or greater, 95% or greater, or 100%) identity of SEQ ID NO: 1 (LDEETGEFL).

Thus, at least one polymer side chain (e.g., the first polymer segment) comprises a therapeutic peptide (i.e., peptide). The peptide comprises any suitable number of amino acid units so long as the peptide comprises a sequence having 75% or greater (e.g., 80% or greater, 85% or greater, 90% or greater, 95% or greater, or 100%) sequence identity of SEQ ID NO: 1 (LDEETGEFL). In keeping with an aspect of the invention, the therapeutic peptide comprises at least 7 amino acid units. For example, the peptide comprises 7 or more amino acid units, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid units. Alternatively, or in addition, the peptide can comprise 100 or less amino acid units, for example, 90 or less, 80 or less, 70 or less, 60 or less, 59 or less, 58 or less, 57 or less, 56 or less, 55 or less, 54 or less, 53 or less, 52 or less, 51 or less, 50 or less, 49 or less, 48 or less, 47 or less, 46 or less, 45 or less, 44 or less, 43 or less, 42 or less, 41 or less, 40 or less, 39 or less, 38 or less, 37 or less, 36 or less, 35 or less, 34 or less 33 or less, 32 or less, or 31 or less amino acid units. Thus, the peptide can comprise a number of amino acid units bounded by any two of the aforementioned endpoints. For example, the peptide can comprise 7 to 100 amino acid units, for example, 7 to 90, 7 to 80, 7 to 70, 7 to 60, 7 to 50, 7 to 40, 7 to 30, 7 to 20, 7 to 16, 7 to 15, 7 to 14, 8 to 100, 8 to 90, 8 to 80, 8 to 70, 8 to 60, 8 to 50, 8 to 40, 8 to 30, 8 to 20, 8 to 16, 8 to 15, 8 to 14, 9 to 100, 9 to 90, 9 to 80, 9 to 70, 9 to 60, 9 to 50, 9 to 40, 9 to 30, 9 to 20, 9 to 16, 9 to 15, 9 to 14, 10 to 16, 10 to 15, 10 to 14, 11 to 16, 11 to 15, 11 to 14, 12 to 16, 12 to 15, or 12 to 14 amino acid units. In some embodiments, the peptide comprises 11 to 16 amino acids. In certain embodiments, the peptide comprises 11 to 15 amino acids or 12 to 14 amino acids.

The peptide can have any suitable structure (e.g., primary, secondary, tertiary, or quaternary structure) described herein. The peptide can be a branched peptide, a linear peptide, cyclic peptide, or a cross-linked peptide. In some embodiments, the polymer is characterized by a structure wherein at least a portion of the peptide is linked to the polymer backbone group via an enzymatically degradable linker, such a matrix metalloproteinase (MMP) cleavage sequence, cathepsin B cleavage sequence, ester bond, reductive sensitive bond-disulfide bond, pH sensitive bond-imine bond or any combinations of these. In other embodiments, the polymer is characterized by a structure wherein at least a portion of the peptide side-chain is linked to the polymer backbone or consists of a degradable or triggerable linker. In some embodiments, the peptide and/or polymer further comprises a tag for imaging and/or analysis. For example, the peptide and/or polymer can further comprise a dye, radiolabeling, an imaging agent, tritiation, and the like.

In some embodiments, the peptide comprising a sequence having 75% or greater (e.g., 80% or greater, 85% or greater, 90% or greater, 95% or greater, or 100%) sequence identity of SEQ ID NO: 1 (LDEETGEFL) further comprises a charge modulating domain. The charge modulating domain can be any suitable amino acid domain, which increases the positive charge of the peptide. For example, the charge modulating domain can be a TAT sequence, a glycine-serine domain, a cationic residue domain, or a combination thereof. In some embodiments, the charge modulating domain is a glycine-serine domain, a cationic residue domain, or a combination thereof. In certain embodiments, the charge modulating domain is a cationic residue domain having from 2 to 7 amino acid residues selected from lysine, arginine, histidine, and a combination thereof. In preferred embodiments, the charge modulating domain modulates the peptide to have a net positive charge.

In some embodiments, the peptide comprises a sequence having 85% or greater sequence identity of SEQ ID NO: 1 (LDEETGEFL). In certain embodiments, the peptide comprises a sequence having 75% or greater or 85% or greater sequence identity of SEQ ID NO: 1 (LDEETGEFL) has a point mutation to comprise a proline residue and/or a point mutation to delete a glutamate residue. In preferred embodiments, the peptide comprises SEQ ID NO: 1 (LDEETGEFL) or SEQ ID NO: 2 (LDPETGEFL). In other embodiments, the peptide comprises SEQ ID NO: 137 (LDPTGEFL) or SEQ ID NO: 138 (LDPETGFL).

In an embodiment, the peptide is selected from SEQ ID NO: 1-SEQ ID NO: 136, SEQ ID NO: 140, and SEQ ID NO: 141, optionally wherein the peptide is selected from SEQ ID NO: 3-SEQ ID NO: 136.

In some embodiments, the polymer is characterized by the formula (FX1a), (FX1b), (FX1c), (FX1d); (FX1e); (FX1f); or (FX1g):

$Q^1$-T-$Q^2$ (FX1a);

$Q^1$-T-$[S]_h$-$Q^2$ (FX1b);

$Q^1$-$[S]_h$-T-$Q^2$ (FX1c);

$Q^1$-$[S]_i$-T-$[S]_h$-$Q^2$ (FX1d);

$Q^1$-$[S]_i$-T-$[S]_h$-T-$Q^2$ (FX1e);

$Q^1$-T-$[S]_i$-T-$[S]_h$-$Q^2$ (FX1f); or $Q^1$-T-$[S]_i$-T-$[S]_h$-T-$Q^2$ (FX1g);

wherein each T is independently the first polymer segment comprising the first repeating units and each S is independently an additional polymer segment; $Q^1$ is a first backbone terminating group; $Q^2$ is a second backbone terminating group; and wherein h is zero or an integer selected over the range of 1 to 1000 (e.g., 1 to 500, 1 to 250, 1 to 100, or 1 to 50) and i is zero or an integer selected over the range of 1 to 1000 (e.g., 1 to 500, 1 to 250, 1 to 100, or 1 to 50). In an embodiment, the polymer is characterized by any of formulas (FX1a)-(FX1g), wherein each -T- is independently —$[Y^1]_m$—; wherein each $Y^1$ is independently the first repeating unit of the first polymer segment; and each m is independently an integer selected from the range 0 to 1000 (e.g., 0 or 1 to 500, 1 to 250, 1 to 100, or 1 to 50), provided that at least one m is an integer selected from the range 1 to 1000 (e.g., 1 to 500, 1 to 250, 1 to 100, or 1 to 50). In certain embodiments, each of the first polymer segment backbone group and/or the additional polymer segment backbone group is a substituted or unsubstituted polymerized norbornene, olefin, cyclic olefin, norbornene anhydride, cyclooctene, cyclopentadiene, styrene, acrylamide, or acrylate.

In certain embodiments, the polymer is characterized by the formula (FX2a), (FX2b), or (FX2c):

(FX2a)

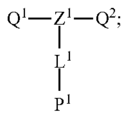

(FX2b)

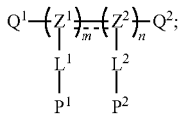

or (FX2c)

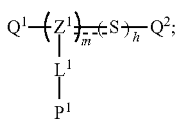

wherein each $Z^1$ is independently a first polymer backbone group and each $Z^2$ is independently a second polymer backbone group; each S is independently a repeating unit having a composition different from the first repeating unit; $Q^1$ is a first backbone terminating group and $Q^2$ is a second backbone terminating group; each $L^1$ is independently a first linking group, each $L^2$ is independently a second linking group; each $P^1$ is the peptide; wherein each $P^2$ is a polymer side chain having a composition different from that of $P^1$; wherein each $P^2$ is a polymer side chain having a composition different from that of $P^1$; and wherein each m is independently an integer selected from the range of 2 to 1000 (e.g., 2 to 500, 2 to 250, 2 to 100, or 2 to 50); wherein each n is each independently an integer selected from the range of 0 to 1000 (e.g., 0 to 500, 0 to 250, 0 to 100, or 0 to 50); and wherein h are each independently an integer selected from the range of 0 to 1000 (e.g., 0 to 500, 0 to 250, 0 to 100, or 0 to 50). In certain embodiments, each of the first polymer backbone group and/or the second polymer backbone group is a substituted or unsubstituted polymerized norbornene, olefin, cyclic olefin, norbornene anhydride, cyclooctene, cyclopentadiene, styrene, acrylamide, or acrylate.

For each of the polymers characterized by the formula (FX2a), (FX2b), or (FX2c), described herein, it will be understood that the first polymer backbone group units, the second polymer backbone group units, and the repeating unit having a composition different from the first repeating unit can be arranged in any suitable order. For example, the first polymer backbone group units, the second polymer backbone group units, and the repeating unit having a composition different from the first repeating unit can be arranged as a random polymer, block polymer, brush, brush block, alternating, segmented, grafted, tapered and other architectures. In other words, variables "m", "n", and "h" merely define the total number of that particular monomer in the polymer and do not imply any particular order.

In certain embodiments, for each of the polymers characterized by the formula (FX2a), (FX2b), and (FX2c), each of $Z^1$ and $Z^2$ can be any suitable monomer capable of undergoing ring opening metathesis or cross metathesis. For example, each of $Z^1$ and $Z^2$ can independently be a substituted or unsubstituted norbornene, oxanorbornene, olefin, cyclic olefin, cyclooctene, or cyclopentadiene. In some embodiments, each of the first polymer backbone group and/or the second polymer backbone group is a polymerized norbornene dicarboxyimide monomer. In preferred embodiments, each polymer backbone group of the polymer is a polymerized norbornene dicarboxyimide monomer.

Thus, for each of the polymers characterized by the formula (FX2a), (FX2b), and (FX2c), each $Z^1$ connected to $L^1$, and $P^1$ or a combination thereof can independently be characterized by the formula (FX3a) or (FX3b):

(FX3a)

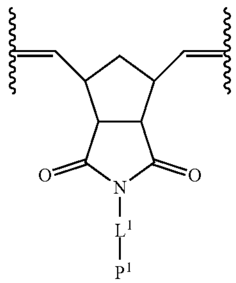

or

-continued (FX3b)

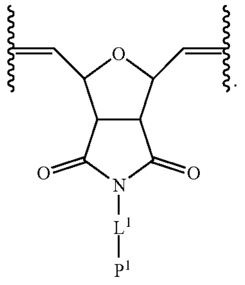

and when present, each $Z^2$ connected to $L^2$, and $P^2$ or a combination thereof can independently be characterized by the formula (FX4a) or (FX4b)

(FX4a)

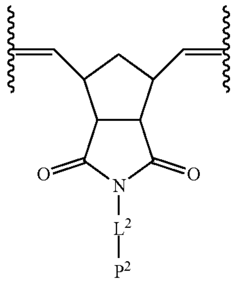

or (FX4b)

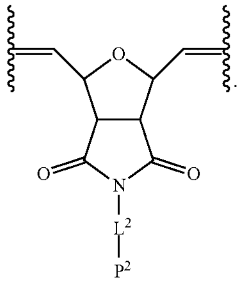

In certain embodiments of the polymers characterized by the formula (FX2a), (FX2b), and (FX2c), each $Z^1$ connected to $L^1$, and $P^1$ or a combination thereof is independently characterized by the formula (FX3a):

(FX3a)

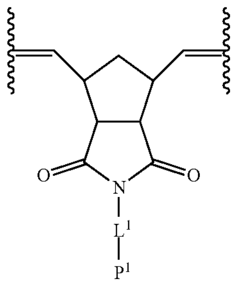

and/or each $Z^2$ connected to $L^2$, and $P^2$ or a combination thereof is independently characterized by the formula (FX4a):

(FX4a)

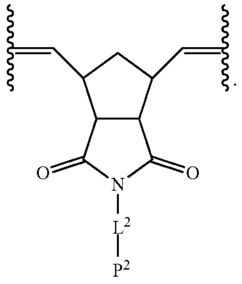

For each of the polymers characterized by the formula (FX1a), (FX1b), (FX1c), (FX1d), (FX1e), (FX1f), (FX1g), (FX2a), (FX2b), and (FX2c), each of $Q^1$ and $Q^2$ can independently be selected from a hydrogen, $C_1$-$C_{30}$ alkyl, $C_3$-$C_{30}$ cycloalkyl, $C_5$-$C_{30}$ aryl, $C_5$-$C_{30}$ heteroaryl, $C_1$-$C_{30}$ acyl, $C_1$-$C_{30}$ hydroxyl, $C_1$-$C_{30}$ alkoxy, $C_2$-$C_{30}$ alkenyl, $C_2$-$C_{30}$ alkynyl, $C_5$-$C_{30}$alkylaryl, —$CO_2R^3$, —$CONR^4R^5$, —$COR^6$, —$SOR^7$, —$OSR^8$, —$SO_2R^9$, —$OR^{10}$, —$SR^{11}$, —$NR^{12}R^{13}$, —$NR^{14}COR^{15}$, $C_1$-$C_{30}$ alkyl halide, phosphonate, phosphonic acid, silane, siloxane, silsesquioxane, $C_2$-$C_{30}$ halocarbon chain, $C_2$-$C_{30}$ perfluorocarbon, $C_2$-$C_{30}$ polyethylene glycol, a metal, or a metal complex, wherein each of $R^3$-$R^{15}$ is independently H, $C_5$-$C_{10}$ aryl or $C_1$-$C_{10}$ alkyl.

For each of the polymers characterized by the formula (FX2a), (FX2b), and (FX2c), each of $L^1$ and $L^2$ can be any suitable linking group. For example, each of $L^1$ and $L^2$ can independently be selected from a single bond, an oxygen, and groups having an alkyl group, an alkenylene group, an arylene group, an alkoxy group, an acyl group, a triazole group, a diazole group, a pyrazole group, and combinations thereof. In certain embodiments, each of $L^1$ and $L^2$ is independently selected from a single bond, —O—, $C_1$-$C_{10}$ alkyl, $C_2$-$C_{10}$ alkenylene, $C_3$-$C_{10}$ arylene, $C_1$-$C_{10}$ alkoxy, $C_1$-$C_{10}$ acyl and combinations thereof.

For each of the polymers characterized by the formula (FX2a), (FX2b), and (FX2c), each $P^2$ is a polymer side chain having a composition different from that of $P^1$. Thus, $P^2$ can be any suitable side chain capable of being incorporated into the polymer with $P^1$. In some embodiments, $P^2$ is a peptide or protein other than $P^1$. Thus, the polymer can comprise two different peptide or protein units. In some embodiments, $P^2$ is a nonionic polymer selected from a polyalkylene glycol, a polyetheramine, a polyethylene oxide/polypropylene oxide copolymer, a polysaccharide, and combinations thereof. In certain embodiments, the nonionic polymer is a polyalkylene glycol (e.g., polyethylene glycol (PEG) or polypropylene oxide (PPO)), a polyethylene oxide/polypropylene oxide copolymer, or a combination thereof. In preferred embodiments, the nonionic polymer is a polyethylene glycol (PEG). Thus, in some embodiments, each $Z^2$ connected to $L^2$, and $P^2$ or a combination thereof is independently characterized by the formula (FX7a) or (FX7b):

(FX7a)

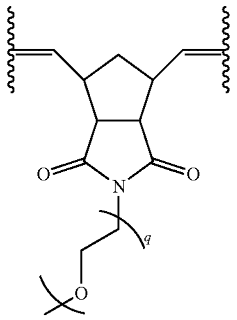

or (FX7a)

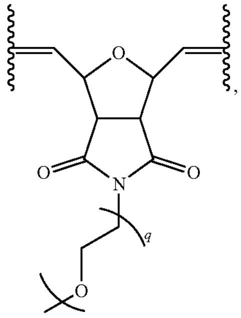

, wherein q is an integer from 1 to 500 (e.g., 1 to 250, 1 to 100, 1 to 50, 1 to 25, 1 to 10, or 1 to 6).

For each of the polymers characterized by the formula (FX2a), (FX2b), and (FX2c), each S is independently a repeating unit having a composition different from the first repeating unit. Thus, S can be any monomer unit capable of being incorporated into the polymer with $P^1$. In some embodiments, S comprises a nonionic polymer selected from a polyalkylene glycol, a polyetheramine, a polyethylene oxide/polypropylene oxide copolymer, a polysaccharide, and combinations thereof. In certain embodiments, the nonionic polymer is a polyalkylene glycol (e.g., polyethylene glycol (PEG) or polypropylene oxide (PPO)), a polyethylene oxide/polypropylene oxide copolymer, or a combination thereof. In preferred embodiments, the nonionic polymer is a polyethylene glycol (PEG). Thus, in some embodiments, each S is independently characterized by the formula (FX7a) or (FX7b):

(FX7a)

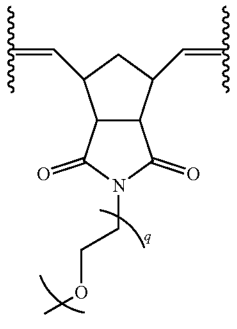

or

-continued (FX7a)

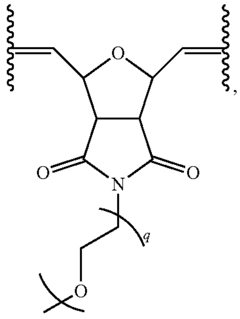

, wherein q is an integer from 1 to 500 (e.g., 1 to 250 1 to 100, 1 to 50, 1 to 25, 1 to 10, or 1 to 6)

In certain embodiments, the polymer is characterized by the formula (FX2a), (FX2b), or (FX2c):

(FX2a)

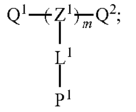

(FX2b)

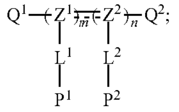

or (FX2c)

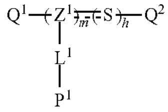

wherein each $Z^1$ is independently a first polymer backbone group and each $Z^2$ is independently a second polymer backbone group; each S is independently a repeating unit having a composition different from the first repeating unit; $Q^1$ is a first backbone terminating group and $Q^2$ is a second backbone terminating group; each $L^1$ is independently a first linking group, each $L^2$ is independently a second linking group; each $P^1$ is the polymer side chain comprising the peptide; wherein each $P^2$ is a polymer side chain having a composition different from that of $P^1$; each m is independently an integer selected from the range of 2 to 100; each n is independently an integer selected from the range of 0 to 100; and each h is independently an integer selected from the range of 0 to 100, provided that each of the first polymer backbone group and/or the second polymer backbone group is a polymerized norbornene dicarboxyimide monomer, and wherein the peptide comprises a sequence having 75% or greater (e.g., 80% or greater, 85% or greater, 90% or greater, 95% or greater, or 100%) sequence identity of SEQ ID NO: 1 (LDEETGEFL) or SEQ ID NO: 2 (LDPETGEFL). In certain embodiments, the peptide is SEQ ID NO: 72 (LD-PETGEFLRRRR). In some embodiments, the polymer further fulfills (i) and/or (ii) of the following properties:

(i) the polymer has a degree of polymerization of 5 to 100, and (ii) the polymer has a peptide density of greater than 50%, as defined by the following formula:

$$\frac{P^1}{P^1+P^2+S}\times 100.$$

In preferred embodiments, the polymer fulfills both of properties (i) and (ii) above.

In some specific embodiments, the polymer comprises one or more peptides and/or proteins other than the therapeutic peptide described herein (i.e., one or more additional peptides and/or proteins). For example, each polymer segment S of formula (FX1a), (FX1b), (FX1c), (FX1d); (FX1e); (FX1f); or (FX1g) can independently comprise a peptide or protein other than the therapeutic peptide described herein. Similarly, each $P^2$ of formula (FX2a), (FX2b), or (FX2c) can independently comprise a peptide or protein other than the therapeutic peptide described herein.

The one or more additional peptides and/or proteins can be any suitable peptide or protein, having any suitable function. For example, the one or more additional peptides and/or proteins can be an additional therapeutic peptide (e.g., an additional therapeutic peptide described herein), a cell-penetrating agent (e.g., a cell-penetrating peptide), a targeting agent (e.g., a target-specific peptide to a tissue or cell type), a therapeutically synergistic disease-specific peptide (e.g. a peptide known or thought to be therapeutic for a disease state, such as but not limited to, neurodegenerative disease), an antibody, or a combination thereof. The additional peptides and/or proteins can be linked to the polymer backbone by any suitable means. In some embodiments, the additional peptides and/or proteins are linked to the polymer backbone via an enzymatically degradable linker (i.e., linking group or linking moiety). Examples of suitable cleavable, degradable or triggerable linkers include enzyme cleavable sequences such as one or more matrix metalloproteinase (MMP) cleavage sequence, cathepsin B cleavage sequence, ester bond, reductive sensitive bond-disulfide bond, pH sensitive bond-imine bond, among others.

The one or more additional peptides and/or proteins can have any suitable number of amino acid units. For example, the one or more additional peptides and/or proteins can comprise 2 or more amino acid units, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid units. Alternatively, or in addition, the one or more additional peptides and/or proteins can comprise 100 or less amino acid units, for example, 90 or less, 80 or less, 70 or less, 60 or less, 59 or less, 58 or less, 57 or less, 56 or less, 55 or less, 54 or less, 53 or less, 52 or less, 51 or less, 50 or less, 49 or less, 48 or less, 47 or less, 46 or less, 45 or less, 44 or less, 43 or less, 42 or less, 41 or less, 40 or less, 39 or less, 38 or less, 37 or less, 36 or less, 35 or less, 34 or less 33 or less, 32 or less, or 31 or less amino acid units. Thus, the one or more additional peptides and/or proteins can comprise a number of amino acid units bounded by any two of the aforementioned endpoints. For example, the one or more additional peptides and/or proteins can comprise 2 to 100 amino acid units, for example, 2 to 90, 2 to 80, 2 to 70, 2 to 60, 5 to 100, 5 to 90, 5 to 80, 5 to 70, 5 to 60, 3 to 60, 3 to 59, 4 to 58, 5 to 57, 6 to 56, 7 to 55, 8 to 54, 9 to 53, 10 to 52, 11 to 51, 12 to 50, 13 to 49, 14 to 48, 15 to 47, 16 to 46, 17 to 45, 18 to 44, 19 to 43, 20 to 42, 21 to 41, 22 to 42, 23 to 41, 24 to 40, 25 to 39, 26 to 38, 27 to 37, 28 to 36, 29 to 35, 30 to 34, or 31 to 33 amino acid units. In certain embodiments, the one or more additional peptides and/or proteins comprises 5 to 100 amino acids. In preferred embodiments, the one or more additional peptides and/or proteins comprises 8 to 60 amino acid.

The one or more additional peptides and/or proteins can have any suitable structure (e.g., primary, secondary, tertiary, or quaternary structure). Additionally, the one or more additional peptides and/or proteins can be branched, linear, cyclic, or cross-linked. In some embodiments, the one or more additional peptides and/or proteins is a charge modulating domain. For example, the one or more additional peptides and/or proteins can be or can comprise a TAT sequence, a glycine-serine domain, a cationic residue domain, or a combination thereof, or optionally a glycine-serine domain, a cationic residue domain, or a combination thereof. In certain embodiments, the one or more additional peptides and/or proteins modulates the charge of the polymer to have a net positive charge. Without wishing to be bound by any particular theory, it is believed that the net positive charge increases the cellular uptake of the polymer comprising the peptide.

In some specific embodiments, the polymer comprises a tag for imaging and/or analysis. For example, each polymer segment S of formula (FX1a), (FX1b), (FX1c), (FX1d); (FX1e); (FX1f); or (FX1g) can independently comprise a tag for imaging and/or analysis. Similarly, each $P^2$ of formula (FX2a), (FX2b), or (FX2c) can independently comprise a tag for imaging and/or analysis. For example, the polymer can comprise a dye, radiolabeling, an imaging agent, tritiation, and the like.

After polymerization the inventive polymers may be characterized using any suitable technique(s). Typically, the inventive polymers are characterized by size-exclusion chromatography with multiangle light scattering (SEC-MALS), sometimes referred to as gel permeation chromatography (GPC), to ascertain degree of polymerization (DP) and molecular weight distribution (dispersity or Mw/Mn). Alternatively, or in addition to, the inventive polymers may be characterized by SDS-PAGE to ascertain degree of polymerization (DP) and molecular weight. Preferably, there is suitable agreement between the obtained DP and the theoretical DP based on the initial monomer-to-initiator ratio ($[M]_0/[I]_0$).

The inventive polymer can have any suitable degree of polymerization. If the degree of polymerization is too low, the polymer may not be resistant to enzymatic cleavage by proteases or may be cleared too rapidly from the body since the polymer's molecular weight would be lower than the clearance threshold through the kidney. Alternatively, if the degree of polymerization is too high, the peptide side chain groups displayed on the polymer may be too dense to engage their biological targets such as cell receptors, enzymes, etc. Typically, the polymer has a degree of polymerization of 2 to 1000 (e.g., 2 to 500, 2 to 250, 2 to 100, 2 to 50, 2 to 30, 5 to 1000, 5 to 500, 5 to 250, 5 to 100, 5 to 50, 5 to 30, 20 to 500, 20 to 250, 20 to 100, 20 to 50, or 20 to 30). In certain embodiments, the polymer has a degree of polymerization of 5 to 100. In preferred embodiments, the polymer has a degree of polymerization of 5 to 50. For example, the polymer can have a degree of polymerization of 5 or about 5, a degree of polymerization of 15 or about 15 (e.g., 17), a degree of polymerization of 30 or about 30, or a degree of polymerization of 50 or about 50. In certain embodiments, the polymer has a degree of polymerization of at least 20. Without wishing to be bound by any particular theory, it is believed that a degree of polymerization of at least 20 allows for the protein-like polymer to bridge the gap between both Kelch domains of a Keap1 homodimer, thereby increasing binding interactions by stably binding both Kelch domains simultaneously.

The inventive polymer can have any suitable weight average molecular weight. The polymers can have a weight average molecular weight of 2,000 kDa or less, for example, 1,800 kDa or less, 1,600 kDa or less, 1,400 kDa or less, 1,200 kDa or less, 1,000 kDa or less, 900 kDa, or less, 800 kDa, or less, 700 kDa or less, 600 kDa or less, 500 kDa or less, 250 kDa or less, 100 kDa or less, or 50 kDa or less. Alternatively, or in addition, the polymers can have a weight average molecular weight of 500 Da or more, for example, 1 kDa or more, 5 kDa or more, or 10 kDa or more. Thus, the polymers can have a weight average molecular weight bounded by any two of the aforementioned endpoints. For example, the polymers can have a weight average molecular weight of from 500 Da to 2,000 kDa, from 500 Da to 1,000 kDa, from 500 Da to 500 kDa, from 500 Da to 100 kDa, from 500 Da to 50 kDa, 1 kDa to 2,000 kDa, from 1 kDa to 1,000 kDa, from 1 kDa to 500 kDa, from 1 kDa to 100 kDa, from 1 kDa to 50 kDa, 5 kDa to 2,000 kDa, from 5 kDa to 1,000 kDa, from 5 kDa to 500 kDa, from 5 kDa to 100 kDa, from 5 kDa to 50 kDa, 10 kDa to 2,000 kDa, from 10 kDa to 1,000 kDa, from 10 kDa to 500 kDa, from 10 kDa to 100 kDa, or from 10 kDa to 50 kDa.

Generally, the polymers described herein are characterized by a brush density of greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Brush polymers of certain aspects are characterized by a brush density selected from the range 50% to 100%, optionally some embodiments a brush density selected from the range of 60% to 100%, optionally for some embodiments a brush density selected from the range of 70% to 100%, optionally some embodiments a brush density selected from the range of 80% to 100%, or optionally for some embodiments a brush density selected from the range of 90% to 100%.

The polymer can have any suitable peptide density. The polymer may be characterized by peptide density which refers to the percentage of the repeating units comprising a polymer backbone group covalently linked to at least one peptide. Thus, for each of the polymers characterized by the formula (FX2a), (FX2b), and (FX2c), the polymer density can be defined by the following formula:

$$\frac{P^1}{P^1 + P^2 + S} \times 100.$$

Generally, the polymers described herein are characterized by a peptide density of greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Brush polymers of certain aspects are characterized by a peptide density selected from the range 50% to 100%, optionally some embodiments a peptide density selected from the range of 60% to 100%, optionally for some embodiments a peptide density selected from the range of 70% to 100%, optionally some embodiments a peptide density selected from the range of 80% to 100%, or optionally for some embodiments a peptide density selected from the range of 90% to 100%. In some embodiments, the brush density is equivalent to the peptide density.

In another aspect, the invention provides a pharmaceutical composition comprising one or more peptides and/or one or more polymers described herein. In some embodiments, the composition comprises one or more pharmaceutically acceptable excipients. For example, the peptides and/or polymers of the invention can be formulated for parenteral administration, such as intravenous (IV) administration or administration into a body cavity or lumen of an organ. Alternatively, the peptides and/or polymers can be injected intra-tumorally. Formulations for injection will commonly comprise a solution of the peptide and/or polymer dissolved in a pharmaceutically acceptable carrier. Among the acceptable vehicles and solvents that can be employed are water and an isotonic sodium chloride. In addition, sterile fixed oils can conventionally be employed as a solvent or suspending medium. For this purpose, any bland fixed oil can be employed including synthetic monoglycerides or diglycerides. In addition, fatty acids such as oleic acid can likewise be used in the preparation of injectables. These solutions are sterile and generally free of undesirable matter. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the peptide and/or polymer in these formulations can vary widely, and will be selected primarily based on fluid volumes, viscosities, body weight, and the like, in accordance with the particular mode of administration selected and the patient's needs. In certain embodiments, the concentration of a peptide and/or polymer in a solution formulation for injection will range from 0.1% (w/w) to 10% (w/w) or about 0.1% (w/w) to about 10% (w/w).

In some embodiments, the composition further comprises an additional Keap1 inhibitor or Nrf2 inducer. For example the composition can further comprise an additional small molecule drug such as dimethyl fumarate, tert-butylhydroquinone, DL-sulforaphane, or the like. Other small molecule Keap1 inhibitors or Nrf2 inducers will be readily apparent to those skill in the art. In certain embodiments, the composition further comprises an additional Keap1 inhibiting peptide. In other words, the composition can comprise a protein-like polymer described herein and an additional peptide.

In another aspect, the invention provides a method of treating or managing a condition comprising administering to a subject an effective amount of a peptide, polymer, and/or pharmaceutical composition described herein. The peptide, polymer, and/or pharmaceutical composition can be administered by oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. In some embodiments, the peptide, polymer, and/or pharmaceutical composition is administered intravenously, subcutaneously, intramuscularly, topically, orally, or a combination thereof.

The methods described herein can comprise contacting a target tissue of the subject with the peptide and/or polymer or a metabolite or product thereof, contacting a target cell of the subject with the peptide and/or polymer or a metabolite or product thereof, and/or contacting a target receptor of the subject with the peptide and/or polymer or a metabolite or product thereof. In preferred embodiments, the peptides and/or polymers described herein pass through the cell membrane and contact an intracellular target. Without wishing to be bound by any particular theory, it is believe that the peptide/polymer structure and charge described herein play an integral role in providing cell permeability.

In some embodiments, the methods described herein interrupt the protein-protein interaction between Nuclear factor (erythroid-derived 2)-like 2 (Nrf2) and Kelch-like ECH-Associating protein 1 (Keap1) (e.g., by inhibiting binding to the ETGE motif of Nrf2). Without wishing to be bound by any particular theory, inhibiting Keap1/Nrf2 binding can enhance the antioxidant and anti-inflammatory response to provide beneficial effects in both the central nervous system (CNS) and/or the non-central nervous system. Thus, the methods described herein can be used to treat and/or manage a condition associated with an inflammatory state, increased oxidative stress, autoimmune pathophysiology, chemo-preventative measures, neurodegeneration, or a combination thereof.

The method includes administering a therapeutically effective amount of a peptide, polymer, and/or composition described herein to a subject in need thereof. For example, the methods can include administering the peptide, polymer, and/or composition to provide a dose of from 10 ng/kg to 50 mg/kg to the subject. For example, the peptide and/or polymer dose can range from 5 mg/kg to 50 mg/kg, from 10 μg/kg to 5 mg/kg, or from 100 μg/kg to 1 mg/kg. The peptide and/or polymer dose can also lie outside of these ranges, depending on the particular peptide and/or polymer as well as the type of disease being treated. Frequency of administration can range from a single dose to multiple doses per week, or more frequently. In some embodiments, the peptide and/or polymer is administered from about once per month to about five times per week. In some embodiments, the peptide and/or polymer is administered once per week.

In some embodiments, the methods described herein can be used to treat or manage an autoimmune disease. For example, the methods described herein can be used to treat or manage multiple sclerosis, systemic lupus erythematous, Sjogren syndrome, rheumatoid arthritis, vitiligo, psoriasis, or the like.

In some embodiments, the methods described herein can be used to treat or manage a respiratory disease. For example, the methods described herein can be used to treat or manage COPD, emphysema, potential treatment for smokers, idiopathic pulmonary fibrosis, chronic sarcoidosis, hypersensitivity pneumonitis, or the like.

In some embodiments, the methods described herein can be used to treat or manage a gastrointestinal disease. For example, the methods described herein can be used to treat or manage ulcerative colitis, ulcers, prevent acetaminophen toxicity, non-alcoholic steatohepatitis, primary biliary cholangitis, cirrhosis, type 2 diabetes, diabetic nephropathy, or the like.

In some embodiments, the methods described herein can be used to treat or manage a cardiovascular disease. For example, the methods described herein can be used to treat or manage cardiac ischemia-reperfusion injury, heart failure, atherosclerosis, or the like.

In some embodiments, the methods described herein can be used to treat or manage a neurodegenerative disease. For example, the methods described herein can be used to treat or manage Alzheimer's disease, Parkinson's disease, amyotrophic lateral sclerosis (ALS), Huntington's disease, Friedreich ataxia, frontotemporal lobar degeneration, or the like.

The invention may be further set forth and understood in view of the following non-limiting examples and embodiments which one having skill in the art will readily understand are intended to illustrate specific aspects of the invention.

Example 1

This example demonstrates the enhanced binding affinity of peptide sequences of the invention.

Peptide sequences SEQ ID NO: 72 (LDPETGEFLRRRR), SEQ ID NO: 129 (LDPETGEFLKKRR), SEQ ID NO: 116 (LDPETGEFLKRKR), SEQ ID NO: 1 (LDEETGEFL), SEQ ID NO: 139 (DERLRERPLTGFR), and SEQ ID NO: 140 (YGRKKRRLDPETGEFL) were evaluated using in silico experiments with AutoDock Vina software, which is capable of docking simulation as well as binding energy predictions. The binding affinities calculated for binding of Keap1 are shown in FIG. 1.

As is apparent from the results set forth in FIG. 1, each of sequences SEQ ID NO: 72 (LDPETGEFLRRRR), SEQ ID NO: 129 (LDPETGEFLKKRR), and SEQ ID NO: 116 (LDPETGEFLKRKR) exhibited enhanced binding affinity relative to the native Nrf2 sequence SEQ ID NO: 1 (LDEETGEFL). These results show that addition of lysine residues and/or arginine residues can increase the binding affinity of the native Nrf2 sequence.

Example 2

This example demonstrates the effect on binding interactions exhibited by a peptide sequence of the invention, having a point mutation to delete a glutamate residue.

Figure 2:
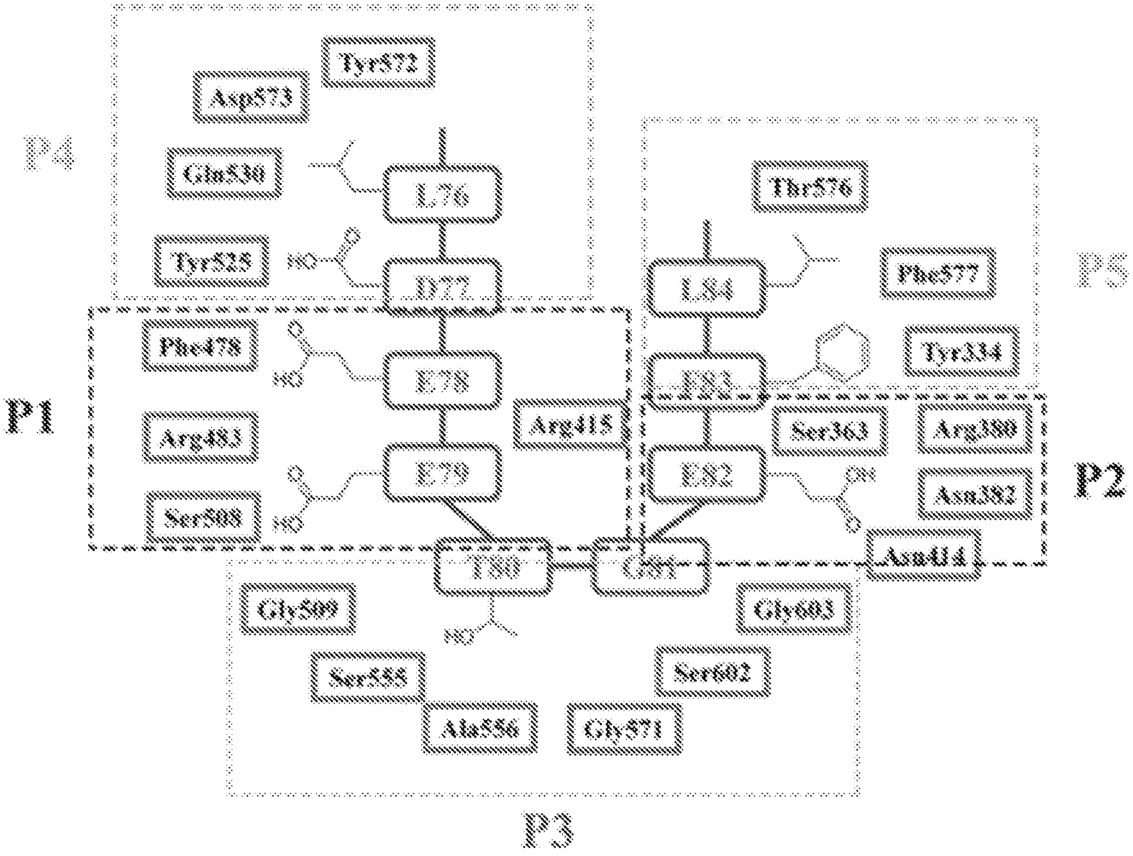
FIG. 2 shows documented binding interactions P1-P5 within the pocket of the Kelch domain, established by the interaction between the Nrf2 peptide and Keap1 protein. See, for example, Lu et al. ("Binding thermodynamics and kinetics guided optimization of potent Keap1-Nrf2 peptide inhibitors," *RSC Advances,* 5:85983-7 (2015)).
Figure 3:
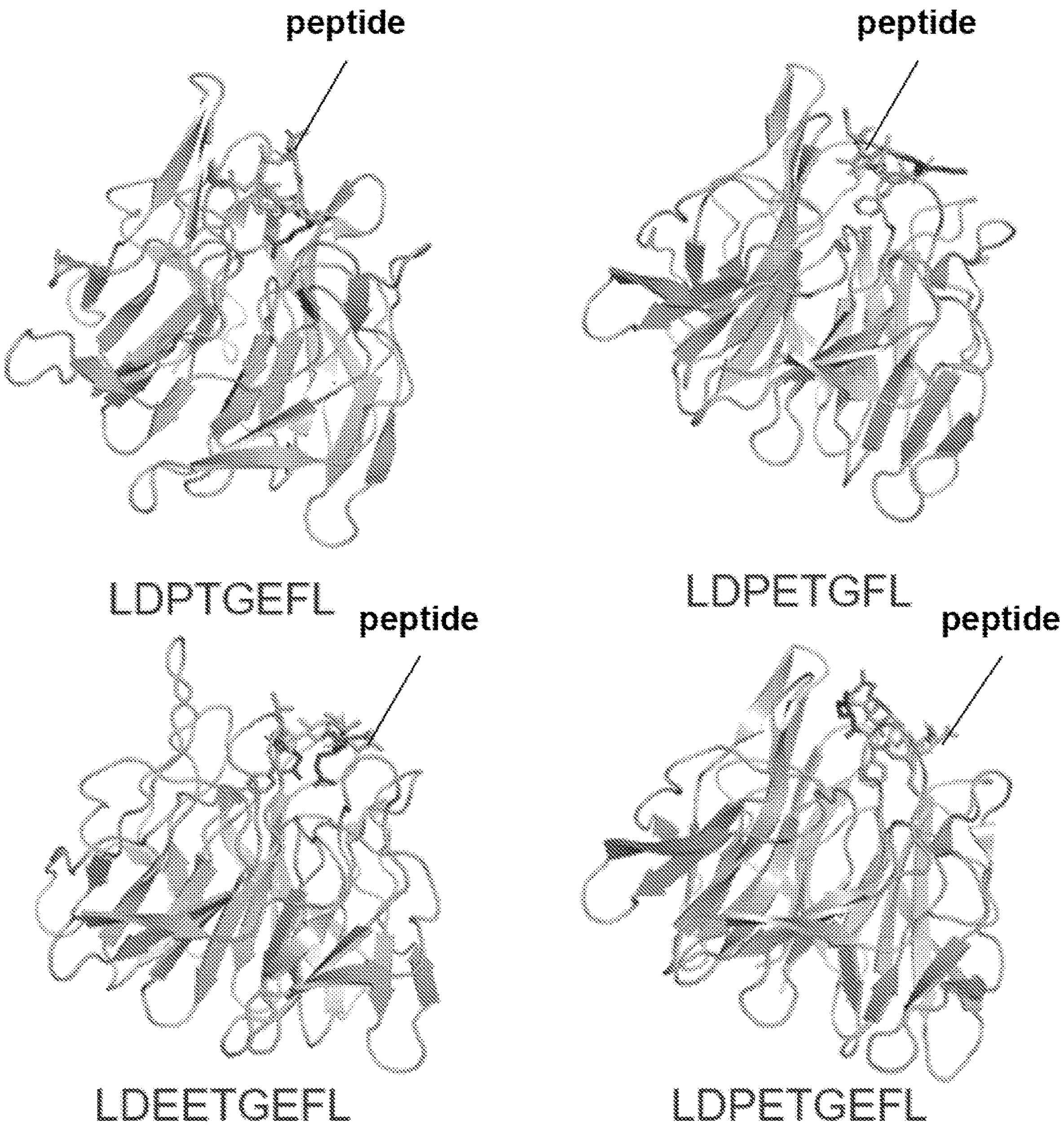
FIG. 3 depicts four different peptide sequences, namely, SEQ ID NO: 137 (LDPTGEFL), SEQ ID NO: 138 (LDPETGFL), SEQ ID NO: 1 (LDEETGEFL), and SEQ ID NO: 2 (LDPETGEFL), as described in Example 2.

Peptide sequences SEQ ID NO: 137 (LDPTGEFL), SEQ ID NO: 138 (LDPETGFL), SEQ ID NO: 1 (LDEETGEFL), and SEQ ID NO: 2 (LDPETGEFL), depicted in FIG. 3 were evaluated using in silico simulations with CABS-Dock software, which is capable of simultaneous prediction of binding sites and protein-peptide docking through coarse-gain methods. Documented binding interactions P1-P5 within the pocket of the Kelch domain of the Keap1 protein, as depicted in FIG. 2, were simulated for each of peptide sequences SEQ ID NO: 137 (LDPTGEFL), SEQ ID NO: 138 (LDPETGFL), SEQ ID NO: 1 (LDEETGEFL), and SEQ ID NO: 2 (LDPETGEFL), and the results are set forth in FIGS. 7A-7C.

Figure 7A:
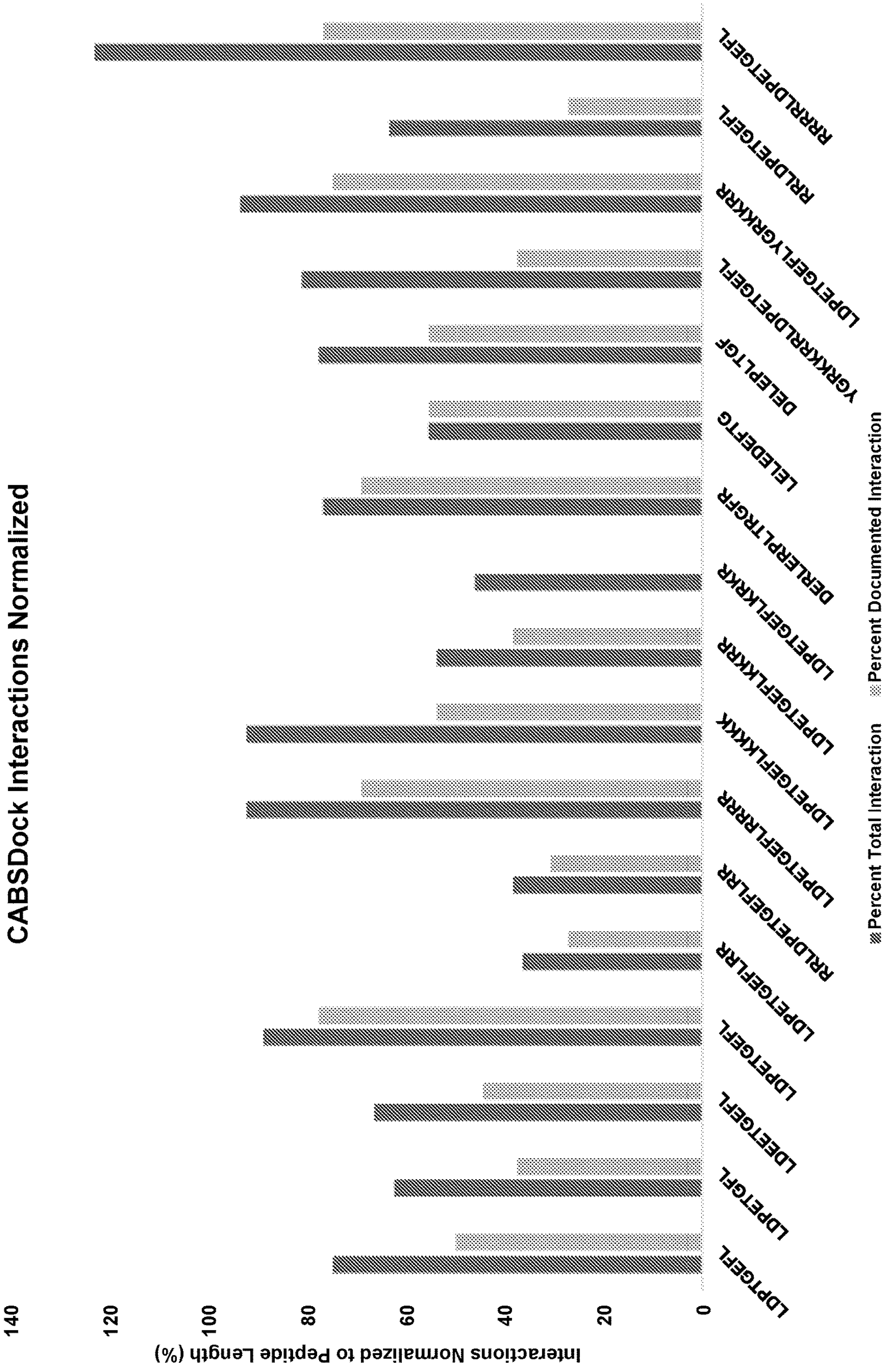
FIG. 7A shows (i) the normalized overall binding interactions with P1-P5 within the pocket of the Kelch domain and (ii) the normalized interactions with documented Keap1 residues within the pocket of the Kelch domain, exhibited by the peptide sequences shown in FIGS. 1 and 3-6 and described in Examples 1-5, as well as additional peptide sequences SEQ ID NO: 143 (DERLERPLTRGFR), SEQ ID NO: 144 (LELEDEFTG), and SEQ ID NO: 145 (DELEPLTGF). The sequences in FIG. 7A (in order as shown in the figure) are: SEQ ID NO: 137, SEQ ID NO: 138, SEQ ID NO: 1, SEQ ID NO: 2, SEQ ID NO: 70, SEQ ID NO: 78, SEQ ID NO: 72, SEQ ID NO: 95, SEQ ID NO: 129, SEQ ID NO: 116, SEQ ID NO: 143, SEQ ID NO: 144, SEQ ID NO: 145, SEQ ID NO: 140, SEQ ID NO: 141, SEQ ID NO: 74, and SEQ ID NO: 76.
Figure 7C:
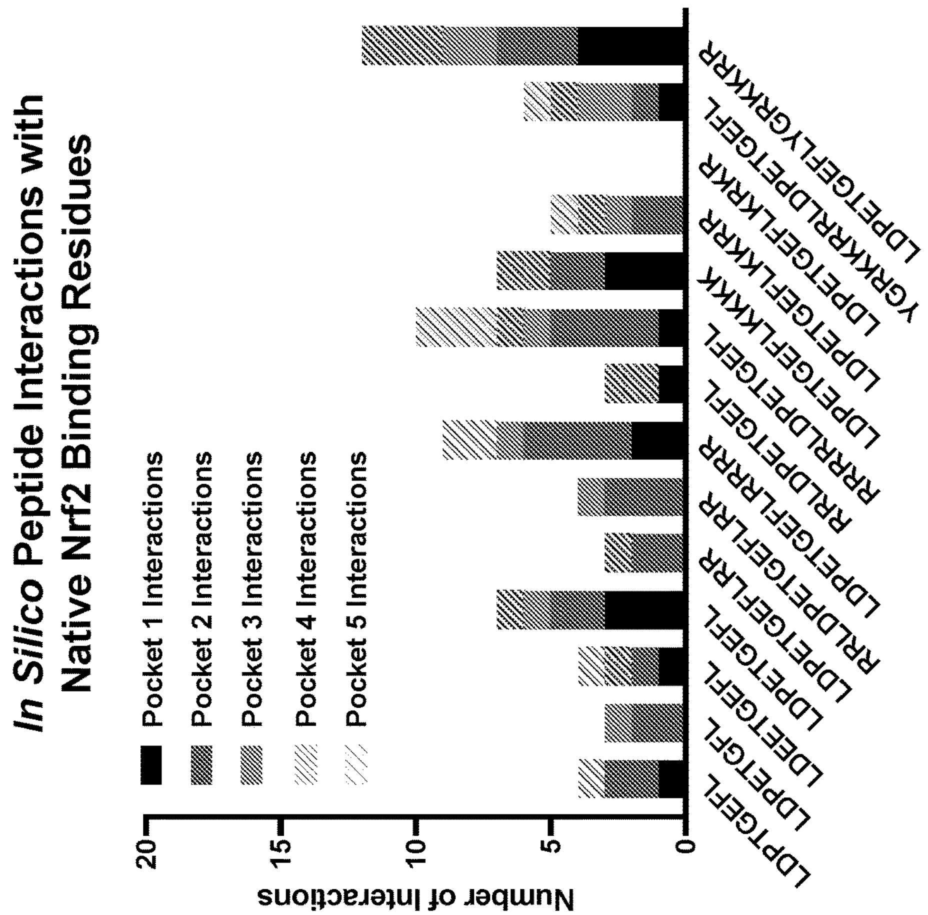
FIG. 7C shows the specific in silico peptide interactions with P1-P5 within the pocket of the Kelch domain, exhibited by the peptide sequences shown in FIGS. 1 and 3-6 and described in Examples 1-5. The sequences in FIG. 7C (in order as shown in the figure) are: SEQ ID NO: 137, SEQ ID NO: 138, SEQ ID NO: 1, SEQ ID NO: 2, SEQ ID NO: 70, SEQ ID NO: 78, SEQ ID NO: 72, SEQ ID NO: 74, SEQ ID NO: 76, SEQ ID NO: 95, SEQ ID NO: 129, SEQ ID NO: 116, SEQ ID NO: 140 and SEQ ID NO: 141.
Figure 7B:
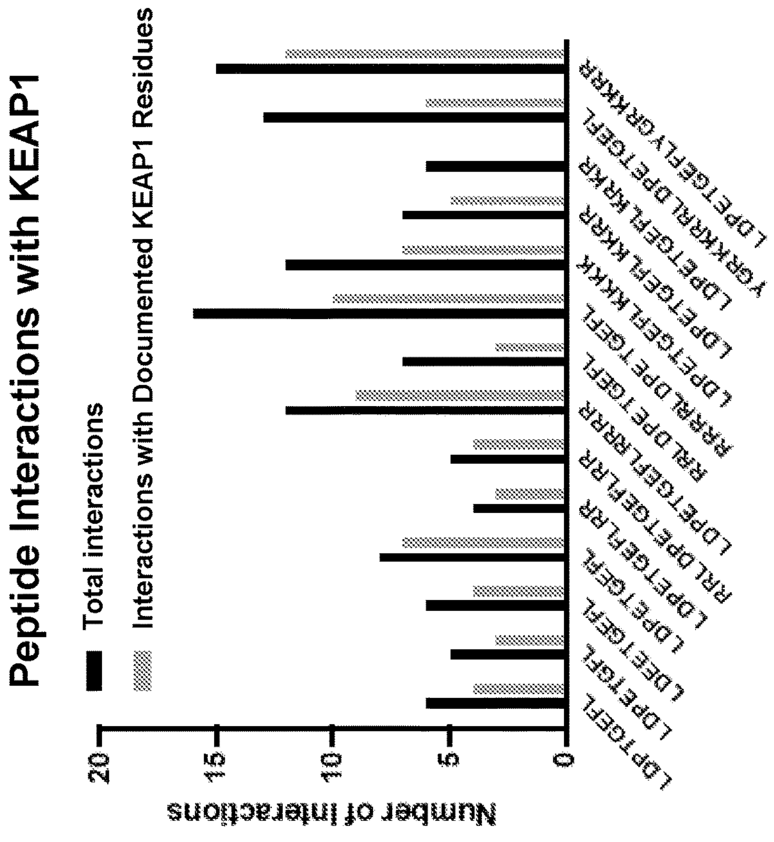
FIG. 7B shows (i) the overall binding interactions with P1-P5 within the pocket of the Kelch domain and (ii) the interactions with documented Keap1 residues within the pocket of the Kelch domain, exhibited by the peptide sequences shown in FIGS. 1 and 3-6 and described in Examples 1-5. The sequences in FIG. 7B (in order as shown in the figure) are: SEQ ID NO: 137, SEQ ID NO: 138, SEQ ID NO: 1, SEQ ID NO: 2, SEQ ID NO: 70, SEQ ID NO: 78, SEQ ID NO: 72, SEQ ID NO: 74, SEQ ID NO: 76, SEQ ID NO: 95, SEQ ID NO: 129, SEQ ID NO: 116, SEQ ID NO: 140 and SEQ ID NO: 141.

As is apparent from the results set forth in FIGS. 7A-7C, SEQ ID NO: 137 (LDPTGEFL) and SEQ ID NO: 138 (LDPETGFL), having a point mutation to delete a glutamate residue, had reduced interactions with most, if not all, of the P1-P5 interactions relative to SEQ ID NO: 1 (LDEETGEFL) and SEQ ID NO: 2 (LDPETGEFL). These results show that removal of glutamate residues can reduce the overall interactions with Keap1 relative to the native Nrf2 sequence and the proline modified native Nrf2 sequence SEQ ID NO: 2 (LDPETGEFL).

Example 3

This example demonstrates the effect on binding interactions exhibited by a peptide sequence of the invention, having arginine residue modifications.

Figure 4:
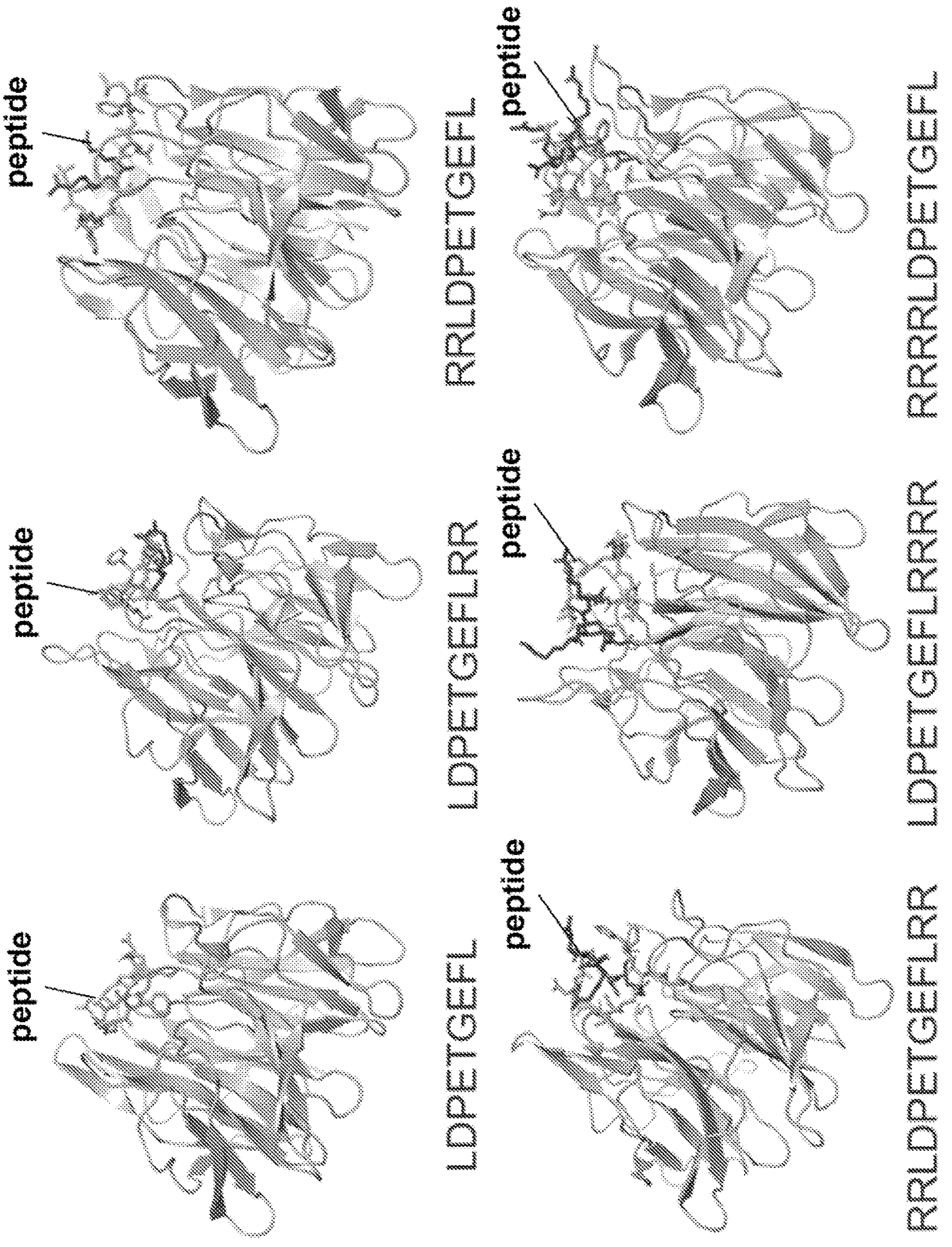
FIG. 4 depicts six different peptide sequences, namely, SEQ ID NO: 2 (LDPETGEFL), SEQ ID NO: 70 (LDPETGEFLRR), SEQ ID NO: 74 (RRLDPETGEFL), SEQ ID NO: 78 (RRLDPETGEFLRR), SEQ ID NO: 72 (LDPETGEFLRRRR), and SEQ ID NO: 76 (RRRRLDPETGEFL), as described in Example 3.

Peptide sequences SEQ ID NO: 2 (LDPETGEFL), SEQ ID NO: 70 (LDPETGEFLRR), SEQ ID NO: 74 (RRLD- PETGEFL), SEQ ID NO: 78 (RRLDPETGEFLRR), SEQ ID NO: 72 (LDPETGEFLRRRR), and SEQ ID NO: 76 (RRRRLDPETGEFL), depicted in FIG. 4 were evaluated using in silico simulations with CABS-Dock software, which is capable of simultaneous prediction of binding sites and protein-peptide docking through coarse-gain methods. Documented binding interactions P1-P5 within the pocket of the Kelch domain of the Keap1 protein, as depicted in FIG. 2, were simulated for each of peptide sequences SEQ ID NO: 2 (LDPETGEFL), SEQ ID NO: 70 (LDPETGEFLRR), SEQ ID NO: 74 (RRLDPETGEFL), SEQ ID NO: 78 (RRLDPETGEFLRR), SEQ ID NO: 72 (LDPETGEFLRRRR), and SEQ ID NO: 76 (RRRRLDPETGEFL), and the results are set forth in FIGS. 7A-7C.

As is apparent from the results set forth in FIGS. 7A-7C, SEQ ID NO: 72 (LDPETGEFLRRRR), SEQ ID NO: 76 (RRRRLDPETGEFL), and SEQ ID NO: 78 (RRLDPETGEFLRR), having a sum total of four arginine residues added to the beginning or end of the proline modified native Nrf2 sequence SEQ ID NO: 2 (LDPETGEFL), had increased interactions with most, if not all, of the P1-P5 interactions relative to SEQ ID NO: 2 (LDPETGEFL), SEQ ID NO: 70 (LDPETGEFLRR), and SEQ ID NO: 74 (RRLDPETGEFL). In addition, SEQ ID NO: 76 (RRRRLDPETGEFL) and SEQ ID NO: 72 (LDPETGEFLRRRR), having four arginine residues added to the beginning and end of the proline modified native Nrf2 sequence SEQ ID NO: 2 (LDPETGEFL), respectively, had the highest amount of interactions with P1-P5 amongst the six sequences tested.

These results show that addition of arginine residues can increase the overall interactions with Keap1 relative to the proline modified native Nrf2 sequence SEQ ID NO: 2 (LDPETGEFL).

Example 4

This example demonstrates the effect on binding interactions exhibited by a peptide sequence of the invention, having lysine residue modifications.

Figure 5:
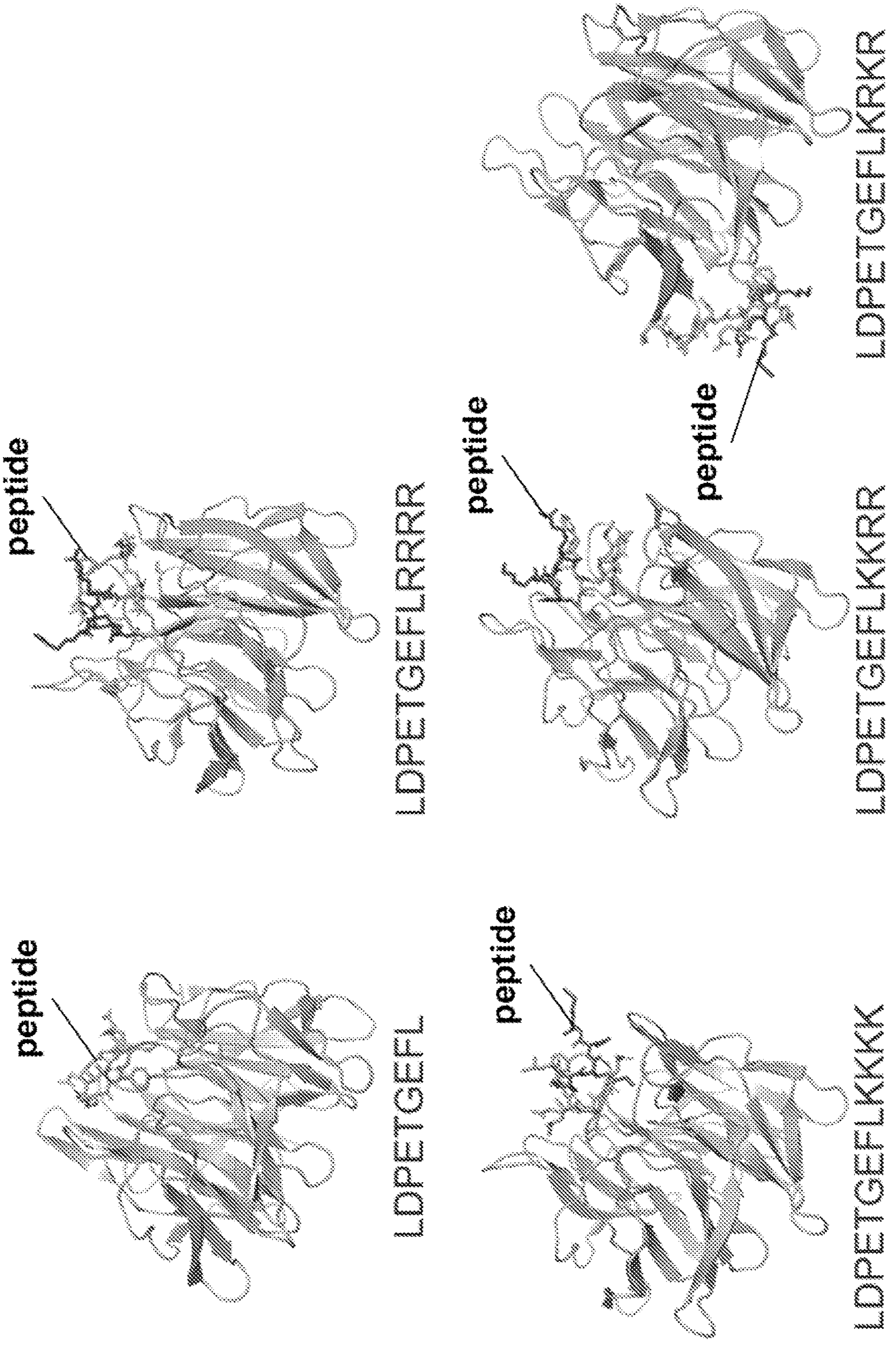
FIG. 5 depicts five different peptide sequences, namely, SEQ ID NO: 2 (LDPETGEFL), SEQ ID NO: 72 (LDPETGEFLRRRR), SEQ ID NO: 95 (LDPETGEFLKKKK), SEQ ID NO: 129 (LDPETGEFLKKRR), and SEQ ID NO: 116 (LDPETGEFLKRKR) as described in Example 4.

Peptide sequences SEQ ID NO: 2 (LDPETGEFL), SEQ ID NO: 72 (LDPETGEFLRRRR), SEQ ID NO: 95 (LDPETGEFLKKKK), SEQ ID NO: 129 (LDPETGEFLKKRR), and SEQ ID NO: 116 (LDPETGEFLKRKR), depicted in FIG. 5 were evaluated using in silico simulations with CABS-Dock software, which is capable of simultaneous prediction of binding sites and protein-peptide docking through coarse-gain methods. Documented binding interactions P1-P5 within the pocket of the Kelch domain of the Keap1 protein, as depicted in FIG. 2, were simulated for each of peptide sequences SEQ ID NO: 2 (LDPETGEFL), SEQ ID NO: 72 (LDPETGEFLRRRR), SEQ ID NO: 95 (LDPETGEFLKKKK), SEQ ID NO: 129 (LDPETGEFLKKRR), and SEQ ID NO: 116 (LDPETGEFLKRKR), and the results are set forth in FIGS. 7A-7C.

As is apparent from the results set forth in FIGS. 7A-7C, SEQ ID NO: 95 (LDPETGEFLKKKK), having four lysine residues added to end of the proline modified native Nrf2 sequence SEQ ID NO: 2 (LDPETGEFL), had a similar amount of interactions relative to SEQ ID NO: 72 (LDPETGEFLRRRR), having four arginine residues added to the end of the proline modified native Nrf2 sequence SEQ ID NO: 2 (LDPETGEFL).

These results show that addition of lysine residues can increase the overall interactions with Keap1 relative to the proline modified native Nrf2 sequence SEQ ID NO: 2 (LDPETGEFL).

Example 5

This example demonstrates the effect on binding interactions exhibited by a peptide sequence of the invention, having a TAT sequence modification.

Figure 6:
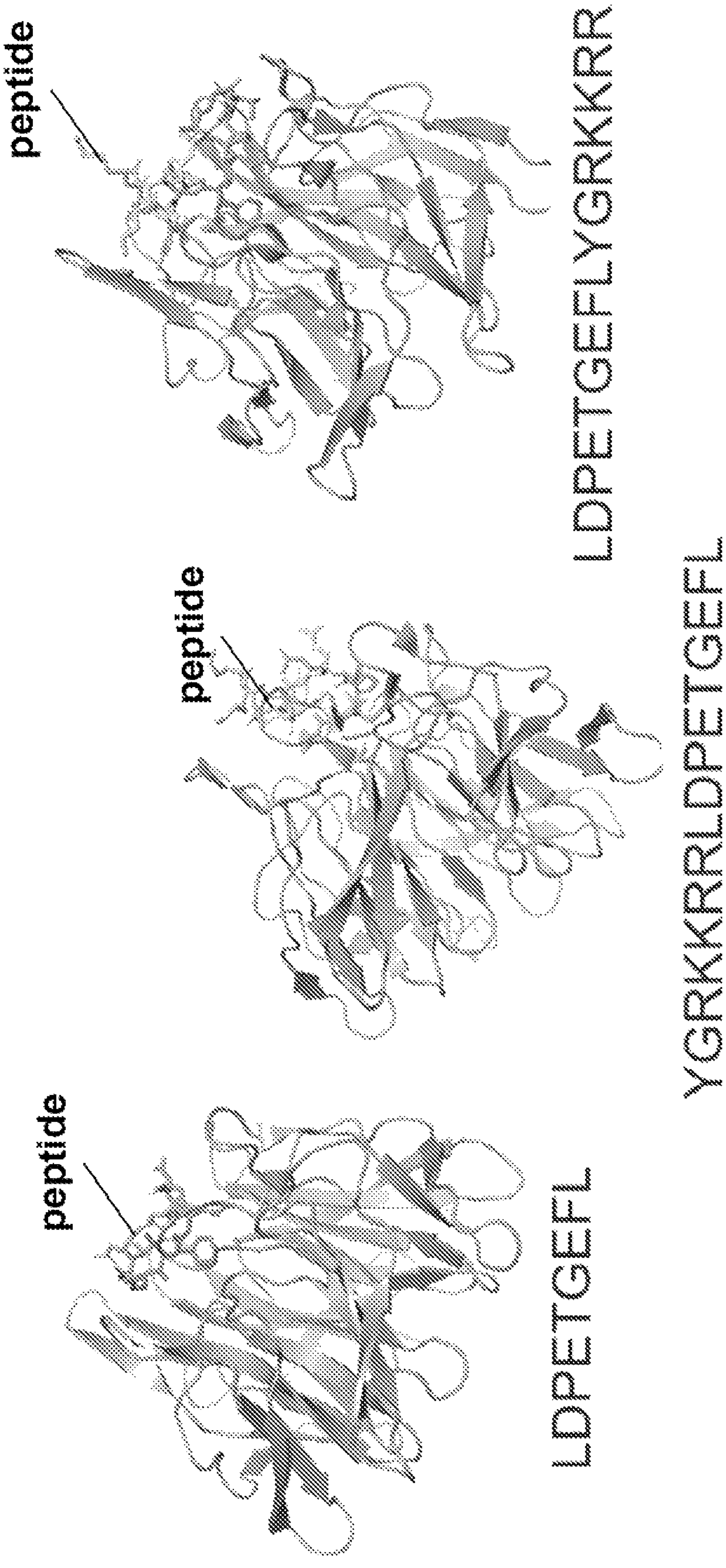
FIG. 6 depicts three different peptide sequences, namely, SEQ ID NO: 2 (LDPETGEFL), SEQ ID NO: 140 (YGRKKRRLDPETGEFL), and SEQ ID NO: 141 (LDPETGEFLYGRKKRR), as described in Example 5.

Peptide sequences SEQ ID NO: 2 (LDPETGEFL), SEQ ID NO: 140 (YGRKKRRLDPETGEFL), and SEQ ID NO: 141 (LDPETGEFLYGRKKRR), depicted in FIG. 6 were evaluated using in silico simulations with CABS-Dock software, which is capable of simultaneous prediction of binding sites and protein-peptide docking through coarse-gain methods. Documented binding interactions P1-P5 within the pocket of the Kelch domain of the Keap1 protein, as depicted in FIG. 2, were simulated for each of peptide sequences SEQ ID NO: 2 (LDPETGEFL), SEQ ID NO: 140 (YGRKKRRLDPETGEFL), and SEQ ID NO: 141 (LDPETGEFLYGRKKRR), and the results are set forth in FIGS. 7A-7C, and more particularly in the normalized results at FIG. 7A, which account for the increased peptide length resulting from the addition of the TAT sequence.

As is apparent from the normalized results set forth in FIG. 7A, SEQ ID NO: 140 (YGRKKRRLDPETGEFL) and SEQ ID NO: 141 (LDPETGEFLYGRKKRR), having TAT sequences added to the beginning or end of the proline modified native Nrf2 sequence SEQ ID NO: 2 (LDPETGEFL), had a similar amount of interactions relative to SEQ ID NO: 2 (LDPETGEFL), when the increased peptide length is accounted for.

These results show that addition of a TAT sequence does not diminish the overall number of interactions with Keap1 when added to the proline modified native Nrf2 sequence SEQ ID NO: 2 (LDPETGEFL).

To further exemplify the results set forth in Examples 1-5, FIG. 7A shows (i) the normalized overall binding interactions with P1-P5 within the pocket of the Kelch domain and (ii) the normalized interactions with documented Keap1 residues within the pocket of the Kelch domain, exhibited by the peptide sequences shown in FIGS. 1 and 3-6 and described in Examples 1-5, as well as additional peptide sequences SEQ ID NO: 143 (DERLERPLTRGFR), SEQ ID NO: 144 (LELEDEFTG), and SEQ ID NO: 145 (DELEPLTGF). Similarly, FIG. 7B shows (i) the overall binding interactions with P1-P5 within the pocket of the Kelch domain and (ii) the interactions with documented Keap1 residues within the pocket of the Kelch domain, exhibited by the peptide sequences shown in FIGS. 1 and 3-6 and described in Examples 1-5. In addition, FIG. 7C shows the specific in silico peptide interactions with P1-P5 within the pocket of the Kelch domain, exhibited by the peptide sequences shown in FIGS. 1 and 3-6 and described in Examples 1-5.

Example 6

This example shows the in silico modeling of the complex formed between the Kelch domain and ProPepR peptide SEQ ID NO: 72 (LDPETGEFLRRRR).

Figures 8A, 8B, 8C:
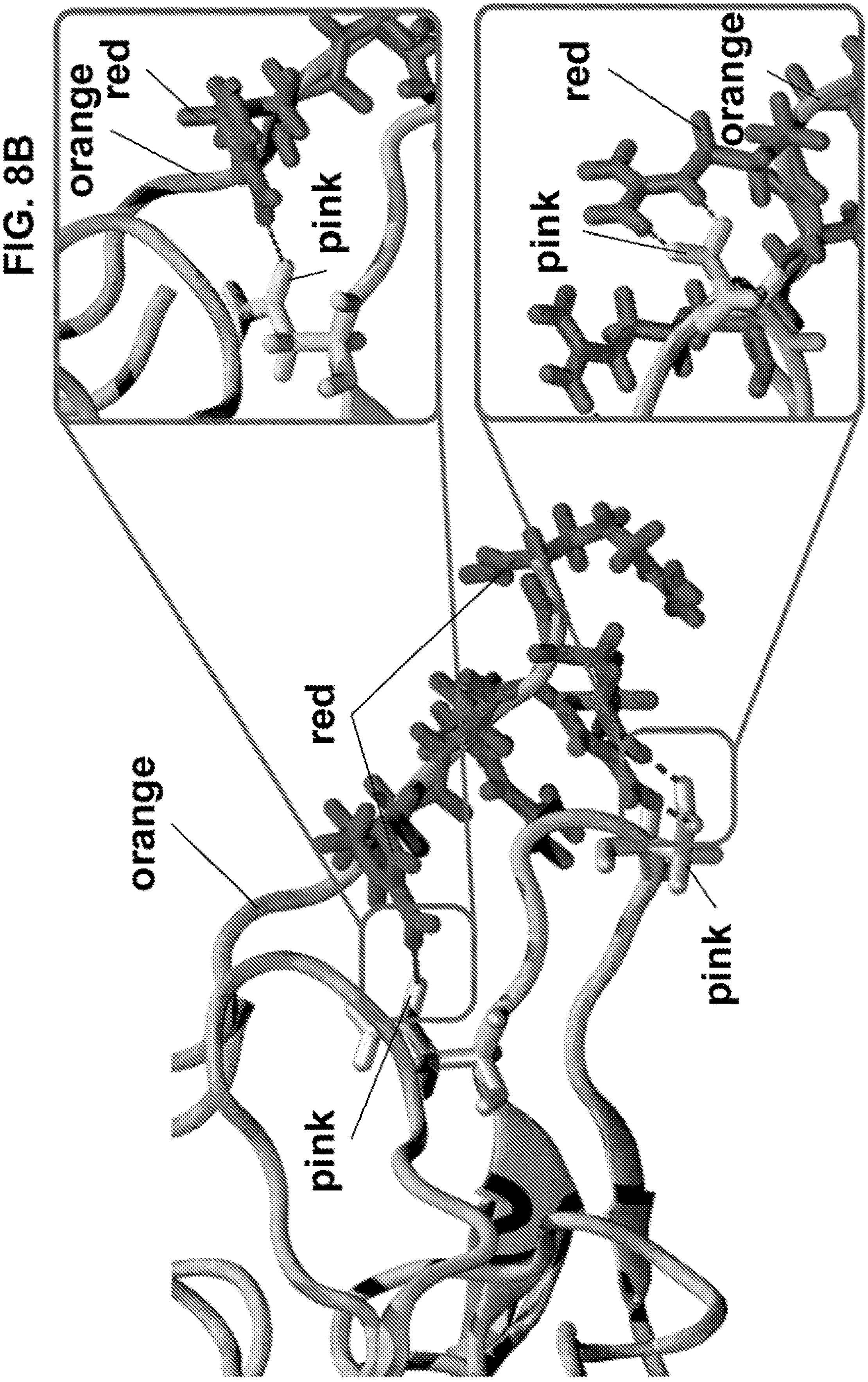
FIGS. 8A-8C show the structure analysis of the complex of a Kelch domain with SEQ ID NO: 72 (LDPETGEFLRRRR) also annotated as ProPepR peptide from an All-Atom simulation (Teal—Kelch; Orange—ProPepR peptide; Red—Arg tail of ProPepR peptide; and Pink—interacting residues). In particular.

The binding between the Keap1 Kelch domain and ProPepR peptide SEQ ID NO: 72 (LDPETGEFLRRRR) was modeled using classical All-Atom MD simulations performed with GROMACS 2016.3, and the results are set forth in FIGS. 8A-8C.

The structures depicted in FIGS. 8A-8C support the theory that the arginine tail of ProPepR peptide SEQ ID NO: 72 (LDPETGEFLRRRR) enhances the Kelch-peptide binding compared with ProPep peptide SEQ ID NO: 2 (LDPETGEFL) via strong Coulombic interactions and hydrogen bonds with the adjacent residues on the Kelch domain ($Asn_{382}$ and $Asp_{385}$). More particularly, FIG. 8B shows that the 1st Arg residue (red) forms a hydrogen bond with $Asn_{382}$ (pink), and FIG. 8C shows that the 3rd Arg residue (red) forms salt bridge with $Asp_{385}$ (pink).

To further demonstrate the benefits of the arginine tale on the Kelch-peptide binding, the binding energies between the peptide Arg tails and the Kelch domain from the All-Atom simulations of (i) the Kelch domain/ProPepR peptide SEQ ID NO: 72 (LDPETGEFLRRRR) complex (i.e., four arginine residues "RRRR") and (ii) the Kelch domain/ProPepR peptide SEQ ID NO: 70 (LDPETGEFLRR) complex (i.e., two arginine residues "RR") are provided in Table 1.

TABLE 1

Comparative Binding to Kelch Domain of RRRR vs. RR

| | Peptide - Kelch | Coulombic (kJ/mol) | Lennard-Jones (kJ/mol) |
|---|---|---|---|
| RRRR | $Arg_3$ - $Asp_{385}$ | −120.8 ± 68.7 | 3.5 ± 9.8 |
| | $Arg_1$ -$Asn_{382}$ | −0.13 ± 1.5 | −0.21 ± 0.23 |
| | Arg tail - ($Asn_{382}$-$Thr_{388}$) | −152.6 ± 57.4 | −50.2 ± 13.4 |
| RR | $Arg_1$ -$Asn_{382}$ | −0.022 ± 1.8 | −0.10 ± 0.14 |
| | Arg tail - ($Asn_{382}$-$Thr_{388}$) | −36.6 ± 34.8 | −29.6 ± 13.1 |

As shown in Table 1, the Coulombic interaction between the $3^{rd}$ Arg on RRRR and Kelch $Asp_{385}$ contributes to about 80% of the Arg tail—Kelch domain interaction and contributes to about 15% of the total binding affinity of the peptide SEQ ID NO: 72 (LDPETGEFLRRRR) and the Kelch domain. These results show that the longer Arg tail of SEQ ID NO: 72 (LDPETGEFLRRRR) strengthens the peptide—Kelch domain binding relative to SEQ ID NO: 70 (LDPETGEFLRR). Thus, the additional Coulombic interactions and hydrogen bond formed by the terminal arginine residues of SEQ ID NO: 72 (LDPETGEFLRRRR) enhance binding over LDPETGEFL and LDPETGEFLRR.

Example 7

This examples shows the binding specificity between the Kelch domain and the following four peptides: ProPep SEQ ID NO: 2 (LDPETGEFL), ProPepR SEQ ID NO: 72 (LDPETGEFLRRRR), ScrambleR SEQ ID NO: 146 (DELEPLTGFRRRR), Full Scramble SEQ ID NO: 143 (DERLERPLTRGFR).

Binding specificity calculations and modeling were performed using Alphafold-multimer 2.1.1 for peptides ProPep SEQ ID NO: 2 (LDPETGEFL), ProPepR SEQ ID NO: 72 (LDPETGEFLRRRR), ScrambleR SEQ ID NO: 146 (DELEPLTGFRRRR), Full Scramble SEQ ID NO: 143 (DERLERPLTRGFR), and the results are set forth in FIGS. 9A-9D, respectively.

Figure 9A:
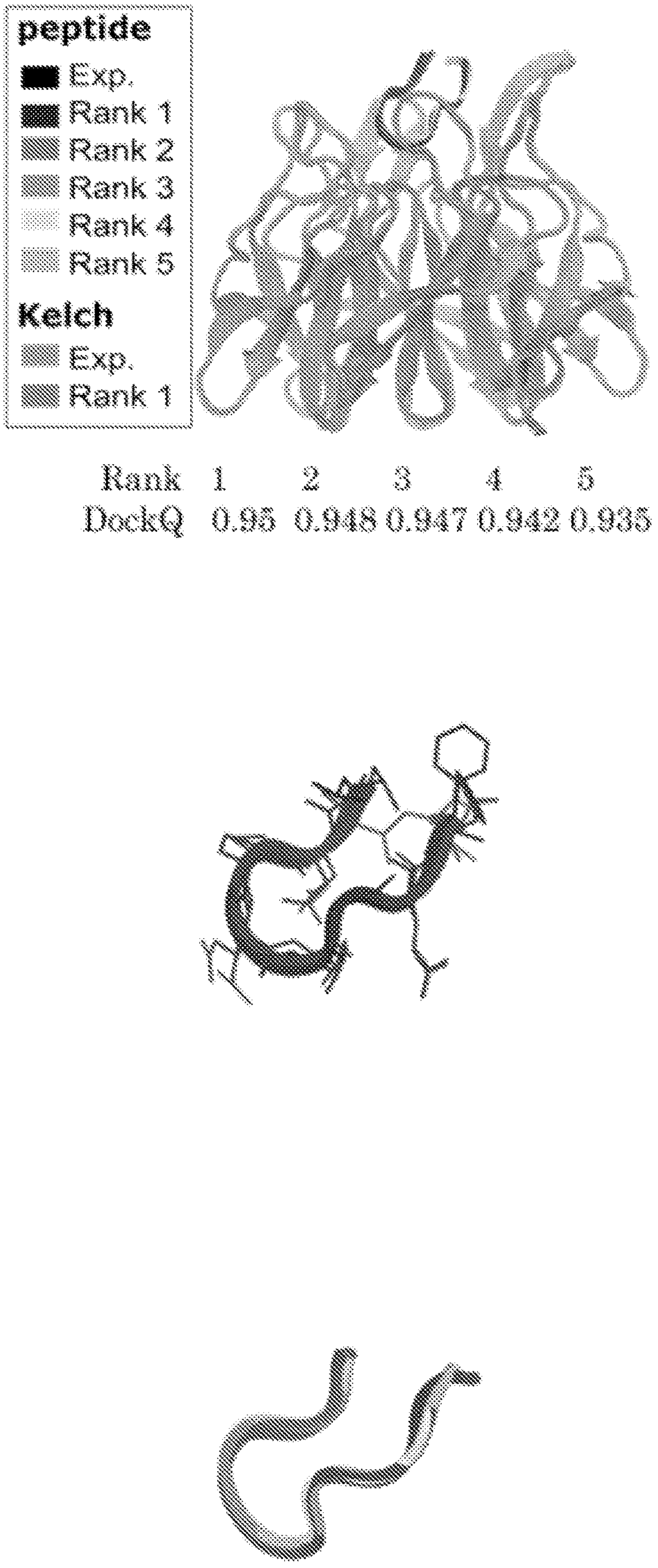
FIGS. 9A-9D show the predicted Kelch-peptide complex structures using Alphafold-multimer for peptides (FIG. 9A) SEQ ID NO: 2 (LDPETGEFL), (FIG. 9B) SEQ ID NO: 72 (LDPETGEFLRRRR), (FIG. 9C) SEQ ID NO: 146 (DELEPLTGFRRRR), and (FIG. 9D) SEQ ID NO: 143 (DERL- ERPLTRGFR). Shown in the top row of FIGS. 9A-9D are the five predicted structures (Ranks 1-5) and the experimental structure (PDB ID: 6T7V[2]), which are aligned using the backbone atoms of the Kelch domain only. Also included are the model confidence scores (1≥DockQ≥0) for the five predicted structures where a higher score (e.g., Rank 1) stands for a higher confidence. Shown in the middle row of FIGS. 9A-9D are the most probable structures (Rank 1) of the peptides, superimposed with the experimental structure of 6T7V. Note SEQ ID NO: 2 (LDPETGEFL) is the peptide which binds the Kelch domain in 6T7V. The side chains are also included for comparison. Shown in the bottom row are the five predicted structures (backbone only) for each peptide, superimposed with the experimental structure of SEQ ID NO: 2 (LDPETGEFL) in 6T7V.
Figure 9B:
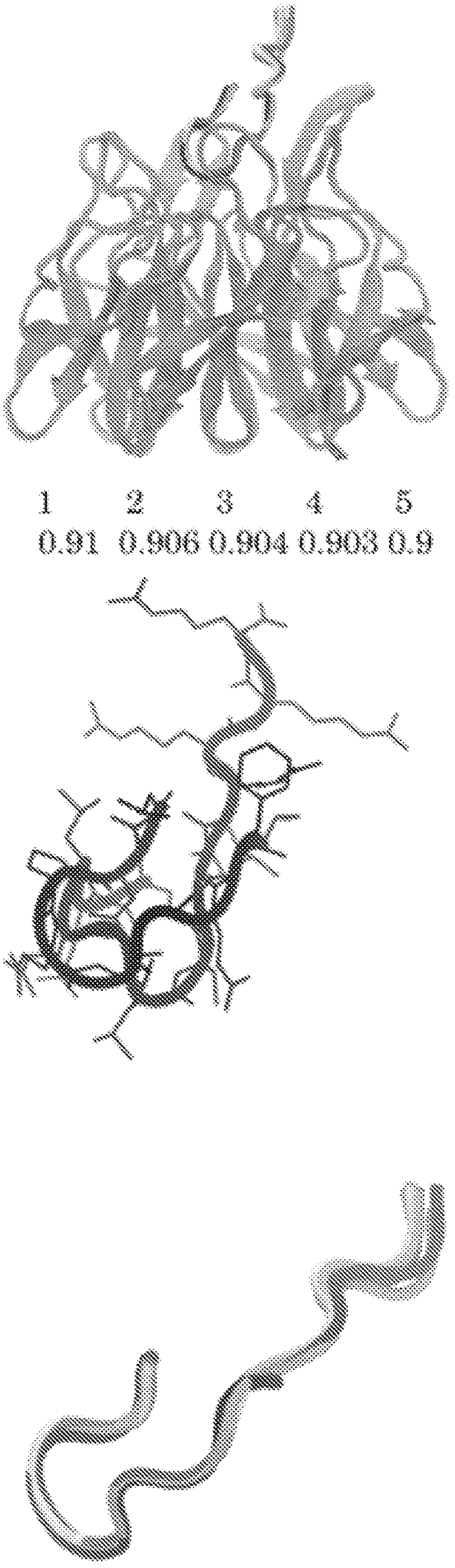
Figure 9C:
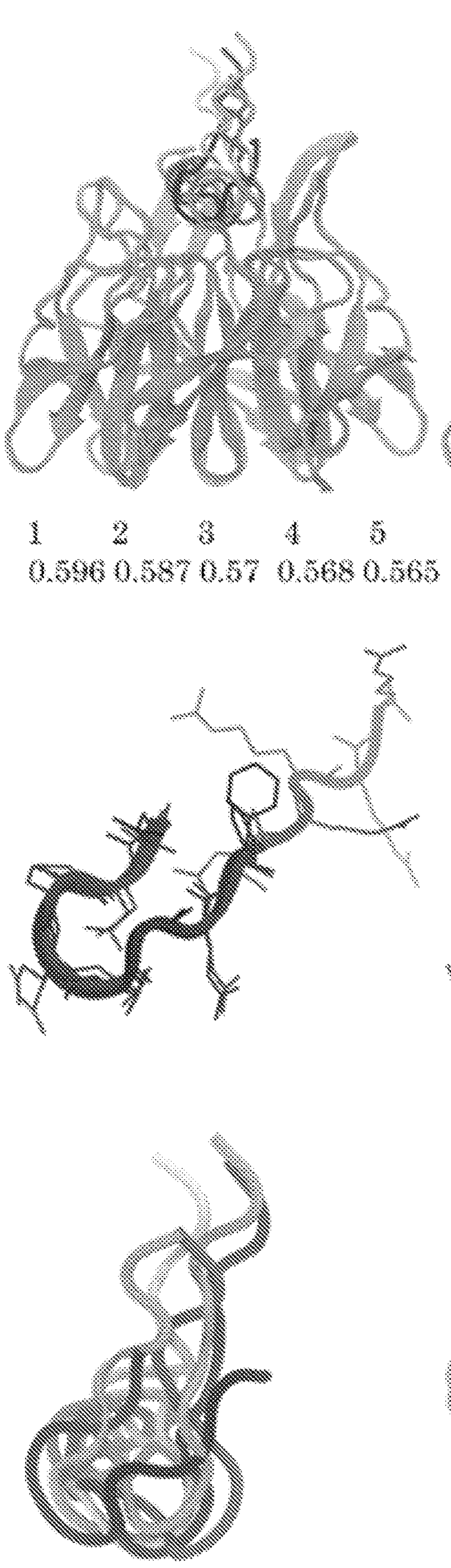
Figure 9D:
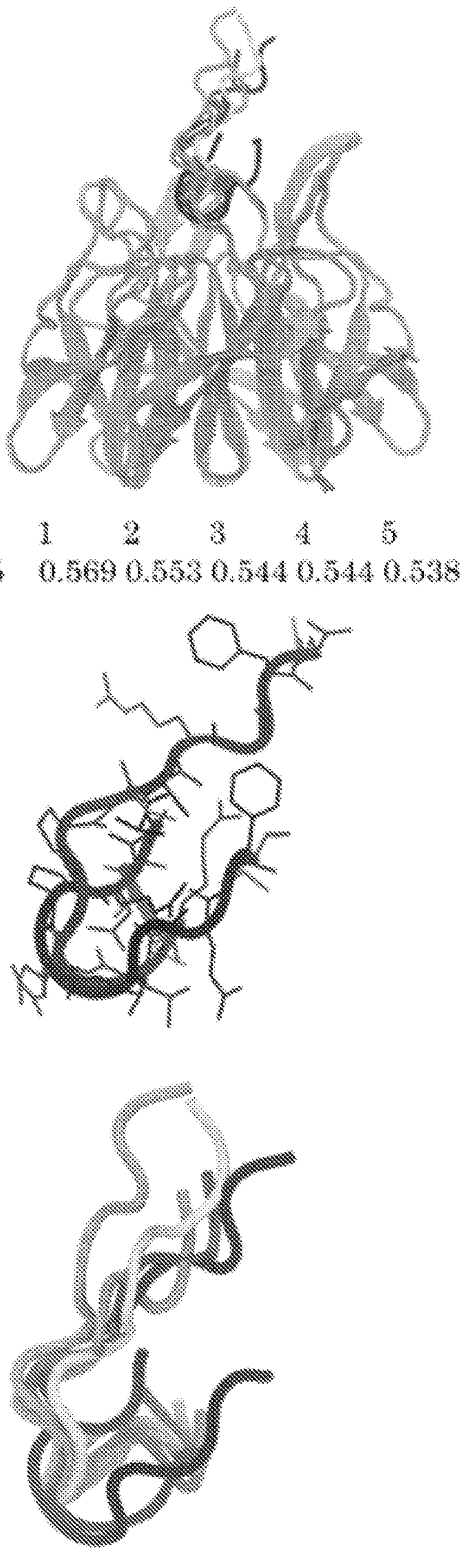

As shown in the top row in FIGS. 9A-9D, Alphafold-multimer provides the top five predicted structures (Ranks 1-5) for the peptides when complexed with the experimental structure of the protein (PDB ID: 6T7V), which are aligned using the backbone atoms of the Kelch domain only. Also provided in the top row of FIGS. 9A-9D, are the model confidence scores (1≥DockQ≥0) for the five predicted structures where a higher score (e.g., Rank 1) stands for a higher confidence. As evidenced by FIGS. 9A and 9B, these five predicted structures are highly preserved for peptides ProPep SEQ ID NO: 2 (LDPETGEFL) and ProPepR SEQ ID NO: 72 (LDPETGEFLRRRR), suggesting their specific binding feature with the Kelch domain. However, FIGS. 9C and 9B show that the five predicted structures are random with low DockQ scores indicating that the binding of ScrambleR SEQ ID NO: 146 (DELEPLTGFRRRR) and Full Scramble SEQ ID NO: 143 (DERLERPLTRGFR) with the Kelch domain is less stable.

FIGS. 9A-9D also show (middle row) the most probable structures (Rank 1) of the peptides, superimposed with the experimental structure of the peptide that binds with the experimental structure of the protein 6T7V. Note that SEQ ID NO: 2 (LDPETGEFL) is the peptide which binds the Kelch domain in 6T7V. The side chains have been included in these structures for comparison. Similar to the middle row of FIGS. 9A-9D, the bottom row of FIGS. 9A-9D shows the five predicted structures (backbone only) for each peptide, superimposed with the experimental structure of SEQ ID NO: 2 (LDPETGEFL) which binds the Kelch domain in 6T7V.

These results show that the Kelch-peptide binding structures are highly preserved for ProPep SEQ ID NO: 2 (LDPETGEFL) and ProPepR SEQ ID NO: 72 (LDPETGEFLRRRR), evidencing the specific binding feature of these two Kelch-peptide complexes. In contrast, these results show that ScrambleR SEQ ID NO: 146 (DELEPLTGFRRRR) and Full Scramble SEQ ID NO: 143 (DERLERPLTRGFR) exhibit non-specific Kelch-peptide binding. In other words, the binding specificity of ProPepR with the Keap1 Kelch domain was confirmed to rely on the specific amino acid sequence rather than the general composition of the peptide which did not generate intense binding.

Example 8

This example shows the Coulombic and Lennard-Jones binding interactions with the Kelch domain exhibited by SEQ ID NO: 1 (LDEETGEFL), SEQ ID NO: 2 (LDPETGEFL), SEQ ID NO: 70 (LDPETGEFLRR), SEQ ID NO: 72 (LDPETGEFLRRRR), SEQ ID NO: 146 (DELEPLTGFRRRR), and SEQ ID NO: 143 (DERLERPLTRGFR).

The binding between the Keap1 Kelch domain and peptides with SEQ ID NO: 1 (LDEETGEFL), SEQ ID NO: 2 (LDPETGEFL), SEQ ID NO: 70 (LDPETGEFLRR), SEQ ID NO: 72 (LDPETGEFLRRRR), SEQ ID NO: 146 (DELEPLTGFRRRR), and SEQ ID NO: 143 (DERLERPLTRGFR) were modeled using classical All-Atom MD simulations performed with GROMACS 2016.3. The Lennard-Jones (LJ) interactions and Coulombic interactions were monitored for 200 ns, and the results are set forth at the bottom of FIGS. 10A-10F. In addition, the final simulation snapshot (i.e., at the end of 200 ns) for each Kelch-peptide complex is provided at the top of FIGS. 10A-10F. The other molecules and ions (e.g., water, $Na^+$, and $Cl^-$) are omitted for display, and the average values of the interaction energies are listed next to the plot.

As is apparent from the results set forth in FIGS. 10A-10F, the Kelch-peptide complex predominantly consisted of Coulombic interactions inasmuch as both the Kelch domain and the peptides are highly charged. Compared to SEQ ID NO: 1 (LDEETGEFL), the proline-substitution in SEQ ID NO: 2 (LDPETGEFL) enhanced binding with the Kelch domain. Among the six peptides tested, SEQ ID NO: 72 (LDPETGEFLRRRR) had the strongest binding with the Kelch domain. In addition, the results set forth in FIGS. 10A-10F show that SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR) exhibited stronger Kelch-peptide binding than scrambled peptides SEQ ID NO: 146 (DELEPLTGFRRRR) and SEQ ID NO: 143 (DERLERPLTRGFR). These results are consistent with the Alphafold-multimer results set forth in Example 7 and FIGS. 41A-41D.

Figure 10A:
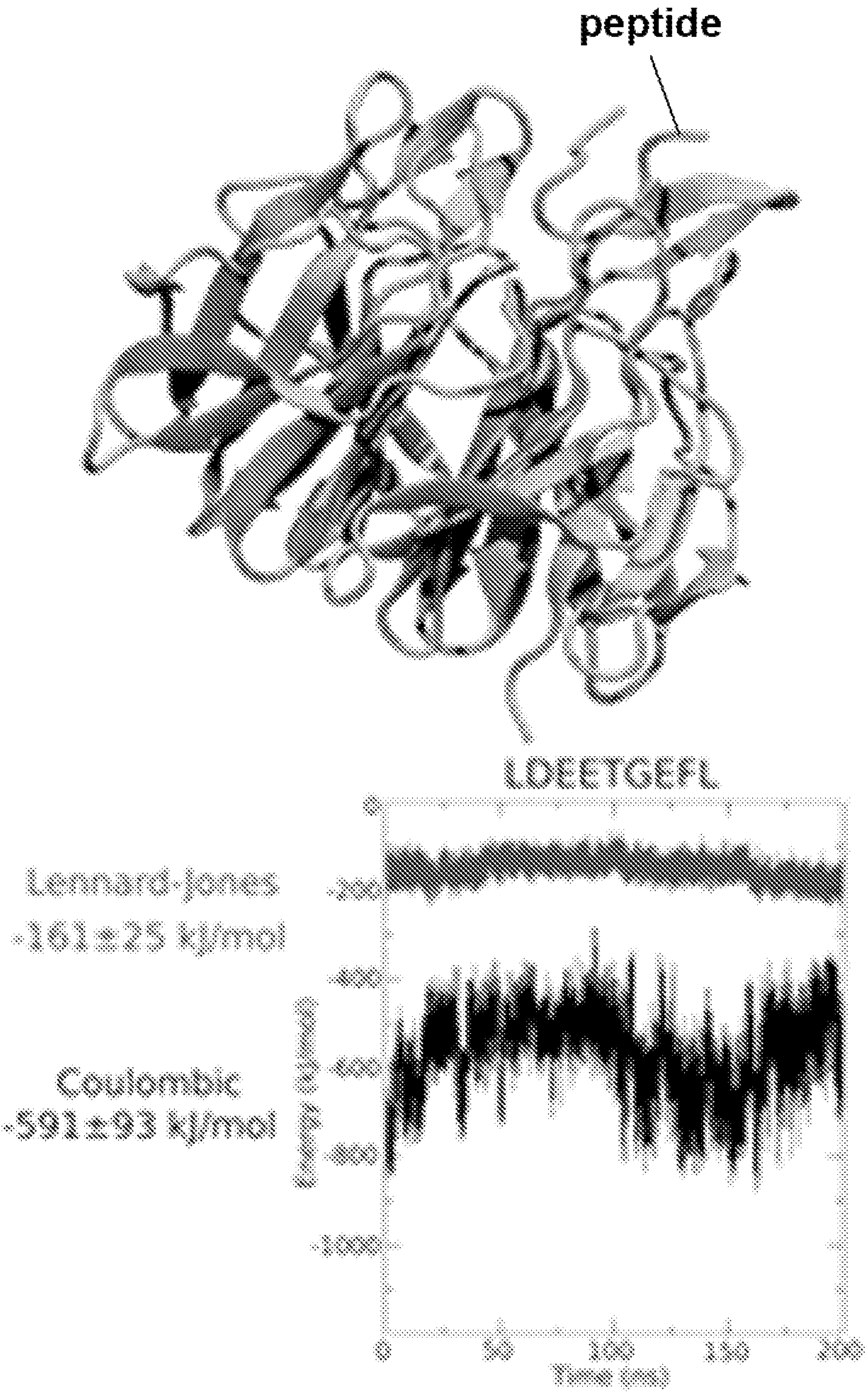
FIGS. 10A-10F show All-Atom simulation results of the Kelch domain with each peptide (FIG. 10A) SEQ ID NO: 1 (LDEETGEFL), (FIG. 10B) SEQ ID NO: 2 (LDPETGEFL), (FIG. 10C) SEQ ID NO: 70 (LDPETGEFLRR), (FIG. 10D) SEQ ID NO: 72 (LDPETGEFLRRRR), (FIG. 10E) SEQ ID NO: 146 (DELEPLTGFRRRR), and (FIG. 10F) SEQ ID NO: 143 (DERLERPLTRGFR). Subfigures in the top row are the last simulation snapshots demonstrating the Kelch-peptide binding structures where the other molecules (e.g., water, $Na^+$, and $Cl^-$) are omitted for display. Subfigures in the bottom row are the Coulombic and Lennard-Jones interaction energies between the Kelch domain and the peptide through the simulations.
Figure 10B:
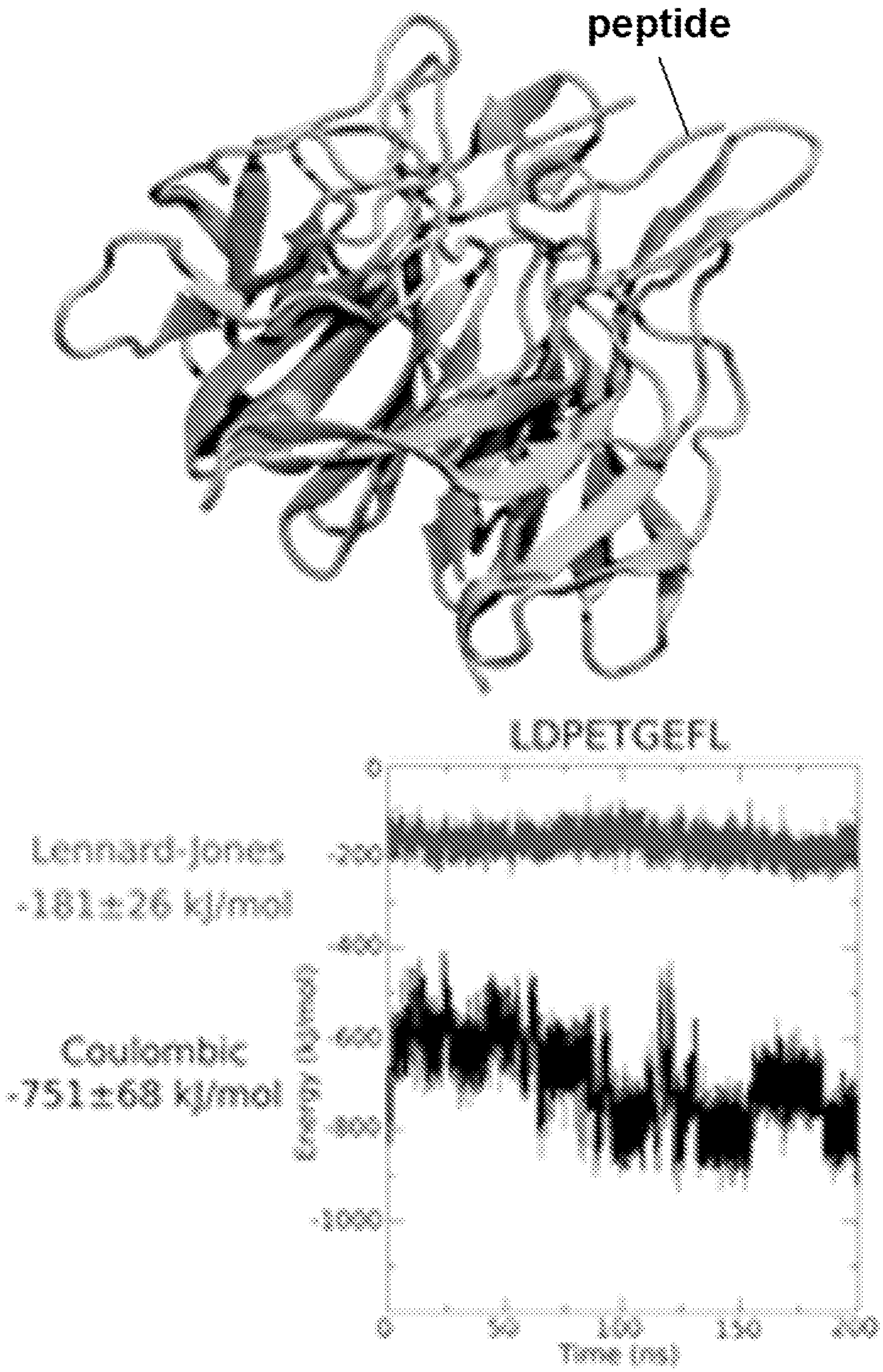
Figure 10C:
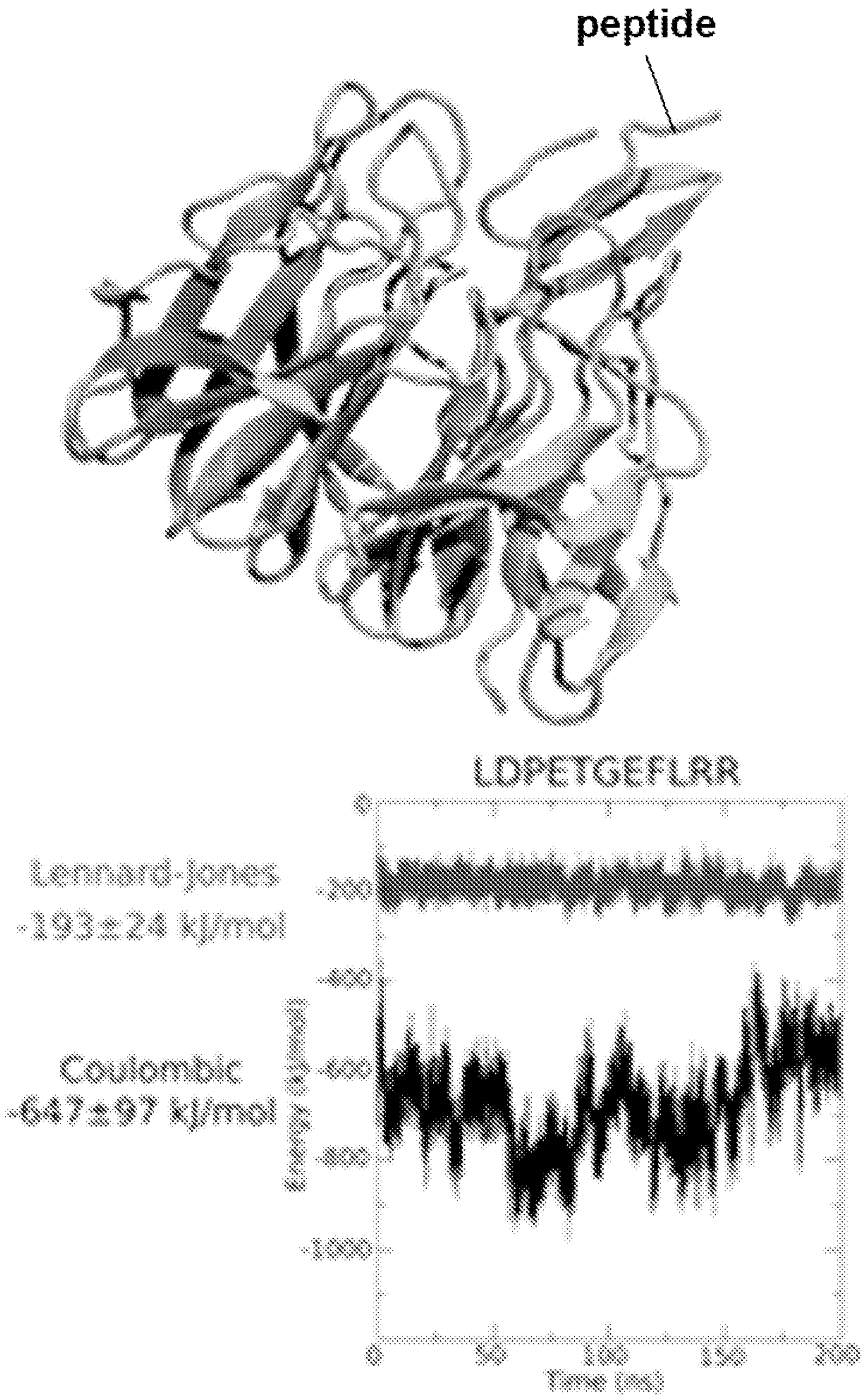
Figure 10D:
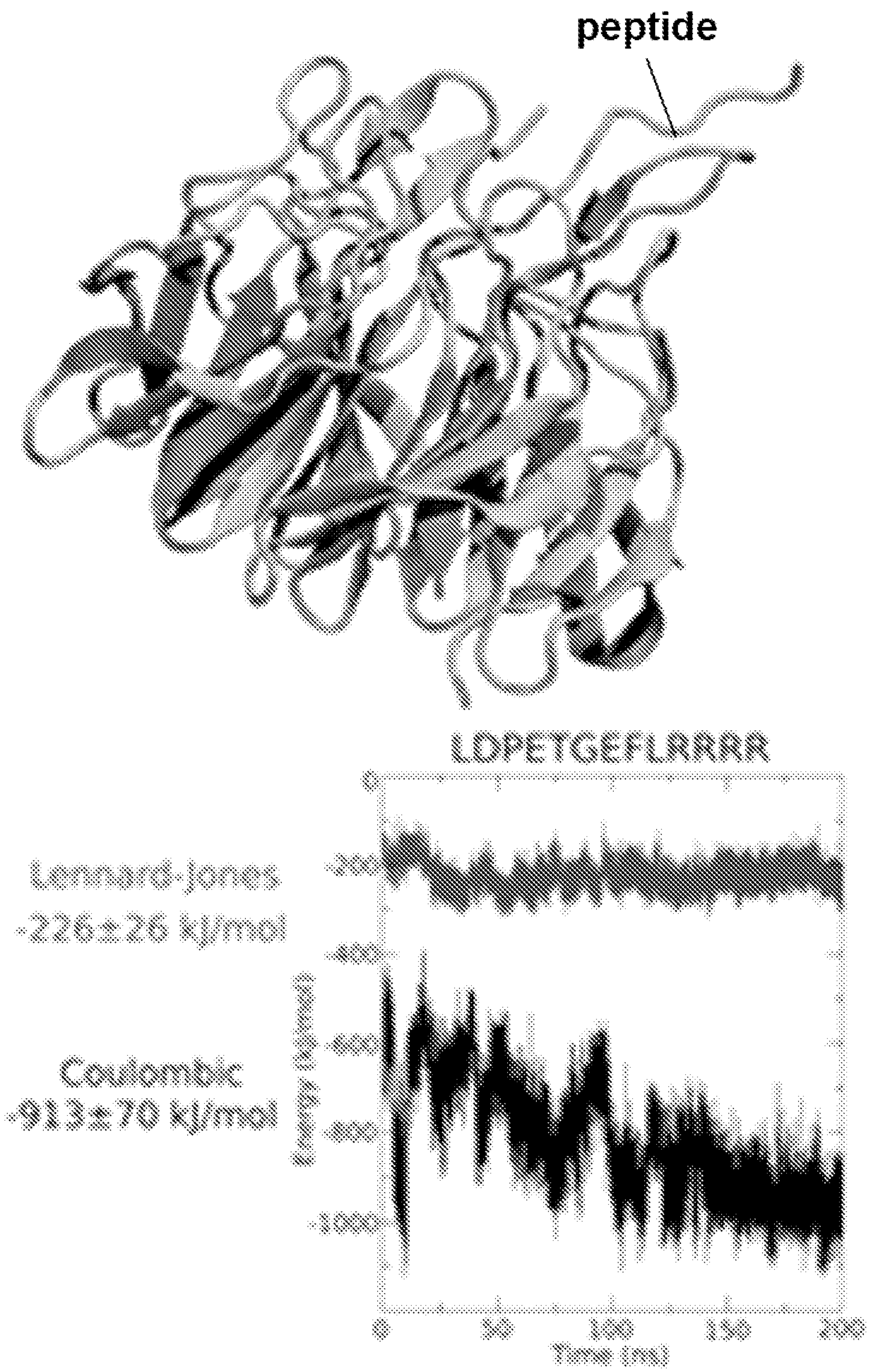

In addition, FIGS. 10B and 10D show that the arginine tail enhances the Kelch-peptide binding via strong of the Coulombic interactions and hydrogen bonds with the adjacent residues on the Kelch domain (i.e., Asn382 and Asp385). See, for example, SEQ ID NO: 72 (LDPETGEFLRRRR) (FIG. 10D) with an average Coulombic binding energy of approximately −913 kJ/mol as compared to SEQ ID NO: 2 (LDPETGEFL) (FIG. 10B) with an average Coulombic binding energy of approximately −751 kJ/mol. The cooperative effect of the Coulombic interactions and hydrogen bonds boosts the binding affinity between the peptide and the Kelch domain. In that regard, SEQ ID NO: 72 (LDPETGEFLRRRR) exhibits approximately ~1.5 times the affinity to the Kelch domain relative to SEQ ID NO: 70 (LDPETGEFLRR), which only forms a single hydrogen bond between the first Arg residue and the Kelch domain.

Figure 10E:
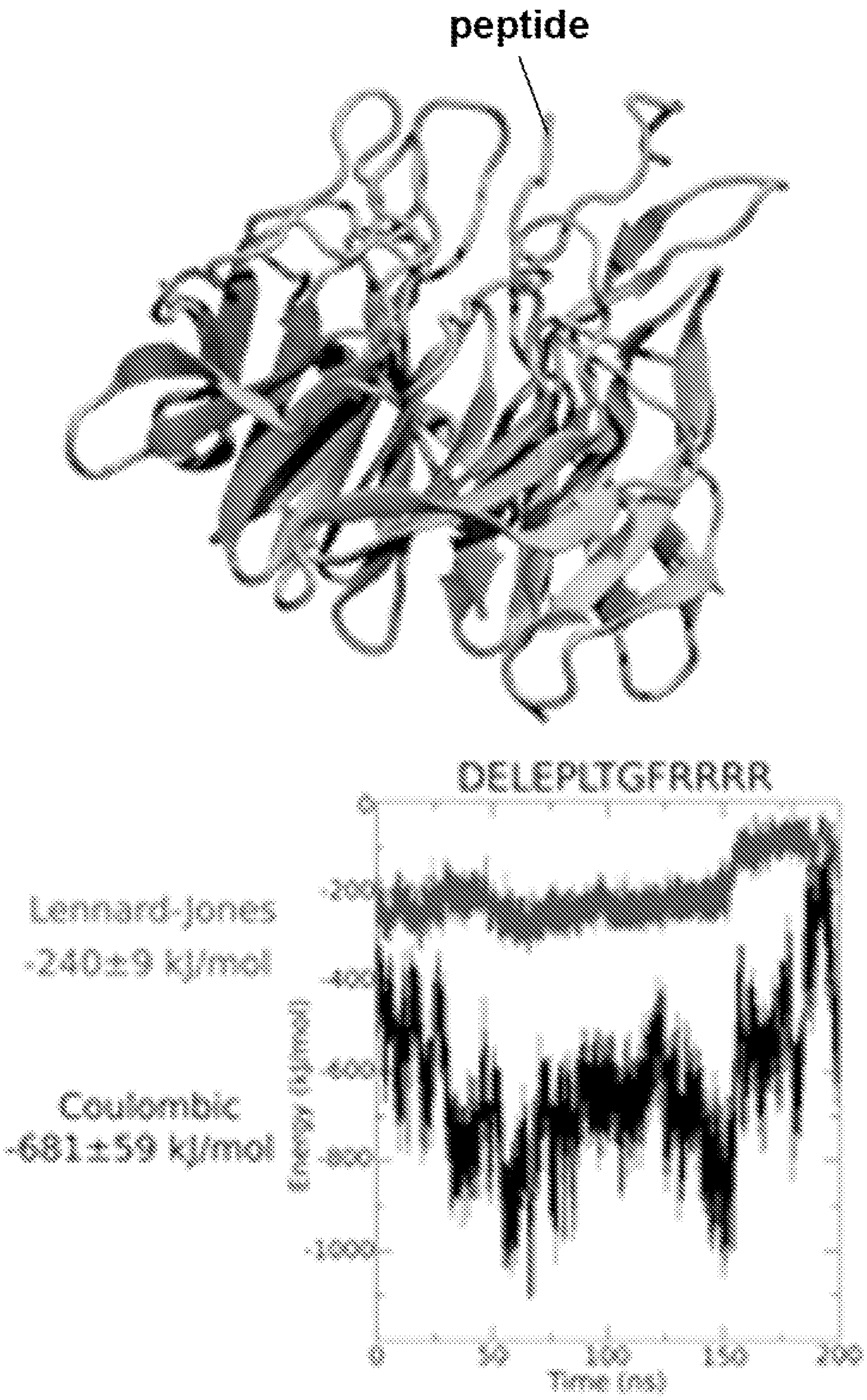
Figure 10F:
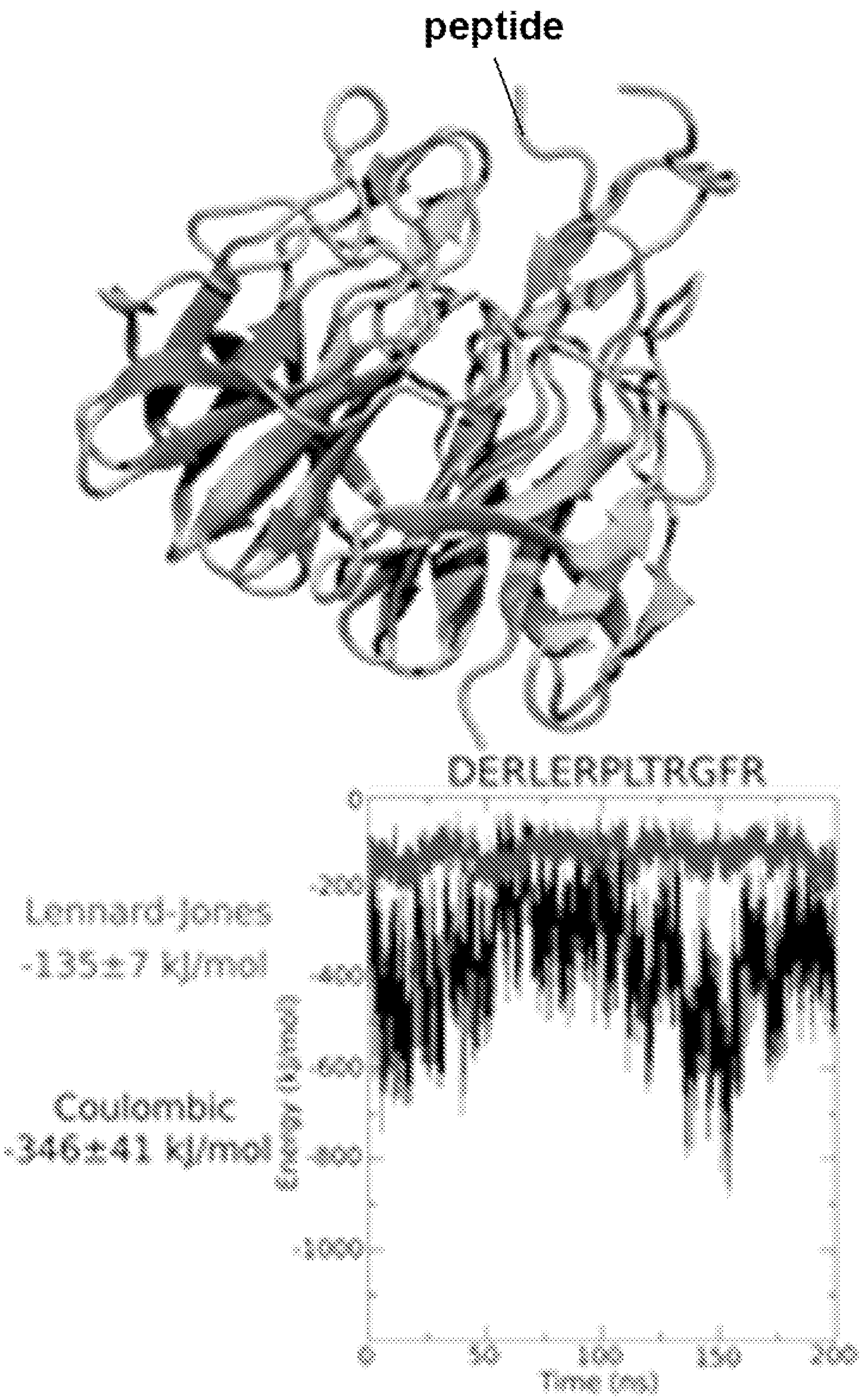

The final simulation snapshots provided in FIGS. 10E and 10F show that the ScrambleR peptide SEQ ID NO: 146 (DELEPLTGFRRRR) keeps the approximate U-shape on the docked region, while the Full Scramble peptide SEQ ID NO: 143 (DERLERPLTRGFR) is greatly deformed. See FIGS. 10E and 10F, respectively. The energy analysis indicated that binding between the ScrambleR peptide or the Full Scramble peptide and the Kelch domain is still favorable but the binding affinity was much weaker when compared to SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR). In particular, the ScrambleR peptide exhibited approximately 80% of the binding strength SEQ ID NO: 72 (LDPETGEFLRRRR) and the Full Scramble peptide exhibited approximately 43% of the binding strength of SEQ ID NO: 72 (LDPETGEFLRRRR).

To further probe the energy contribution provided by the arginine tail, the Lennard-Jones (LJ) interactions and Coulombic interactions were analyzed further for SEQ ID NO: 72 (LDPETGEFLRRRR) and SEQ ID NO: 146 (DELEPLTGFRRRR). More particularly, the binding energies between the arginine tails and the Kelch domain were measured and the results are set forth in Table 2.

TABLE. 2

Comparative Binding to Kelch Domain by Arginine Tails

| | Coulombic (KJ/mol) | Lennard-Jones (KJ/mol) |
|---|---|---|
| SEQ ID NO: 72 (LDPETGEFLRRRR) | −152.6 ± 57.4 | −50.2 ± 13.4 |
| SEQ ID NO: 146 (DELEPLTGFRRRR) | −168 ± 54 | −72 ± 14 |

The results set forth in Table 2 show that the arginine tail of SEQ ID NO: 146 (DELEPLTGFRRRR) contributed approximately 26% to total binding affinity such that the binding for the ScrambleR peptide was comparable to SEQ ID NO: 72 (LDPETGEFLRRRR). However, when this contribution from the arginine tail is accounted for, these results show that the middle amino acids of SEQ ID NO: 146 (DELEPLTGFRRRR), that were responsible for inhibiting the Kelch domain, only contributed approximately 60% of the binding affinity of the middle amino acids for SEQ ID NO: 72 (LDPETGEFLRRRR). These results show that the middle amino acid for the ScrambleR peptide, which are responsible for inhibiting the Kelch domain, do not bind as strongly as the middle amino acids for SEQ ID NO: 72 (LDPETGEFLRRRR).

Example 9

This example shows the MARTINI binding energies for the complex between the Kelch domain and peptides: SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR).

MARTINI coarse-grained simulations were generated from the All-Atom structures provided in Example 8 using martinize.py downloaded at http://cgmartini.nl/. The structures were solvated in water separately and sodium chloride salt (0.15 M) was added. Energy minimization were first performed on the initial structure for 500 steps with the steepest descent algorithm. Subsequently, 4 equilibration runs were carried out to fully equilibrate the system with the same MD integrator, V-rescale thermostat, and Berendsen barostat but different time steps (10 fs, 15 fs, 15 fs, and 15 fs) and position restraint force constants on the protein backbone (1000, 1000, 100, 10). Finally, each production run was performed for 3 μs with a time step of 15 fs. V-rescale thermostat and Parrinello-Rahman barostat were used to preserve temperature and pressure. The results for SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR) are set forth in FIG. 11.

Figure 11:
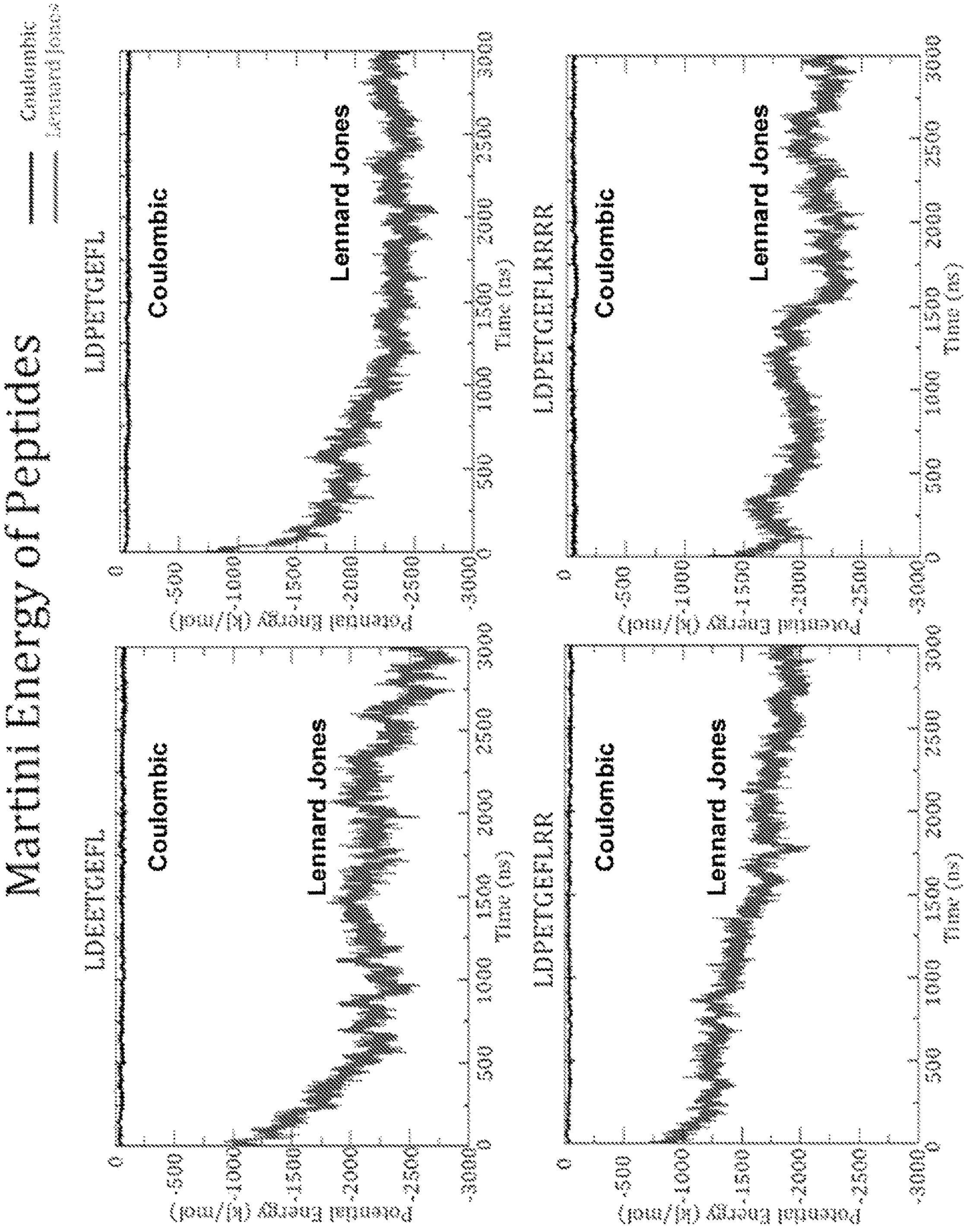
FIG. 11 shows the MARTINI interaction energy simulations between the Kelch domain and peptides: SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR).

The results provided in FIG. 11 show that the MARTINI binding energies for the complex between the Kelch domain and peptides: SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR) all converged after approximately 1.5 μs and were highly negative. These results demonstrate a stable binding behavior and indicate that the interaction between these four peptides and the Kelch domain is favorable.

Example 10

Figure 12A:
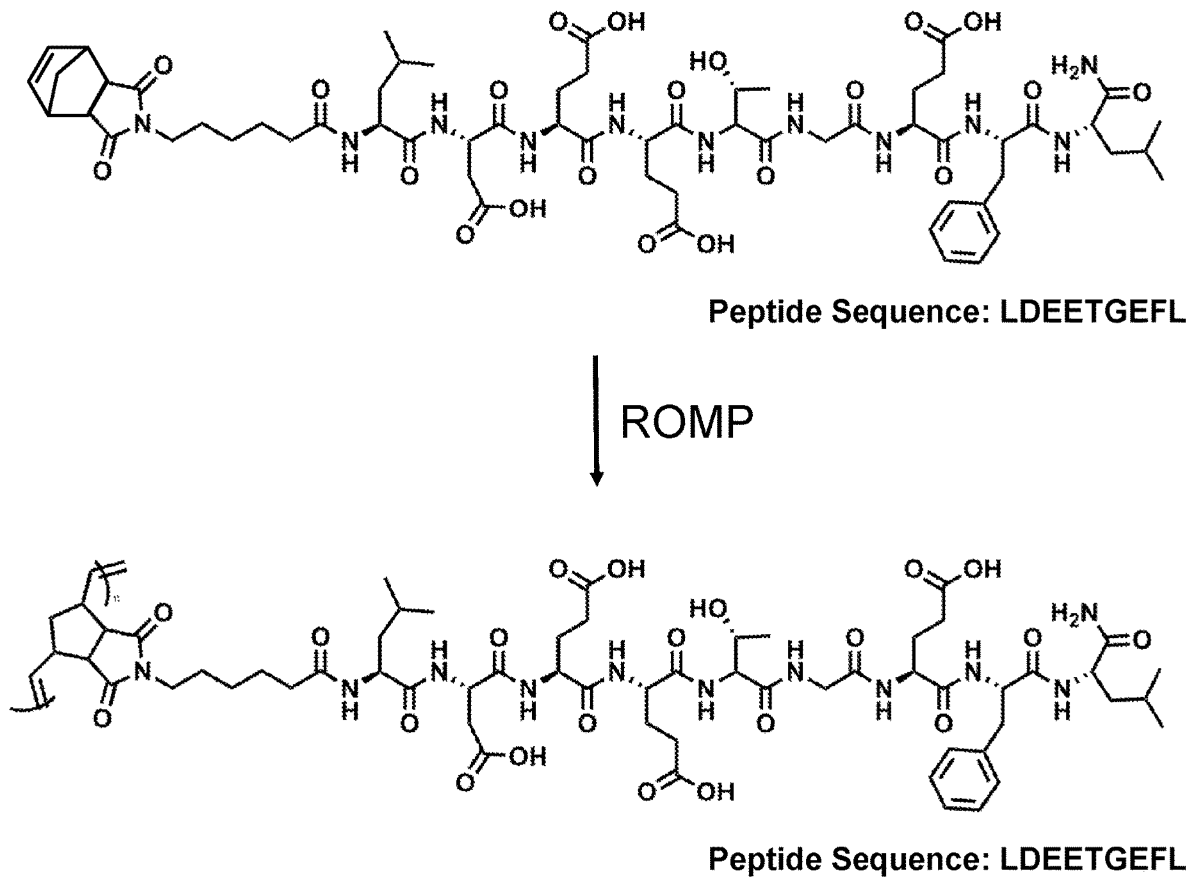
FIG. 12A shows the ring-opening metathesis polymerization (ROMP) of a polynorbornene dicarboxyimide monomer comprising SEQ ID NO: 1 (LDEETGEFL) to form a polynorbornene dicarboxyimide-based brush polymer comprising the peptide SEQ ID NO: 1 (LDEETGEFL), as described in Example 10.

This example provides an exemplary synthesis of a polynorbornene dicarboxyimide-based brush polymer comprising the peptide SEQ ID NO: 1 (LDEETGEFL), as depicted in FIG. 12A.

Peptide SEQ ID NO: 1 (LDEETGEFL) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 12A was prepared by amide coupling to N-(hexanoic acid)-cis-5-norbornene-exo-dicarboximide at the N-terminus of peptide SEQ ID NO: 1 (LDEETGEFL). Following completion of the synthesis, the peptide or peptide monomer was cleaved from the resin by treatment with TFA/$H_2O$/TIPS in a 9.5:2.5:2.5 ratio for 2 to 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide monomer was confirmed by ESI-MS or MALDI-ToF MS and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 12D. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 12B:
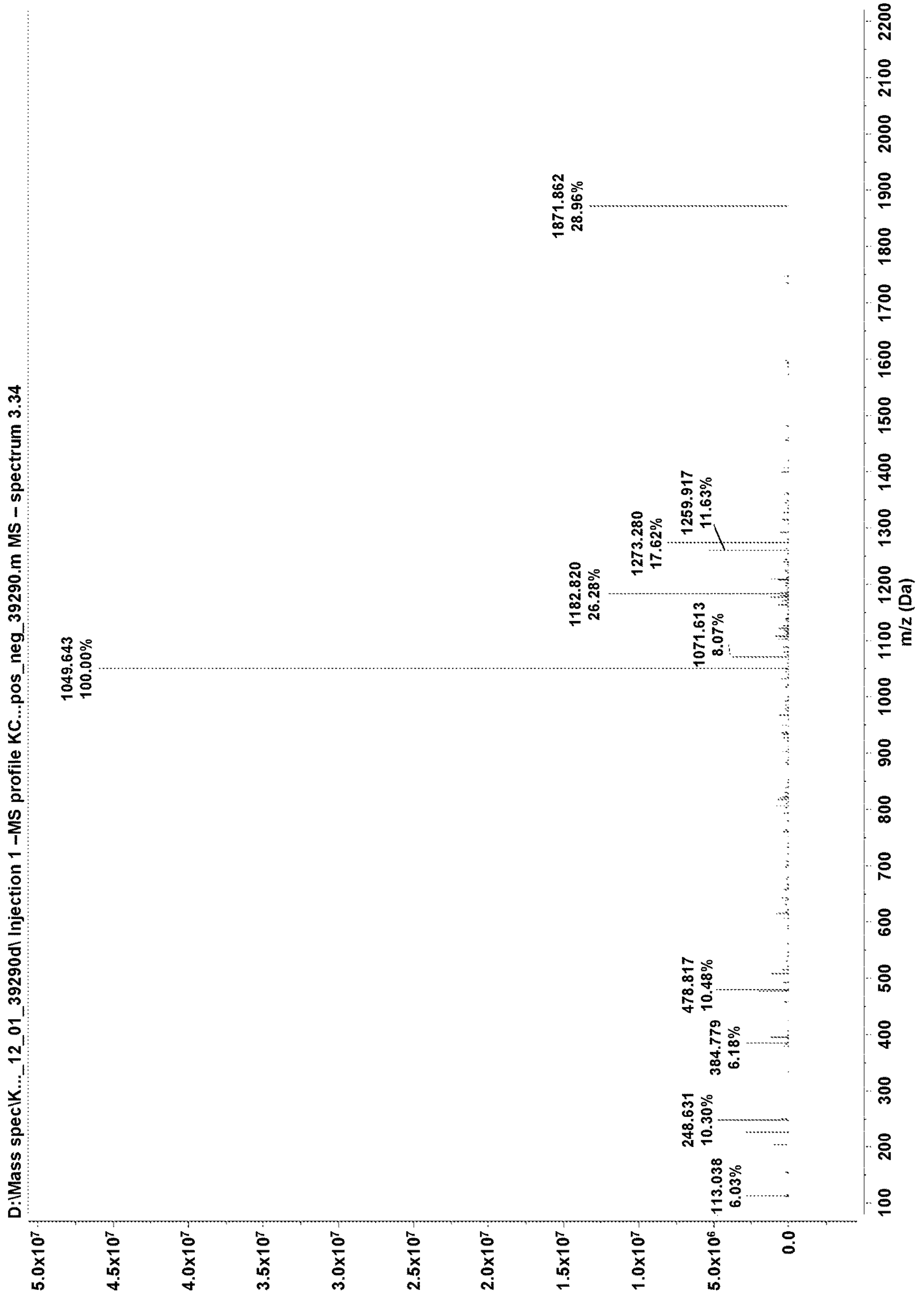
FIG. 12B shows the mass spectrum for the SEQ ID NO: 1 (LDEETGEFL) peptide as measured by electrospray ionization (ESI) mass spectrometry.
Figure 12C:
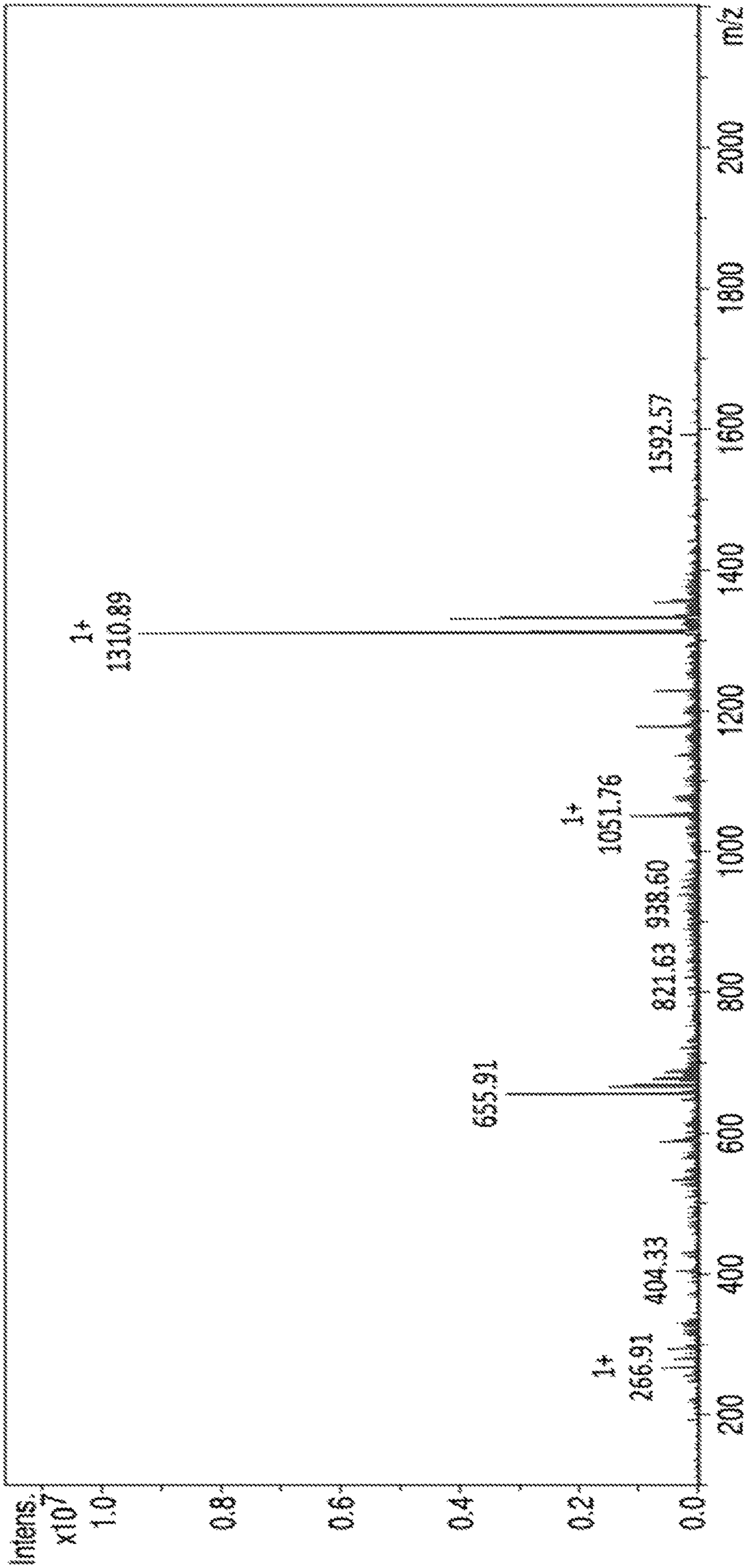
FIG. 12C shows the mass spectrum for the polynorbornene dicarboxyimide monomer comprising SEQ ID NO: 1 (LDEETGEFL) as measured by electrospray ionization (ESI) mass spectrometry.
Figure 12D:
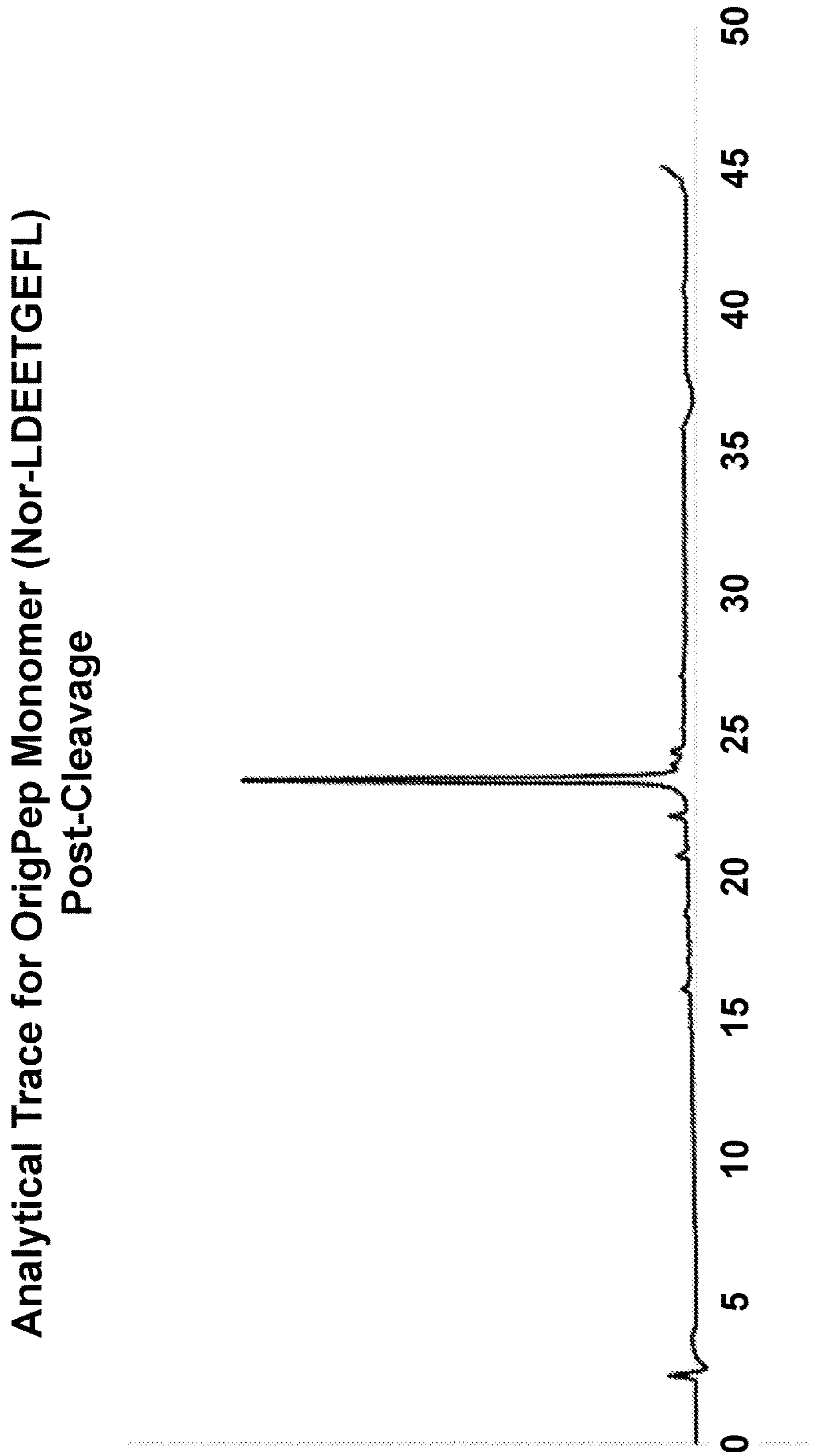
FIG. 12D shows the high-performance liquid chromatography (HPLC) analytical trace for the polynorbornene dicarboxyimide monomer comprising SEQ ID NO: 1 (LDEETGEFL).

The identity of the SEQ ID NO: 1 (LDEETGEFL) peptide was confirmed by electrospray ionization (ESI) mass spectrometry with a mass of 1050 Da, as evidenced by FIG. 12B. The identity of the polynorbornene dicarboxyimide monomer comprising SEQ ID NO: 1 (LDEETGEFL) was confirmed by electrospray ionization (ESI) mass spectrometry with a mass of 1310 Da, as evidenced by FIG. 12C.

Polymerizations were carried out in a glovebox under $N_2$ by mixing the monomer and ROMP catalyst (e.g., Grubbs, Hoveyda-Grubbs, or Schrock) in respective ratio (e.g., 5:1, 10:1, or 15:1) in dry DMF to generate a polymer with desired degree of polymerization. For example, a DP of 10 involved mixing the monomer (0.0125 mmol, 10 equiv, 25 mM) with the ROMP catalyst (e.g., Grubbs, Hoveyda-Grubbs, or Schrock) (0.00125 mmol, 1 equiv, 2.5 mM) in dry DMF (0.5 mL).

Figure 12E:
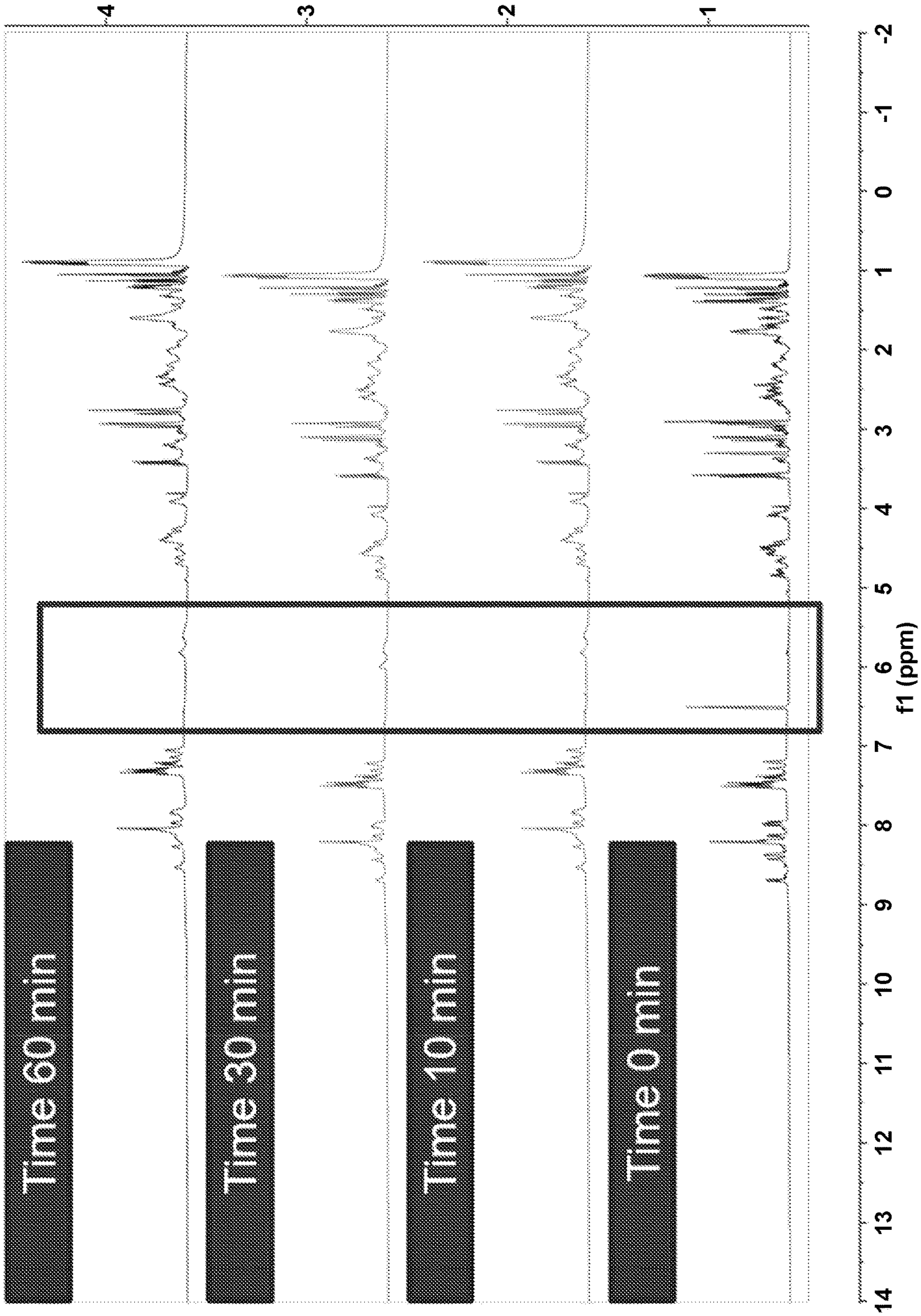
FIG. 12E depicts the polymerization reaction of polynorbornene dicarboxyimide-based SEQ ID NO: 1 (LDEETGEFL) peptide monomer prepared according to Example 10, and the $^1$H NMR spectra for the time course experiments monitoring the polymerization reaction. The disappearance of the resonance at δ=6.5 ppm corresponding to the olefin protons of the monomer and the coincident appearance of resonances δ=5-6 ppm, which correspond to the cis and trans olefin protons of the polymer backbone.

The polymerization reaction was monitored using $^1H$ NMR spectroscopy by measuring the consumption of the peptide monomer and to determine the time period required to reach completion. Termination was done with ethyl vinyl ether (10 eq.) for 30 minutes at room temperature with stirring. FIG. 12E depicts the polymerization reaction of polynorbornene dicarboxyimide-based SEQ ID NO: 1 (LDEETGEFL) peptide monomer prepared according to this example, and the $^1H$ NMR spectra for the time course experiments monitoring the polymerization reaction. The disappearance of the resonance at δ=6.5 ppm corresponding to the olefin protons of the monomer and the coincident appearance of resonances δ=5-6 ppm, which correspond to the cis and trans olefin protons of the polymer backbone.

The resulting polymer was directly characterized by SEC-MALS. The polymer was precipitated with cold ether and collected by centrifugation and dried overnight. The PLPs were further purified using dialysis in regenerated cellulose (3500 Da pore size) and 2 liters of miliQ water over a 48 hour period. The water was renewed at 24 hours and at 48 hours the dialyzed materials were collected, sterile filtered using a 0.22-micron PES filter, and lyophilized.

Figure 12F:
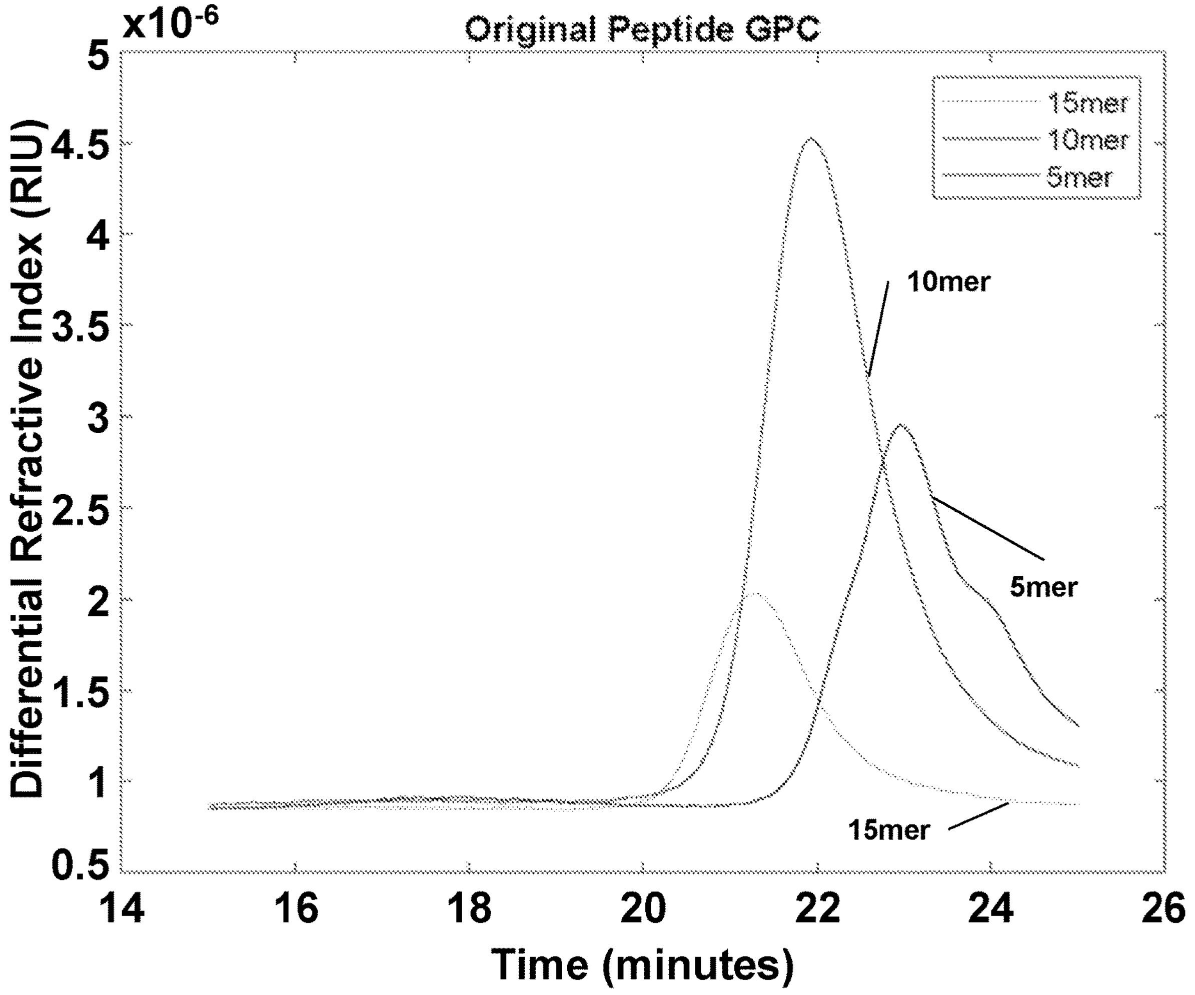
FIG. 12F shows the differential refractive index, as determined by size-exclusion chromatography (SEC-MALS) coupled with multiangle light scattering, for the approximate 5mer, 10mer, and 15mer of the polynorbornene dicarboxyimide-based brush polymer, as prepared in Example 10.

Polymer dispersities ($M_w/M_n$) and molecular weights ($M_n$) were determined by size-exclusion chromatography coupled with multiangle light scattering (SEC-MALS). To this end, SEC was performed on a Phenomenex Phenogel 5u 10, 1K-75K, 300×7.80 mm column in series with a Phenomenex Phenogel 5u 10, 10K-1000K, 300×7.80 mm column, which ran with 0.05 M LiBr in DMF as the running buffer (flow rate of 0.75 mL/min) using a Shimadzu pump. The instrument was also equipped with a MALS detector (DAWN™ HELEOS™, Wyatt Technology) and a refractive index (RI) detector (Wyatt Optilab T-rEX detector). The entire SEC-MALS set-up was normalized to a 30K MW polystyrene standard. FIG. 12F shows the differential refractive index, as determined by size-exclusion chromatography (SEC-MALS) coupled with multiangle light scattering, for the 5mer, 10mer, and 15mer (approximate) of the polynorbornene dicarboxyimide-based brush polymer, as prepared in this example.

The 5mer, 10mer, and 15mer (approximate) of the polynorbornene dicarboxyimide-based brush polymers (i.e., SEQ ID NO: 1 (LDEETGEFL)) were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

Figure 14:
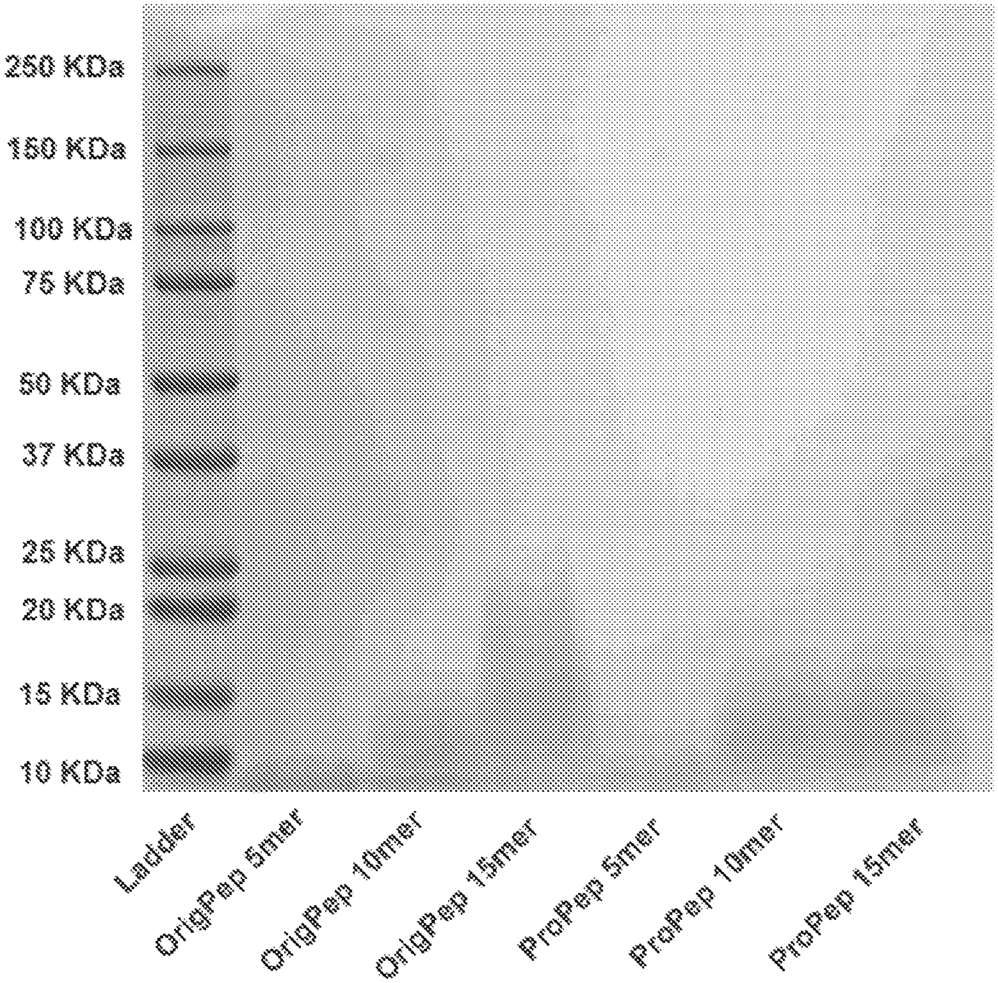
FIG. 14 shows the SDS-PAGE results for the approximate 5mer, 10mer, and 15mer of the polynorbornene dicarboxyimide-based brush polymer (i.e., SEQ ID NO: 1 (LDEETGEFL)), prepared in Example 10, and the approximate 5mer, 10mer, and 15mer of the polynorbornene dicarboxyimide-based brush polymer (i.e., SEQ ID NO: 2 (LDPETGEFL)) prepared in Example 11.

FIG. 14 shows the SDS-PAGE results for the 5mer, 10mer, and 15mer (approximate) of the polynorbornene dicarboxyimide-based brush polymer (i.e., SEQ ID NO: 1 (LDEETGEFL)), prepared in this example, and the 5mer, 10mer, and 15mer (approximate) of the polynorbornene dicarboxyimide-based brush polymer (i.e., SEQ ID NO: 2 (LDPETGEFL)) prepared in Example 11.

Example 11

Figure 13A:
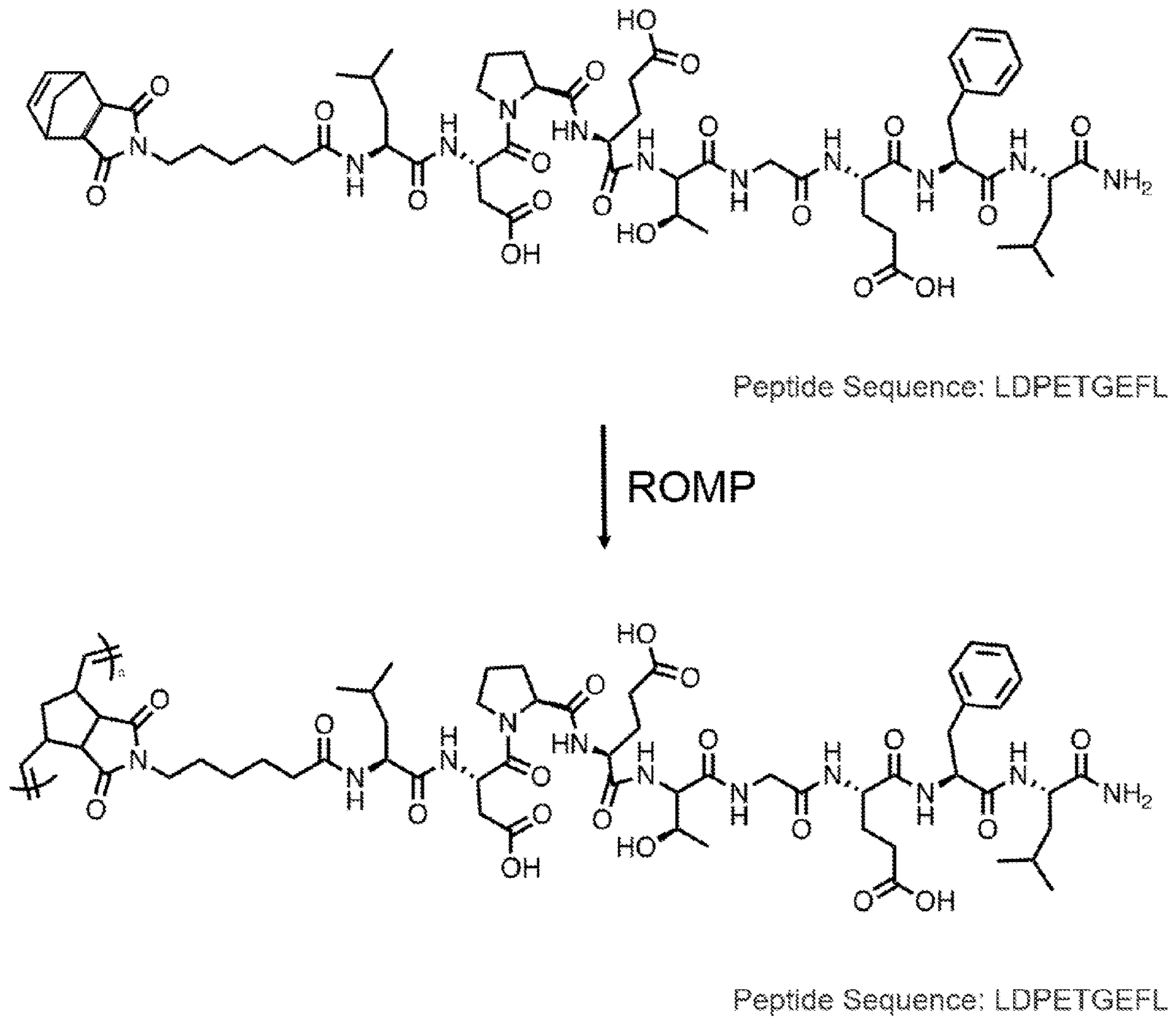
FIG. 13A shows the ring-opening metathesis polymerization (ROMP) of a polynorbornene dicarboxyimide monomer comprising SEQ ID NO: 2 (LDPETGEFL) to form a polynorbornene dicarboxyimide-based brush polymer comprising the peptide SEQ ID NO: 2 (LDPETGEFL), as described in Example 11.

This example provides an exemplary synthesis of a polynorbornene dicarboxyimide-based brush polymer comprising the peptide SEQ ID NO: 2 (LDPETGEFL), as depicted in FIG. 13A.

Peptide SEQ ID NO: 2 (LDPETGEFL) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 13A was prepared by amide coupling to N-(hexanoic acid)-cis-5-norbornene-exo-dicarboximide at the N-terminus of peptide SEQ ID NO: 2 (LDPETGEFL). Following completion of the synthesis, the peptide or peptide monomer was cleaved from the resin by treatment with TFA/$H_2O$/TIPS in a 9.5:2.5:2.5 ratio for 2 to 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide monomer was confirmed by ESI-MS or MALDI-ToF MS and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 13D. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 13B:
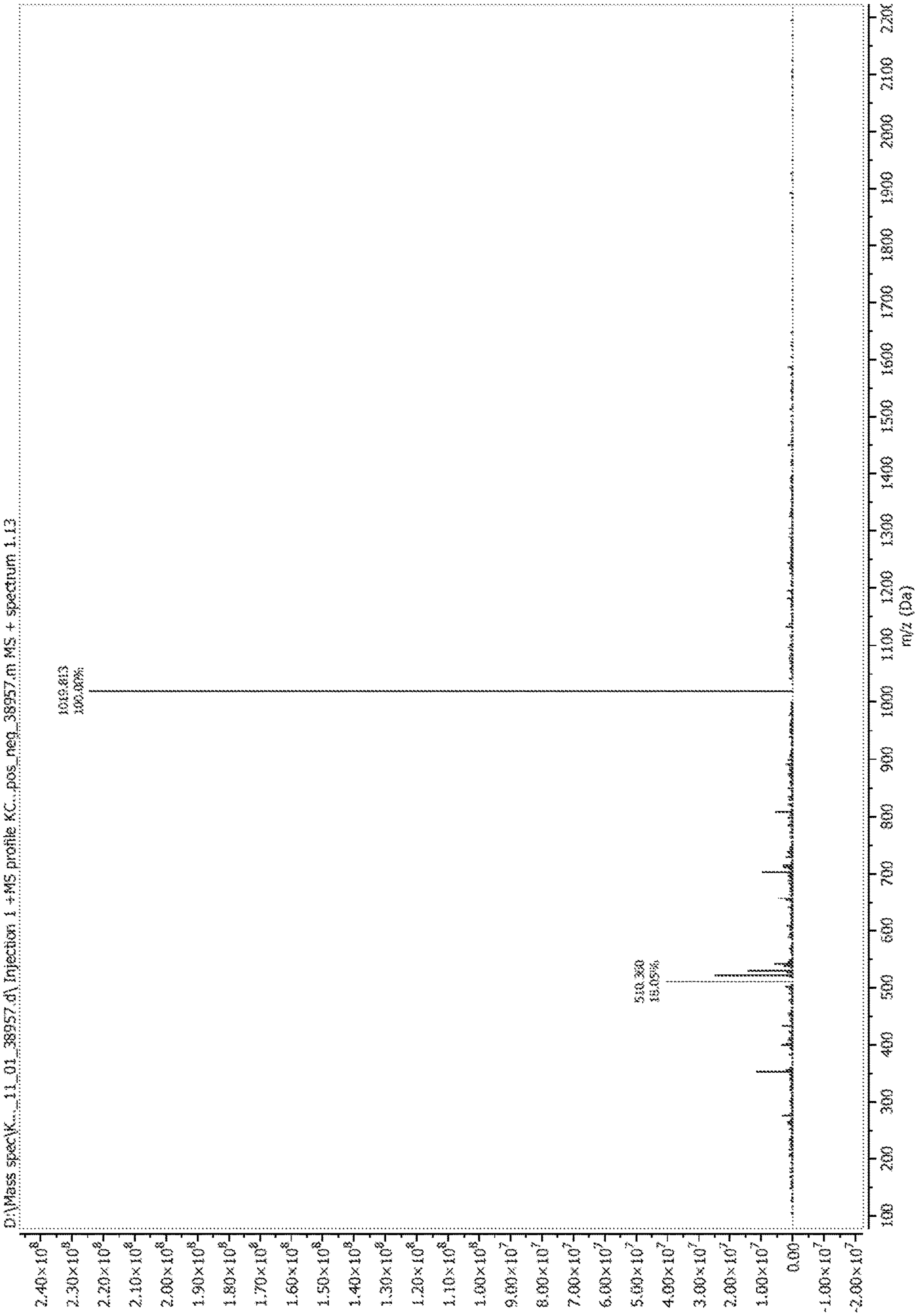
FIG. 13B shows the mass spectrum for the SEQ ID NO: 2 (LDPETGEFL) peptide as measured by electrospray ionization (ESI) mass spectrometry.

The identity of the SEQ ID NO: 2 (LDPETGEFL) peptide was confirmed by electrospray ionization (ESI) mass spectrometry with a mass of 1020 Da, as evidenced by FIG. 13B. The identity of the polynorbornene dicarboxyimide monomer comprising SEQ ID NO: 2 (LDPETGEFL) was confirmed by electrospray ionization (ESI) mass spectrometry with a mass of 1278 Da, as evidenced by FIG. 13C.

Polymerizations were carried out in a glovebox under $N_2$ by mixing the monomer and ROMP catalyst (e.g., Grubbs, Hoveyda-Grubbs, or Schrock) in respective ratio (e.g., 5:1, 10:1, or 15:1) in dry DMF to generate a polymer with desired degree of polymerization. For example, a DP of 10 involved mixing the monomer (0.0125 mmol, 10 equiv, 25 mM) with the ROMP catalyst (e.g., Grubbs, Hoveyda-Grubbs, or Schrock) (0.00125 mmol, 1 equiv, 2.5 mM) in dry DMF (0.5 mL).

The polymerization reaction was monitored using $^1H$ NMR spectroscopy by measuring the consumption of the peptide monomer and to determine the time period required to reach completion. Termination was done with ethyl vinyl ether (10 eq.) for 30 minutes at room temperature with stirring. FIG. 13E depicts the polymerization reaction of polynorbornene dicarboxyimide-based SEQ ID NO: 2 (LDPETGEFL) peptide monomer prepared according to this example, and the $^1H$ NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone.

The resulting polymer was directly characterized by SEC-MALS. The polymer was precipitated with cold ether and collected by centrifugation and dried overnight. The PLPs were further purified using dialysis in regenerated cellulose (3500 Da pore size) and 2 liters of miliQ water over a 48 hour period. The water was renewed at 24 hours and at 48 hours the dialyzed materials were collected, sterile filtered using a 0.22-micron PES filter, and lyophilized.

Polymer dispersities ($M_w/M_n$) and molecular weights ($M_n$) were determined by size-exclusion chromatography coupled with multiangle light scattering (SEC-MALS). To this end, SEC was performed on a Phenomenex Phenogel 5u 10, 1K-75K, 300×7.80 mm column in series with a Phenomenex Phenogel 5u 10, 10K-1000K, 300×7.80 mm column, which ran with 0.05 M LiBr in DMF as the running buffer (flow rate of 0.75 mL/min) using a Shimadzu pump. The instrument was also equipped with a MALS detector (DAWN™ HELEOS™, Wyatt Technology) and a refractive index (RI) detector (Wyatt Optilab T-rEX detector). The entire SEC-MALS set-up was normalized to a 30K MW polystyrene standard. FIG. 13F shows the differential refractive index, as determined by size-exclusion chromatography (SEC-MALS) coupled with multiangle light scattering, for the 5mer, 10mer, and 15mer (approximate) of the polynorbornene dicarboxyimide-based brush polymer, as prepared in this example.

The 5mer, 10mer, and 15mer (approximate) of the polynorbornene dicarboxyimide-based brush polymers (i.e., SEQ ID NO: 2 (LDPETGEFL)) were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

FIG. 14 shows the SDS-PAGE results for the 5mer, 10mer, and 15mer (approximate) of the polynorbornene dicarboxyimide-based brush polymer (i.e., SEQ ID NO: 1 (LDEETGEFL)), prepared in Example 10, and the 5mer, 10mer, and 15mer (approximate) of the polynorbornene dicarboxyimide-based brush polymer (i.e., SEQ ID NO: 2 (LDPETGEFL)) prepared in this example.

Figure 13C:
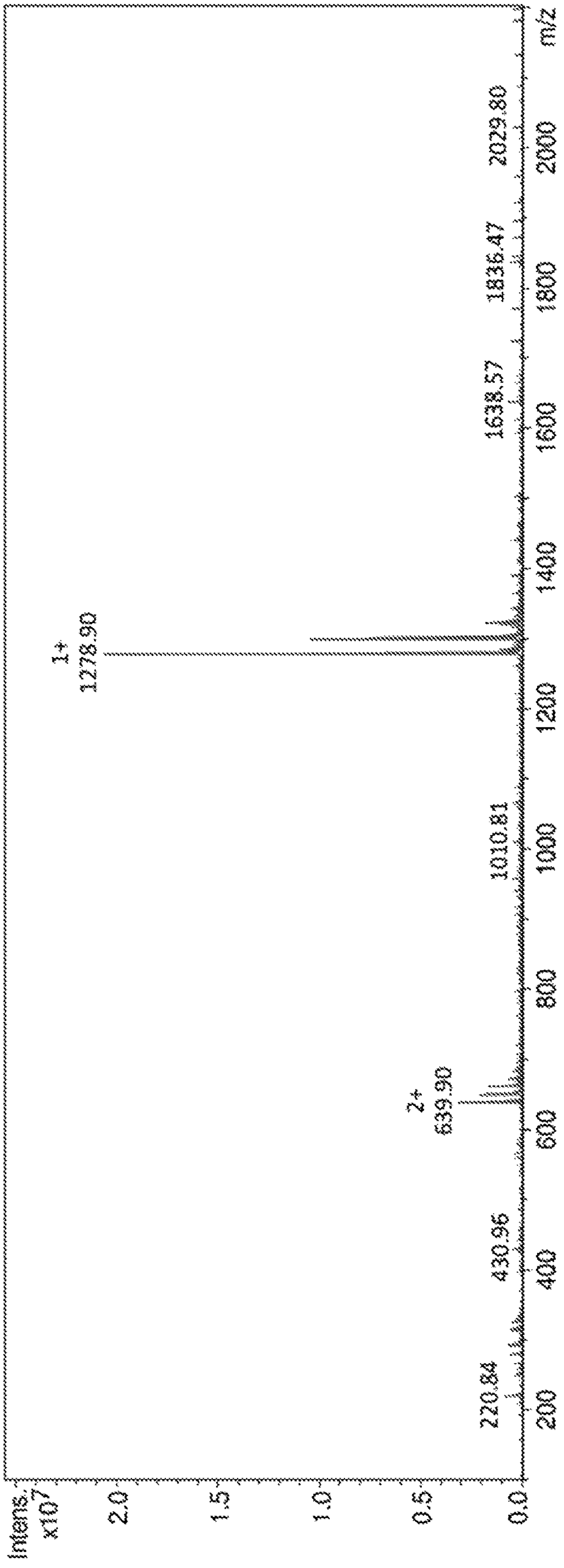
FIG. 13C shows the mass spectrum for the polynorbornene dicarboxyimide monomer comprising SEQ ID NO: 2 (LDPETGEFL) as measured by electrospray ionization (ESI) mass spectrometry.
Figure 13D:
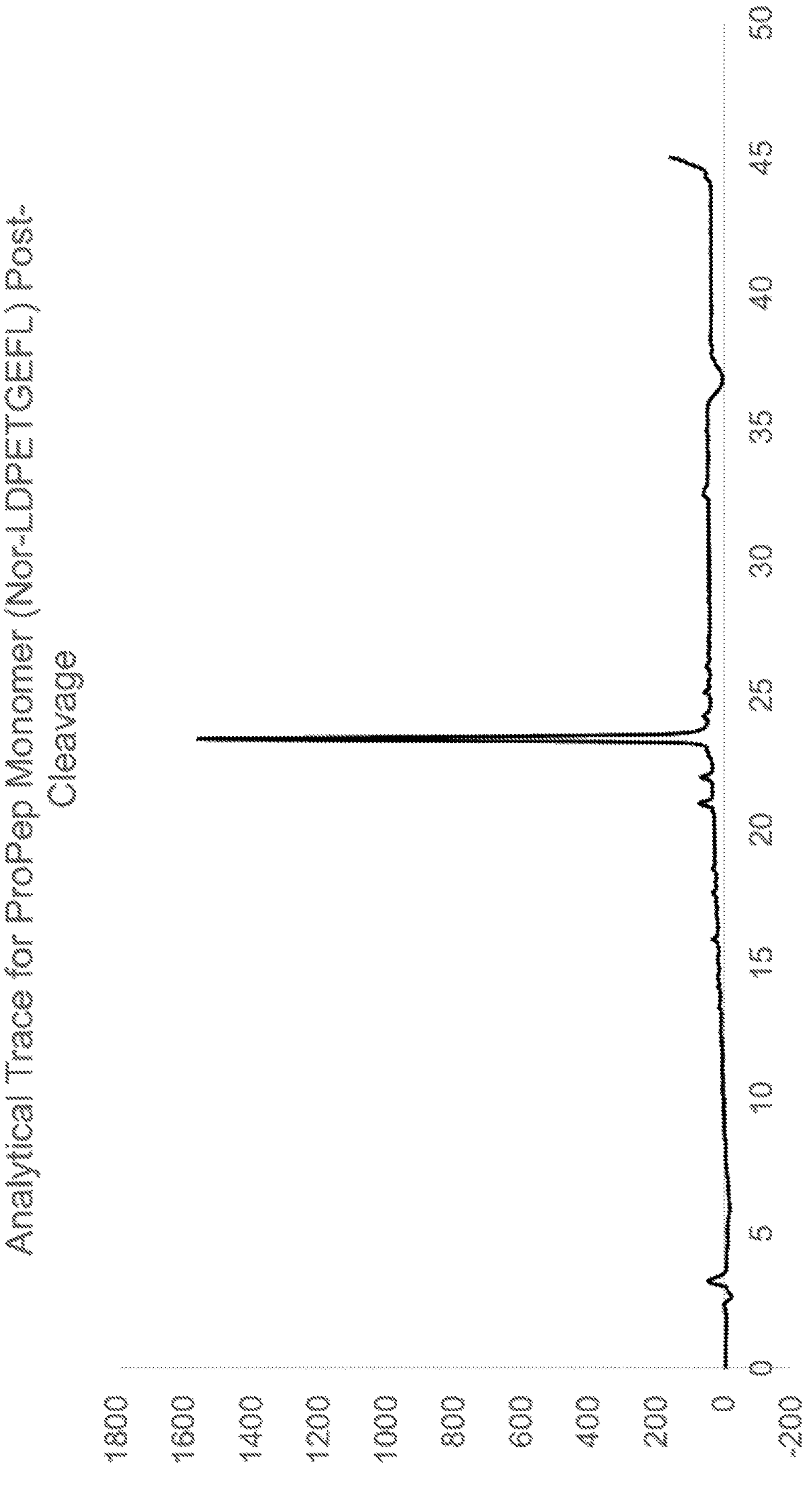
FIG. 13D shows the high-performance liquid chromatography (HPLC) analytical trace for the polynorbornene dicarboxyimide monomer comprising SEQ ID NO: 2 (LDPETGEFL).
Figure 13E:
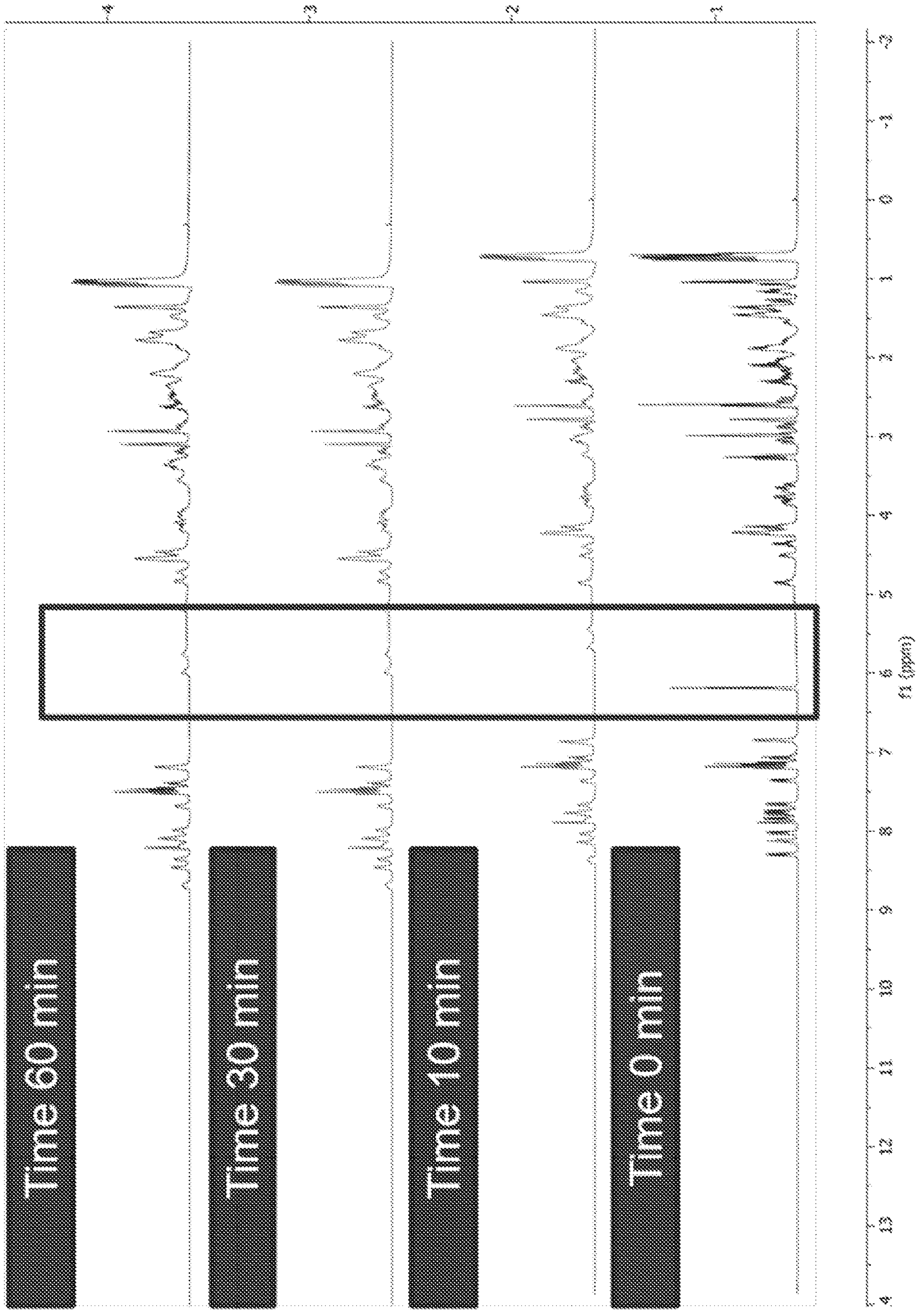
FIG. 13E depicts the polymerization reaction of polynorbornene dicarboxyimide-based SEQ ID NO: 2 (LDPETGEFL) peptide monomer prepared according to Example 11, and the $^1$H NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone.
Figure 13F:
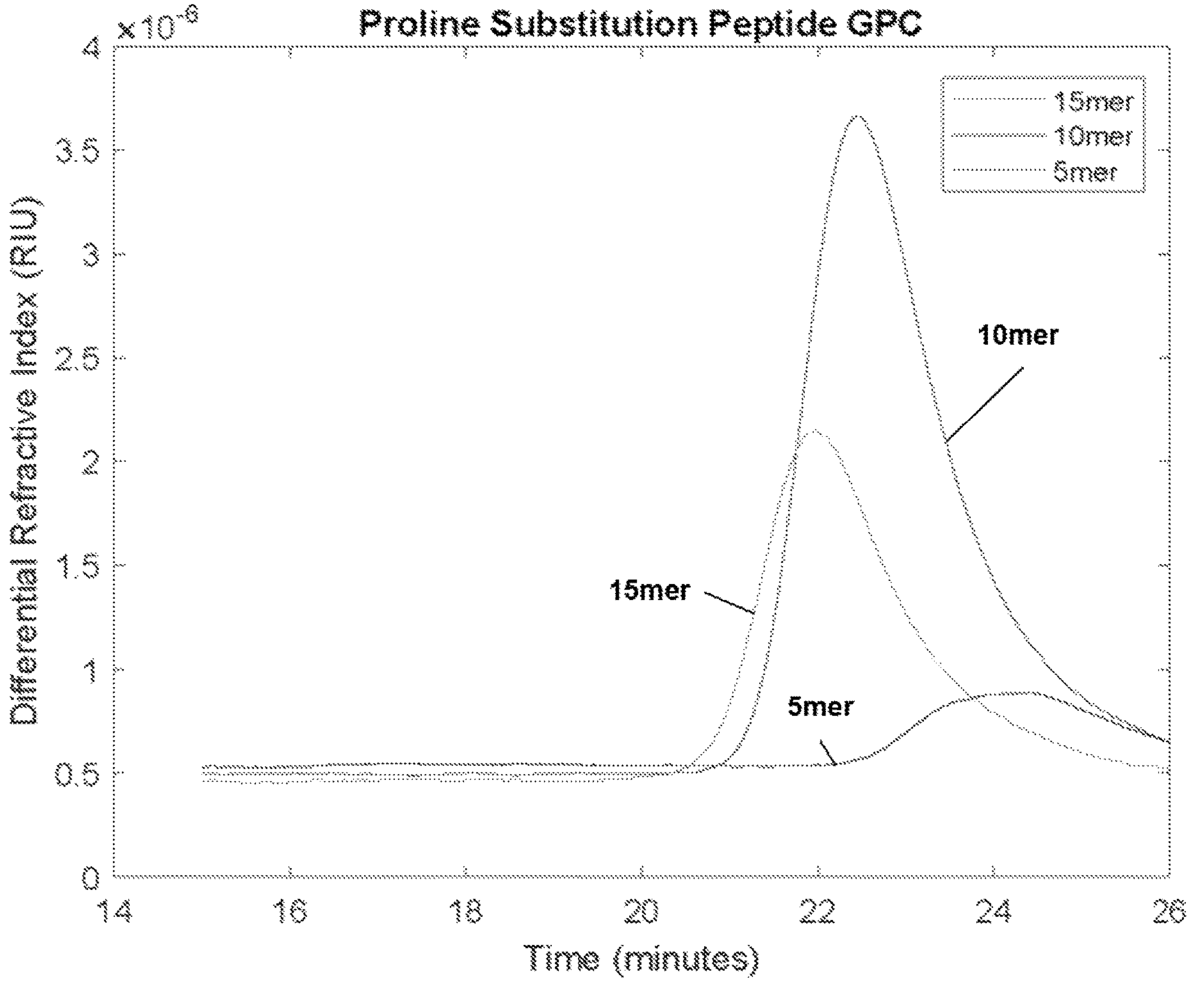
FIG. 13F shows the differential refractive index, as determined by size-exclusion chromatography (SEC-MALS) coupled with multiangle light scattering, for the approximate 5mer, 10mer, and 15mer of the polynorbornene dicarboxyimide-based brush polymer, as prepared in Example 11.
Figure 13G:
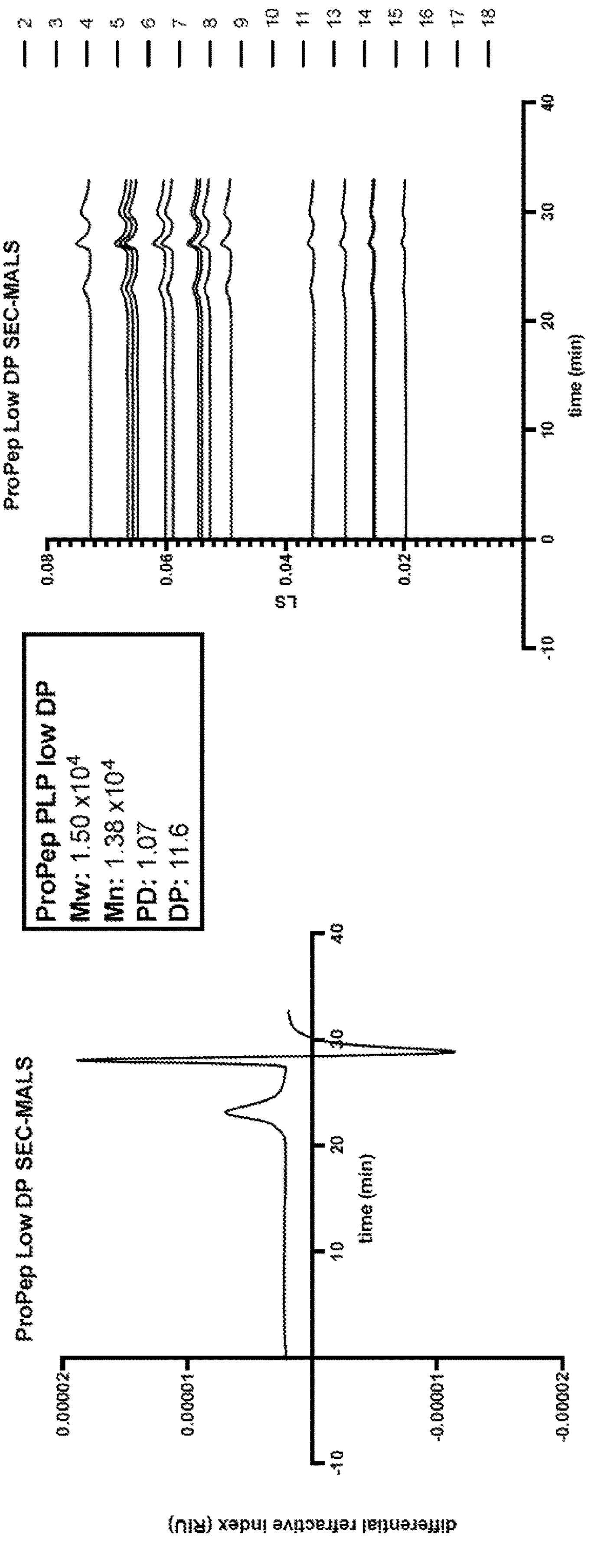
FIG. 13G shows the differential refractive index, as determined by size-exclusion chromatography (SEC-MALS) coupled with multiangle light scattering, for a low degree of polymerization (LowDP) polynorbornene dicarboxyimide-based brush polymer (DP=average of about 11.6) comprising the SEQ ID NO: 2 (LDPETGEFL) peptide monomer, as prepared in Example 11.

More particularly, FIG. 13G shows the differential refractive index, as determined by size-exclusion chromatograph (SEC-MALS) coupled with multiangle light scattering, for a particular low degree of polymerization (LowDP) protein-like polymer prepared in this example. More specifically, a low degree of polymerization (DP=average of about 11.6) polynorbornene dicarboxyimide-based brush polymer comprising the SEQ ID NO: 2 (LDPETGEFL) peptide monomer was prepared and the analytical properties are set forth in FIG. 13G.

Figure 13H:
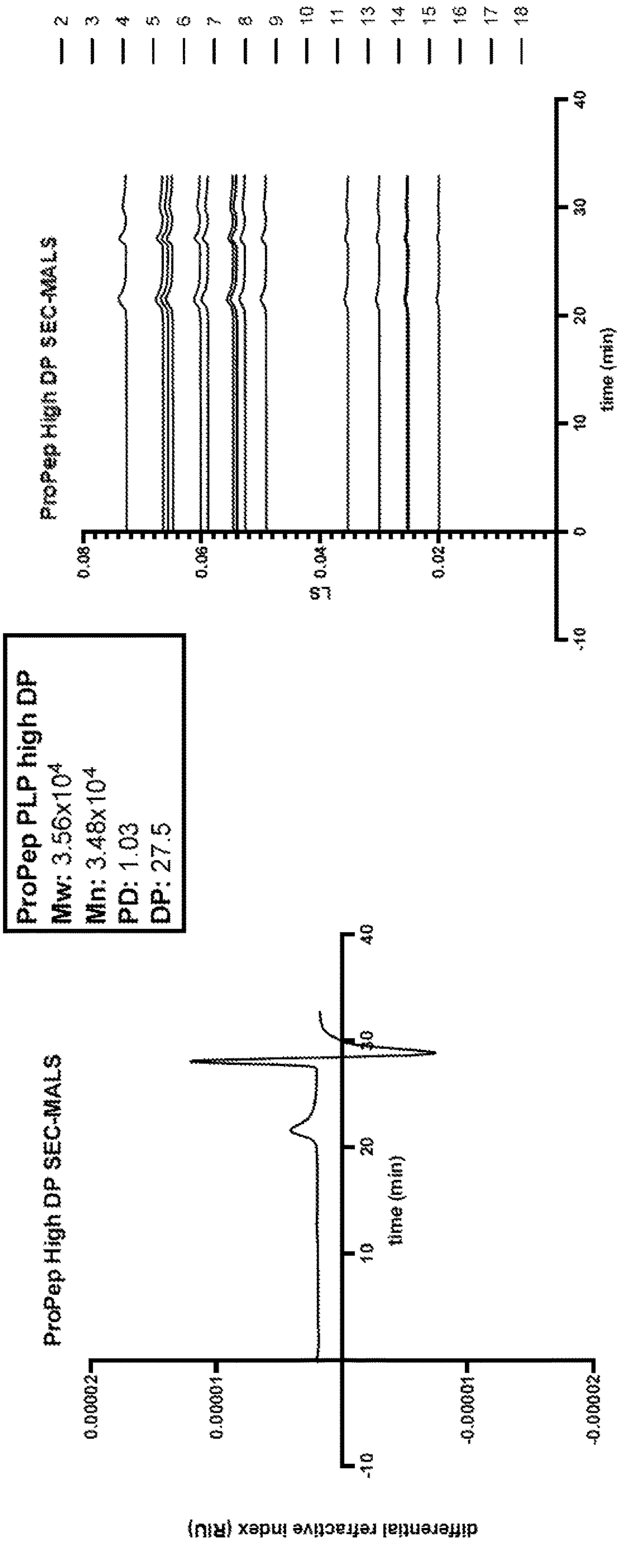
FIG. 13H shows the differential refractive index, as determined by size-exclusion chromatography (SEC-MALS) coupled with multiangle light scattering, for a high degree of polymerization (HighDP) polynorbornene dicarboxyimide-based brush polymer (DP=average of about 27.5) comprising the SEQ ID NO: 2 (LDPETGEFL) peptide monomer, as prepared in Example 11.

In addition, FIG. 13H shows the differential refractive index, as determined by size-exclusion chromatograph (SEC-MALS) coupled with multiangle light scattering, for a particular high degree of polymerization (HighDP) protein-like polymer prepared in this example. More specifically, a high degree of polymerization (DP=average of about 22.5) polynorbornene dicarboxyimide-based brush polymer comprising the SEQ ID NO: 2 (LDPETGEFL) peptide monomer was prepared and the analytical properties are set forth in FIG. 13H.

Example 12

Figure 15A:
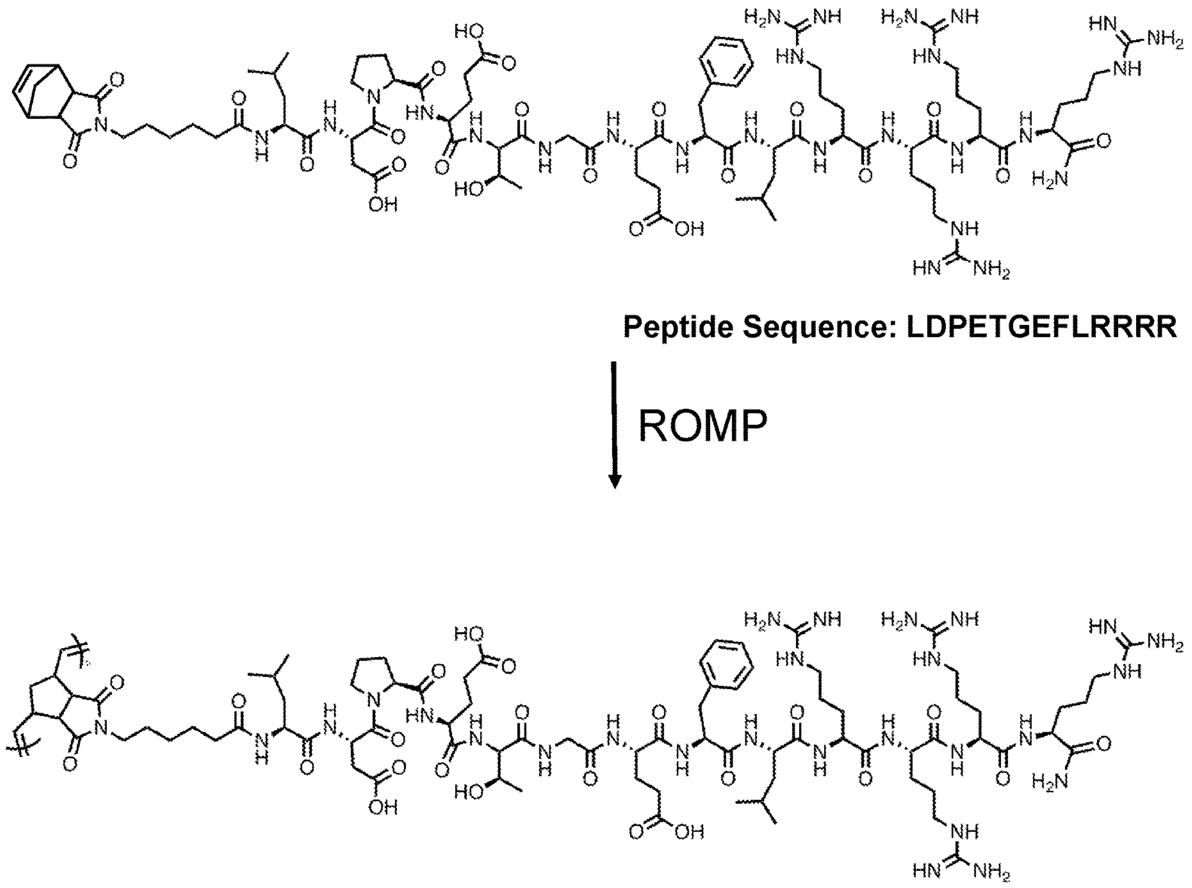
FIG. 15A shows the ring-opening metathesis polymerization (ROMP) of a polynorbornene dicarboxyimide monomer comprising SEQ ID NO: 72 (LDPETGEFLRRRR) to form a polynorbornene dicarboxyimide-based brush polymer comprising the peptide SEQ ID NO: 72 (LDPETGEFLRRRR), as described in Example 12.

This example provides an exemplary synthesis of a polynorbornene dicarboxyimide-based brush polymer comprising the peptide SEQ ID NO: 72 (LDPETGEFLRRRR), as depicted in FIG. 15A.

Peptide SEQ ID NO: 72 (LDPETGEFLRRRR) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 15A was prepared by amide coupling to N-(hexanoic acid)-cis-5-norbornene-exo-dicarboximide at the N-terminus of peptide SEQ ID NO: 72 (LDPETGEFLRRRR). Following completion of the synthesis, the peptide or peptide monomer was cleaved from the resin by treatment with TFA/$H_2O$/TIPS in a 9.5:2.5:2.5 ratio for 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide or peptide monomer was confirmed by ESI-MS or MALDI-ToF MS and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 15D. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 15B:
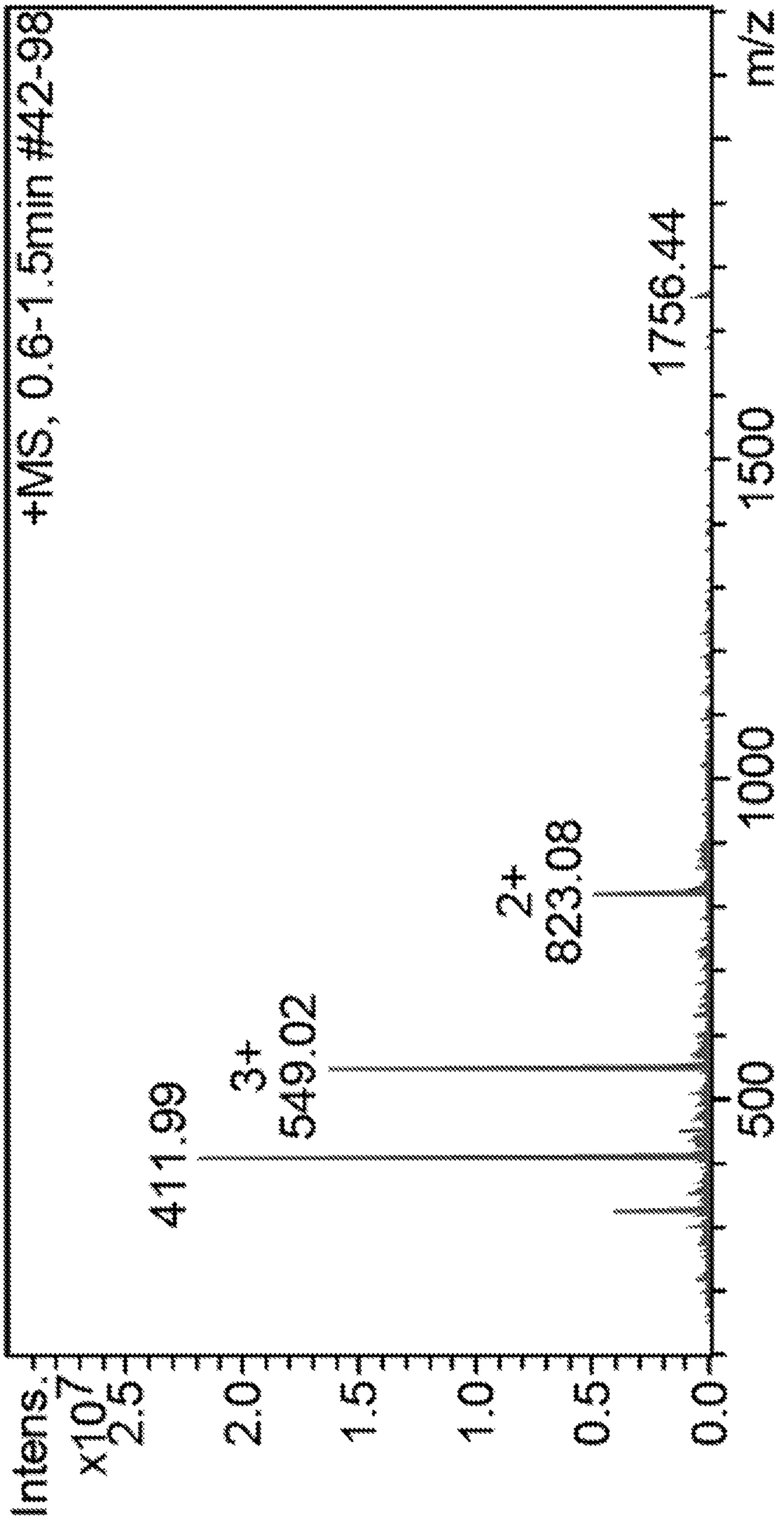
FIG. 15B shows the mass spectrum for the SEQ ID NO: 72 (LDPETGEFLRRRR) peptide as measured by electrospray ionization (ESI) mass spectrometry.
Figure 15C:
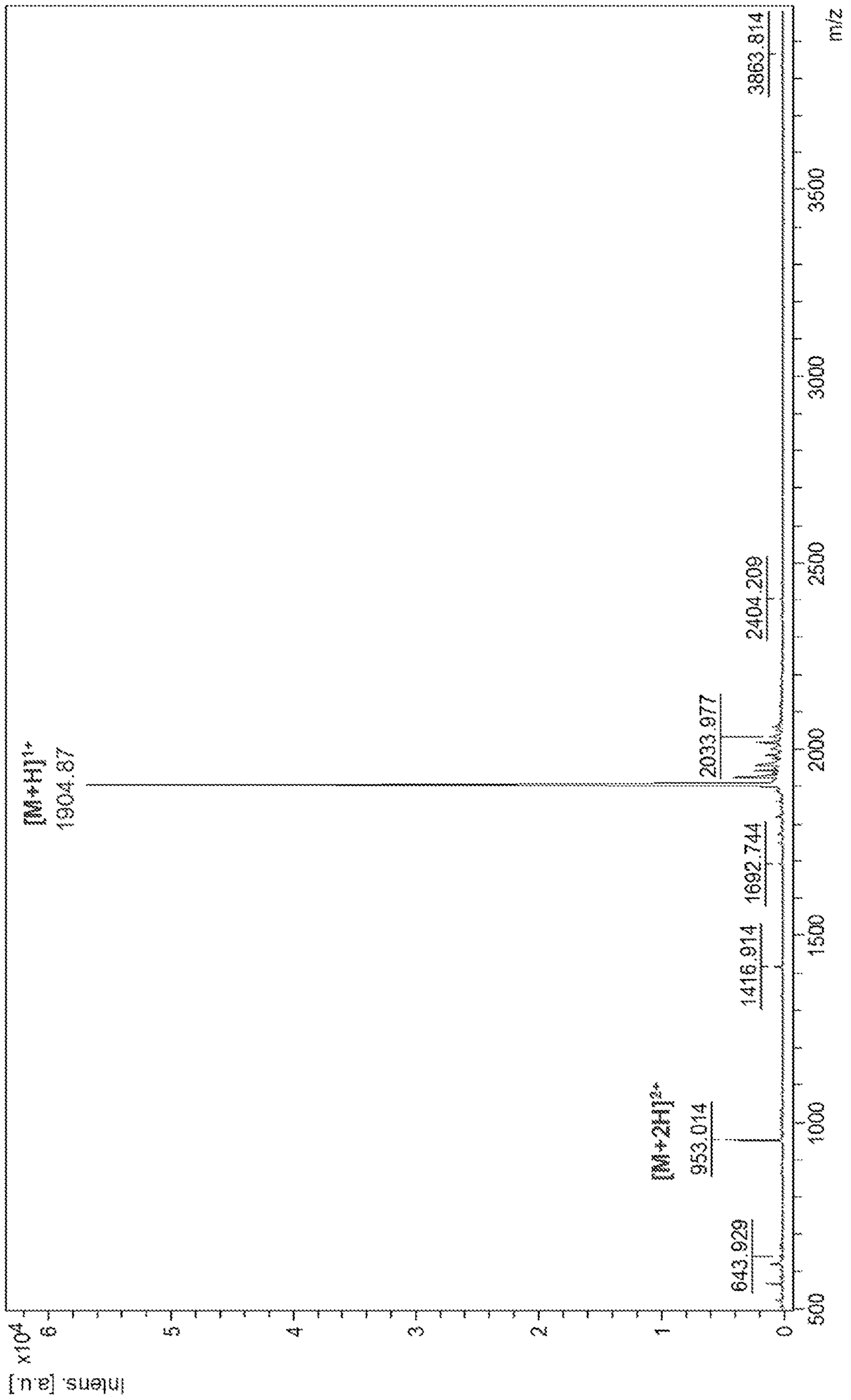
FIG. 15C shows the mass spectrum for the polynorbornene dicarboxyimide monomer comprising SEQ ID NO: 72 (LDPETGEFLRRRR) as measured by MALDI mass spectrometry.
Figure 15D:
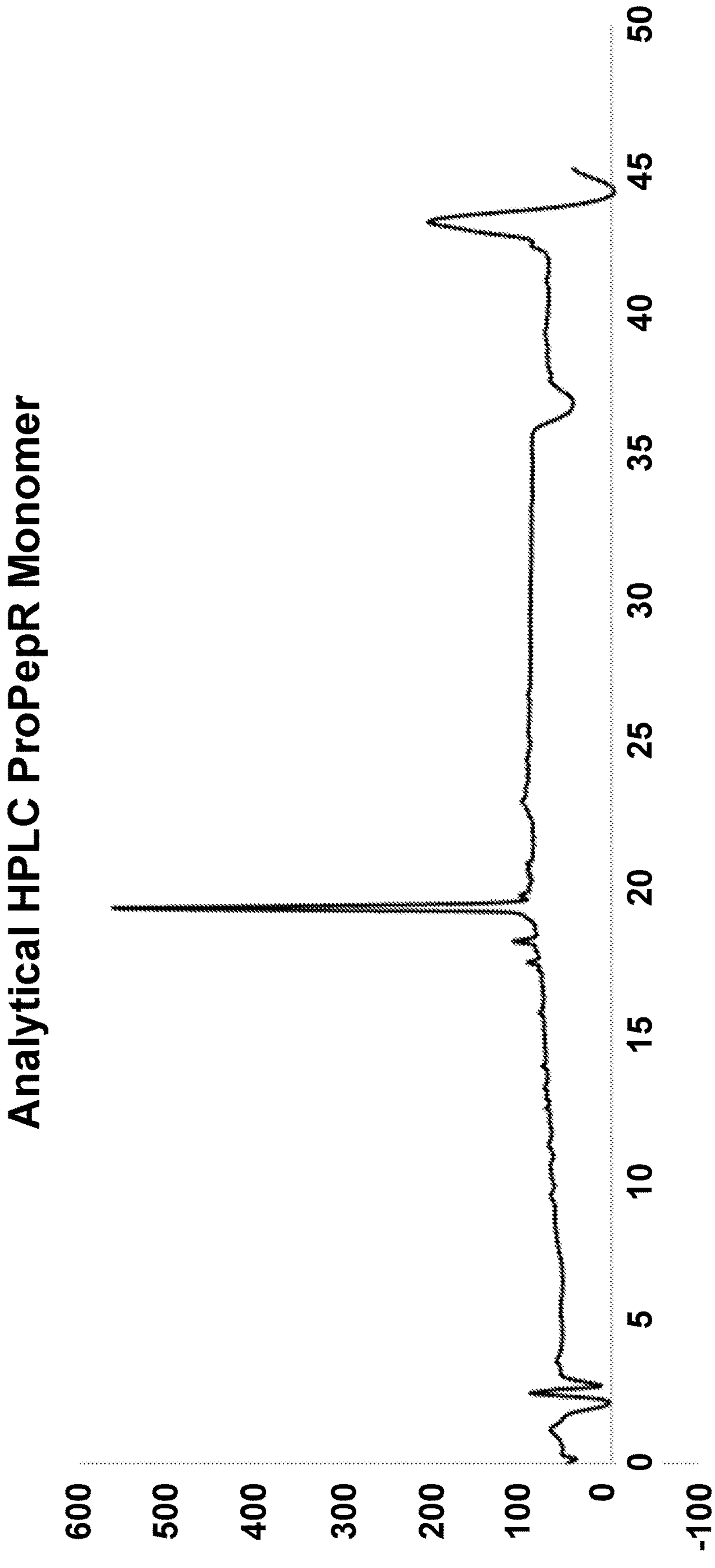
FIG. 15D shows the high-performance liquid chromatography (HPLC) analytical trace for the polynorbornene dicarboxyimide monomer comprising SEQ ID NO: 72 (LDPETGEFLRRRR).

The identity of the SEQ ID NO: 72 (LDPETGEFLRRRR) peptide was confirmed by ESI mass spectrometry with a mass $[M+2H]^{2+}$ of 823 Da (i.e., 1646 Da), as evidenced by FIG. 15B. The identity of the polynorbornene dicarboxyimide monomer comprising SEQ ID NO: 72 (LDPETGEFLRRRR) was confirmed by MALDI mass spectrometry with a mass of 1904 Da, as evidenced by FIG. 15C.

Purified monomers were polymerized in dry, degassed 1M LiCl dimethylformamide using a ROMP catalyst (e.g., Grubbs, Hoveyda-Grubbs, or Schrock) in respective ratio (e.g., 15:1) to generate a polymer with the desired degree of polymerization. For example, a theoretical desired degree of polymerization (DP) of 15 for a homopolymer a monomer stock of 30 mM was added to a catalyst stock of 2 mM of equal volume to generate a final reaction solution with 15 equivalents of monomer (15 mM, 100 mg, 0.078 mmol): 1 equivalent of catalyst (1 mM, 3.79 mg, 0.005 mmol) in 5.2 mL total of dry, degassed 1M LiCl DMF. The reaction was left at room temperature under stirring in a glove box under nitrogen gas. A portion of the reaction can be aliquoted for dye labeling through the addition of a Cy5.5 monomer block. For example, to dye label ¼ of the reaction, 1 equivalent of Cy5.5 monomer (1.08 mg, 0.0013 mmol) in 1.3 mL 1M LiCl DMF was added to 1.3 mL of the initial reaction. Dye block additions were left for 30 min at room temperature with stirring in the glovebox under nitrogen gas.

Figure 15E:
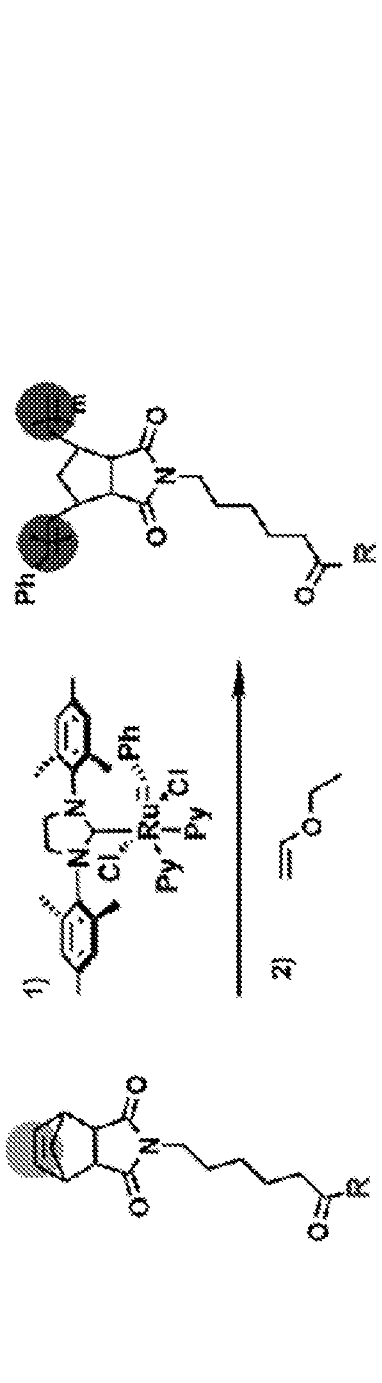
FIG. 15E depicts the polymerization reaction of polynorbornene dicarboxyimide-based SEQ ID NO: 72 (LDPETGEFLRRRR) peptide monomer prepared according to Example 12, and the $^1$H NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone.
Figure 15E:
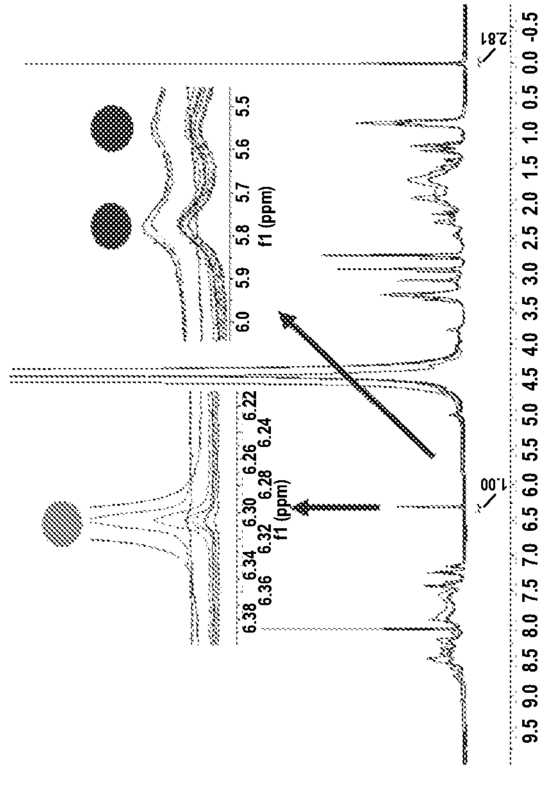

The polymerization reaction was monitored using $^1H$ NMR spectroscopy by measuring the consumption of the peptide monomer and to determine the time period required to reach completion. Termination was done with ethyl vinyl ether (10 eq.) for 30 min at room temperature with stirring. FIG. 15E depicts the polymerization reaction of polynorbornene dicarboxyimide-based SEQ ID NO: 72 (LDPETGEFLRRRR) peptide monomer prepared according to this example, and the $^1H$ NMR spectra for the time course experiments monitoring the polymerization reaction. The disappearance of the resonance at $\delta$=6.3 ppm corresponding to the olefin protons of the monomer and the coincident appearance of resonances $\delta$=5-6 ppm, which correspond to the cis and trans olefin protons of the polymer backbone.

Figure 15F:
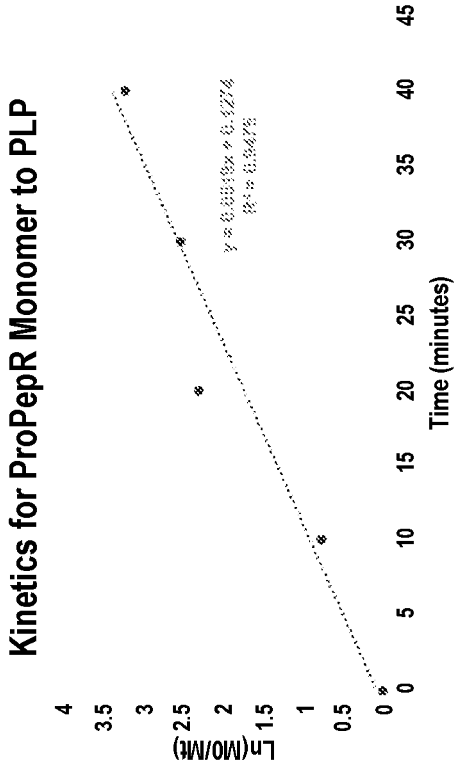
FIG. 15F shows the kinetics of the polymerization reaction for a low degree of polymerization (LowDP) polynorbornene dicarboxyimide-based brush polymer (DP=average of about 11.6), comprising polynorbornene dicarboxyimide-based SEQ ID NO: 72 (LDPETGEFLRRRR) peptide monomer, prepared according to Example 12.
Figure 15G:
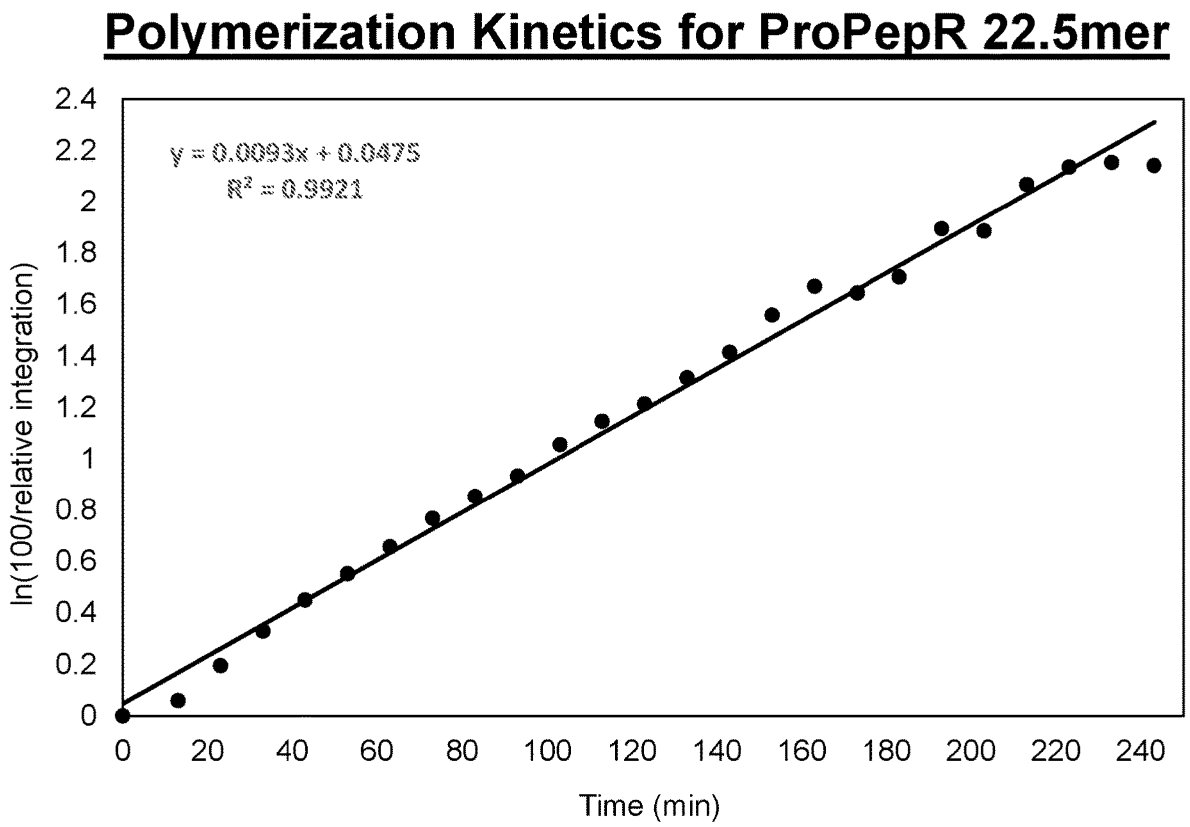
FIG. 15G shows the kinetics of the polymerization reaction for a high degree of polymerization (HighDP) polynorbornene dicarboxyimide-based brush polymer (DP=average of about 22.5), comprising polynorbornene dicarboxyimide-based SEQ ID NO: 72 (LDPETGEFLRRRR) peptide monomer, prepared according to Example 12.

In addition to monitoring the polymerization reaction by using $^1H$ NMR spectroscopy, the kinetics of the polymerization reaction were plotted for a particular low degree of polymerization (LowDP) protein-like polymer prepared in this example. In particular, FIG. 15F shows that kinetics of the polymerization reaction for a low degree of polymerization (DP=average of about 11.6) polynorbornene dicarboxyimide-based brush polymer comprising the SEQ ID NO: 72 (LDPETGEFLRRRR) peptide monomer. Similarly, the kinetics of the polymerization reaction were plotted for a particular high degree of polymerization (HighDP) protein-like polymer prepared in this example. In particular, FIG. 15G shows that kinetics of the polymerization reaction for a high degree of polymerization (DP=average of about 22.5) polynorbornene dicarboxyimide-based brush polymer comprising the SEQ ID NO: 72 (LDPETGEFLRRRR) peptide monomer.

Following polymerization, the polymer was precipitated with cold ether and collected by centrifugation and dried overnight. The PLPs were further purified using dialysis in regenerated cellulose (3500 Da pore size) and 2 liters of miliQ water over a 48 hour period. The water was renewed at 24 hours and at 48 hours the dialyzed materials were collected, sterile filtered using a 0.22-micron PES filter, and lyophilized.

Figure 15H:
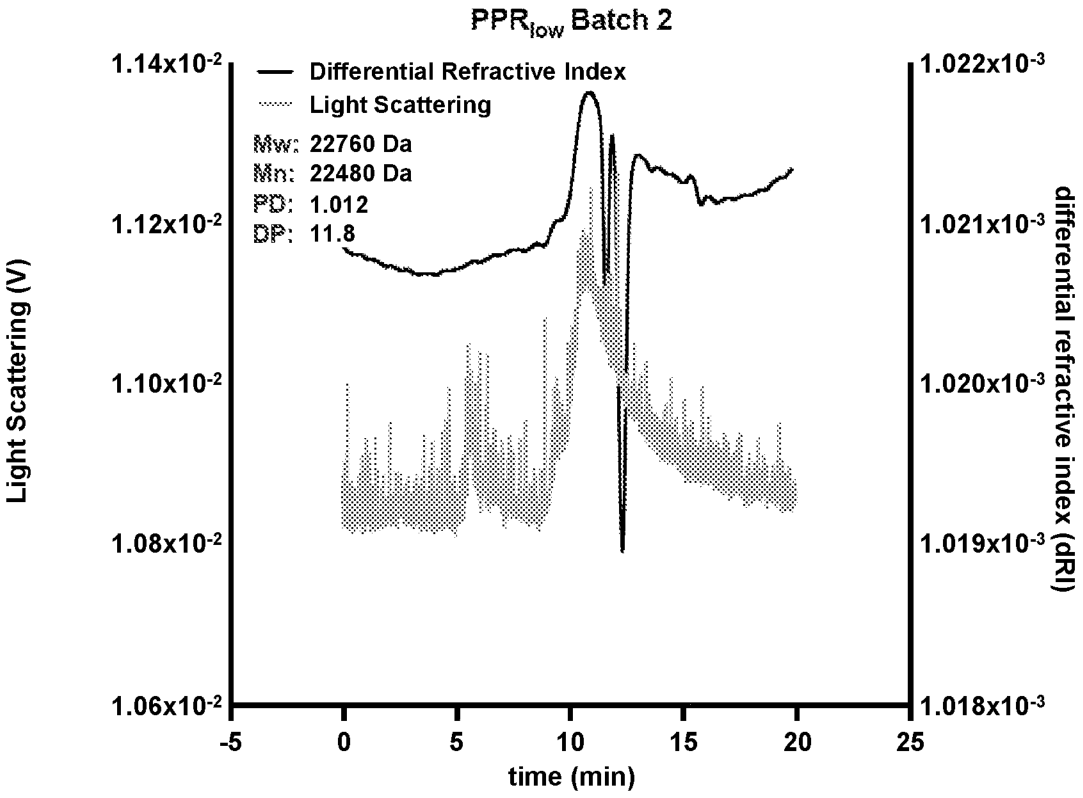
FIG. 15H shows the differential refractive index, as determined by aqueous gel permeation chromatography (GPC), for a particular batch of a low degree of polymerization (LowDP) polynorbornene dicarboxyimide-based brush polymer, comprising polynorbornene dicarboxyimide-based SEQ ID NO: 72 (LDPETGEFLRRRR) peptide monomer, as prepared in Example 12.
Figure 15I:
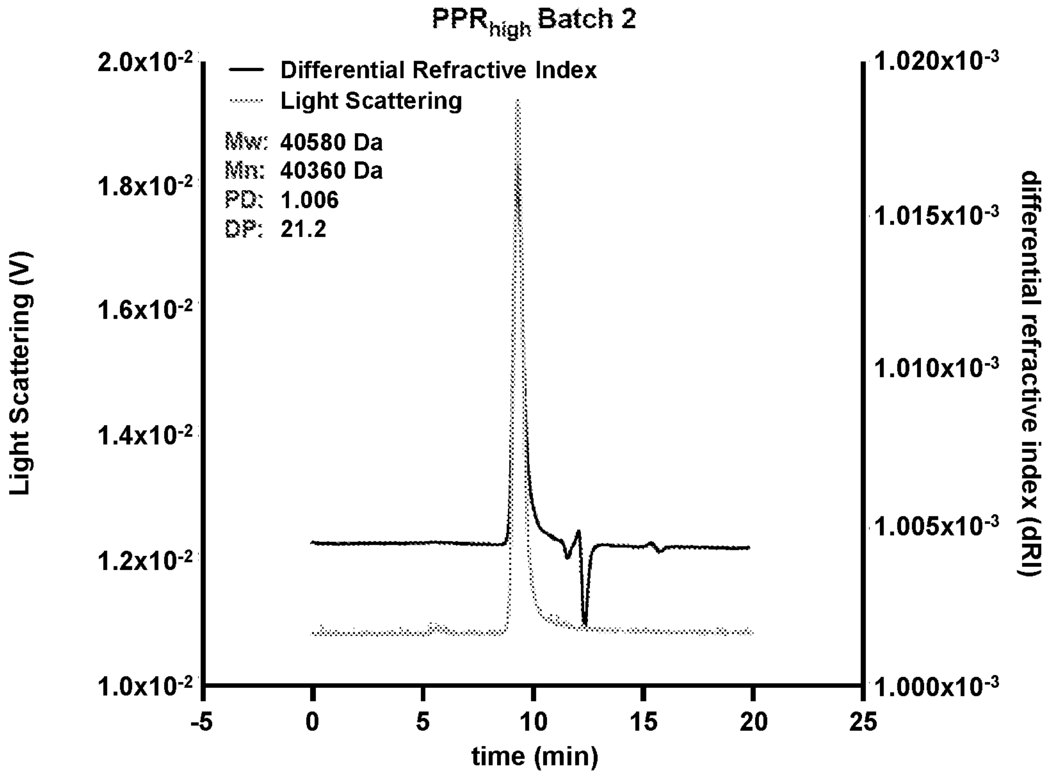
FIG. 15I shows the differential refractive index, as determined by aqueous gel permeation chromatography (GPC), for a particular batch of a high degree of polymerization (HighDP) polynorbornene dicarboxyimide-based brush polymer, comprising polynorbornene dicarboxyimide-based SEQ ID NO: 72 (LDPETGEFLRRRR) peptide monomer, as prepared in Example 12.

The analytical properties and differential refractive index of the low degree of polymerization (DP=average of about 11.6) polynorbornene dicarboxyimide-based brush polymer comprising the SEQ ID NO: 72 (LDPETGEFLRRRR) peptide monomer were determined by aqueous gel permeation chromatography (GPC), and the results are set forth in FIG. 15H. In addition, the analytical properties and differential refractive index of the high degree of polymerization (DP=average of about 22.5) polynorbornene dicarboxyimide-based brush polymer comprising the SEQ ID NO: 72 (LDPETGEFLRRRR) peptide monomer were determined by aqueous GPC, and the results are set forth in FIG. 15I.

Polymer dispersities ($M_w/M_n$) and molecular weights ($M_n$) were determined by aqueous phase gel permeation chromatography (GPC). To this end, aqueous phase GPC measurements were performed using a TOSOH Biosciences TSKgel G500$PW_{XL}$-CP column (7.8 mm ID×30 cm, 10 μm) with 0.1 M sodium nitrate buffer containing 0.1% TFA as the mobile phase with a flow rate of 1.0 mL/min. Detection consisted of a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software.

The polymers were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

Figure 18:
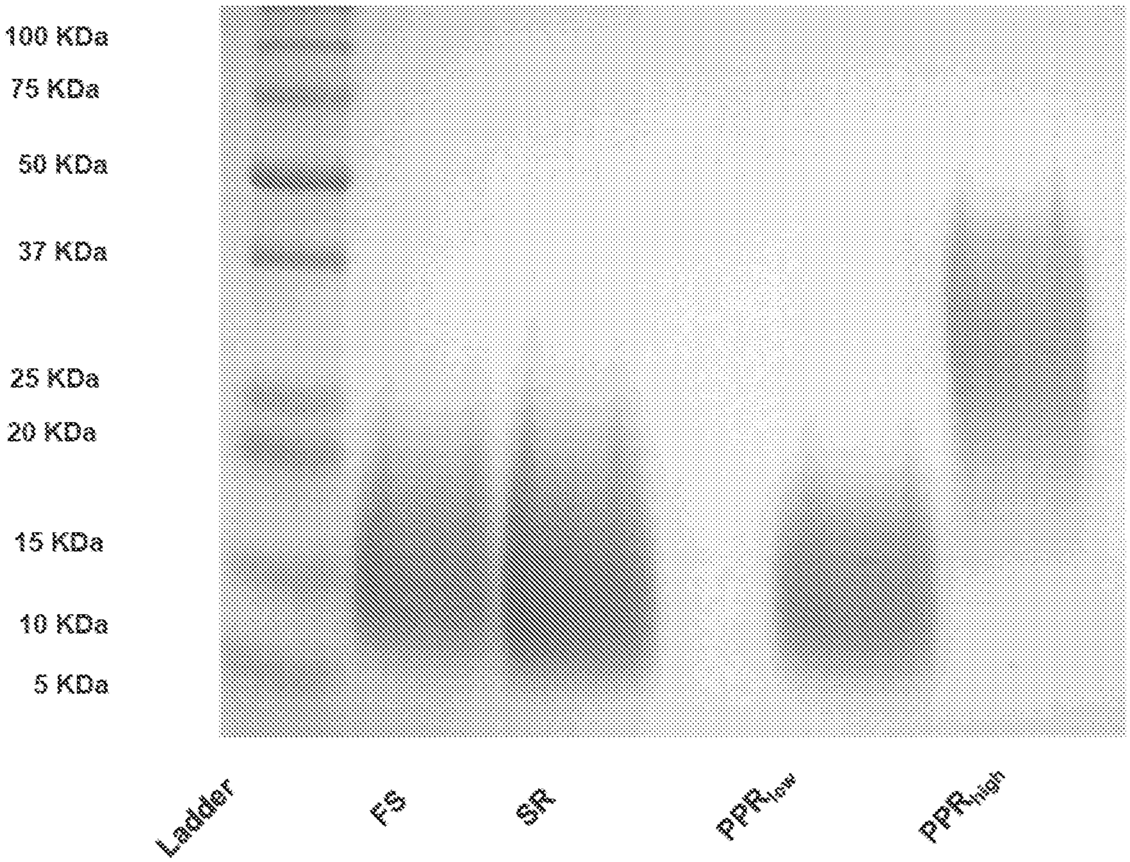
FIG. 18 shows the SDS-PAGE results for the full scramble polynorbornene dicarboxyimide-based brush polymer ("FS") comprising polynorbornene dicarboxyimide-based SEQ ID NO: 143 (DERLERPLTRGFR) peptide monomer prepared in Example 13, the scrambleRRRR polynorbornene dicarboxyimide-based brush polymer ("SR") comprising polynorbornene dicarboxyimide-based SEQ ID NO: 146 (DELEPLTGFRRRR) peptide monomer prepared in Example 14, the low degree of polymerization (LowDP) polynorbornene dicarboxyimide-based brush polymer ("$PPR_{low}$"—DP=average of about 11.6) comprising polynorbornene dicarboxyimide-based SEQ ID NO: 72 (LDPETGEFLRRRR) peptide monomer prepared in Example 12, and the high degree of polymerization (HighDP) polynorbornene dicarboxyimide-based brush polymer ("$PPR_{high}$"—DP=average of about 22.5) comprising polynorbornene dicarboxyimide-based SEQ ID NO: 72 (LDPETGEFLRRRR) peptide monomer prepared in Example 12.

FIG. 18 shows the SDS-PAGE results for the full scramble polynorbornene dicarboxyimide-based brush polymer ("FS") comprising polynorbornene dicarboxyimide-based SEQ ID NO: 143 (DERLERPLTRGFR) peptide monomer prepared in Example 13, the scrambleRRRR polynorbornene dicarboxyimide-based brush polymer ("SR") comprising polynorbornene dicarboxyimide-based SEQ ID NO: 146 (DELEPLTGFRRRR) peptide monomer prepared in Example 14, the low degree of polymerization (LowDP) polynorbornene dicarboxyimide-based brush polymer ("$PPR_{low}$"—DP=average of about 11.6) comprising polynorbornene dicarboxyimide-based SEQ ID NO: 72 (LDPETGEFLRRRR) peptide monomer prepared in this example, and the high degree of polymerization (HighDP) polynorbornene dicarboxyimide-based brush polymer ("$PPR_{high}$"—DP=average of about 22.5) comprising polynorbornene dicarboxyimide-based SEQ ID NO: 72 (LDPETGEFLRRRR) peptide monomer prepared in this example.

Example 13

Figure 16A:
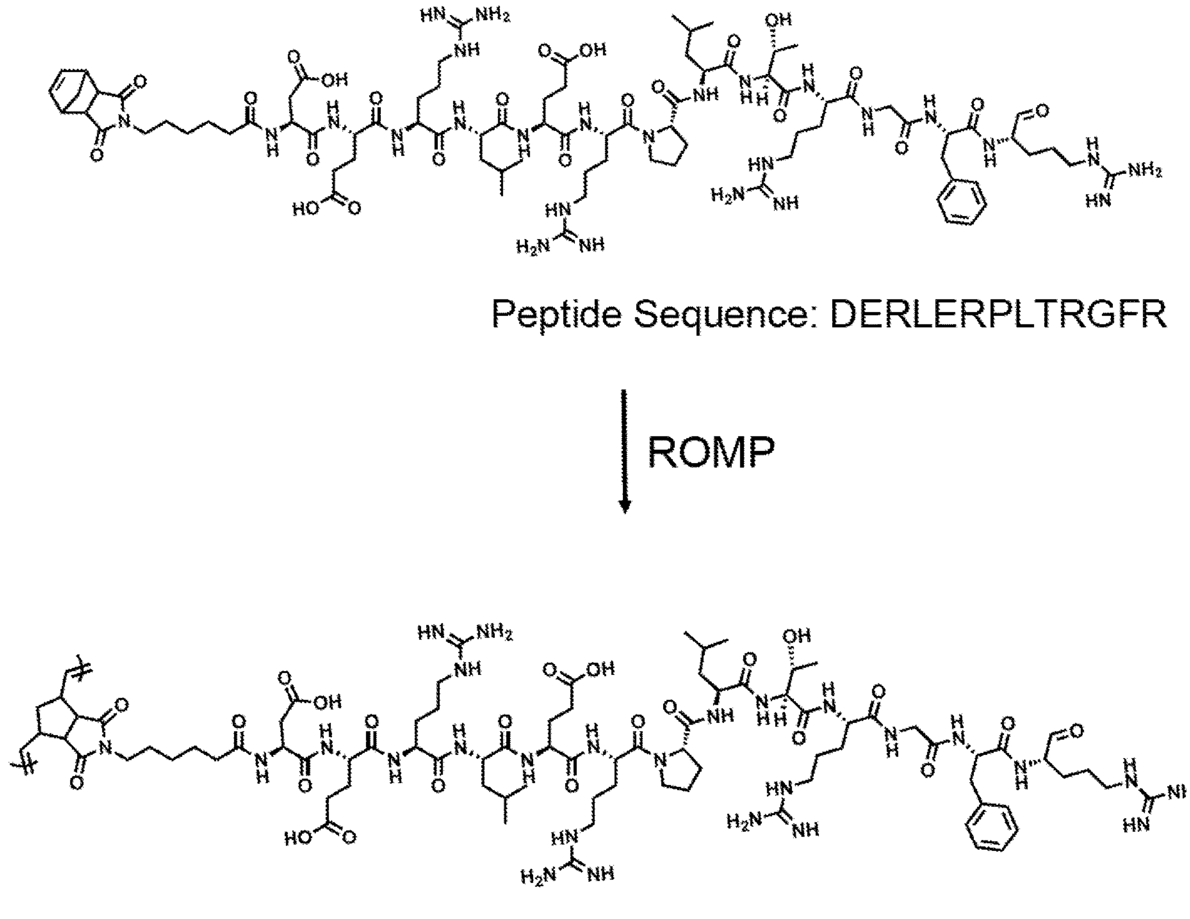
FIG. 16A shows the ring-opening metathesis polymerization (ROMP) of a polynorbornene dicarboxyimide monomer comprising SEQ ID NO: 143 (DERLERPLTRGFR) to form a polynorbornene dicarboxyimide-based brush polymer comprising the peptide SEQ ID SEQ ID NO: 143 (DERLERPLTRGFR), as described in Example 13.

This example provides an exemplary synthesis of a polynorbornene dicarboxyimide-based brush polymer comprising the scrambled peptide SEQ ID NO: 143 (DERLERPLTRGFR), as depicted in FIG. 16A. In other words, this example provides an exemplary synthesis of a polynorbornene dicarboxyimide-based brush polymer comprising a fully scrambled version of peptide SEQ ID NO: 72 (LDPETGEFLRRRR).

Fully scrambled peptide SEQ ID NO: 143 (DERLERPLTRGFR) (DP=average of about 8.7) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 16A was prepared by amide coupling to N-(hexanoic acid)-cis-5-norbornene-exo-dicarboximide at the N-terminus of peptide SEQ ID NO: 143 (DERLERPLTRGFR). Following completion of the synthesis, the peptide or peptide monomer was cleaved from the resin by treatment with TFA/$H_2O$/TIPS in a 9.5:2.5:2.5 ratio for 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide or peptide monomer was confirmed by ESI-MS or MALDI-ToF MS and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 16C. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 16B:
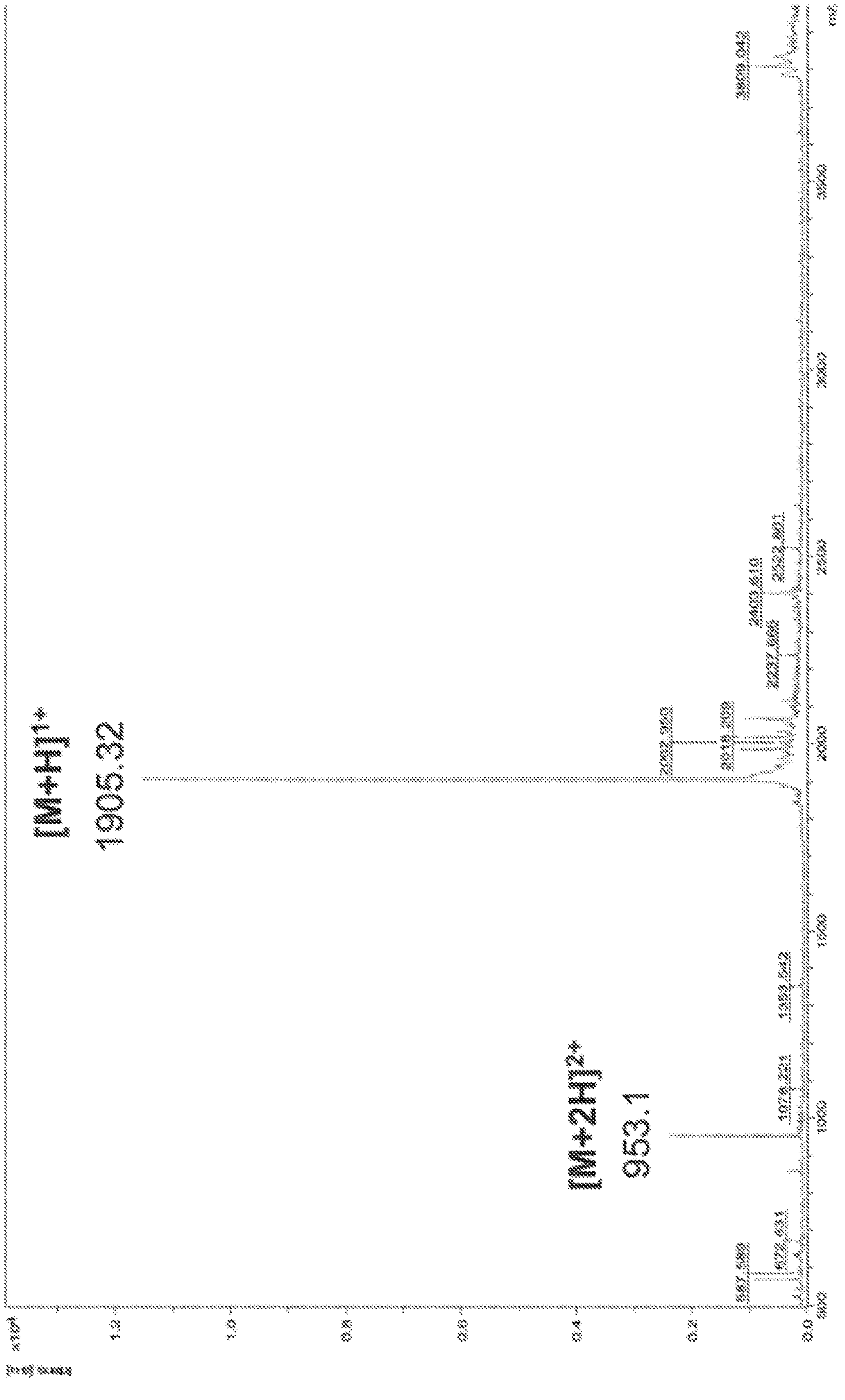
FIG. 16B shows the mass spectrum for the polynorbornene dicarboxyimide monomer comprising SEQ ID NO: 143 (DERLERPLTRGFR) as measured by MALDI mass spectrometry.
Figure 16C:
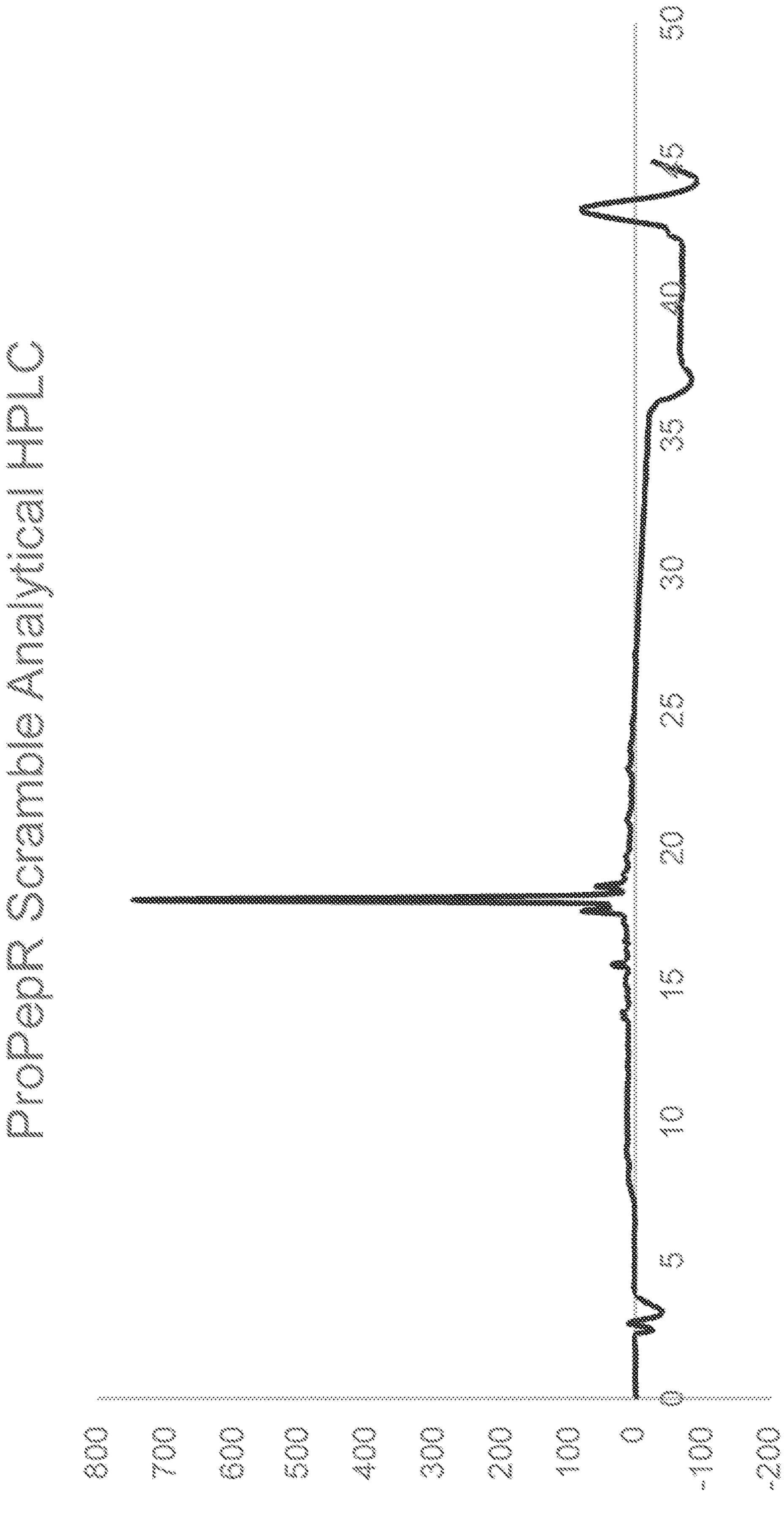
FIG. 16C shows the high-performance liquid chromatography (HPLC) analytical trace for the polynorbornene dicarboxyimide monomer comprising SEQ ID NO: 143 (DERLERPLTRGFR).

The identity of the polynorbornene dicarboxyimide monomer comprising SEQ ID NO: 143 (DERLERPLTRGFR) was confirmed by MALDI mass spectrometry with a mass of 1904 Da, as evidenced by FIG. 16B.

Purified monomers were polymerized in dry, degassed 1M LiCl dimethylformamide using a ROMP catalyst (e.g., Grubbs, Hoveyda-Grubbs, or Schrock) in respective ratio (e.g., 15:1) to generate a polymer with the desired degree of polymerization. For example, a theoretical desired degree of polymerization (DP) of 15 for a homopolymer a monomer stock of 30 mM was added to a catalyst stock of 2 mM of equal volume to generate a final reaction solution with 15 equivalents of monomer (15 mM, 100 mg, 0.078 mmol): 1 equivalent of catalyst (1 mM, 3.79 mg, 0.005 mmol) in 5.2 mL total of dry, degassed 1M LiCl DMF. The reaction was left at room temperature under stirring in a glove box under nitrogen gas. A portion of the reaction can be aliquoted for dye labeling through the addition of a Cy5.5 monomer block. For example, to dye label 14 of the reaction, 1 equivalent of Cy5.5 monomer (1.08 mg, 0.0013 mmol) in 1.3 mL 1M LiCl DMF was added to 1.3 mL of the initial reaction. Dye block additions were left for 30 min at room temperature with stirring in the glovebox under nitrogen gas.

Figure 16E:
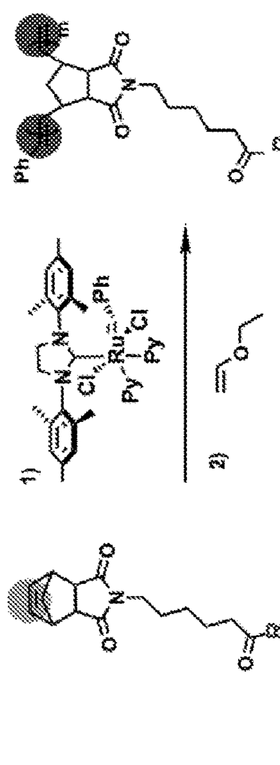
FIG. 16E shows the kinetics of the polymerization reaction for a full scramble polynorbornene dicarboxyimide-based brush polymer, comprising polynorbornene dicarboxyimide-based SEQ ID NO: 143 (DERLERPLTRGFR) peptide monomer, prepared according to Example 13.
Figure 16E:
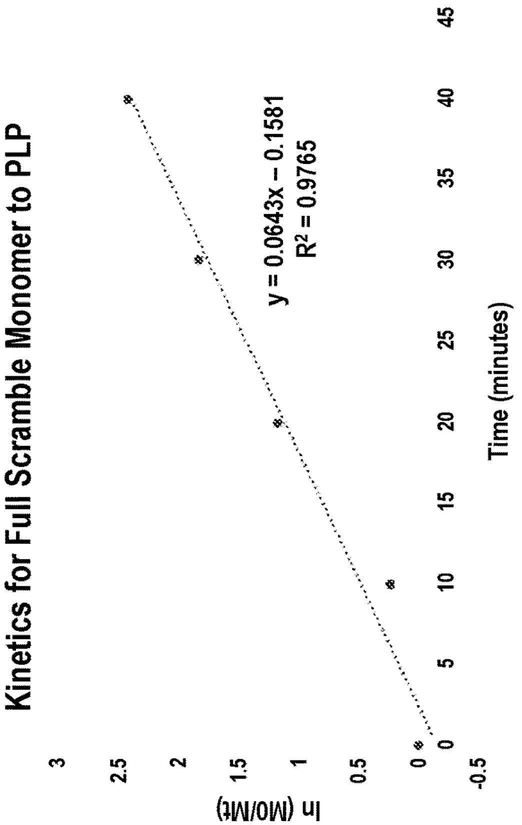
Figure 16D:
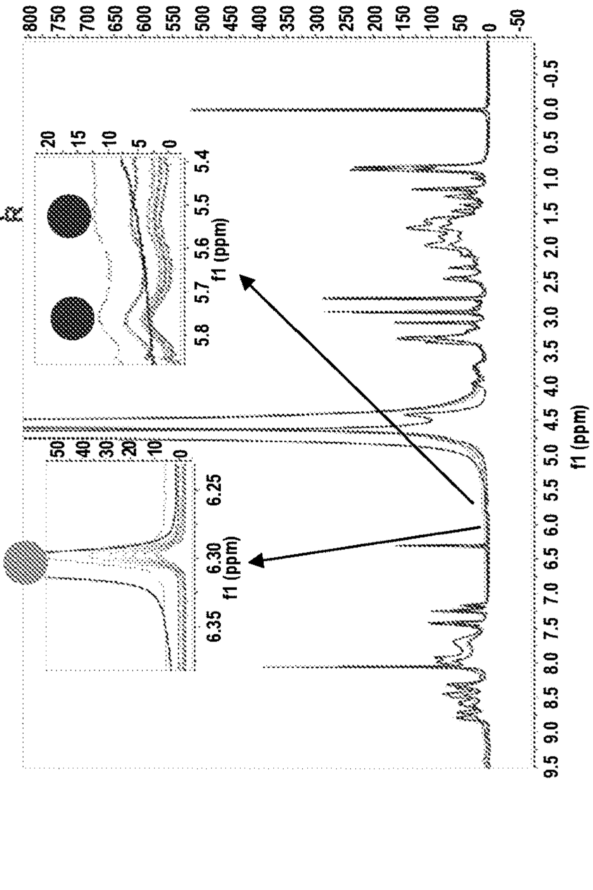
FIG. 16D depicts the polymerization reaction of polynorbornene dicarboxyimide-based SEQ ID NO: 143 (DERLERPLTRGFR) peptide monomer prepared according to Example 13, and the $^1$H NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone.

The polymerization reaction was monitored using $^1H$ NMR spectroscopy by measuring the consumption of the peptide monomer and to determine the time period required to reach completion. Termination was done with ethyl vinyl ether (10 eq.) for 30 minutes at room temperature with stirring. FIG. 16D depicts the polymerization reaction of polynorbornene dicarboxyimide-based SEQ ID NO: 143 (DERLERPLTRGFR) peptide monomer prepared according to this example, and the $^1H$ NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone. In addition to monitoring the polymerization reaction by using $^1H$ NMR spectroscopy, the kinetics of the polymerization reaction were plotted, and the results are set forth in FIG. 16E.

Following polymerization, the polymer was precipitated with cold ether and collected by centrifugation and dried overnight. The PLPs were further purified using dialysis in regenerated cellulose (3500 Da pore size) and 2 liters of miliQ water over a 48 hour period. The water was renewed at 24 hours and at 48 hours the dialyzed materials were collected, sterile filtered using a 0.22-micron PES filter, and lyophilized.

Figure 16F:
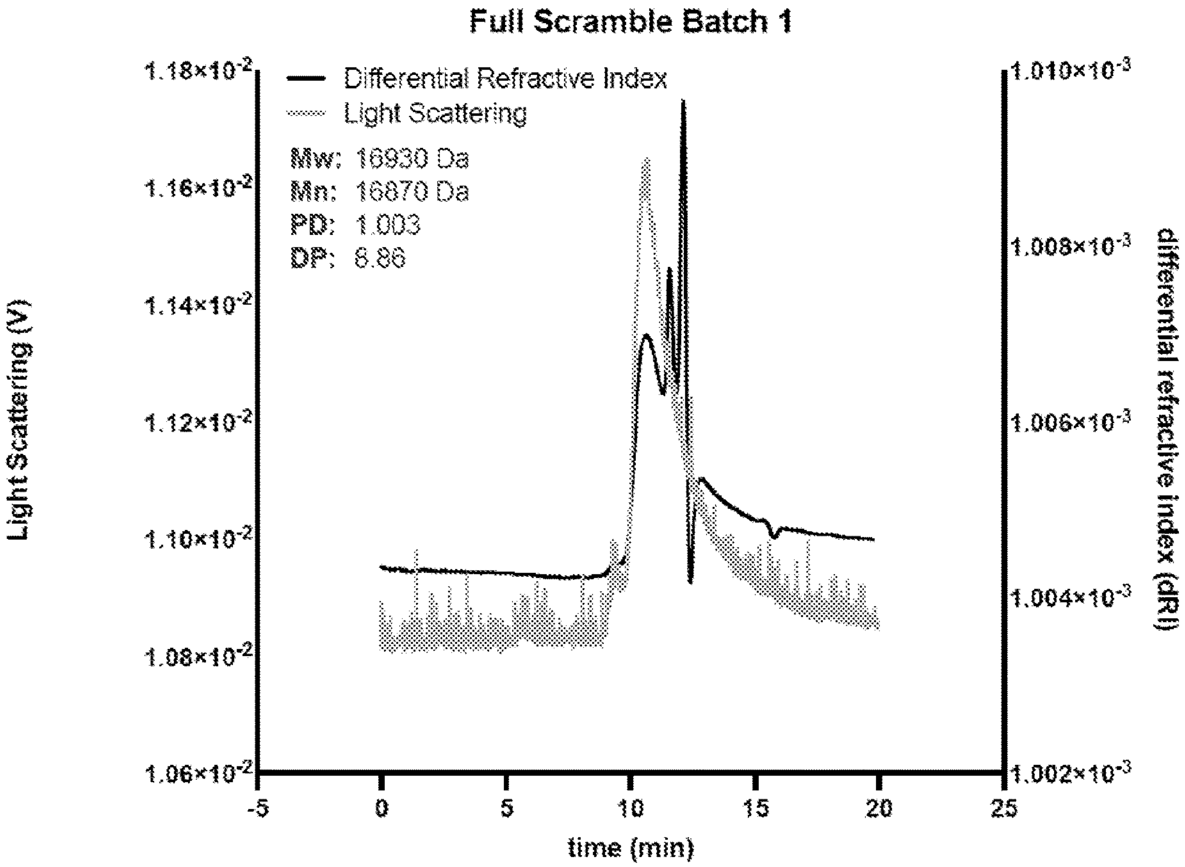
FIG. 16F shows the differential refractive index, as determined by aqueous gel permeation chromatography (GPC), for a particular batch of a polynorbornene dicarboxyimide-based brush polymer, comprising polynorbornene dicarboxyimide-based SEQ ID NO: 143 (DERLERPLTRGFR) peptide monomer, as prepared in Example 13.

In addition to monitoring the polymerization reaction by using $^1H$ NMR spectroscopy, the analytical properties and differential refractive index of the polynorbornene dicarboxyimide-based brush polymer, comprising polynorbornene dicarboxyimide-based SEQ ID NO: 143 (DERLERPLTRGFR) peptide monomer were determined by aqueous gel permeation chromatography (GPC), and the results for a particular batch are set forth in FIG. 16F.

Polymer dispersities ($M_w/M_n$) and molecular weights ($M_n$) were determined by aqueous phase gel permeation chromatography (GPC). To this end, aqueous phase GPC measurements were performed using a TOSOH Biosciences TSKgel G500$PW_{XL}$-CP column (7.8 mm ID×30 cm, 10 μm) with 0.1 M sodium nitrate buffer containing 0.1% TFA as the mobile phase with a flow rate of 1.0 mL/min. Detection consisted of a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software.

The polymers were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample)

and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

FIG. 18 shows the SDS-PAGE results for the full scramble polynorbornene dicarboxyimide-based brush polymer ("FS") comprising polynorbornene dicarboxyimide-based SEQ ID NO: 143 (DERLERPLTRGFR) peptide monomer prepared in this example, the scrambleRRRR polynorbornene dicarboxyimide-based brush polymer ("SR") comprising polynorbornene dicarboxyimide-based SEQ ID NO: 146 (DELEPLTGFRRRR) peptide monomer prepared in Example 14, the low degree of polymerization (LowDP) polynorbornene dicarboxyimide-based brush polymer ("$PPR_{low}$"—DP=average of about 11.6) comprising polynorbornene dicarboxyimide-based SEQ ID NO: 72 (LDPETGEFLRRRR) peptide monomer prepared in Example 12, and the high degree of polymerization (HighDP) polynorbornene dicarboxyimide-based brush polymer ("$PPR_{high}$"—DP=average of about 22.5) comprising polynorbornene dicarboxyimide-based SEQ ID NO: 72 (LDPETGEFLRRRR) peptide monomer prepared in Example 12.

Example 14

Figure 17A:
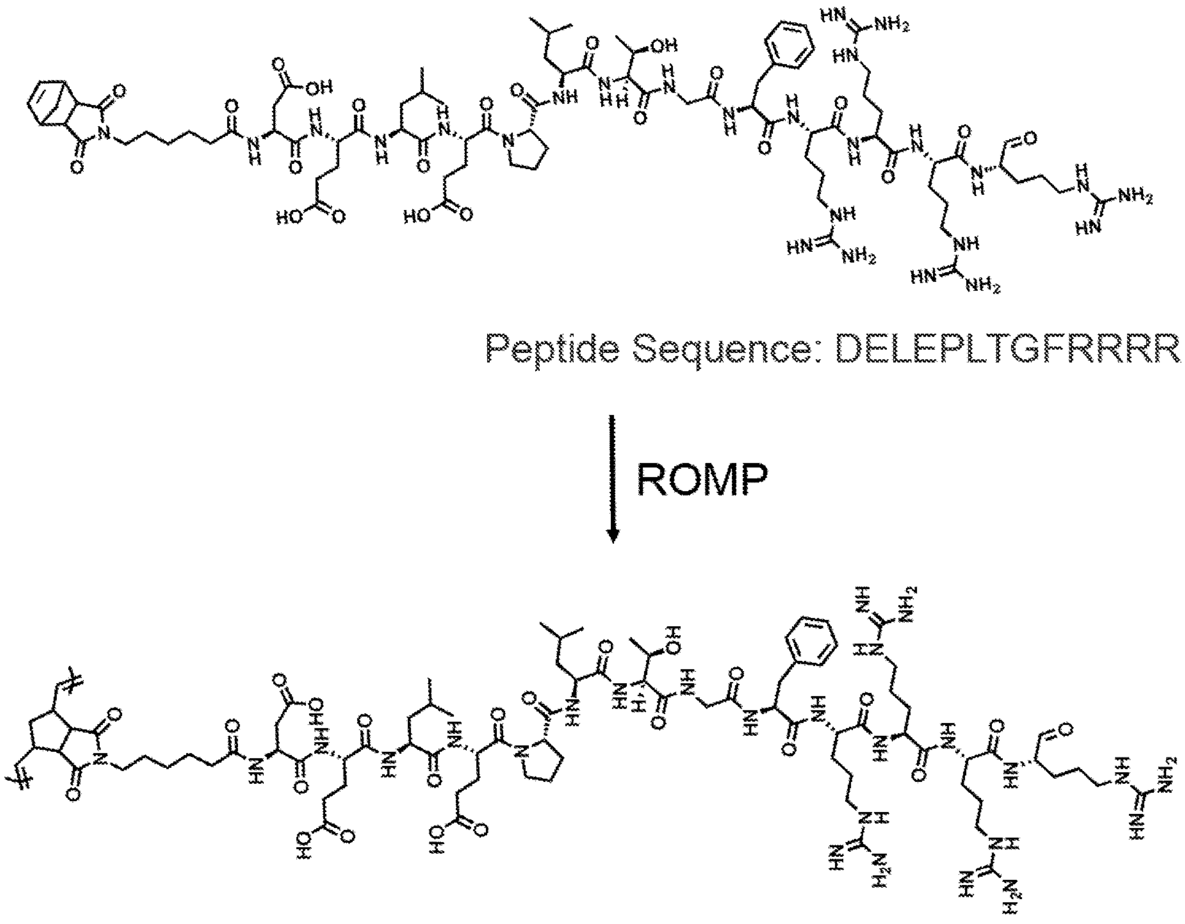
FIG. 17A shows the ring-opening metathesis polymerization (ROMP) of a polynorbornene dicarboxyimide monomer comprising SEQ ID NO: 146 (DELEPLTGFRRRR) to form a polynorbornene dicarboxyimide-based brush polymer comprising the peptide SEQ ID NO: 146 (DELEPLTGFRRRR), as described in Example 14.

This example provides an exemplary synthesis of a polynorbornene dicarboxyimide-based brush polymer comprising the scrambleRRRR (or "ScrambleR") peptide SEQ ID NO: 146 (DELEPLTGFRRRR), as depicted in FIG. 17A. In other words, this example provides an exemplary synthesis of a polynorbornene dicarboxyimide-based brush polymer comprising a semi scrambled version of peptide SEQ ID NO: 72 (LDPETGEFLRRRR), where the four arginine residues remain at the terminus.

ScrambleRRRR peptide SEQ ID NO: 146 (DELEPLTGFRRRR) (DP=average of about 10.2) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 17A was prepared by amide coupling to N-(hexanoic acid)-cis-5-norbornene-exo-dicarboximide at the N-terminus of peptide SEQ ID NO: 146 (DELEPLTGFRRRR). Following completion of the synthesis, the peptide or peptide monomer was cleaved from the resin by treatment with TFA/$H_2O$/TIPS in a 9.5:2.5:2.5 ratio for 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide or peptide monomer was confirmed by ESI-MS or MALDI-ToF MS and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 17C. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 17B:
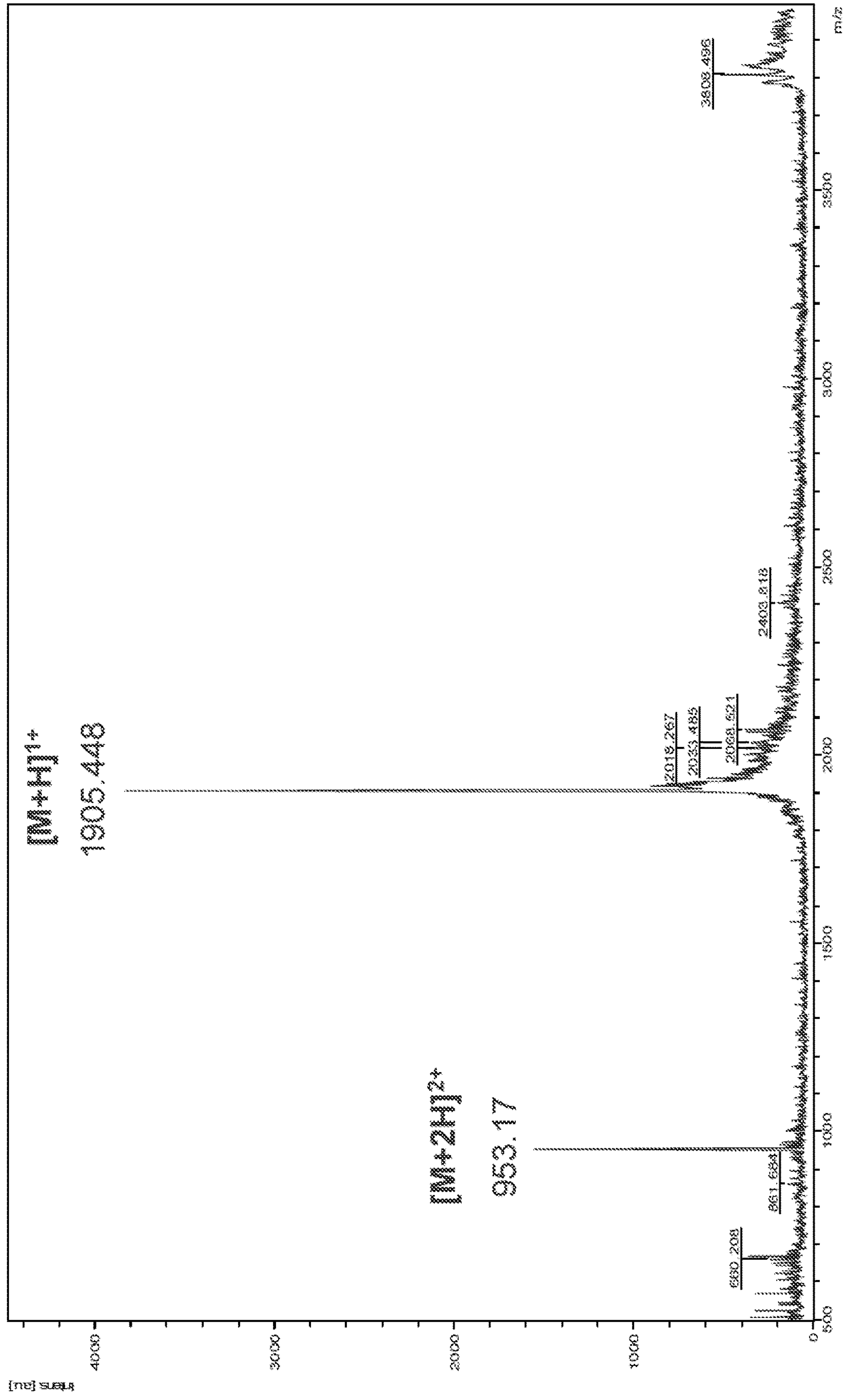
FIG. 17B shows the mass spectrum for the polynorbornene dicarboxyimide monomer comprising SEQ ID NO: 146 (DELEPLTGFRRRR) as measured by MALDI mass spectrometry.
Figure 17C:
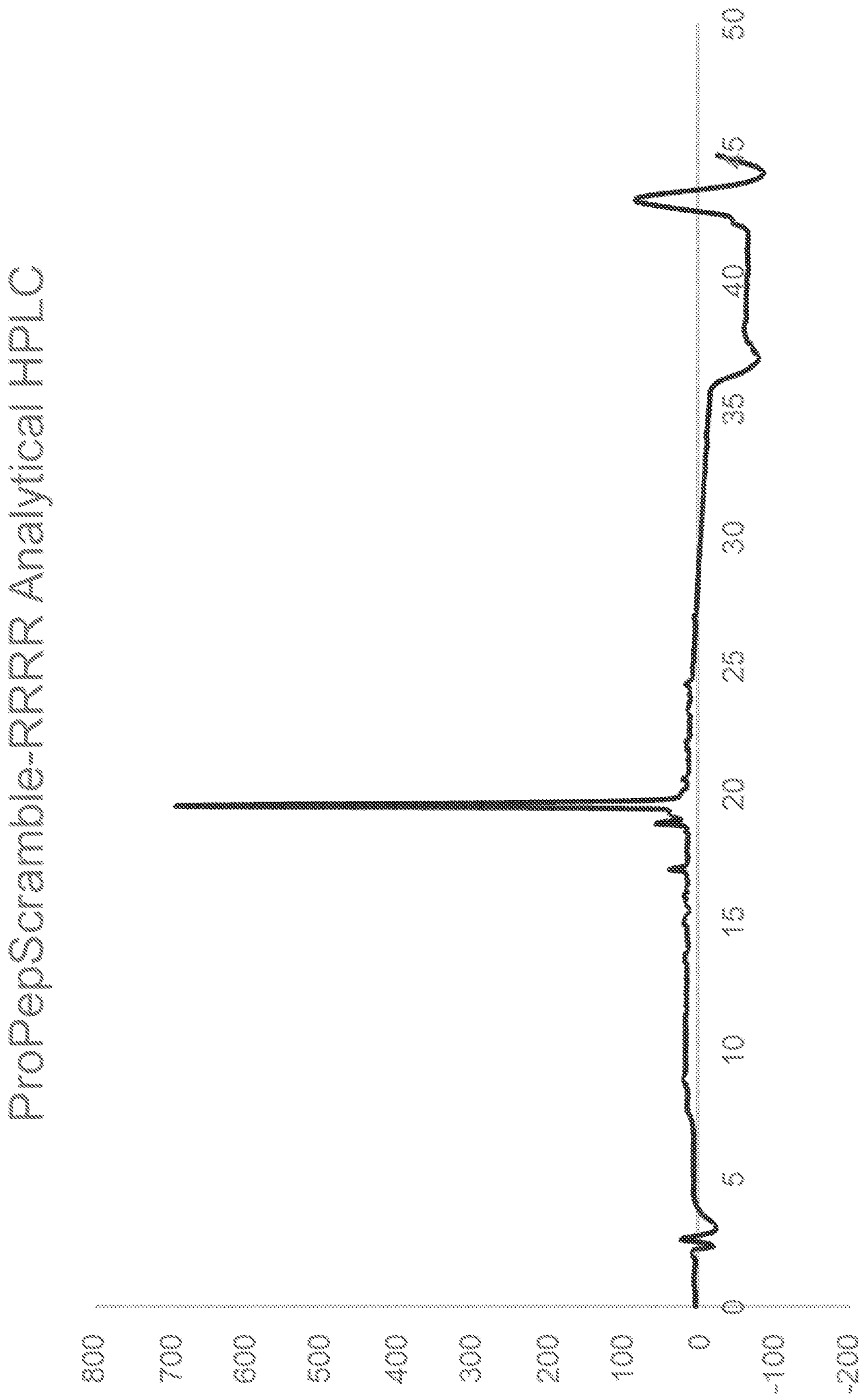
FIG. 17C shows the high-performance liquid chromatography (HPLC) analytical trace for the polynorbornene dicarboxyimide monomer comprising SEQ ID NO: 146 (DELEPLTGFRRRR).

The identity of the polynorbornene dicarboxyimide monomer comprising SEQ ID NO: 146 (DELEPLTGFRRRR) was confirmed by MALDI mass spectrometry with a mass of 1904 Da, as evidenced by FIG. 17B.

Purified monomers were polymerized in dry, degassed 1M LiCl dimethylformamide using a ROMP catalyst (e.g., Grubbs, Hoveyda-Grubbs, or Schrock) in respective ratio (e.g., 15:1) to generate a polymer with the desired degree of polymerization. For example, a theoretical desired degree of polymerization (DP) of 15 for a homopolymer a monomer stock of 30 mM was added to a catalyst stock of 2 mM of equal volume to generate a final reaction solution with 15 equivalents of monomer (15 mM, 100 mg, 0.078 mmol): 1 equivalent of catalyst (1 mM, 3.79 mg, 0.005 mmol) in 5.2 mL total of dry, degassed 1M LiCl DMF. The reaction was left at room temperature under stirring in a glove box under nitrogen gas. A portion of the reaction can be aliquoted for dye labeling through the addition of a Cy5.5 monomer block. For example, to dye label ¼ of the reaction, 1 equivalent of Cy5.5 monomer (1.08 mg, 0.0013 mmol) in 1.3 mL 1M LiCl DMF was added to 1.3 mL of the initial reaction. Dye block additions were left for 30 min at room temperature with stirring in the glovebox under nitrogen gas.

Figure 17D:
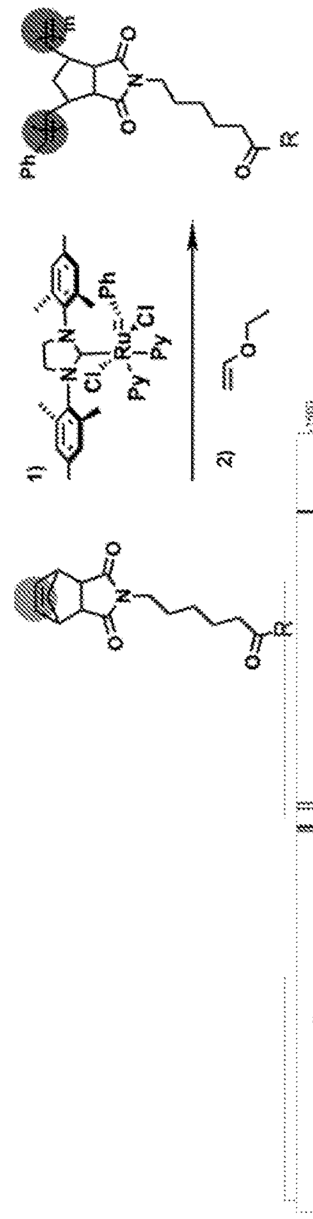
FIG. 17D depicts the polymerization reaction of polynorbornene dicarboxyimide-based SEQ ID NO: 146 (DELEPLTGFRRRR) peptide monomer prepared according to Example 14, and the $^1$H NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone.
Figure 17D:
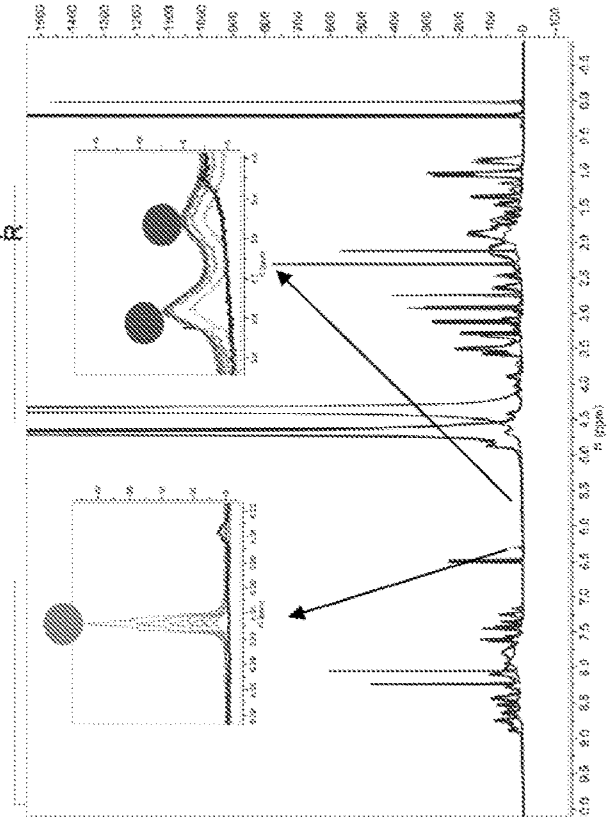
Figure 17E:
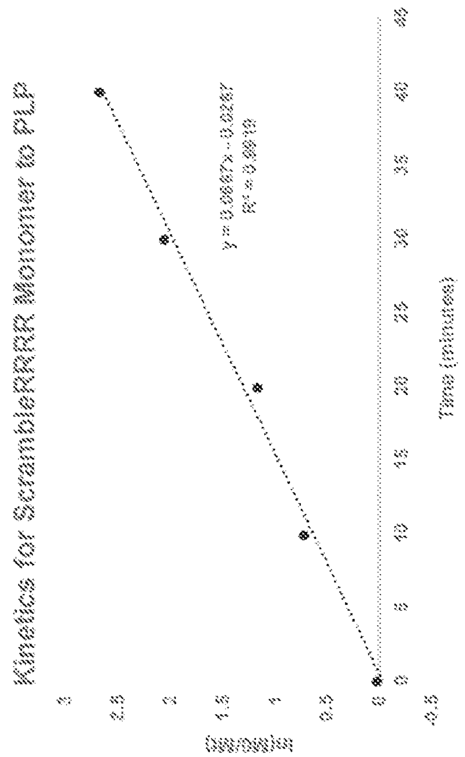
FIG. 17E shows the kinetics of the polymerization reaction for a scrambleRRRR polynorbornene dicarboxyimide-based brush polymer, comprising polynorbornene dicarboxyimide-based SEQ ID NO: 146 (DELEPLTGFRRRR) peptide monomer, prepared according to Example 14.

The polymerization reaction was monitored using $^1$H NMR spectroscopy by measuring the consumption of the peptide monomer and to determine the time period required to reach completion. Termination was done with ethyl vinyl ether (10 eq.) for 30 minutes at room temperature with stirring. FIG. 17D depicts the polymerization reaction of polynorbornene dicarboxyimide-based SEQ ID NO: 146 (DELEPLTGFRRRR) peptide monomer prepared according to this example, and the $^1$H NMR spectra for the time course experiments monitoring the polymerization reaction. The disappearance of the resonance at δ=6.3 ppm corresponding to the olefin protons of the monomer and the coincident appearance of resonances δ=5-6 ppm, which correspond to the cis and trans olefin protons of the polymer backbone. In addition to monitoring the polymerization reaction by using $^1$H NMR spectroscopy, the kinetics of the polymerization reaction were plotted, and the results are set forth in FIG. 17E.

Following polymerization, the polymer was precipitated with cold ether and collected by centrifugation and dried overnight. The PLPs were further purified using dialysis in regenerated cellulose (3500 Da pore size) and 2 liters of miliQ water over a 48 hour period. The water was renewed at 24 hours and at 48 hours the dialyzed materials were collected, sterile filtered using a 0.22-micron PES filter, and lyophilized.

Figure 17F:
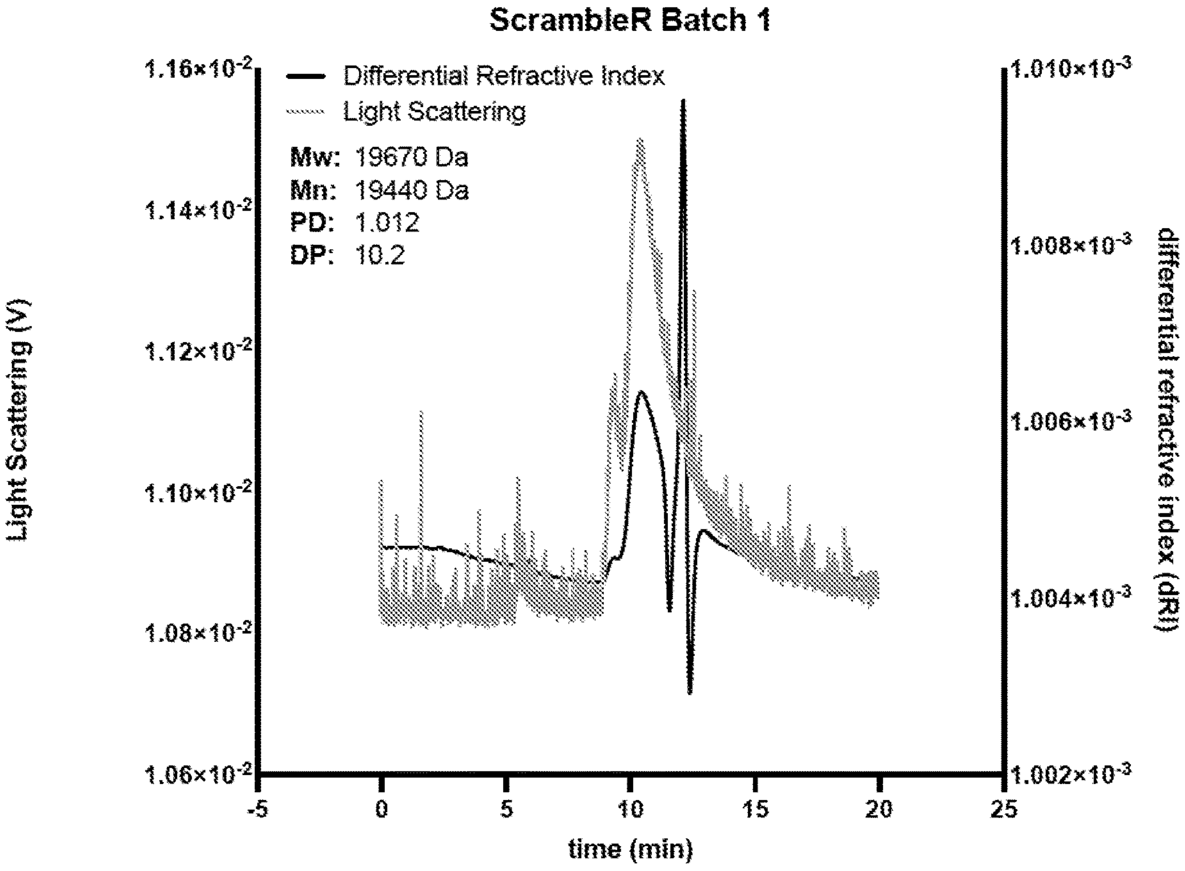
FIG. 17F shows the differential refractive index, as determined by aqueous gel permeation chromatography (GPC), for a particular batch of a polynorbornene dicarboxyimide-based brush polymer, comprising polynorbornene dicarboxyimide-based SEQ ID NO: 146 (DELEPLTGFRRRR) peptide monomer, as prepared in Example 14.

In addition to monitoring the polymerization reaction by using $^1$H NMR spectroscopy, the analytical properties and differential refractive index of the polynorbornene dicarboxyimide-based brush polymer, comprising polynorbornene dicarboxyimide-based SEQ ID NO: 146 (DELEPLTGFRRRR) peptide monomer were determined by aqueous gel permeation chromatography (GPC), and the results for a particular batch are set forth in FIG. 17F.

Polymer dispersities ($M_w/M_n$) and molecular weights ($M_n$) were determined by aqueous phase gel permeation chromatography (GPC). To this end, aqueous phase GPC measurements were performed using a TOSOH Biosciences TSKgel G500PW$_{XL}$-CP column (7.8 mm ID×30 cm, 10 μm) with 0.1 M sodium nitrate buffer containing 0.1% TFA as the mobile phase with a flow rate of 1.0 mL/min. Detection consisted of a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software.

The polymers were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

FIG. 18 shows the SDS-PAGE results for the full scramble polynorbornene dicarboxyimide-based brush polymer ("FS") comprising polynorbornene dicarboxyimide-based SEQ ID NO: 143 (DERLERPLTRGFR) peptide monomer prepared in Example 13, the scrambleRRRR polynorbornene dicarboxyimide-based brush polymer ("SR") comprising polynorbornene dicarboxyimide-based SEQ ID NO: 146 (DELEPLTGFRRRR) peptide monomer prepared in this example, the low degree of polymerization (LowDP) polynorbornene dicarboxyimide-based brush polymer ("PPR$_{low}$"—DP=average of about 11.6) comprising polynorbornene dicarboxyimide-based SEQ ID NO: 72 (LDPETGEFLRRRR) peptide monomer prepared in Example 12, and the high degree of polymerization (HighDP) polynorbornene dicarboxyimide-based brush polymer ("PPR$_{high}$"—DP=average of about 22.5) comprising polynorbornene dicarboxyimide-based SEQ ID NO: 72 (LDPETGEFLRRRR) peptide monomer prepared in Example 12.

Example 15

Figure 19A:
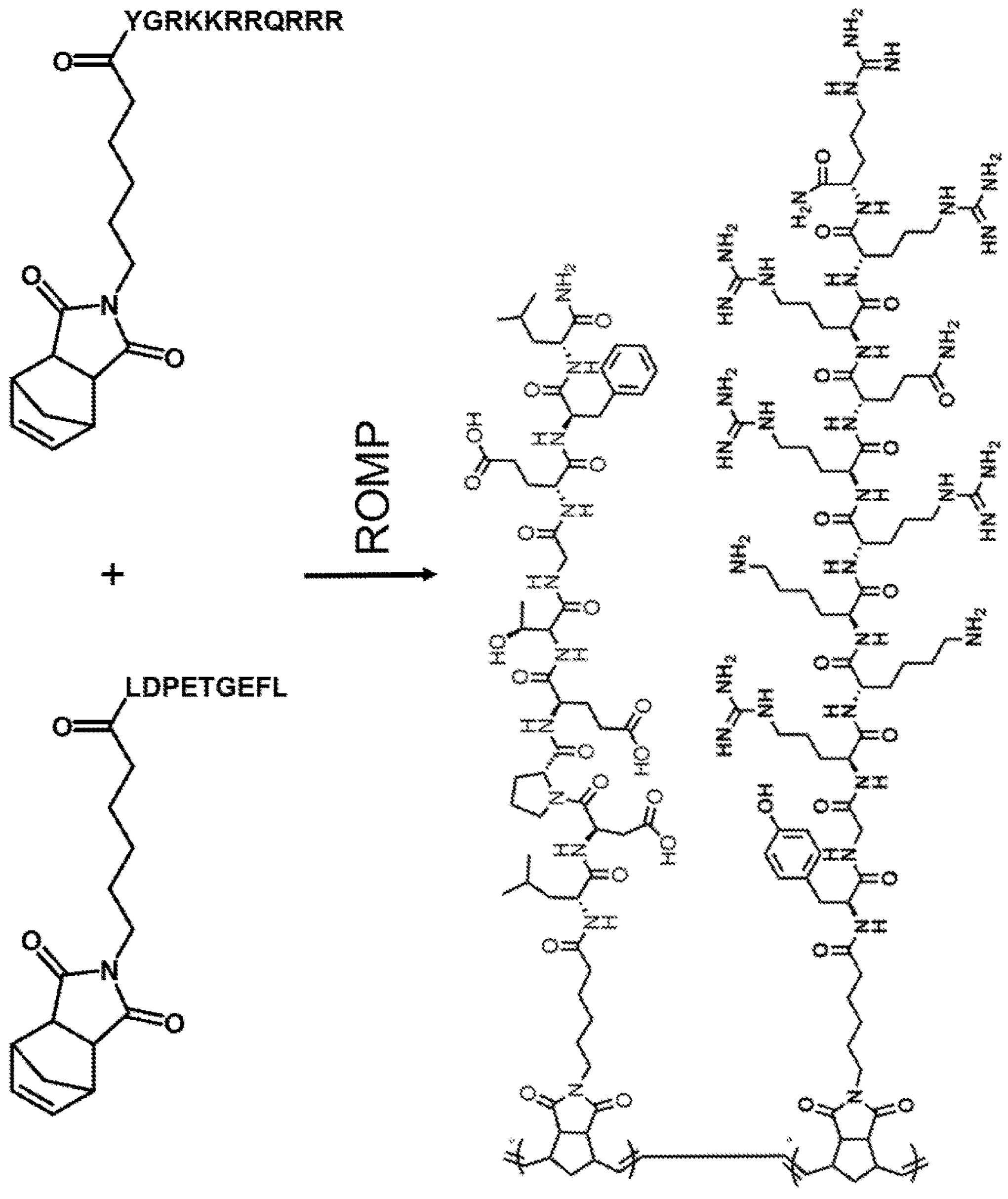
FIG. 19A shows the ring-opening metathesis polymerization (ROMP) of a polynorbornene dicarboxyimide monomer comprising SEQ ID NO: 2 (LDPETGEFL) and a polynorbornene dicarboxyimide monomer comprising TAT peptide SEQ ID NO: 142 (YGRKKRRQRRR) to form a polynorbornene dicarboxyimide-based brush polymer comprising peptide SEQ ID NO: 2 (LDPETGEFL) and TAT peptide SEQ ID NO: 142 (YGRKKRRQRRR), as described in Example 15.

This example provides an exemplary synthesis of a polynorbornene dicarboxyimide-based brush polymer comprising peptide SEQ ID NO: 2 (LDPETGEFL) and TAT peptide SEQ ID NO: 142 (YGRKKRRQRRR), as depicted in FIG. 19A.

Peptide SEQ ID NO: 2 (LDPETGEFL) and TAT peptide SEQ ID NO: 142 (YGRKKRRQRRR) were synthesized using standard solid phase peptide synthesis (SPPS) procedures on an AAPPTec Focus XC automated synthesizer. The peptides were prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomers depicted in FIG. 19A was prepared by amide coupling to N-(hexanoic acid)-cis-5-norbornene-exo-dicarboximide at the N-terminus of peptide SEQ ID NO: 2 (LDPETGEFL) and TAT peptide SEQ ID NO: 142 (YGRKKRRQRRR). Following completion of the synthesis, the peptide or peptide monomer was cleaved from the resin by treatment with TFA/$H_2O$/TIPS in a 9.5:2.5:2.5 ratio for 4 hours. The peptide or monomer was then filtered, precipitated and centrifuged in cold ether and dried overnight under vacuum. Cleaved monomers and peptides were characterized via analytical HPLC and mass spectrometry and then purified by RP-HPLC. The identity of the peptide monomer was confirmed by ESI-MS or MALDI-ToF MS and purity was verified by observation of a single peak in the analytical RP-HPLC chromatogram.

The purity of the peptide monomers were verified by scale RP-HPLC, where a single peak in the chromatogram of a newly purified peptide monomer was taken as an indication of a pure material. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomers were purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

The identity of the polynorbornene dicarboxyimide monomer comprising SEQ ID NO: 2 (LDPETGEFL) was confirmed by electrospray ionization (ESI) mass spectrometry with a mass of 1278 Da, as evidenced by FIG. 13C, and as described in Example 11. The identity of the polynorbornene dicarboxyimide monomer comprising TAT peptide SEQ ID NO: 142 (YGRKKRRQRRR) was confirmed by electrospray ionization (ESI) mass spectrometry with a mass of 1817 Da.

Polymerization was carried out in a glovebox under $N_2$ by mixing the monomers and ROMP catalyst (e.g., Grubbs, Hoveyda-Grubbs, or Schrock) in respective ratio (e.g., 10:5) in dry DMF containing LiCl (1 M). For the block copolymers of this example, the two monomers are sequentially added. In particular, the 10:5 ratio (first peptide monomer: second peptide monomer) was synthesized by first adding 10:1 of the first peptide monomer (monomer:catalyst) and polymerizing until near completion, as determined by NMR. Subsequently, the second peptide monomer was added as 5 equivalents based on the initial catalyst. The second block was allowed to polymerize and then the polymer is terminated. For a random copolymer having two different monomers with a degree of polymerization of 15, the first monomer (0.0125 mmol, 10 equiv, 25 mM) and a second monomer (0.00625 mmol, 5 equiv, 12.5 mM) are mixed with the ROMP catalyst (e.g., Grubbs, Hoveyda-Grubbs, or Schrock) (0.00125 mmol, 1 equiv, 2.5 mM) in dry DMF (0.5 mL) containing LiCl (1 M) at the same time.

Figure 19B:
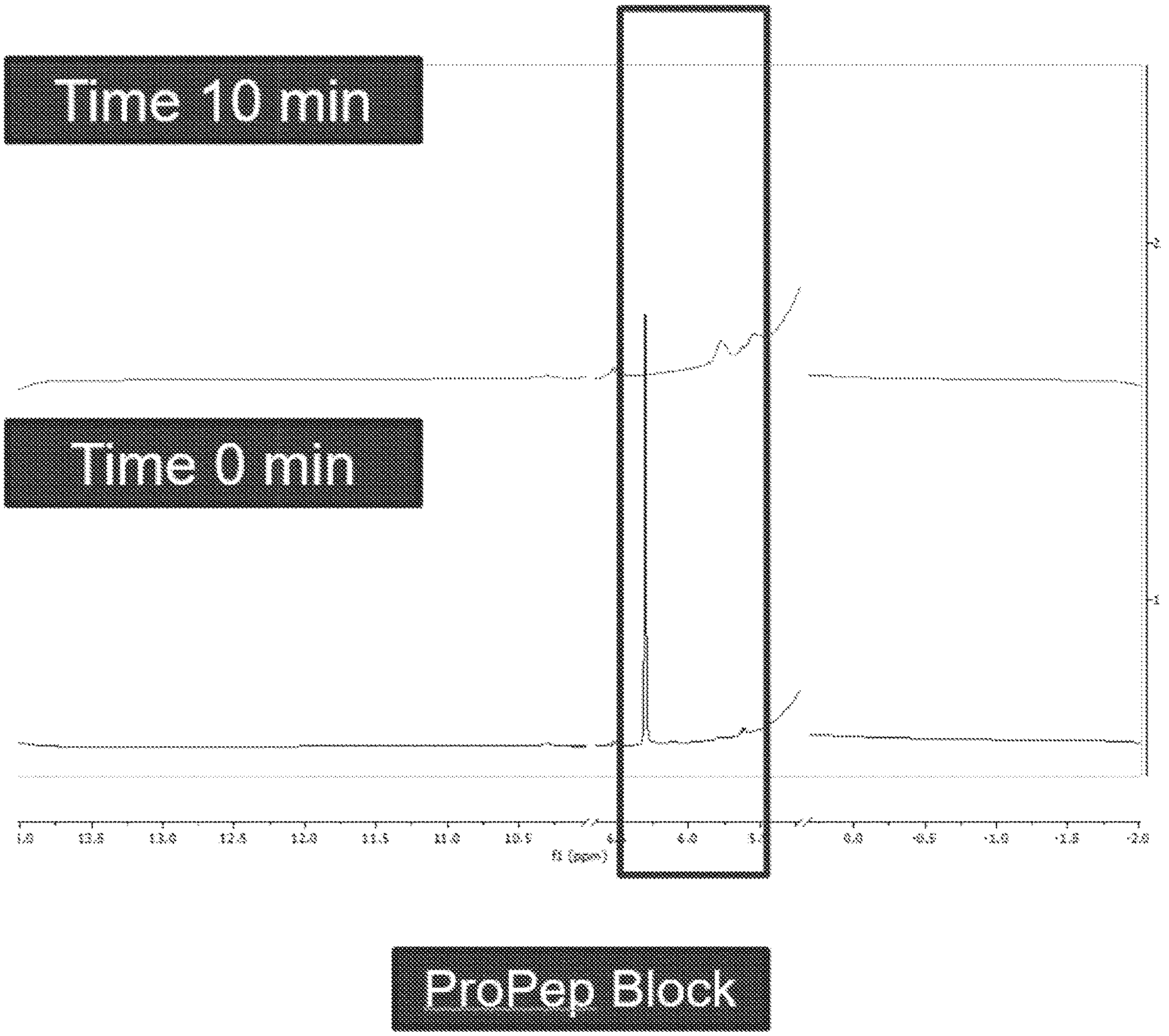
FIGS. 19B and 19C depict the polymerization reaction of polynorbornene dicarboxyimide-based SEQ ID NO: 2 (LDPETGEFL) peptide monomer and polynorbornene dicarboxyimide-based SEQ ID NO: 142 (YGRKKRRQRRR) peptide monomer prepared according to Example 15, and the $^{1}H$ NMR spectra for the time course experiments monitoring the polymerization reaction. The disappearance of the resonance at δ=6.5 ppm corresponding to the olefin protons of the monomer and the coincident appearance of resonances δ=5-6 ppm, which correspond to the cis and trans olefin protons of the polymer backbone.
Figure 19C:
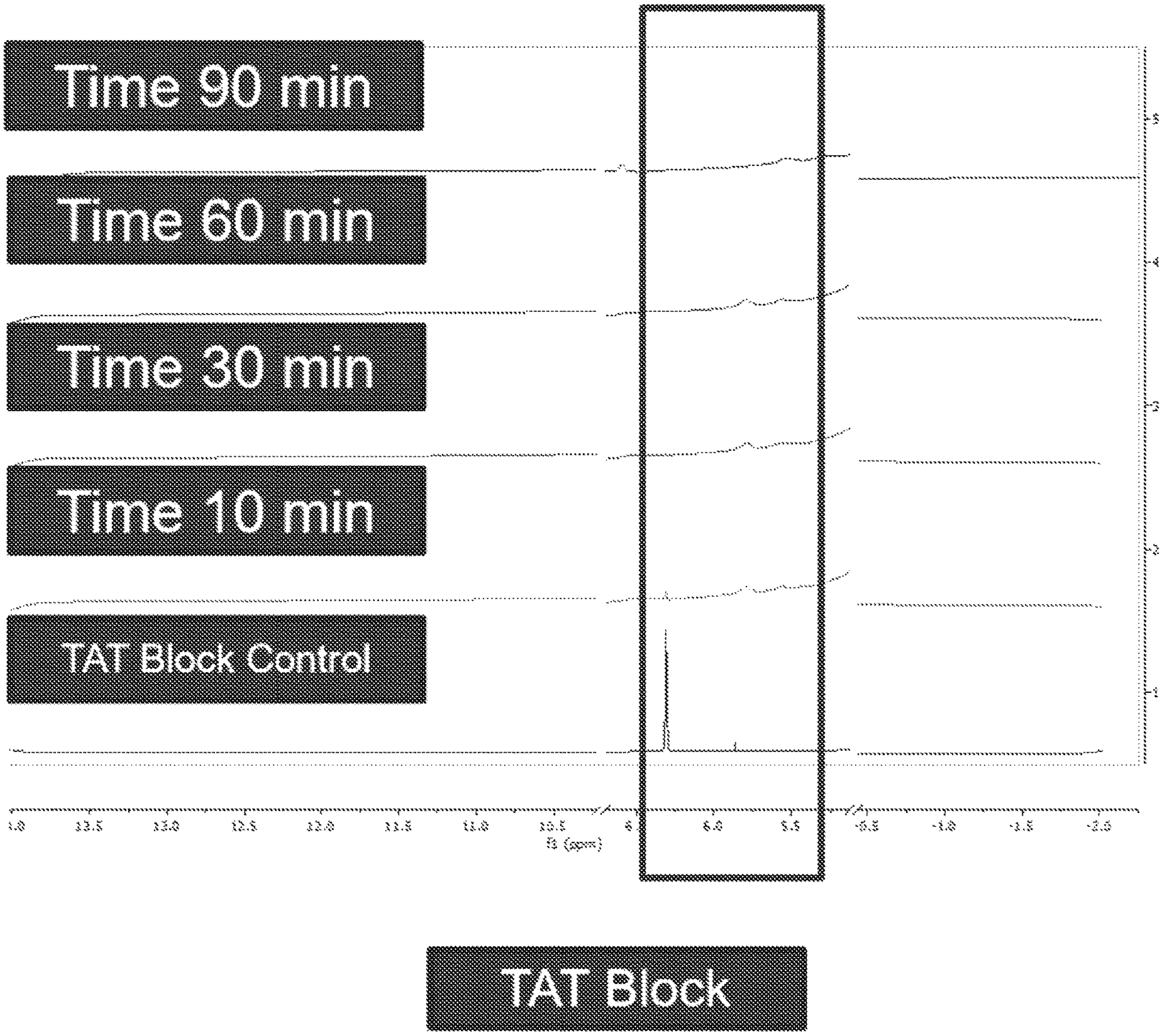

The polymerization reaction was monitored using $^1H$ NMR spectroscopy by measuring the consumption of the peptide monomer and to determine the time period required to reach completion. Termination was done with ethyl vinyl ether (10 eq.) for 30 minutes at room temperature with stirring. FIGS. 19B and 19C depict the polymerization reaction of polynorbornene dicarboxyimide-based SEQ ID NO: 2 (LDPETGEFL) peptide monomer and polynorbornene dicarboxyimide-based SEQ ID NO: 142 (YGRKKRRQRRR) peptide monomer prepared according to this example, and the $^1H$ NMR spectra for the time course experiments monitoring the polymerization reaction. The disappearance of the resonance at δ=6.5 ppm corresponding to the olefin protons of the monomer and the coincident appearance of resonances δ=5-6 ppm, which correspond to the cis and trans olefin protons of the polymer backbone.

Example 16

This example provides an analysis of the three-dimensional structures exhibited by a low degree of polymerization polynorbornene dicarboxyimide-based brush polymer ("ProPepR Low"—DP=average of about 11.6) comprising polynorbornene dicarboxyimide-based SEQ ID NO: 72 (LDPETGEFLRRRR) peptide monomer, a high degree of polymerization polynorbornene dicarboxyimide-based brush polymer ("ProPepR High"—DP=average of about 22.5) comprising polynorbornene dicarboxyimide-based SEQ ID NO: 72 (LDPETGEFLRRRR) peptide monomer, a scrambleRRRR polynorbornene dicarboxyimide-based brush polymer (i.e., "ScrambleR") comprising polynorbornene dicarboxyimide-based SEQ ID NO: 146 (DELEPLTGFRRRR) peptide monomer, and a full scramble polynorbornene dicarboxyimide-based brush polymer (i.e., "Full Scramble") comprising polynorbornene dicarboxyimide-based SEQ ID NO: 143 (DERLERPLTRGFR) peptide monomer.

SAXS experiments were conducted at the 5-ID-D beamline of the Dupont-Northwestern-Dow Collaborative Access Team (DND-CAT) at the Advanced Photon Source, Argonne National Laboratory. PLPs were prepared in miliQ water at 5 mg/mL and loaded into 1.5 mm quartz capillaries for SAXS. The capillaries were then sealed with epoxy to prevent solvent evaporation prior to data acquisition. Capillaries were loaded into a variable temperature multicapillary holder. Two-dimensional scattering patterns were obtained from 10 second exposure using a Rayonix MX170-HS CCD area detector using a 0.5 second exposure time to X-rays with a wavelength of λ=0.7293 Å and a sample-to-detector distance of 8.5 m. The 2D data were azimuthally averaged to yield 1D scattering patterns as intensity versus q. Incoherent background scattering was measured by acquiring scattering patterns for a solvent-loaded capillary in the absence of polymer. The experimental data was fit to a power law of the form $I(q)=A+Bq^{-m}+Cq^2$ and subtracted from the polymer data, where $2 \leq m \leq 4$. The results are set forth in FIGS. 20A-20D.

Figure 20A:
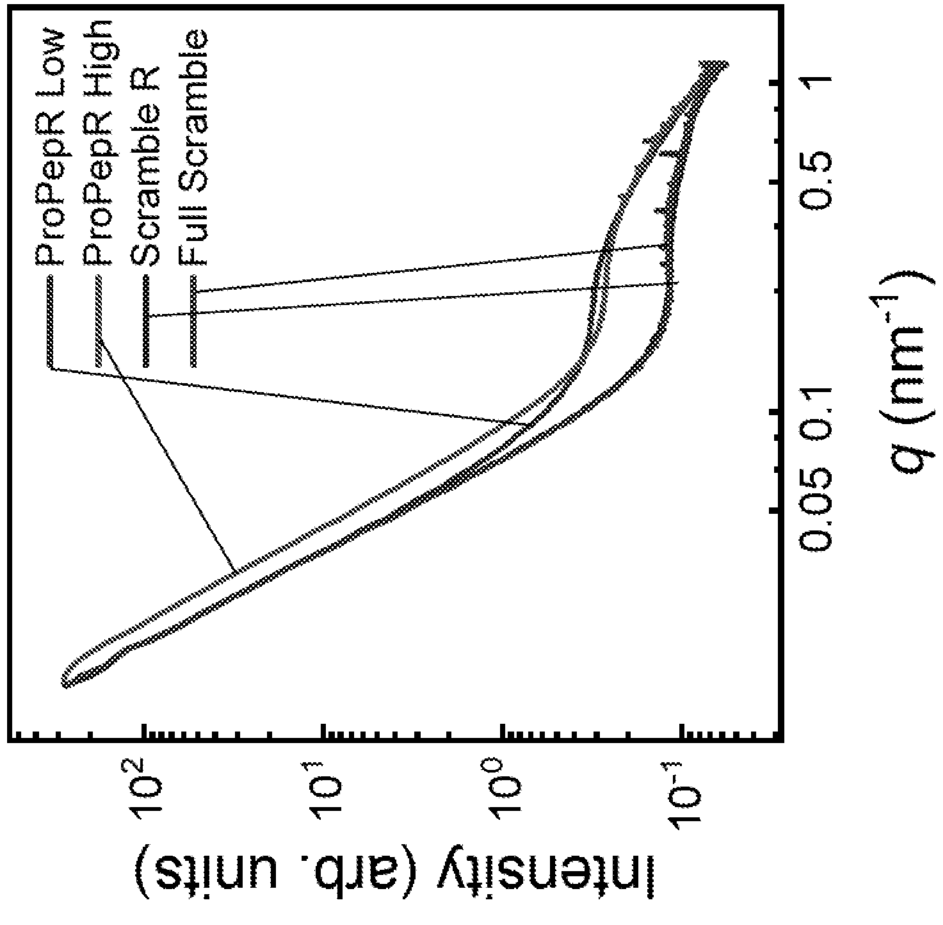
FIG. 20A shows the background subtracted intensity vs. scattering vector plot for (a) a low degree of polymerization polynorbornene dicarboxyimide-based brush polymer ("ProPepR Low"—DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("ProPepR High"—DP=average of about 22.5) comprising polynorbornene dicarboxyimide-based SEQ ID NO: 72 (LDPETGEFLRRRR) peptide monomer, (c) a scrambleRRRR polynorbornene dicarboxyimide-based brush polymer (i.e., "ScrambleR") comprising polynorbornene dicarboxyimide-based SEQ ID NO: 146 (DELEPLTGFRRRR) peptide monomer, and (d) a full scramble polynorbornene dicarboxyimide-based brush polymer (i.e., "Full Scramble") comprising polynorbornene dicarboxyimide-based SEQ ID NO: 143 (DERLERPLTRGFR) peptide monomer, as described in Example 16.

FIG. 20A shows the background subtracted intensity vs. scattering vector plot for the ProPepR PLPs (i.e., ProPepR Low and ProPepR High) and sequence scrambled PLPs (i.e., ScrambleR and Full Scramble) in water. At high q, there is a noticeable shoulder in the spectrum for the ProPepR PLP for both low and high DP that is absent for the sequence scrambled PLPs, which is indicative of more compact, globular structures. These results show that the ScrambleR and Full Scramble PLPs are more extended in water.

Figure 20B:
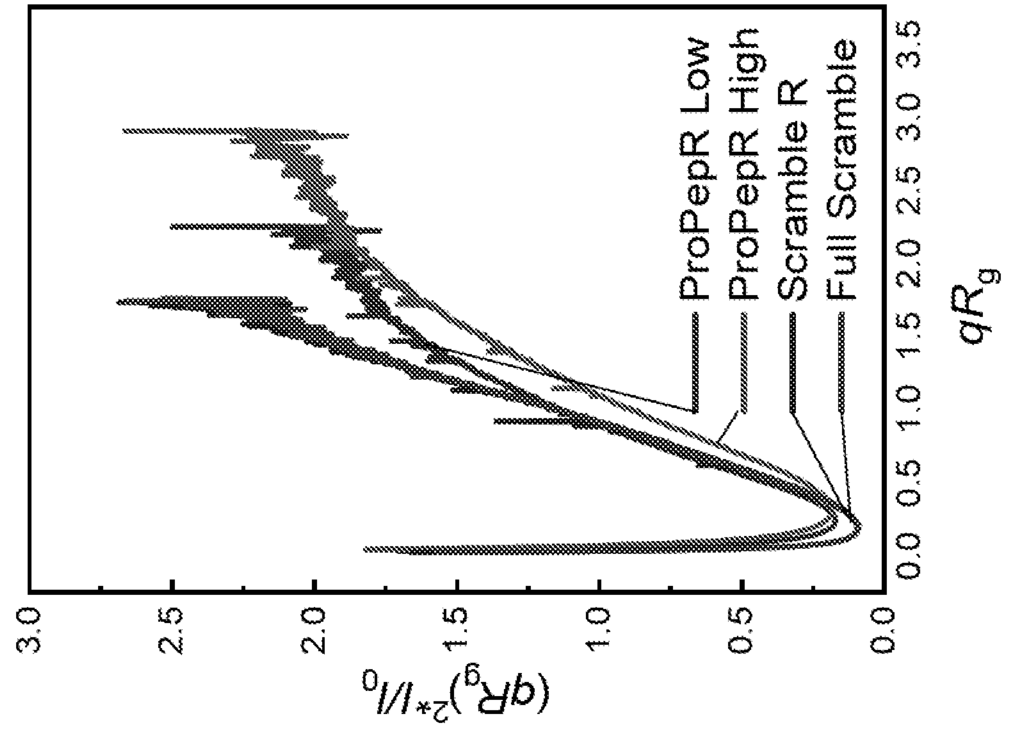
FIG. 20B shows a Kratky plot for (a) a low degree of polymerization polynorbornene dicarboxyimide-based brush polymer ("ProPepR Low"—DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("ProPepR High"—DP=average of about 22.5) comprising polynorbornene dicarboxyimide-based SEQ ID NO: 72 (LDPETGEFLRRRR) peptide monomer, (c) a scrambleRRRR polynorbornene dicarboxyimide-based brush polymer (i.e., "ScrambleR") comprising polynorbornene dicarboxyimide-based SEQ ID NO: 146 (DELEPLTGFRRRR) peptide monomer, and (d) a full scramble polynorbornene dicarboxyimide-based brush polymer (i.e., "Full Scramble") comprising polynorbornene dicarboxyimide-based SEQ ID NO: 143 (DERLERPLTRGFR) peptide monomer, as described in Example 16.

To more closely analyze high q scattering and gain further insight into polymer structure in solution, Kratky plots were constructed, and the results are set forth in FIG. 20B. In that respect, the standard Kratky format, $q^2I$ vs. q, was made dimensionless by multiplying q by $R_g$ to normalize for different coil sizes and by dividing I by I(q=0) to normalize for different molar masses and concentrations. This allows for direct comparison of the topology of the different PLPs, regardless of size and concentration, and observation of trends related to chemistry. A fully collapsed, spherical globule will show a bell-shaped profile in the Kratky format. The local maxima for a sphere occurs at $qR_g=3^{1/2}$ with I/I(0)=1.104. Peaks shifted to higher $qR_g$ and higher I/I(0) are more asymmetric and/or partially unfolded Gaussian coils plateau at I/I(0)=2, while fully extended chains will asymptotically increase.

As shown in FIG. 20B, the Full Scramble and ScrambleR PLPs show an asymptotically increasing intensity in the dimensionless Kratky format indicative of more unfolded and extended chains. In contrast, the ProPepR PLPs exhibit a downturn in intensity at the edge of the SAXS q-range. While these plots are not indicative of fully collapsed globules, they do suggest a slight degree of folding/compaction into asymmetric structures. These results confirm the conclusions provided with respect to FIG. 20A.

Figure 20C:
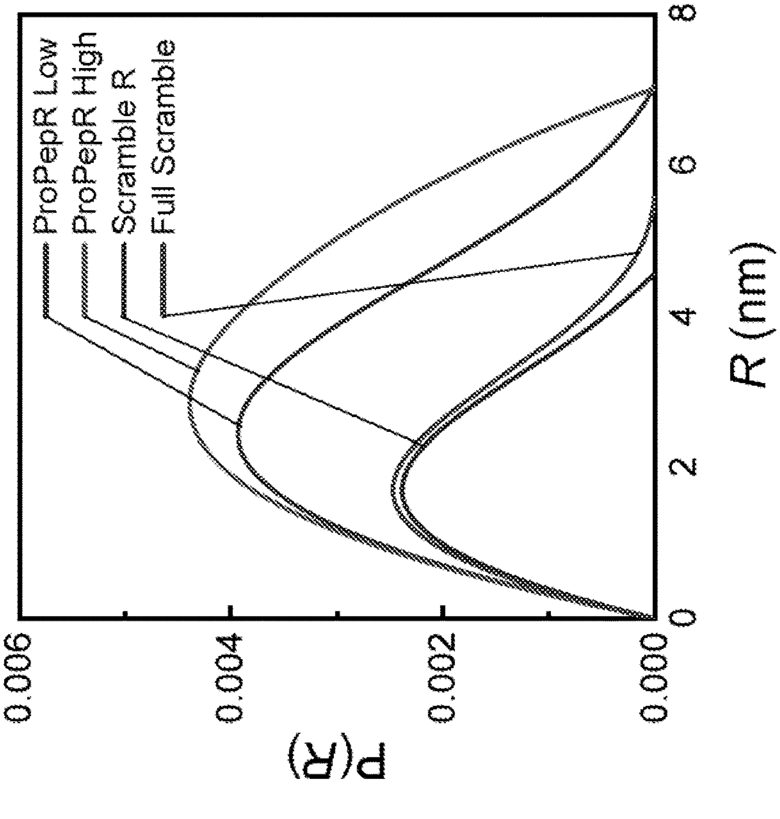
FIG. 20C shows the pair distance distribution functions (PDDFs) for (a) a low degree of polymerization polynorbornene dicarboxyimide-based brush polymer ("ProPepR Low"—DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("ProPepR High"—DP=average of about 22.5) comprising polynorbornene dicarboxyimide-based SEQ ID NO: 72 (LDPETGEFLRRRR) peptide monomer, (c) a scrambleRRRR polynorbornene dicarboxyimide-based brush polymer (i.e., "ScrambleR") comprising polynorbornene dicarboxyimide-based SEQ ID NO: 146 (DELEPLTGFRRRR) peptide monomer, and (d) a full scramble polynorbornene dicarboxyimide-based brush polymer (i.e., "Full Scramble") comprising polynorbornene dicarboxyimide-based SEQ ID NO: 143 (DERLERPLTRGFR) peptide monomer, as described in Example 16.
Figure 20D:
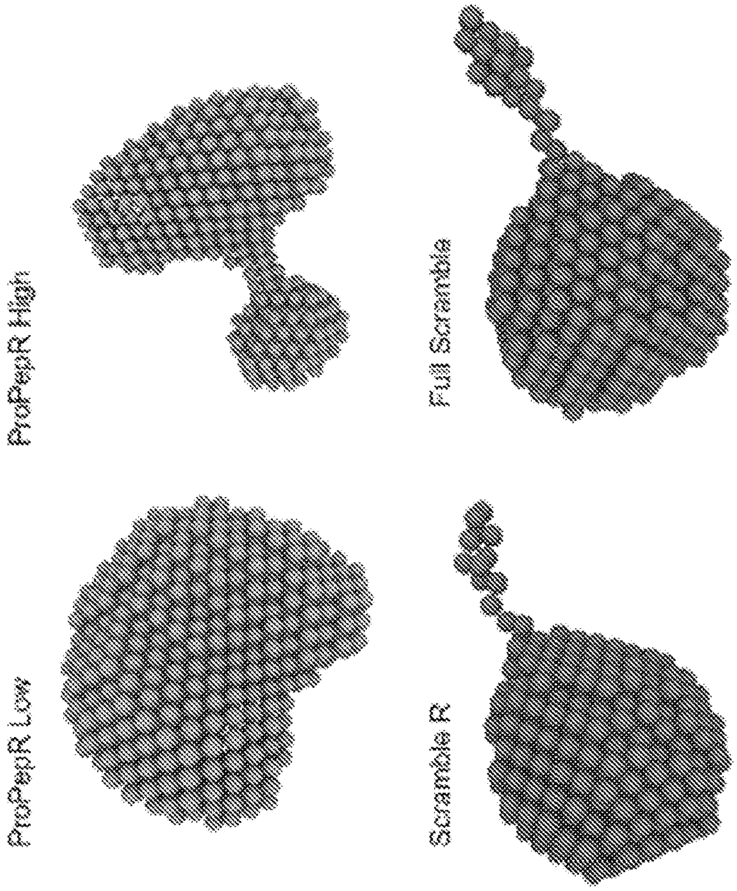
FIG. 20D provides a real space and coarse-grained image for (a) a low degree of polymerization polynorbornene dicarboxyimide-based brush polymer ("ProPepR Low"—DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("ProPepR High"—DP=average of about 22.5) comprising polynorbornene dicarboxyimide-based SEQ ID NO: 72 (LDPETGEFLRRRR) peptide monomer, (c) a scrambleRRRR polynorbornene dicarboxyimide-based brush polymer (i.e., "ScrambleR") comprising polynorbornene dicarboxyimide-based SEQ ID NO: 146 (DELEPLTGFRRRR) peptide monomer, and (d) a full scramble polynorbornene dicarboxyimide-based brush polymer (i.e., "Full Scramble") comprising polynorbornene dicarboxyimide-based SEQ ID NO: 143 (DERLERPLTRGFR) peptide monomer in solution, which were generated using the dammif algorithm in the ATSAS software, as described in Example 16.

To further analyze the probability distribution of mass in space the PLPs, pair distance distribution functions (PDDFs) were plotted and the results are shown in FIG. 20C. The pair distance distribution functions were generated by taking the inverse Fourier transform of scattering data to translate reciprocal space data into real space. The analysis was performed using the $R_g$'s determined by Guinier analysis and the gnom algorithm in ATSAS.

As shown in FIG. 20C, the ProPepR PLPs (i.e., ProPepR Low and ProPepR High) are more flexible and encompass more distinguishable conformations in solution than the sequence scrambled PLPs (i.e., ScrambleR and Full Scramble). Such broad PDDFs are often seen for intrinsically disordered proteins because they are flexible chains that can move between many different conformations in space. In addition, the ProPepR High PLP results in a higher $R_{max}$ than the ProPepR Low PLP, demonstrating that the longer polymer will sample more space. These results show that In summary, the ProPepR PLPs (i.e., ProPepR Low and ProPepR High) are more flexible and more globular than the sequence scrambled PLPs (i.e., ScrambleR and Full Scramble), which seem to behave more like extended/unfolded chains that are comparably rigid and unable to sample many distinguishable conformations.

Using the dammif algorithm in the ATSAS software, a real space and coarse-grained image of the ProPepR PLPs (i.e., ProPepR Low and ProPepR High) and the sequence scrambled PLPs (i.e., ScrambleR and Full Scramble) in solution was generated. The results are set forth in FIG. 20D.

Example 17

Figure 21A:
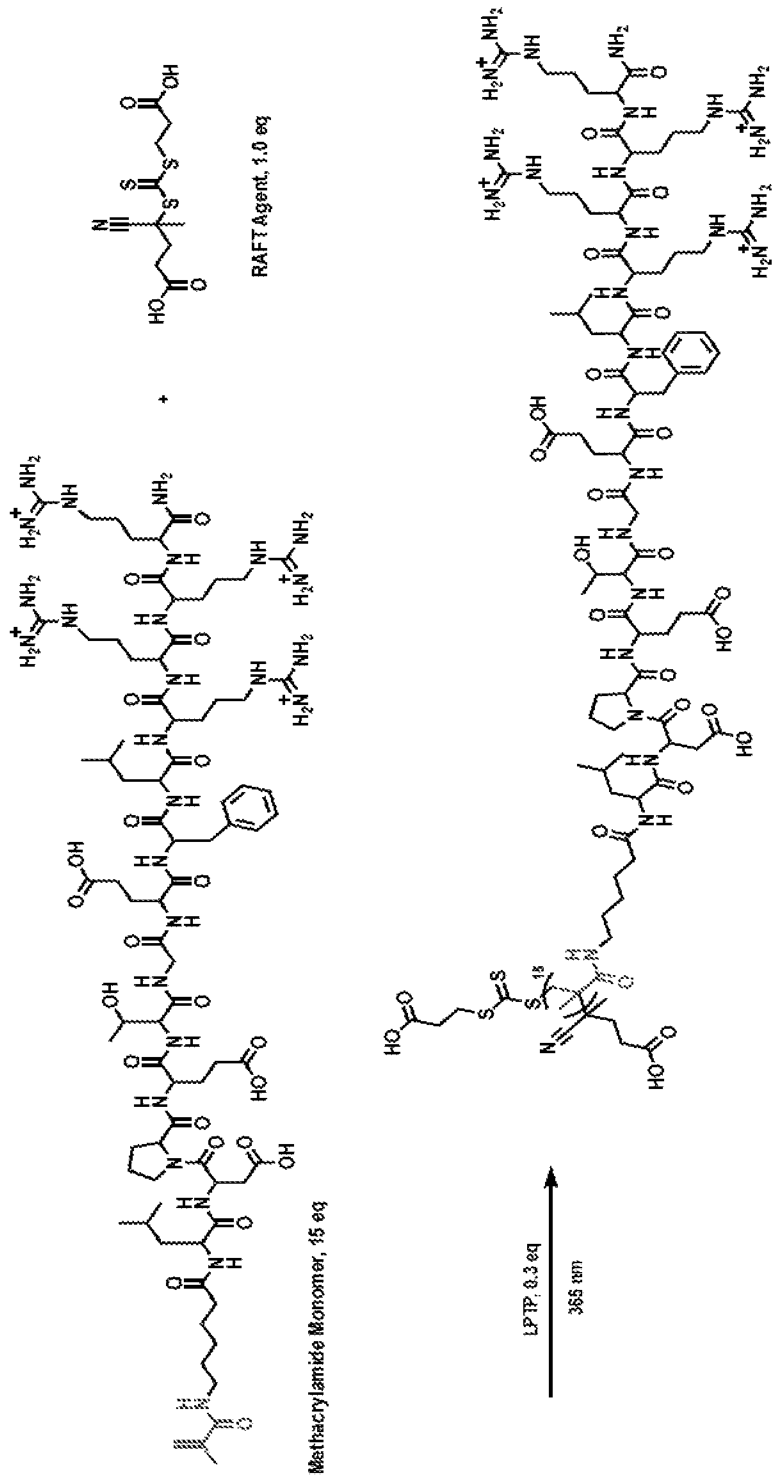
FIG. 21A shows the reversible addition-fragmentation chain-transfer (RAFT) polymerization of a (meth)acrylamide monomer comprising SEQ ID NO: 72 (LDPETGEFLRRRR) to form a (meth)acrylamide-based brush polymer comprising the peptide SEQ ID NO: 72 (LDPETGEFLRRRR), as described in Example 17.

This example provides an exemplary synthesis of a (meth)acrylamide-based brush polymer comprising the peptide SEQ ID NO: 72 (LDPETGEFLRRRR), as depicted in FIG. 21A.

Peptide SEQ ID NO: 72 (LDPETGEFLRRRR) was synthesized using standard solid phase peptide synthesis (SPPS) procedures on an AAPPTec Focus XC automated synthesizer. The peptide was prepared on Rink amide MBHA resin with a typical SPPS procedure involving FMOC deprotection with 20% methylpiperidine in DMF (one 5 min deprotection followed by one 15 min deprotection), and 45 min amide couplings using 3.75 eq. of the FMOC-protected, and side chain-protected amino acid, 4 eq. of HBTU and 8 eq. of DIPEA.

The peptide monomer depicted in FIG. 21A was prepared by adding methacrylic acid (3.0 eq.), HBTU (2.9 eq.), and DIPEA (6.0 eq.) in 12 mL of DMF to the peptide on the resin, and placed on a shaker for 2 hours. The resulting resin was isolated via vacuum filtration and washed with DMF then dichloromethane (DCM) twice. The resin was dried completely then placed in desiccator overnight to yield the (meth)acrylamide monomer with SEQ ID NO: 72 (LDPETGEFLRRRR) peptide on resin.

Following completion of the synthesis, the peptide was cleaved from the resin by treatment with TFA/$H_2O$/TIPS in a 9.5:2.5:2.5 ratio for 3 hours. The peptide monomer was then filtered, precipitated and centrifuged in cold ether. The cleaved monomer was characterized to be fully cleaved and of correct identity using analytical HPLC and MALDI-ToF MS and then purified by RP-HPLC. The identity of the purified peptide monomer was confirmed by MALDI mass spectrometry and purity was verified by observation of a single peak in the analytical RP-HPLC chromatogram.

The purity of the peptide monomer was verified by scale RP-HPLC, where a single peak in the chromatogram of a newly purified peptide monomer was taken as an indication of a pure material. See the high-performance liquid chromatography (HPLC) analytical trace at FIG. 21D. RP-HPLC was performed on a Jupiter Proteo90A Phenomenex column (150×4.60 mm) equipped with a Hitachi-Elite™ LaChrom L2130 pump and a UV-Vis detector (Hitachi-Elite™ LaChrom L-2420) monitoring at 214 nm. The peptide monomer was purified on a preparative-scale Jupiter Proteo90A Phenomenex column (2050×25.0 mm) using an Armen Spot Prep II System and analyzed for purity using a gradient buffer system in which Buffer A is 0.1% TFA in water and Buffer B is 0.1% TFA in acetonitrile.

Figure 21B:
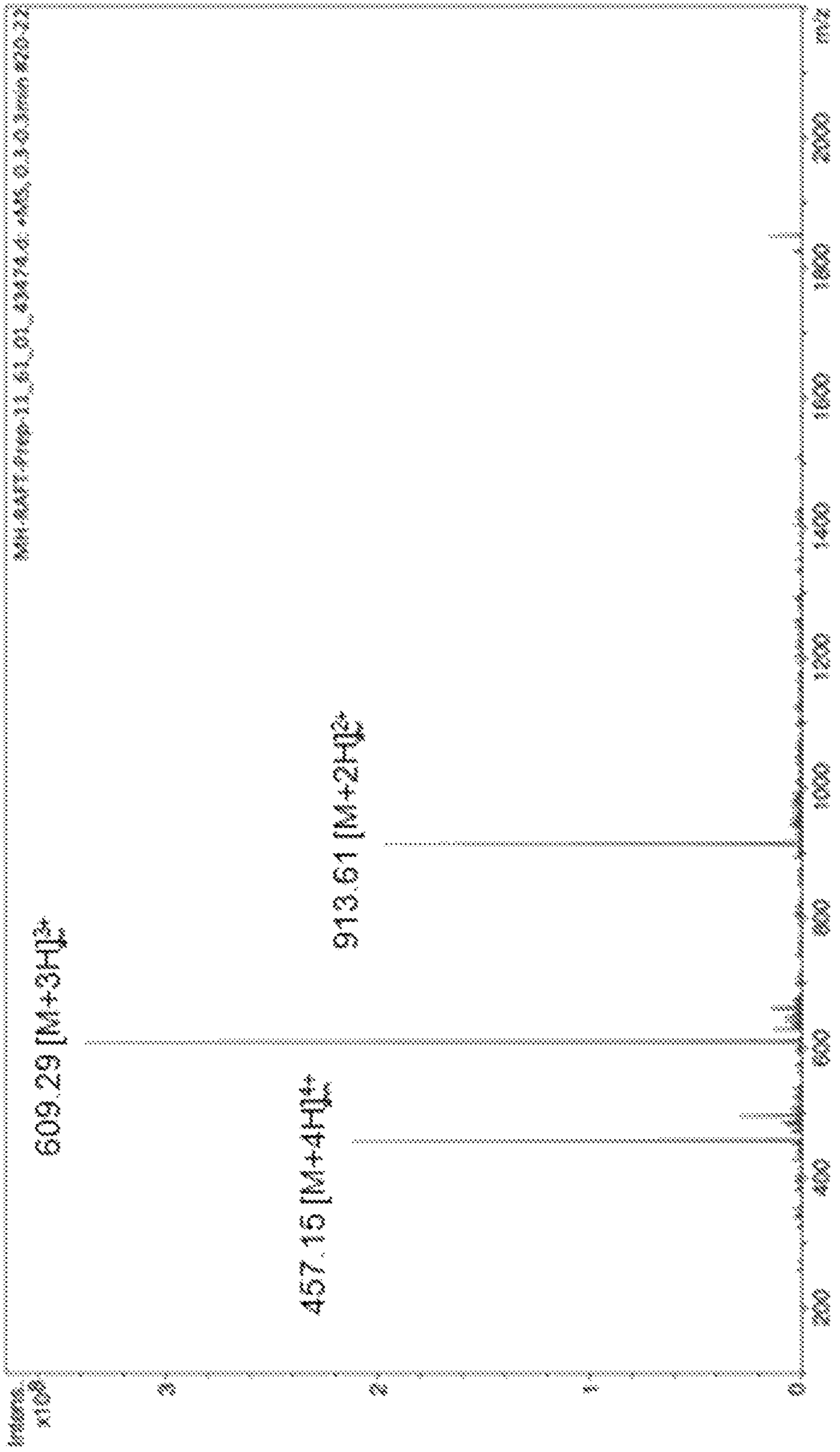
FIG. 21B shows the mass spectrum for the (meth)acrylamide monomer comprising SEQ ID NO: 72 (LDPETGEFLRRRR) as measured by electrospray ionization (ESI) mass spectrometry.
Figure 21C:
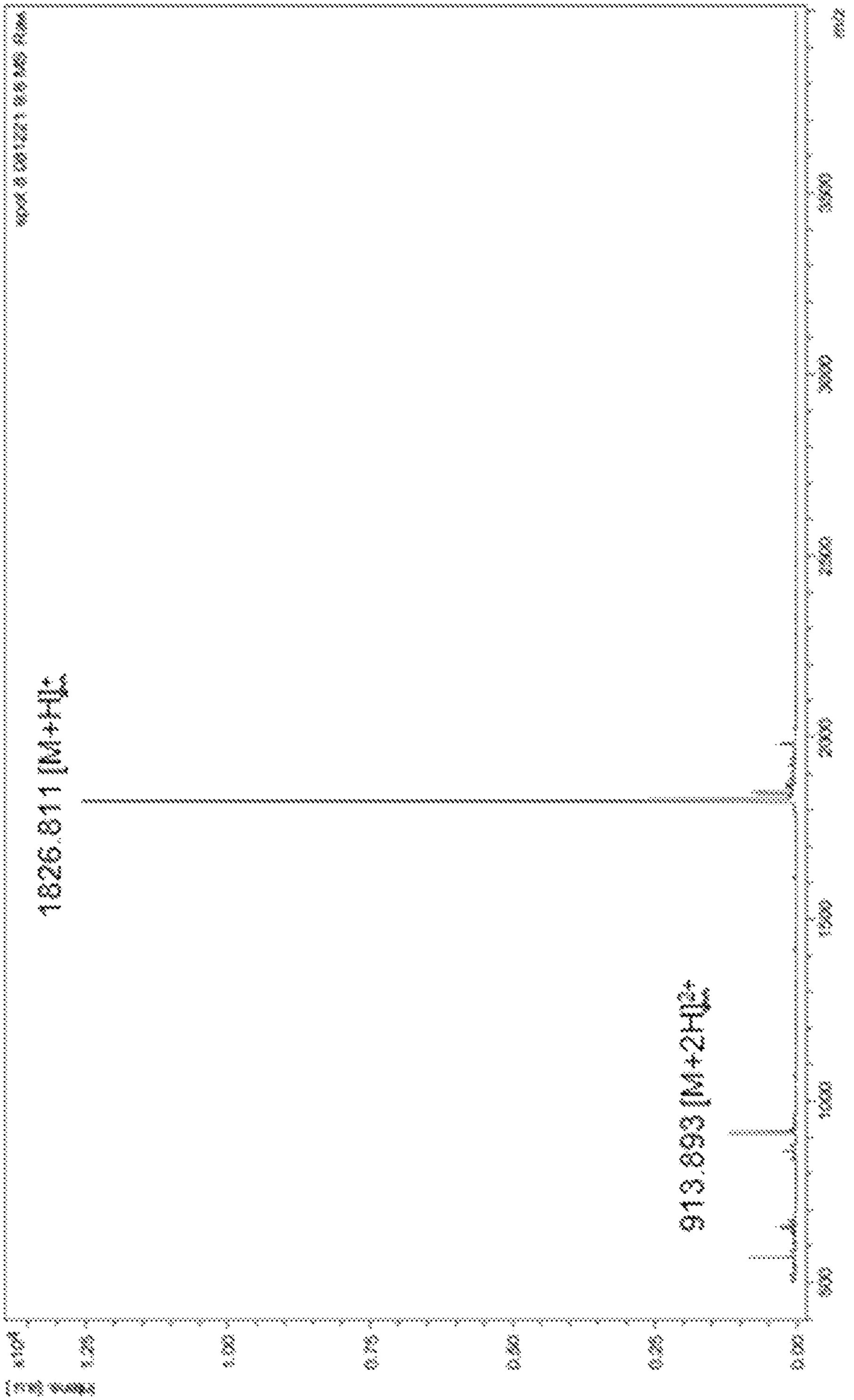
FIG. 21C shows the mass spectrum for the (meth)acrylamide monomer comprising SEQ ID NO: 72 (LDPETGEFLRRRR) as measured by MALDI mass spectrometry.
Figure 21D:
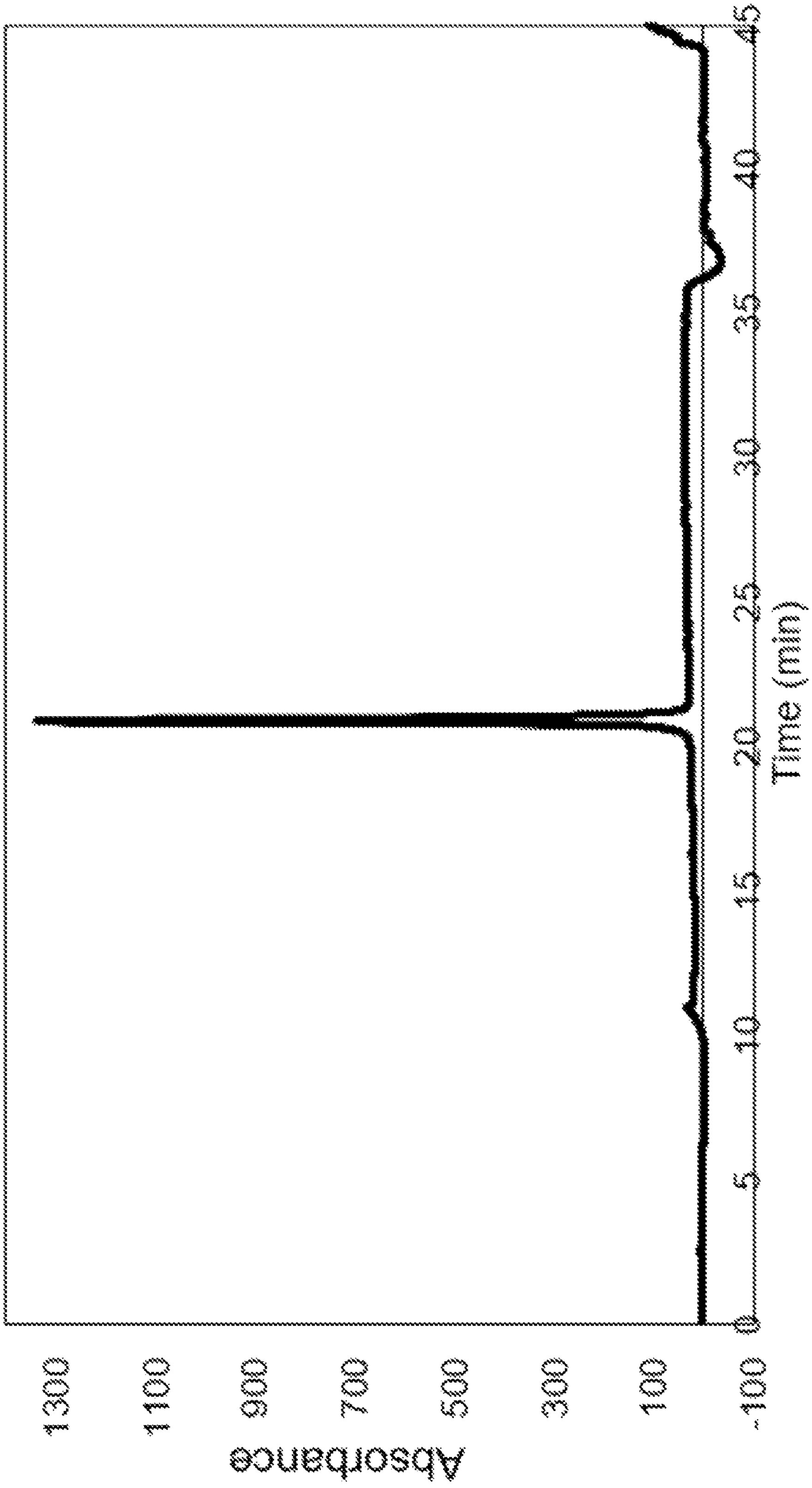
FIG. 21D shows the high-performance liquid chromatography (HPLC) analytical trace for the (meth)acrylamide monomer comprising SEQ ID NO: 72 (LDPETGEFLRRRR).

The identity of the (meth)acrylamide monomer comprising SEQ ID NO: 72 (LDPETGEFLRRRR) was confirmed by ESI mass spectrometry with a mass of 914 $[M+2H]^{2+}$ Da, as evidenced by FIG. 21B. The identity of the (meth) acrylamide monomer comprising SEQ ID NO: 72 (LDPETGEFLRRRR) was further confirmed by MALDI mass spectrometry with a mass of 1827 Da, as evidenced by FIG. 21C.

Polymerizations targeting a theoretical degree of polymerization of 15 were carried out by dissolving purified (meth)acrylamide monomer comprising SEQ ID NO: 72 (LDPETGEFLRRRR) (20 mg, 0.011 mmol, 15 eq.) in 128 μL of 25% acetate buffer (1 M, pH=5) and 75% miliQ water (32 μL acetate buffer, 96 μL miliQ water). To the resulting solution were added 4-(((2 carboxyethyl)thio)carbonothioyl)thio 4-cyano pentanoic acid (RAFT agent, RA, 11.2 μL, 20 mg/mL stock in DMSO, 0.00073 mmol, 1 eq.) and lithium phenyl-2,4,6-trimethylbenzoylphosphinate (LPTP, 10.7 μL, 6 mg/mL stock in miliQ water, 0.00022 mmol, 0.3 eq.) for a total reaction volume of 150 μL. The reaction was degassed by purging with nitrogen for 30 minutes and the resulting mixture was placed in an UV light box (365 nm) for 24 hours. After 24 hours, the vial was removed from UV light and the reaction product was confirmed by $^1$H NMR spectroscopy. Additional experiments, which were monitored using $^1$H NMR spectroscopy, demonstrated that the reaction was complete in as little as 6 hours.

The exemplary procedure above targeted a theoretical DP of 15 based on the monomer:RA molar ratio of 15:1, and resulted in an experimental DP of about 17 and a PDI of about 1.150 as determined by aqueous phase gel permeation chromatography (described below). By changing the monomer:RA molar ratio the theoretical degree of polymerization can be altered. For example, a theoretical DP of 45 was also targeted using a monomer:RA molar ratio of 45:1, which resulted in an experimental DP of about 37 and a PDI of about 1.011 as determined by aqueous phase gel permeation chromatography (described below).

Figure 21E:
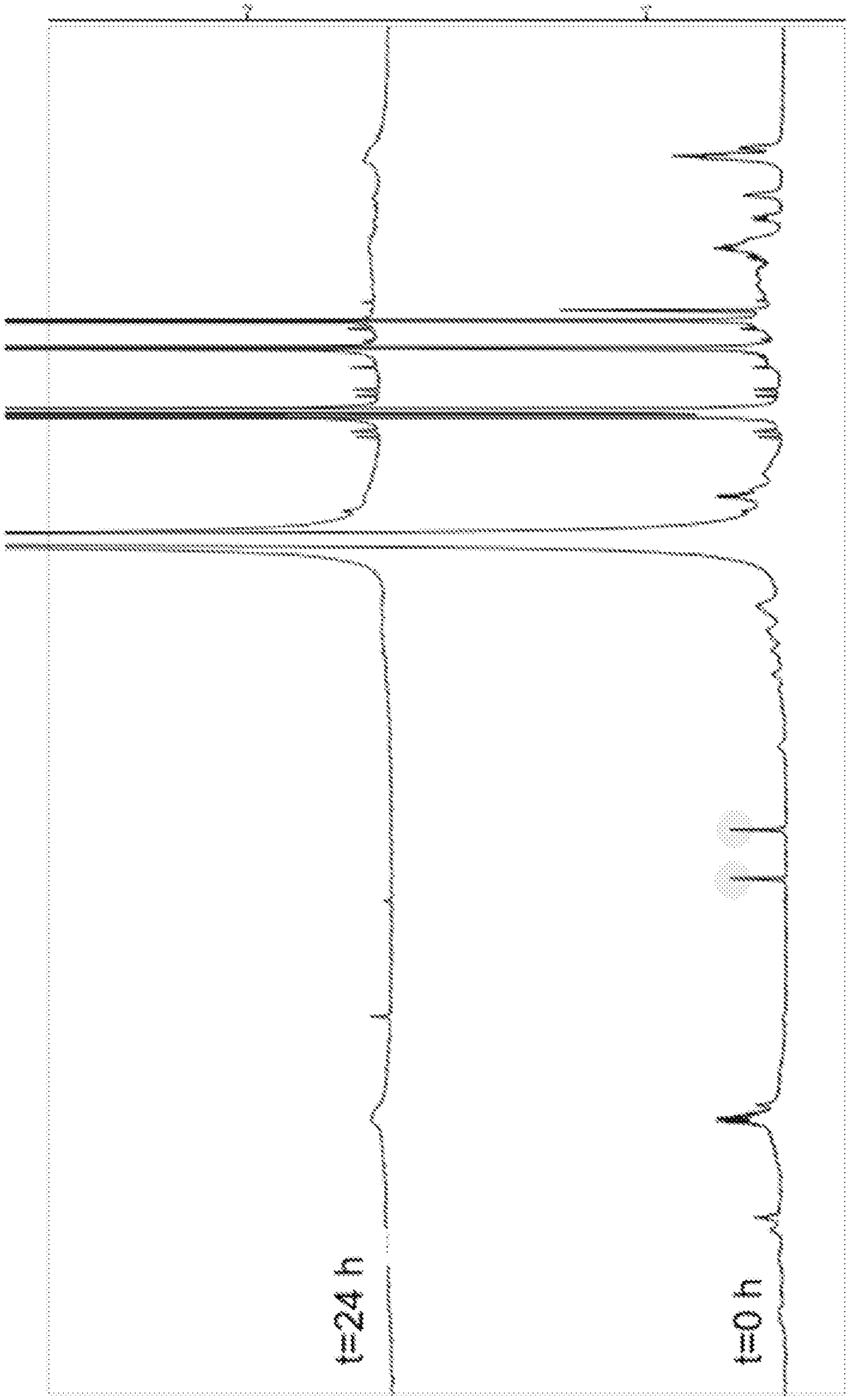
FIGS. 21E and 21F show the $^{1}H$ NMR spectra for the RAFT polymerization of the (meth)acrylamide monomer comprising SEQ ID NO: 72 (LDPETGEFLRRRR) for a degree of polymerization of about 37 (FIG. 21E) and about 17 (FIG. 21F). The disappearance of the resonances at δ=5-6 ppm corresponding to the olefin protons of the monomer indicate completion of the polymerization reaction.
Figure 21F:
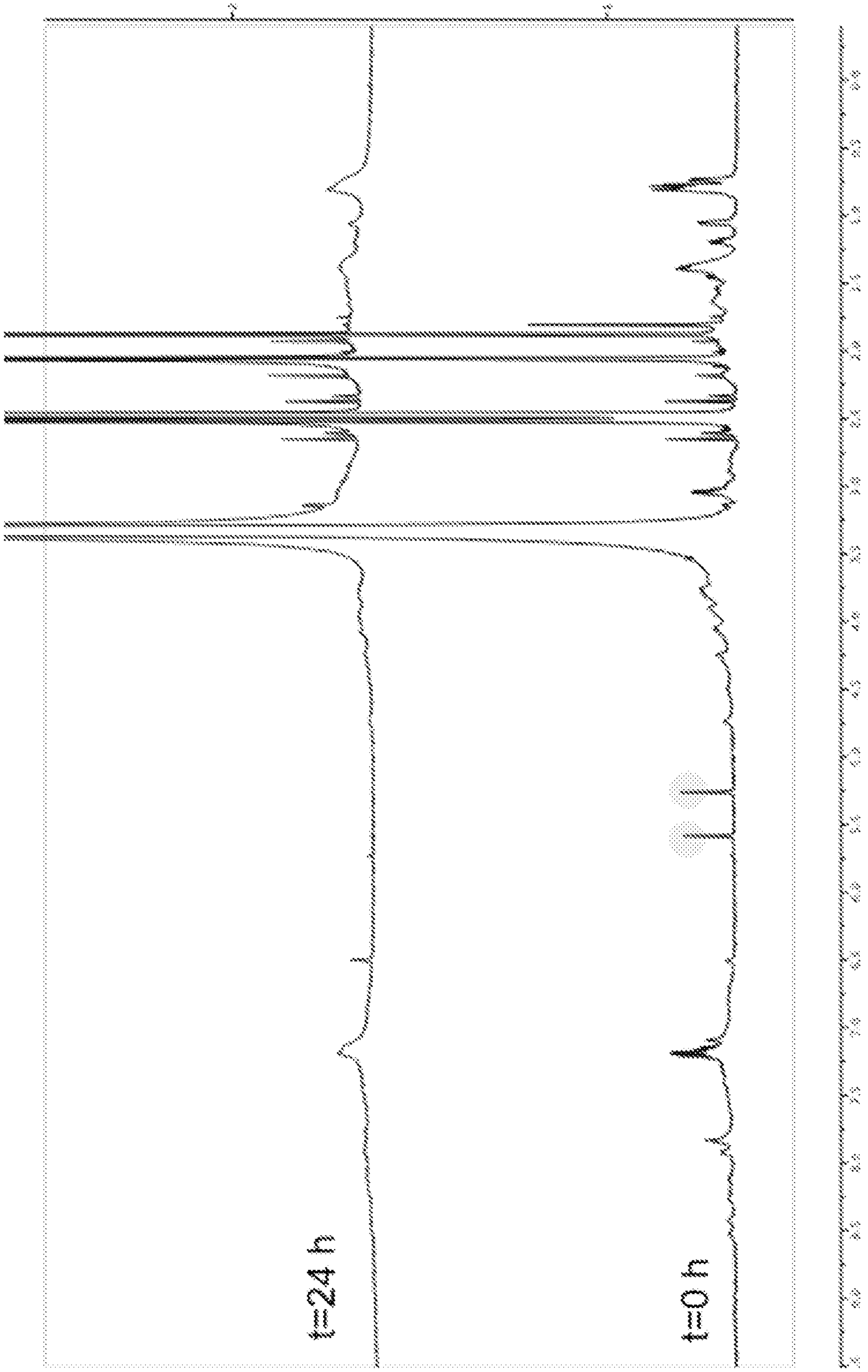

The polymerization reaction was monitored by performing $^1$H NMR spectroscopy at t=0 and t=24 hours and the results for the RAFT polymerization of the (meth)acrylamide monomer comprising SEQ ID NO: 72 (LDPETGEFLRRRR) with a degree of polymerization of about 37 and about 17 are set forth in FIG. 21E and FIG. 21F, respectively.

The disappearance of the resonances at δ=5-6 ppm corresponding to the olefin protons of the monomer indicate completion of the polymerization reaction.

The resulting (meth)acrylamide-based brush polymer comprising the peptide SEQ ID NO: 72 (LDPETGEFLRRRR) was isolated through dialysis. In that respect, miliQ water (3 mL) was added to polymerization reaction and the diluted reaction was carefully transferred into a dialysis bag with a 3,500 MW cut off. The dialysis bag was placed in 2 L of water and dialyzed for 2 days with water being changed after 2 hours, 4 hours, and 24 hours. After dialysis, the polymer was sterile filtered through a 0.22 μm PES filter and isolated as a lyophilized powder.

Figure 21G:
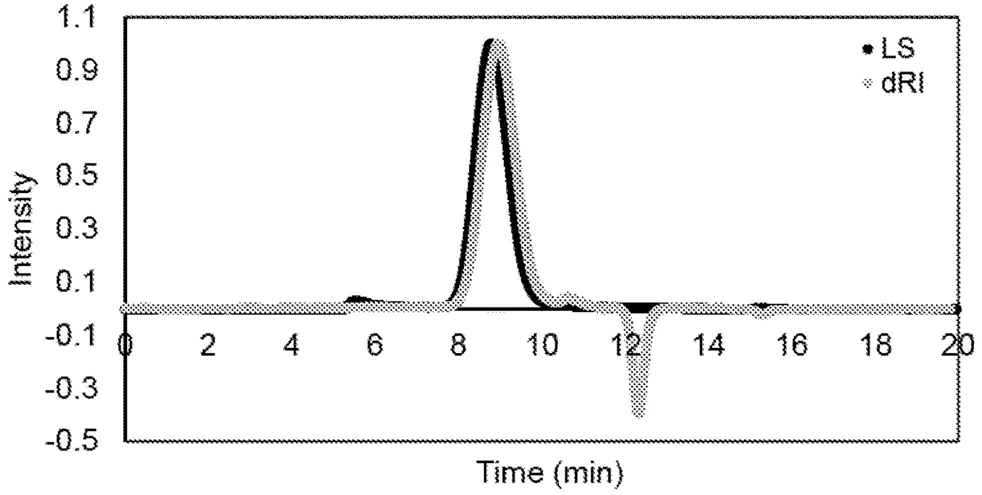
FIGS. 21G-I show the gel permeation chromatography results for the about 37mer (t=24 hours.
Figure 21H:
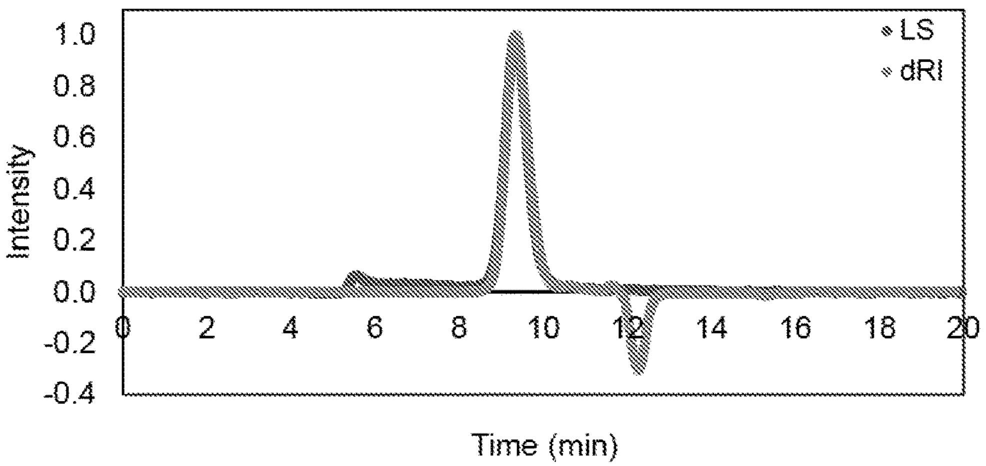
Figure 21I:
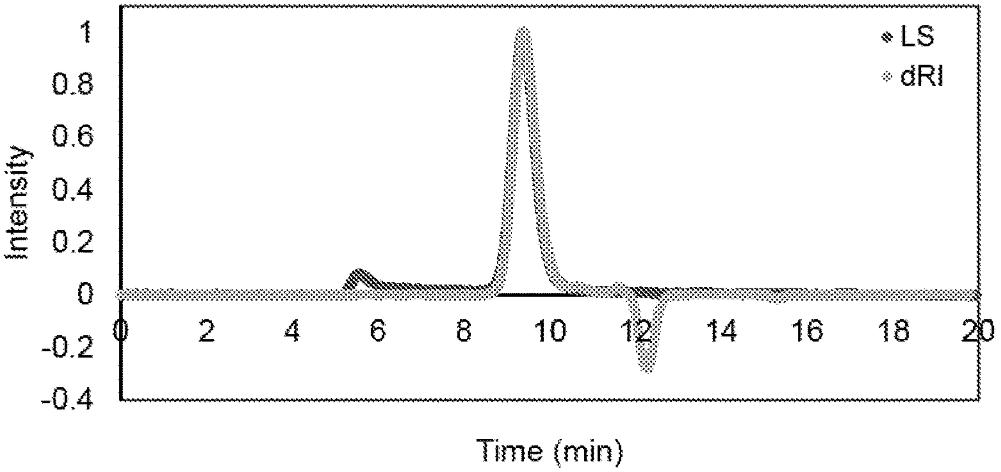

Polymer dispersities ($M_w/M_n$) and molecular weights ($M_n$) were determined by aqueous phase gel permeation chromatography (GPC). To this end, aqueous phase GPC measurements were performed using a TOSOH Biosciences TSKgel G500PW$_{XL}$-CP column (7.8 mm ID×30 cm, 10 μm) with 0.1 M sodium nitrate buffer containing 0.1% TFA as the mobile phase with a flow rate of 1.0 mL/min. Detection consisted of a Wyatt Optilab T-rEX refractive index detector operating at 658 nm and a Wyatt DAWN® HELEOS® II light scattering detector operating at 659 nm. Absolute molecular weights and polydispersities were calculated using the Wyatt ASTRA software. The gel permeation chromatography results for the about 37mer (t=24 hours), about 17mer (t=24 hours), and about 16mer (t=6 hours) of the (meth)acrylamide-based brush polymer (i.e., SEQ ID NO: 72 (LDPETGEFLRRRR)) are set forth in FIGS. 21G-I, respectively.

Figure 21J:
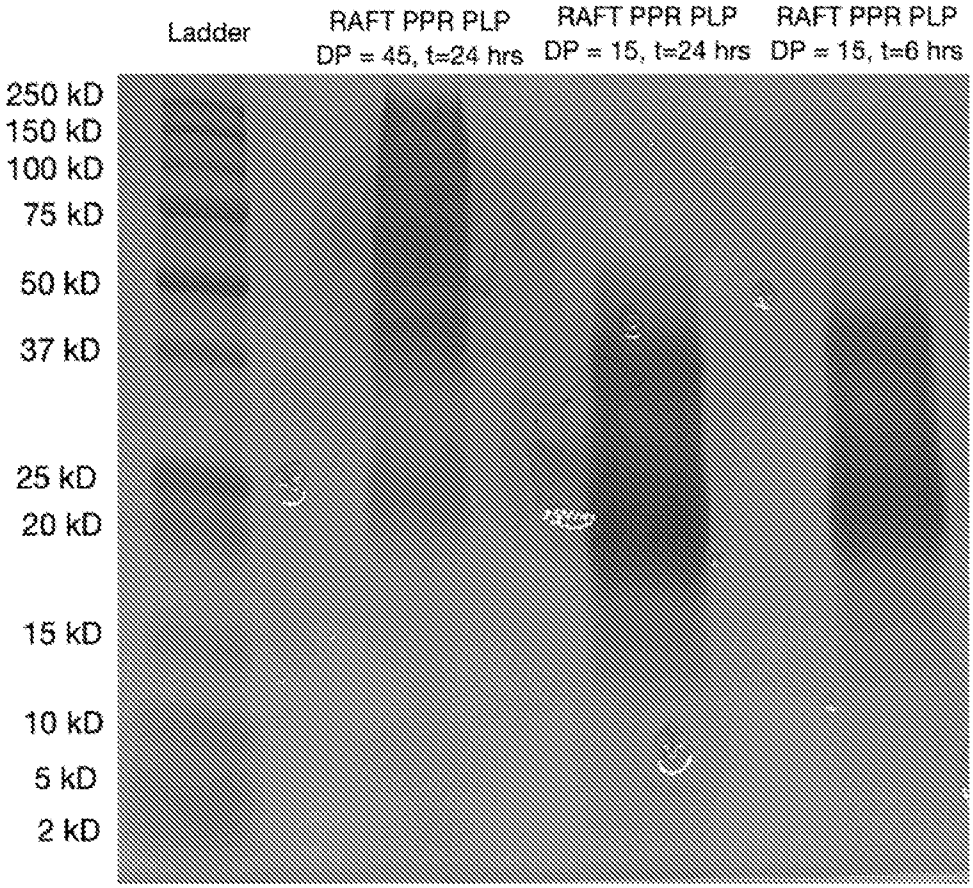
FIG. 21J shows the SDS-PAGE results for the about 37mer (t=24 hours), about 17mer (t=24 hours), and about 16mer (t=6 hours) of the (meth)acrylamide-based brush polymer (i.e., SEQ ID NO: 72 (LDPETGEFLRRRR)), prepared in Example 17.

The polymers were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis. The SDS-PAGE results for the about 37mer (t=24 hours), about 17mer (t=24 hours), and about 16mer (t=6 hours) of the (meth) acrylamide-based brush polymer (i.e., SEQ ID NO: 72 (LDPETGEFLRRRR)) are set forth in FIG. 21J.

Example 18

This example shows the structural effects exhibited by a protein-like polymer (PLP) having (a) a structurally different peptide bound and (b) a structurally different polymer backbone, as determined by circular dichroism (CD).

Figure 22A:
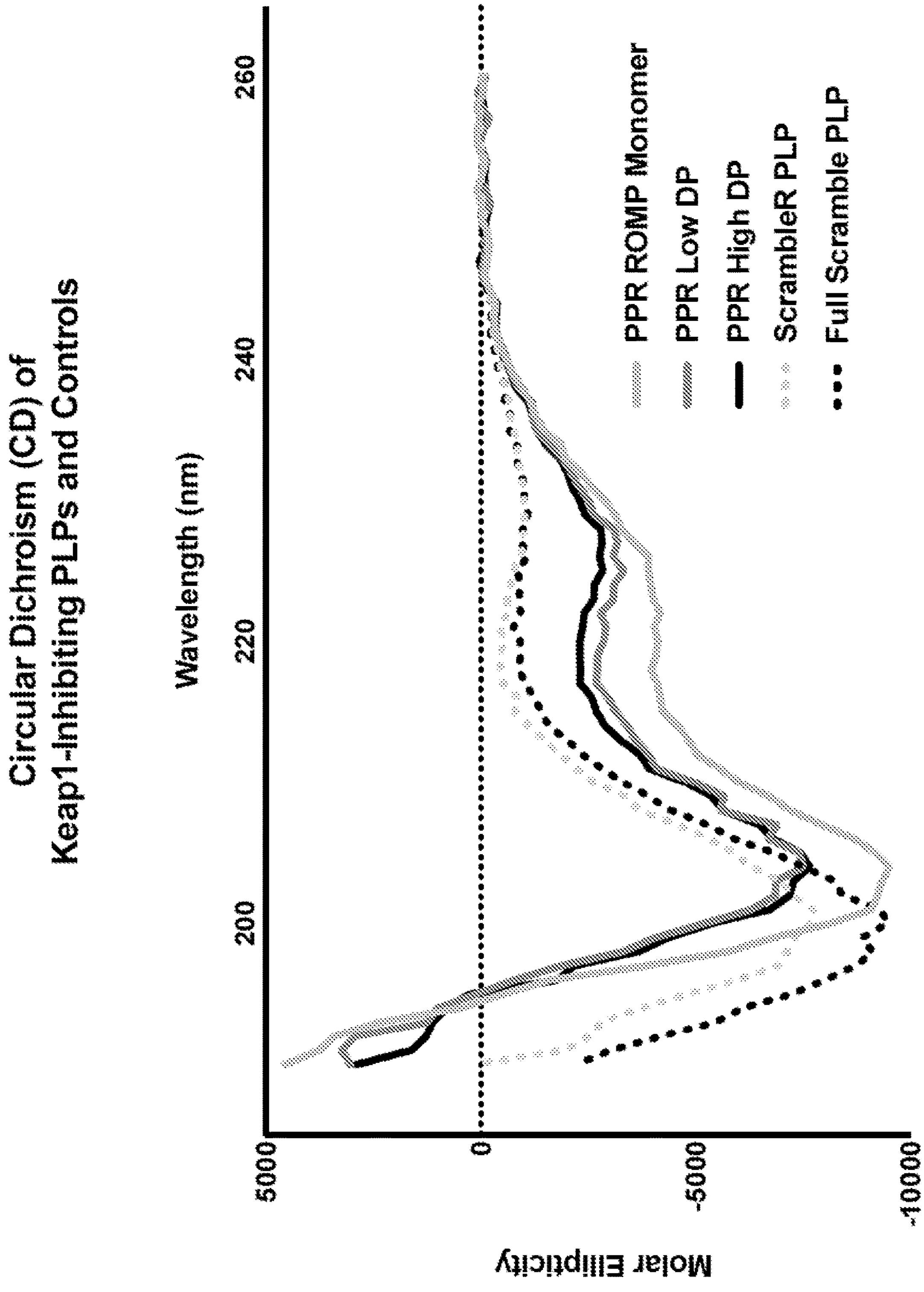
FIG. 22A shows the circular dichroism (CD) of for (a) a polynorbornene dicarboxyimide monomer comprising SEQ ID NO: 72 (LDPETGEFLRRRR) ("PPR ROMP Monomer"), (b) a low degree of polymerization polynorbornene dicarboxyimide-based brush polymer ("PPR Low DP"—DP=average of about 11.6) comprising polynorbornene dicarboxyimide-based SEQ ID NO: 72 (LDPETGEFLRRRR) peptide monomer, (c) a high degree of polymerization polynorbornene dicarboxyimide-based brush polymer ("PPR High DP" DP=average of about 22.5) comprising polynorbornene dicarboxyimide-based SEQ ID NO: 72 (LDPETGEFLRRRR) peptide monomer, (d) a scrambleRRRR polynorbornene dicarboxyimide-based brush polymer (i.e., "ScrambleR PLP") comprising polynorbornene dicarboxyimide-based SEQ ID NO: 146 (DELEPLTGFRRRR) peptide monomer, and (e) a full scramble polynorbornene dicarboxyimide-based brush polymer (i.e., "Full Scramble PLP") comprising polynorbornene dicarboxyimide-based SEQ ID NO: 143 (DERLERPLTRGFR) peptide monomer, as described in Example 18.

The circular dichroism (CD) was taken for (a) a polynorbornene dicarboxyimide monomer comprising SEQ ID NO: 72 (LDPETGEFLRRRR) ("PPR ROMP Monomer"), (b) a low degree of polymerization polynorbornene dicarboxyimide-based brush polymer ("PPR Low DP"—DP=average of about 11.6) comprising polynorbornene dicarboxyimide-based SEQ ID NO: 72 (LDPETGEFLRRRR) peptide monomer, (c) a high degree of polymerization polynorbornene dicarboxyimide-based brush polymer ("PPR High DP"—DP=average of about 22.5) comprising polynorbornene dicarboxyimide-based SEQ ID NO: 72 (LDPETGEFLRRRR) peptide monomer, (d) a scrambleRRRR polynorbornene dicarboxyimide-based brush polymer (i.e., "ScrambleR PLP") comprising polynorbornene dicarboxyimide-based SEQ ID NO: 146 (DELEPLTGFRRRR) peptide monomer, and (e) a full scramble polynorbornene dicarboxyimide-based brush polymer (i.e., "Full Scramble PLP") comprising polynorbornene dicarboxyimide-based SEQ ID NO: 143 (DERLERPLTRGFR) peptide monomer and the results are set forth in FIG. 22A.

As shown in FIG. 22A, the PLPs having different peptide structures, i.e., PPR Low DP (or PPR High DP), ScrambleR PLP, and Full Scramble PLP, have different secondary structures, as evidenced by the difference in shape of the CD spectra. In contrast, PPR Low DP and PPR High DP have the same CD spectrum shape, demonstrating that they have the same secondary structure. Furthermore, the resulting spectra for the PPR ROMP monomer, PPR Low DP, and PPR high DP show similar curves, suggesting despite DP, the secondary structure is maintained.

Figure 22B:
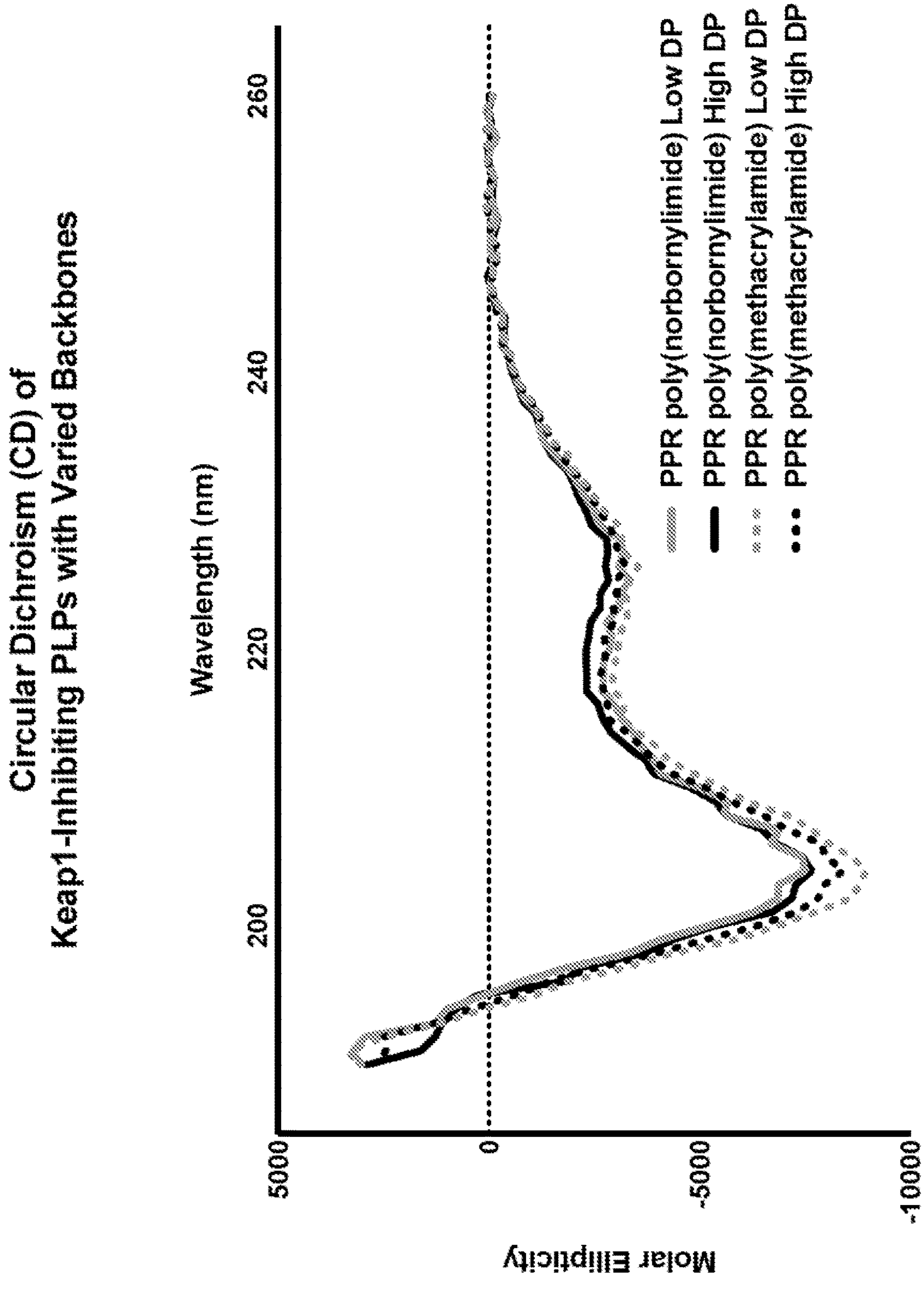
FIG. 22B shows the circular dichroism (CD) of for (a) a low degree of polymerization polynorbornene dicarboxyimide-based brush polymer ("PPR poly(norbornylimide) Low DP"-DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("PPR poly(norbornylimide) High DP"—DP=average of about 22.5) comprising polynorbornene dicarboxyimide-based SEQ ID NO: 72 (LDPETGEFLRRRR) peptide monomer, (c) a low degree of polymerization (meth)acrylamide-based brush polymer ("PPR poly(methacrylamide) Low DP"—DP=average of about 17) comprising (meth)acrylamide-based SEQ ID NO: 72 (LDPETGEFLRRRR) peptide monomer, and (d) a high degree of polymerization (meth) acrylamide-based brush polymer ("PPR poly(methacrylamide) High DP"—DP=average of about 37) comprising (meth)acrylamide-based SEQ ID NO: 72 (LDPETGEFLRRRR) peptide monomer, as described in Example 18.

To demonstrate that the polymer backbone does not affect the secondary structures within the PLP, the circular dichroism (CD) was taken for (a) a low degree of polymerization polynorbornene dicarboxyimide-based brush polymer ("PPR poly(norbornylimide) Low DP"-DP=average of about 11.6) comprising polynorbornene dicarboxyimide-based SEQ ID NO: 72 (LDPETGEFLRRRR) peptide monomer, (b) a high degree of polymerization polynorbornene dicarboxyimide-based brush polymer ("PPR poly(norbornylimide) High DP"—DP=average of about 22.5) comprising polynorbornene dicarboxyimide-based SEQ ID NO: 72 (LDPETGEFLRRRR) peptide monomer, (c) a low degree of polymerization (meth)acrylamide-based brush polymer ("PPR poly(methacrylamide) Low DP"—DP=average of about 17) comprising (meth)acrylamide-based SEQ ID NO: 72 (LDPETGEFLRRRR) peptide monomer, and (d) a high degree of polymerization (meth)acrylamide-based brush polymer ("PPR poly(methacrylamide) High DP"—DP=average of about 37) comprising (meth)acrylamide-based SEQ ID NO: 72 (LDPETGEFLRRRR) peptide monomer and the results are set forth in FIG. 22B.

As shown in FIG. 22B, PPR poly(norbornylimide) Low DP, PPR poly(norbornylimide) High DP, PPR poly(methacrylamide) Low DP, and PPR poly(methacrylamide) High DP have the same CD spectrum shape, demonstrating that they have the same secondary structure. These results show that the polymer backbone does not affect the secondary structure within the PLP. Without wishing to be bound by any particular theory, it is believed that the high peptide: backbone ratio of PLPs which imparts a compound primarily composed of peptides, leads to formation of secondary structures and other three-dimensional configurations that are driven by the peptide sidechain composition and identity.

Example 19

This example provides the binding affinity exhibited by a SEQ ID NO: 2 (LDPETGEFL) peptide (i.e., ProPep Peptide), a polynorbornene dicarboxyimide-based SEQ ID NO: 2 (LDPETGEFL) polymer (i.e., ProPep PLP), a SEQ ID NO: 72 (LDPETGEFLRRRR) peptide (i.e., ProPepR Peptide), and a polynorbornene dicarboxyimide-based SEQ ID NO: 72 (LDPETGEFLRRRR) polymer (i.e., ProPepR PLP), as determined by fluorescence polarization measurements in competitive inhibition screening.

PLPs and controls were assessed for Keap1/Nrf2 disruption using a competitive inhibition screening assay that used fluorescently labeled Nrf2-peptide SEQ ID: 1 (LDEETGEFL) and human recombinant Keap1 (BPS bioscience, San Diego, CA). The assay was carried out according to established protocols. Briefly, test inhibitors (n=3) were added at varying concentrations to wells of a black 96-well plate along with assay buffer, bovine serum albumin (BSA), FAM-Nrf2, and Keap1 and allowed to incubate for 30 minutes at room temperature. The fluorescence polarization (excitation 475-495 nm, emission 518-538 nm) of the samples were measured using the Biotek SynergyNeo2 plate reader. The blank control was assay buffer and inhibitor vehicle. Nrf2 negative binding control included assay buffer, BSA, FAM-Nrf2, and inhibitor vehicle. Nrf2 positive binding control included assay buffer, BSA, FAM-Nrf2, inhibitor vehicle and Keap1. Data was assessed for IC50 values by quantifying percent Nrf2 activity relative to inhibitor concentration by fitting to a nonlinear model for a dose response (absolute IC50) using Prism 9.

Test inhibitors (i) SEQ ID NO: 2 (LDPETGEFL) peptide (shown with a dashed black line), (ii) polynorbornene dicarboxyimide-based SEQ ID NO: 2 (LDPETGEFL) polymer prepared according to Example 11 (shown with a solid black line), (iii) SEQ ID NO: 72 (LDPETGEFLRRRR) peptide (shown with a dashed gray line), and (iv) polynorbornene dicarboxyimide-based SEQ ID NO: 72 (LDPETGEFLRRRR) polymer prepared according to Example 12 (shown with a solid gray line) were added at concentrations ranging from 0.001 to 1000 μM with respect to the peptide, and the percent Nrf2 activity was plotted as a function of inhibitor concentration (μM). The results are set forth in FIG. 23. In addition, the $IC_{50}$ values were calculated as 0.1095 μM (ProPep PLP), 0.3139 μM (ProPep Peptide), 0.05385 μM (ProPepR PLP), and 1.866 μM (ProPepR Peptide).

Figure 23:
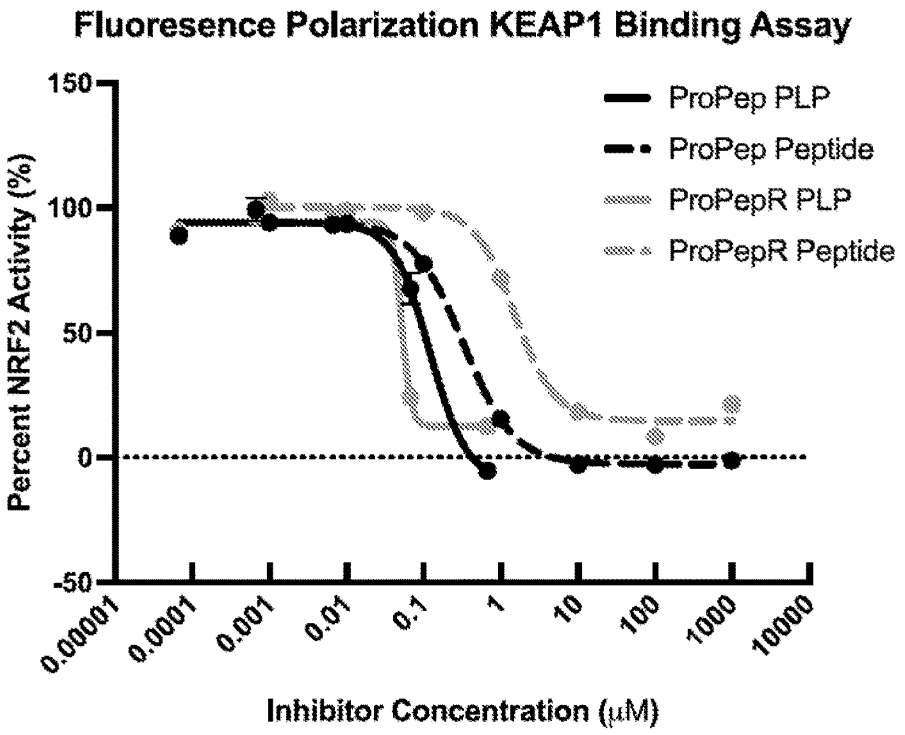
FIG. 23 shows the fluorescence polarization assay for inhibition of Keap1 binding of a fluorescently labeled Nrf2-peptide SEQ ID: 1 (LDEETGEFL), exhibited by SEQ ID NO: 2 (LDPETGEFL) peptide (i.e., ProPep Peptide), polynorbornene dicarboxyimide-based SEQ ID NO: 2 (LDPETGEFL) polymer (i.e., ProPep PLP), SEQ ID NO: 72 (LDPETGEFLRRRR) peptide (i.e., ProPepR Peptide), and polynorbornene dicarboxyimide-based SEQ ID NO: 72 (LDPETGEFLRRRR) polymer (i.e., ProPepR PLP), as described in Example 19.

As is apparent from the results set forth in FIG. 23, the protein-like polymers exhibit comparable binding affinities to Keap1 as compared to free peptides. These results show that adding a SEQ ID NO: 2 (LDPETGEFL) peptide or a SEQ ID NO: 72 (LDPETGEFLRRRR) peptide to a polynorbornene dicarboxyimide-based polymer backbone does not diminish the activity of the peptide. In fact, the PLPs show enhanced binding compared to free peptides alone.

Example 20

This example provides the binding affinity exhibited by a SEQ ID NO: 72 (LDPETGEFLRRRR) peptide (i.e., PPR Free Peptide), a low degree of polymerization polynorbornene dicarboxyimide-based brush polymer ("PPR Low PLP"—DP=average of about 11.6) comprising polynorbornene dicarboxyimide-based SEQ ID NO: 72 (LDPETGEFLRRRR) peptide monomer, a high degree of polymerization polynorbornene dicarboxyimide-based brush polymer ("PPR high PLP"—DP=average of about 22.5) comprising polynorbornene dicarboxyimide-based SEQ ID NO: 72 (LDPETGEFLRRRR) peptide monomer, a full scramble polynorbornene dicarboxyimide-based brush polymer (i.e., Full Scramble PLP) comprising polynorbornene dicarboxyimide-based SEQ ID NO: 143 (DERLERPLTRGFR) peptide monomer, and a scrambleRRRR polynorbornene dicarboxyimide-based brush polymer (i.e., ScrambleR PLP) comprising polynorbornene dicarboxyimide-based SEQ ID NO: 146 (DELEPLTGFRRRR) peptide monomer, as determined by fluorescence polarization measurements in competitive inhibition screening.

PLPs and controls were assessed for Keap1/Nrf2 disruption using a competitive inhibition screening assay that used fluorescently labeled Nrf2-peptide SEQ ID: 1 (LDEETGEFL) and human recombinant Keap1 (BPS bioscience, San Diego, CA). The assay was carried out according to established protocols. Briefly, test inhibitors (n=3) were added at varying concentrations to wells of a black 96-well plate along with assay buffer, bovine serum albumin (BSA), FAM-Nrf2, and Keap1 and allowed to incubate for 30 minutes at room temperature. The fluorescence polarization (excitation 475-495 nm, emission 518-538 nm) of the samples were measured using the Biotek SynergyNeo2 plate reader. The blank control was assay buffer and inhibitor vehicle. Nrf2 negative binding control included assay buffer, BSA, FAM-Nrf2, and inhibitor vehicle. Nrf2 positive binding control included assay buffer, BSA, FAM-Nrf2, inhibitor vehicle and Keap1. Data was assessed for IC50 values by quantifying percent Nrf2 activity relative to inhibitor concentration by fitting to a nonlinear model for a dose response (absolute IC50) using Prism 9.

Test inhibitors (i) SEQ ID NO: 2 (LDPETGEFL) peptide (shown by solid light gray curve), (ii) PPR Low PLP with an average degree of polymerization of about 11.6 prepared according to Example 12 (shown by solid dark gray curve), (iii) PPR High PLP with an average degree of polymerization of about 22.5 prepared according to Example 12 (shown by solid black curve), (iv) Full Scramble PLP comprising polynorbornene dicarboxyimide-based SEQ ID NO: 143 (DERLERPLTRGFR) peptide monomer prepared in Example 13 (shown by light gray dashed curve), and (v) ScrambleR PLP comprising polynorbornene dicarboxyimide-based SEQ ID NO: 146 (DELEPLTGFRRRR) peptide monomer prepared according to Example 14 (shown by black dashed curve) were added at concentrations ranging from 0.001 to 1000 μM, and the percent Nrf2 activity was plotted as a function of inhibitor concentration (μM). The results are set forth in FIG. 24. In addition, the $IC_{50}$ values were calculated as 1432 nM (PPR Free Peptide), 14.96 nM (PPR Low PLP), and 6.242 nM (PPR High PLP). Inasmuch as the Full Scramble peptide and the ScrambleR peptide did not reasonably inhibit Keap1/Nrf2, $IC_{50}$ values were not determined for the Full Scramble PLP and the ScrambleR PLP.

Figure 24:
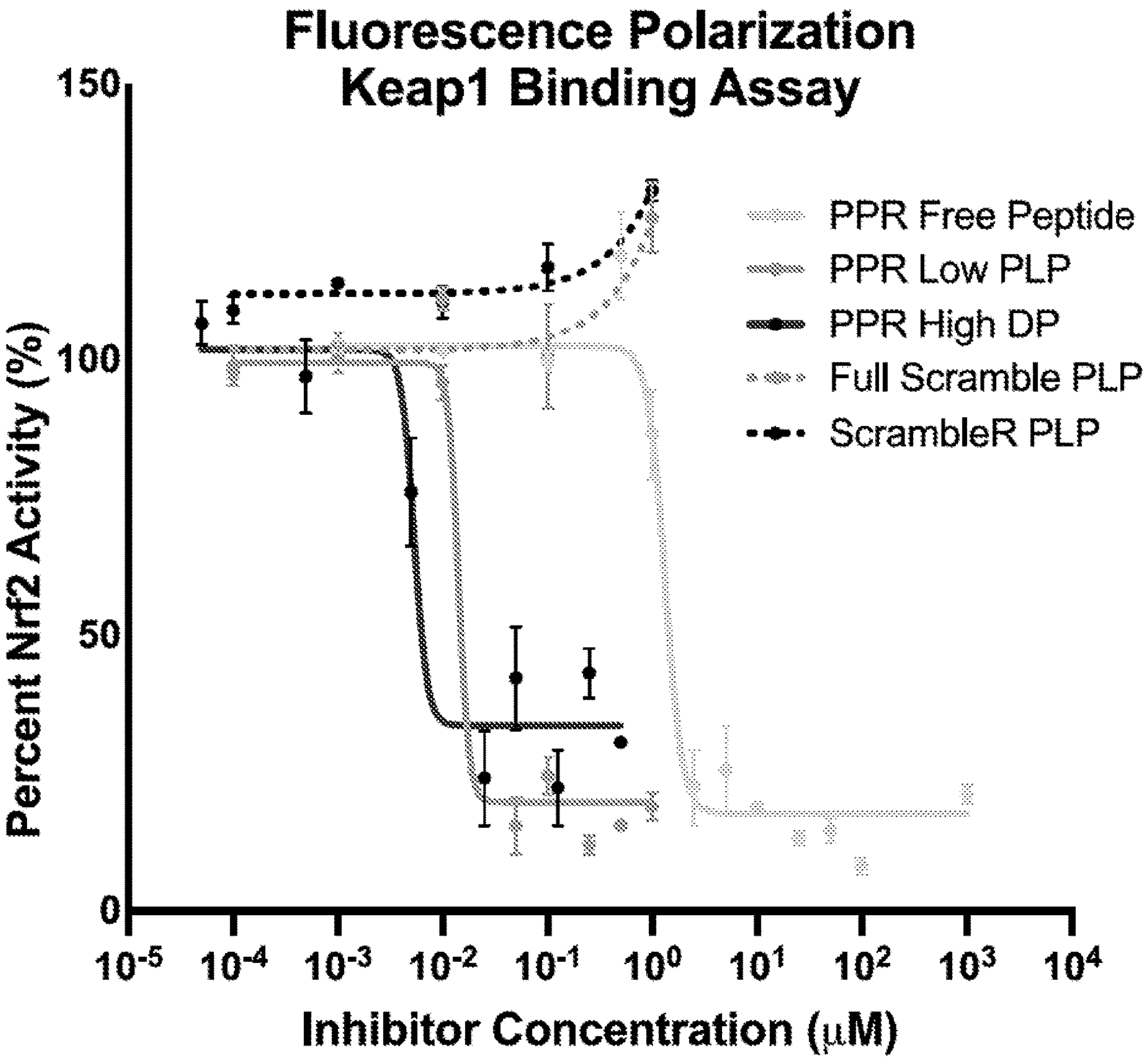
FIG. 24 shows the fluorescence polarization assay for inhibition of Keap1 binding of a fluorescently labeled Nrf2-peptide SEQ ID: 1 (LDEETGEFL), exhibited by SEQ ID NO: 72 (LDPETGEFLRRRR) peptide (i.e., PPR Free Peptide), low degree of polymerization (LowDP) polynorbornene dicarboxyimide-based brush polymer (DP=average of about 11.6) comprising polynorbornene dicarboxyimide-based SEQ ID NO: 72 (LDPETGEFLRRRR) peptide monomer (i.e., PPR Low PLP), high degree of polymerization (HighDP) polynorbornene dicarboxyimide-based brush polymer (DP=average of about 22.5) comprising polynorbornene dicarboxyimide-based SEQ ID NO: 72 (LDPETGEFLRRRR) peptide monomer (i.e., PPR High DP), full scramble polynorbornene dicarboxyimide-based brush polymer comprising polynorbornene dicarboxyimide-based SEQ ID NO: 143 (DERLERPLTRGFR) peptide monomer (i.e., Full Scramble PLP), and scrambleRRRR polynorbornene dicarboxyimide-based brush polymer comprising polynorbornene dicarboxyimide-based SEQ ID NO: 146 (DELEPLTGFRRRR) peptide monomer (i.e., ScrambleR PLP), as described in Example 20.

As is apparent from the results set forth in FIG. 24, the PPR Low PLP and the PPR High PLP exhibited increased binding affinities to Keap1 as compared to the PPR Free peptide. These results show that adding a SEQ ID NO: 72 (LDPETGEFLRRRR) peptide to a polynorbornene dicarboxyimide-based polymer has the potential to increase the binding affinity of the peptide to Keap1. In addition, FIG. 24 shows that Full Scramble PLP and ScrambleR PLP did not inhibit the binding of Nrf2-peptide SEQ ID: 1 (LDEETGEFL) to Keap1 protein, thereby demonstrating that Full Scramble PLP and ScrambleR PLP do not have a high affinity to Keap1 as compared to PPR Low PLP and PPR High PLP. These results show the importance and specificity of the peptide sequence.

Example 21

This example shows the cell uptake in HepG2 (liver) Cells exhibited by a Cy5.5 labeled polynorbornene dicarboxyimide-based protein-like polymer of the invention.

Polynorbornene dicarboxyimide-based SEQ ID NO: 1 (LDEETGEFL) polymer prepared according to Example 10, polynorbornene dicarboxyimide-based SEQ ID NO: 2 (LDPETGEFL) polymer prepared according to Example 11, polynorbornene dicarboxyimide-based SEQ ID NO: 72 (LDPETGEFLRRRR) polymer prepared according to Example 12, PPR Low PLP with an average degree of polymerization of about 11.6 prepared according to Example 12, PPR High PLP with an average degree of polymerization of about 22.5 prepared according to Example 8, Full Scramble PLP comprising polynorbornene dicarboxyimide-based SEQ ID NO: 143 (DERLERPLTRGFR) peptide monomer prepared in Example 13, and ScrambleR PLP comprising polynorbornene dicarboxyimide-based SEQ ID NO: 146 (DELEPLTGFRRRR) peptide monomer prepared according to Example 14 were dye labeled using Cy5.5 monomer blocks added in a 1:15 ratio. Following the addition of the dye blocks, ethyl vinyl ether was added as a terminating agent. The resulting protein-like polymers were purified using dialysis, sterile filtered, lyophilized, and reconcentrated in sterile water prior to cell treatment.

The dye labeled protein-like polymers were analyzed using SDS-PAGE. Samples were prepared for SDS-PAGE in miliQ water at a concentration of 1 mg/ml, and were added to Laemmli sample buffer at a 2:3 ratio (20 μL buffer:30 μL prepared sample) and then heated at 90° C. for 5 minutes. The resulting samples were loaded at 30 μL/well into an AnyKD mini Protean TGX Precast Protein Gel along with 10 μL of the Precision Plus Protein Dual Xtra 2-250 kDa ladder. The gel was run in Tris/Gly/SDS Buffer at 120V until the samples reached the bottom of the gel. PLPs were visualized on the gel using an Instant Coomassie Blue Stain which was applied with shaking at 70 rpm for approximately 15 minutes. Gels were rinsed and imaged for analysis.

Figure 25:
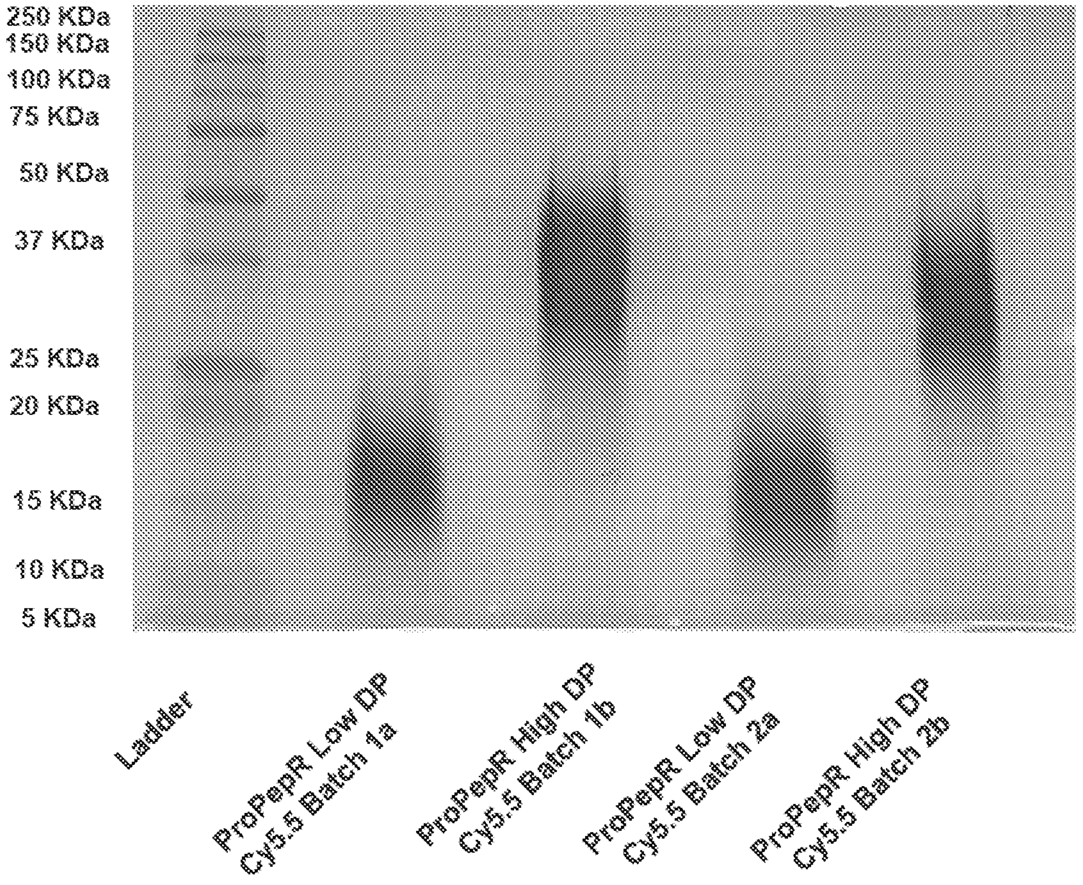
FIG. 25 shows the SDS-PAGE results for the Cy5.5-labeled low degree of polymerization (LowDP) polynorbornene dicarboxyimide-based brush polymer ("ProPepR Low DP Cy5.5"—Batches 1a and 2a), comprising polynorbornene dicarboxyimide-based SEQ ID NO: 72 (LDPETGEFLRRRR) peptide monomer, and the high degree of polymerization (HighDP) polynorbornene dicarboxyimide-based brush polymer ("ProPepR High DP Cy5.5"—Batches 1b and 2b), as prepared according to Example 21.
Figure 26:
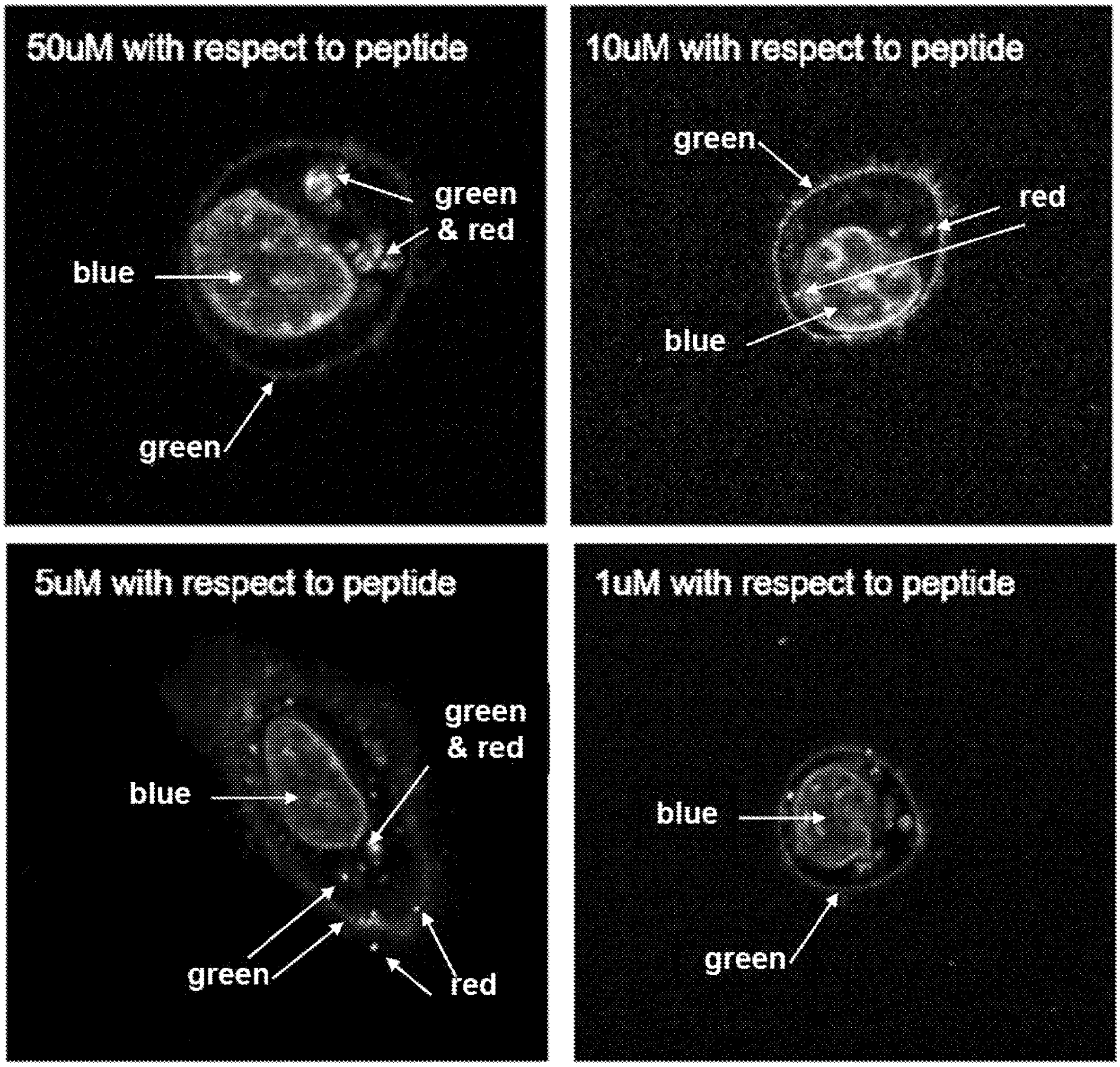
FIG. 26 shows the cell uptake in HepG2 Cells exhibited by a Cy5.5 labeled polynorbornene dicarboxyimide-based SEQ ID NO: 1 (LDEETGEFL) polymer (i.e., OrigPep Homopolymer), imaged using confocal microscopy, as described in Example 21. The cell membranes are shown in green, the nuclei are shown in blue, and the Cy5.5 labeled polynorbornene dicarboxyimide-based SEQ ID NO: 1 (LDEETGEFL) polymers are shown in red. Upper left=50 μM administration with respect to the peptide; Upper right=10 μM administration with respect to the peptide; Lower Left=5 μM administration with respect to the peptide; and Lower right=1 μM administration with respect to the peptide.
Figure 27:
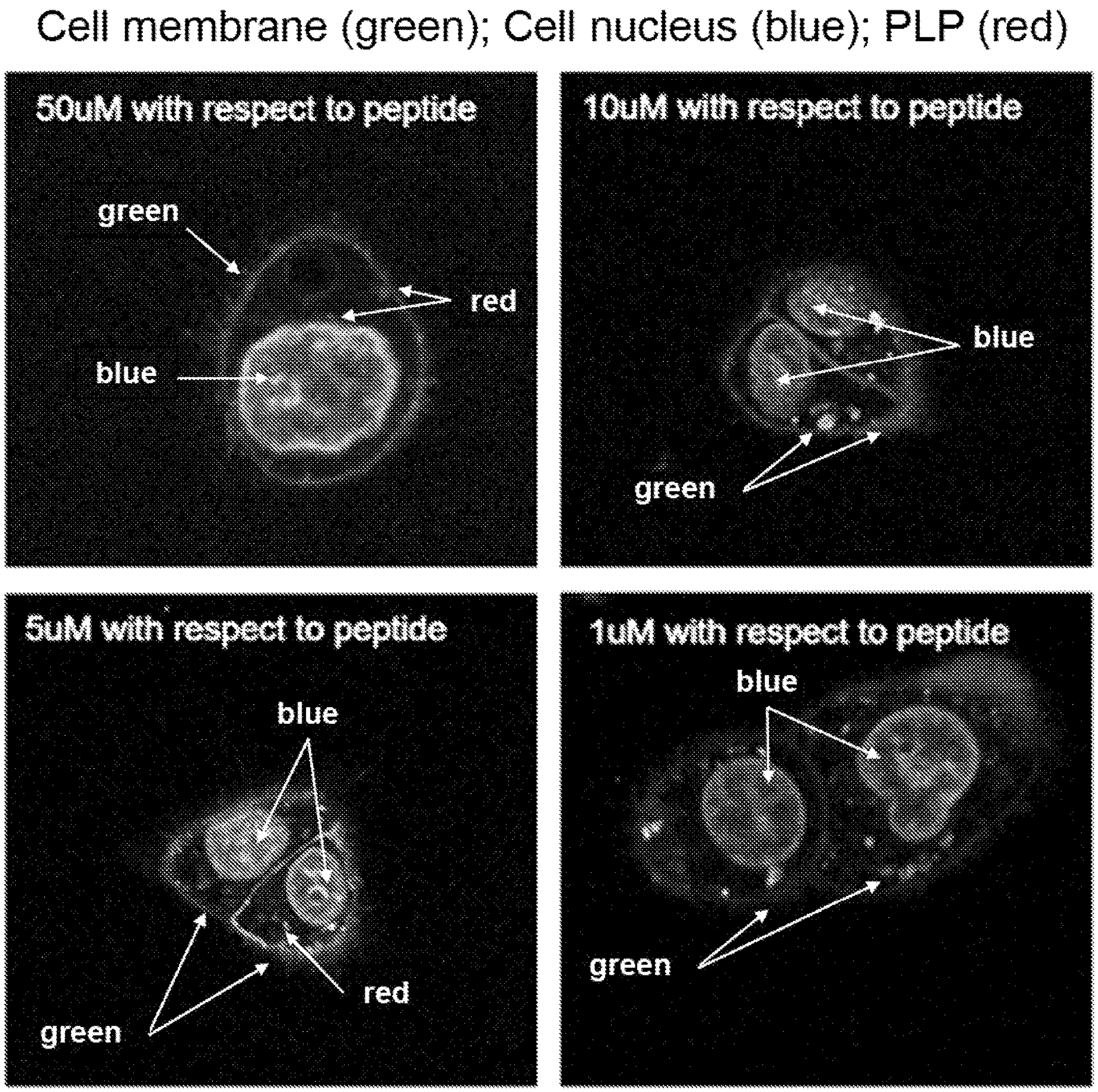
FIG. 27 shows the cell uptake in HepG2 Cells exhibited by a Cy5.5 labeled polynorbornene dicarboxyimide-based SEQ ID NO: 2 (LDPETGEFL) polymer (i.e., ProPep Homopolymer), imaged using confocal microscopy, as described in Example 21. The cell membranes are shown in green, the nuclei are shown in blue, and the Cy5.5 labeled polynorbornene dicarboxyimide-based SEQ ID NO: 2 (LDPETGEFL) polymers are shown in red. Upper left=50 μM administration with respect to the peptide; Upper right=10 μM administration with respect to the peptide; Lower Left=5 μM administration with respect to the peptide; and Lower right=1 μM administration with respect to the peptide.
Figure 28:
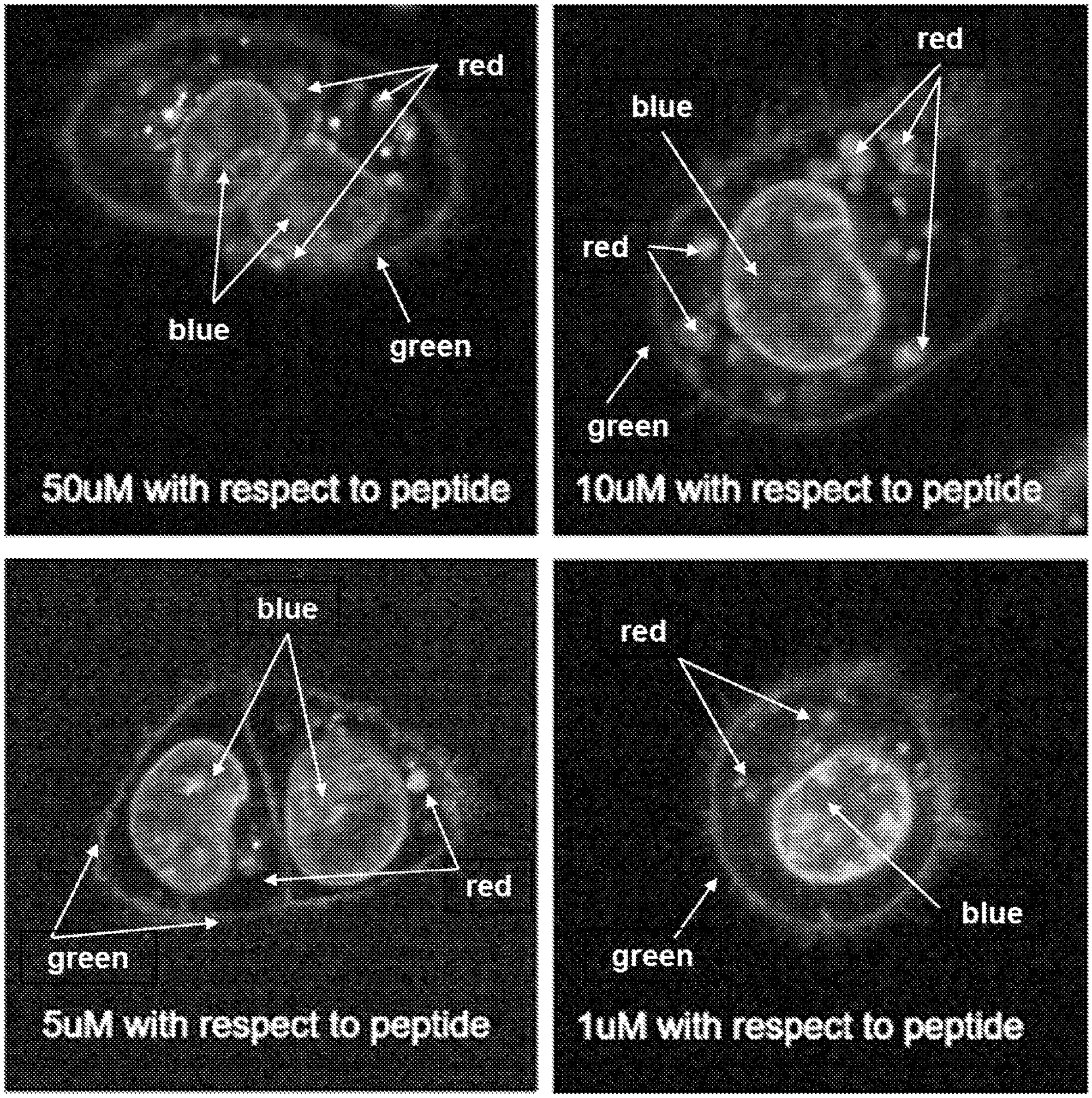
FIG. 28 shows the cell uptake in HepG2 Cells exhibited by a Cy5.5 labeled low degree of polymerization (LowDP) polynorbornene dicarboxyimide-based brush polymer (DP=average of about 11.6) comprising polynorbornene dicarboxyimide-based SEQ ID NO: 72 (LDPETGEFLRRRR) peptide monomer (i.e., ProPrepR Low PLP), imaged using confocal microscopy, as described in Example 21. The cell membranes are shown in green, the nuclei are shown in blue, and the Cy5.5 labeled polynorbornene dicarboxyimide-based SEQ ID NO: 72 (LDPETGEFLRRRR) polymers are shown in red. Upper left=50 μM administration with respect to the peptide; Upper right=10 μM administration with respect to the peptide; Lower Left=5 μM administration with respect to the peptide; and Lower right=1 μM administration with respect to the peptide.
Figure 29:
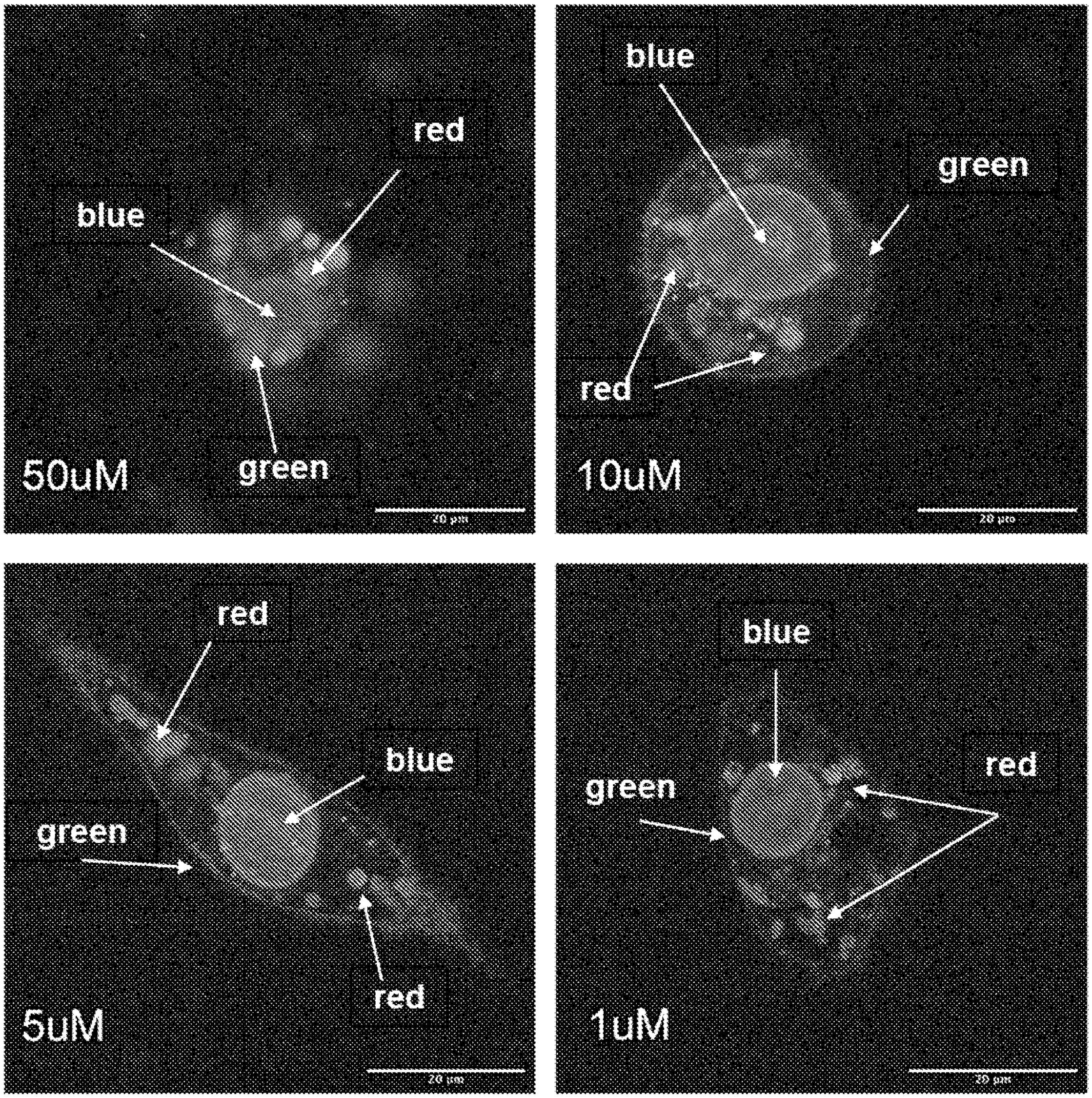
FIG. 29 shows the cell uptake in HepG2 Cells exhibited by a Cy5.5 labeled high degree of polymerization (HighDP) polynorbornene dicarboxyimide-based brush polymer (DP=average of about 22.5) comprising polynorbornene dicarboxyimide-based SEQ ID NO: 72 (LDPETGEFLRRRR) peptide monomer (i.e., ProPrepR High DP), imaged using confocal microscopy, as described in Example 21. The cell membranes are shown in green, the nuclei are shown in blue, and the Cy5.5 labeled polynorbornene dicarboxyimide-based SEQ ID NO: 72 (LDPETGEFLRRRR) polymers are shown in red. Upper left=50 μM administration with respect to the peptide; Upper right=10 μM administration with respect to the peptide; Lower Left=5 μM administration with respect to the peptide; and Lower right=1 μM administration with respect to the peptide.

FIG. 25 shows an exemplary SDS-PAGE result for two separate batches (i.e., batch (a) and batch (b)) of the Cy5.5 labeled PPR Low PLP with an average degree of polymerization of about 11.6 prepared in this example and the Cy5.5 labeled PPR High PLP with an average degree of polymerization of about 22.5 prepared in this example.

The PLPs labeled with Cy5.5 (excitation 683 nm, emission 703 nm) were used to assess cellular uptake and localization. HepG2 cells were cultured using EMEM media and plated in 4-chamber 35 mm round glass-bottom dish for imaging at a cell seeding density of 15,000 cells/well and incubated for 24 hours in a 5% $CO_2$ atmosphere at 37° C. Cells were treated with dye labeled PLP at concentrations of 1, 5, 10 and 50 μM with respect to peptide. Twenty-four hours after treatment, cells were stained using wheat germ agglutinin (excitation 495 nm, emission 519 nm) and Nuc blue (excitation 360 nm, emission 460 nm) to visualize the cell membrane and nucleus respectively. Imaging was accomplished using LEICA SP5 II laser scanning confocal microscope with a 63× oil immersion objective at 1.5× optical zoom. Slice thickness was 0.26 μm with a scan size of 1024×1024 pixels and a scan speed of 400 Hz. The cell nuclei (stained with NucBlu) was imaged using a 358 nm laser with a 15% laser power. Cell imaging for the membrane (stained with wheat germ agglutinin) was accomplished using a 488 nm laser with a 12% laser power. Cy5.5 labeled PLPs were imaged using a 633 nm laser with 12% laser power. Images were analyzed using Fiji ImageJ software.

The images for the Cy5.5 labeled polynorbornene dicarboxyimide-based SEQ ID NO: 1 (LDEETGEFL) polymer, Cy5.5 labeled polynorbornene dicarboxyimide-based SEQ ID NO: 2 (LDPETGEFL) polymer, Cy5.5 labeled low degree of polymerization (LowDP) polynorbornene dicarboxyimide-based brush polymer (DP=average of about 11.6) comprising polynorbornene dicarboxyimide-based SEQ ID NO: 72 (LDPETGEFLRRRR) peptide monomer (i.e., ProPepR Low PLP), and Cy5.5 labeled high degree of polymerization (HighDP) polynorbornene dicarboxyimide-based brush polymer (DP=average of about 22.5) comprising polynorbornene dicarboxyimide-based SEQ ID NO: 72

(LDPETGEFLRRRR) peptide monomer (i.e., ProPepR High DP) treated cells are set forth in FIGS. 26-29, respectively.

As demonstrated by FIGS. 26-29, each of the Cy5.5 labeled polynorbornene dicarboxyimide-based SEQ ID NO: 1 (LDEETGEFL) polymer, Cy5.5 labeled polynorbornene dicarboxyimide-based SEQ ID NO: 2 (LDPETGEFL) polymer, Cy5.5 labeled low degree of polymerization (LowDP) polynorbornene dicarboxyimide-based brush polymer (DP=average of about 11.6) comprising polynorbornene dicarboxyimide-based SEQ ID NO: 72 (LDPETGEFLRRRR) peptide monomer (i.e., ProPrepR Low PLP), and Cy5.5 labeled high degree of polymerization (HighDP) polynorbornene dicarboxyimide-based brush polymer (DP=average of about 22.5) comprising polynorbornene dicarboxyimide-based SEQ ID NO: 72 (LDPETGEFLRRRR) peptide monomer (i.e., ProPepR High DP), respectively, showed at least modest uptake into HepG2 (liver) cells. In addition, as demonstrated by FIGS. 26-29, the Cy5.5 labeled polynorbornene dicarboxyimide-based SEQ ID NO: 72 (LDPETGEFLRRRR) polymer exhibited significantly increased uptake into HepG2 (liver) cells relative to the other two protein-like polymers.

Figure 30:
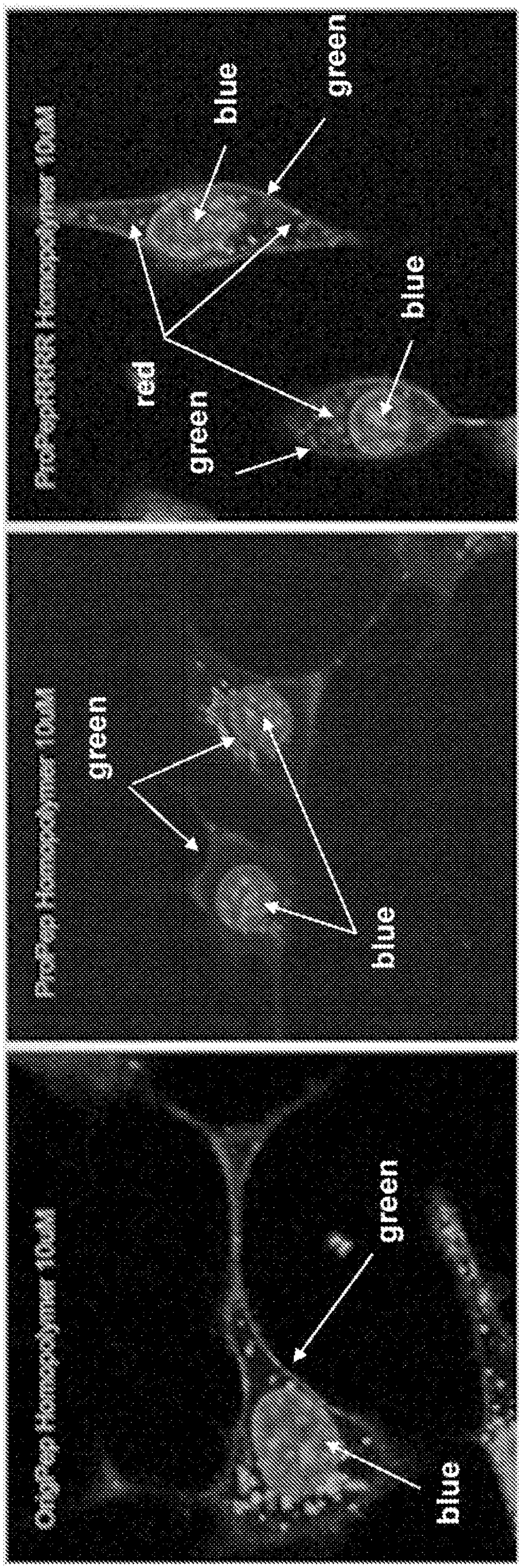
FIG. 30 shows a comparison of the cell uptake in HD95 (Huntington Disease Model Mouse Striatal Neurons) Cells exhibited by 10 μM administration, with respect to the peptide, of a Cy5.5 labeled polynorbornene dicarboxyimide-based SEQ ID NO: 1 (LDEETGEFL) polymer (i.e., OrigPep Homopolymer), a Cy5.5 labeled polynorbornene dicarboxyimide-based SEQ ID NO: 2 (LDPETGEFL) polymer (i.e., ProPep Homopolymer), and a Cy5.5 labeled polynorbornene dicarboxyimide-based SEQ ID NO: 72 (LDPETGEFLRRRR) polymer (i.e., ProPepRRRR Homopolymer), as described in Example 21. The cell membranes are shown in green, the nuclei are shown in blue, and the polymers are shown in red.

In addition, a comparative of the protein-like polymers at a concentration of 10 μM is provided at FIG. 30 in HD95/H Q111 striatal cells (Huntington's disease model cells). For these images, HD95/H Q111 striatal cells (Huntington's disease model cells) were plated at 15 k cells/well into a 4 well confocal dish. Cells were incubated overnight, at which time they were treated with Cy5.5 labeled polynorbornene dicarboxyimide-based SEQ ID NO: 1 (LDEETGEFL) 15mer (approximate) polymer, Cy5.5 labeled polynorbornene dicarboxyimide-based SEQ ID NO: 2 (LDPETGEFL) 15mer (approximate) polymer, and Cy5.5 labeled low degree of polymerization (LowDP) polynorbornene dicarboxyimide-based brush polymer (DP=average of about 11.6) comprising polynorbornene dicarboxyimide-based SEQ ID NO: 72 (LDPETGEFLRRRR) peptide monomer (i.e., ProPrepR Low PLP) at concentrations of 25 μM, 10 μM, 5 μM and 1 μM with respect to peptide. After 24 hours post-treatment, the cells were stained with wheat germ agglutinin 488 and NucBlu and subsequently imaged using confocal microscopy.

These results show that (i) the protein-like polymers of the invention have the ability to penetrate the cell membrane and (ii) the polynorbornene dicarboxyimide-based SEQ ID NO: 72 (LDPETGEFLRRRR) polymer, having a net positive charge, provides the highest uptake into HepG2 (liver) cells and HD95/H Q111 striatal cells (Huntington's disease model cells).

Figure 31:
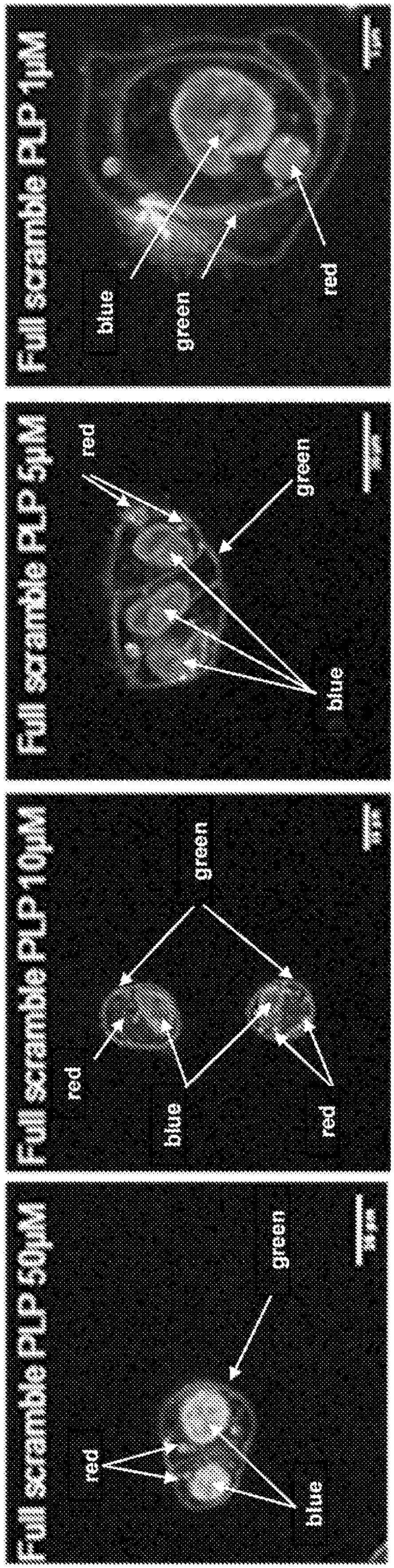
FIG. 31 shows the cell uptake in HepG2 Cells exhibited by a Cy5.5 labeled polynorbornene dicarboxyimide-based SEQ ID NO: 143 (DERLERPLTRGFR) polymer (i.e., Full Scramble PLP), imaged using confocal microscopy, as described in Example 21. The cell membranes are shown in green, the nuclei are shown in blue, and the Cy5.5 labeled polynorbornene dicarboxyimide-based SEQ ID NO: 143 (DERLERPLTRGFR) polymers are shown in red. Far left=50 μM administration with respect to the peptide; Middle left=10 μM administration with respect to the peptide; Middle right=5 μM administration with respect to the peptide; and Far right=1 μM administration with respect to the peptide.
Figure 32:
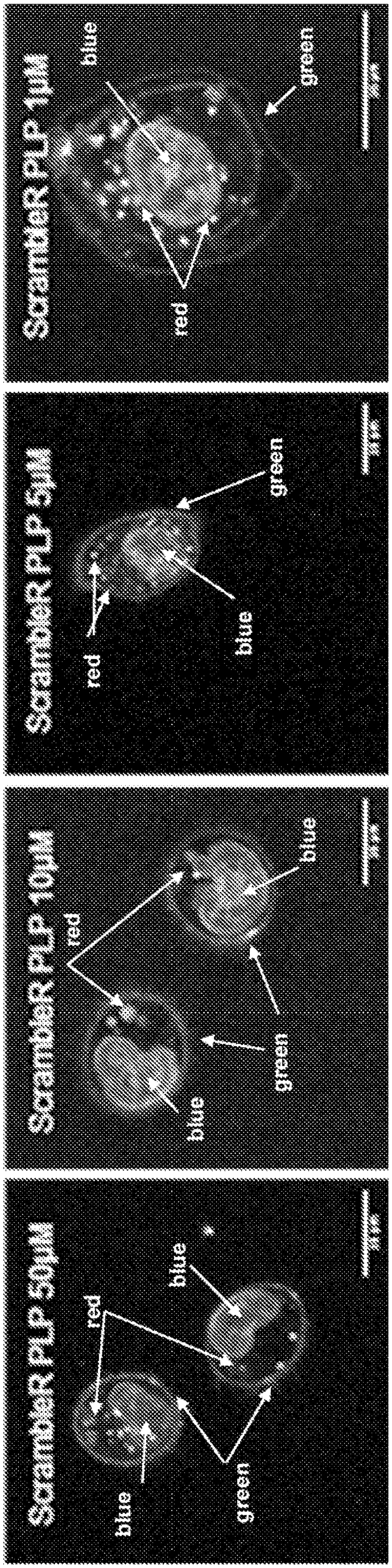
FIG. 32 shows the cell uptake in HepG2 Cells exhibited by a Cy5.5 labeled polynorbornene dicarboxyimide-based SEQ ID NO: 146 (DELEPLTGFRRRR) polymer (i.e., ScrambleR PLP), imaged using confocal microscopy, as described in Example 21. The cell membranes are shown in green, the nuclei are shown in blue, and the Cy5.5 labeled polynorbornene dicarboxyimide-based SEQ ID NO: 146 (DELEPLTGFRRRR) polymer polymers are shown in red. Far left=50 μM administration with respect to the peptide; Middle left=10 μM administration with respect to the peptide; Middle right=5 μM administration with respect to the peptide; and Far right=1 μM administration with respect to the peptide.
Figure 33:
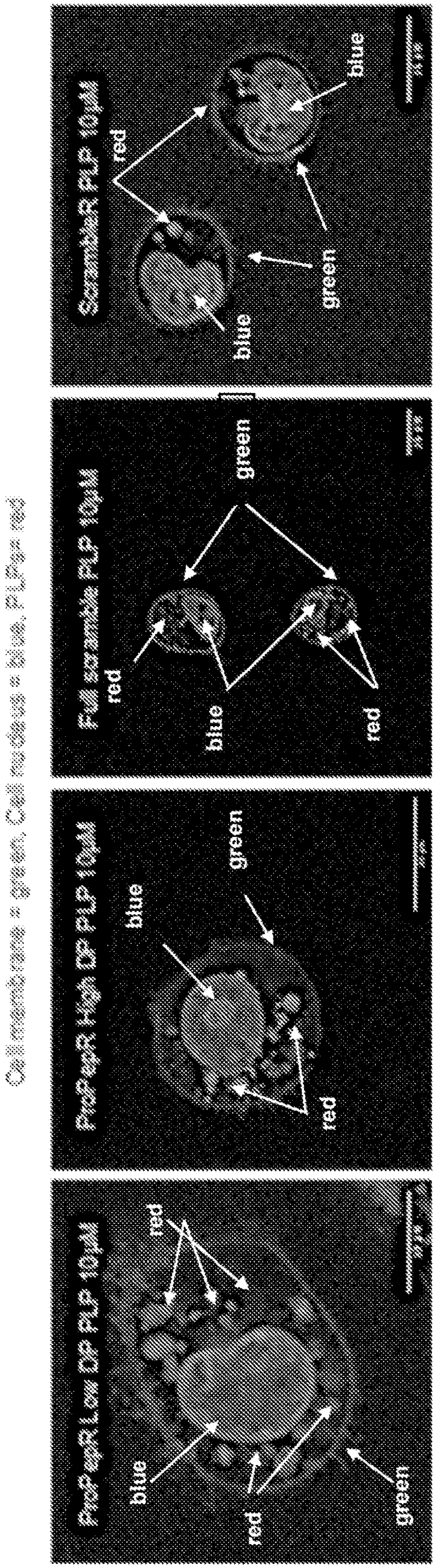
FIG. 33 shows a comparison of the cell uptake in HepG2 Cells exhibited by 10 μM administration, with respect to the peptide, of a low degree of polymerization (DP=average of about 11.6) Cy5.5 labeled polynorbornene dicarboxyimide-based SEQ ID NO: 72 (LDPETGEFLRRRR) polymer (i.e., ProPepR Low DP PLP), a high degree of polymerization (DP=average of about 22.5) Cy5.5 labeled polynorbornene dicarboxyimide-based SEQ ID NO: 72 (LDPETGEFLRRRR) polymer (i.e., ProPepR High DP PLP), a Cy5.5 labeled polynorbornene dicarboxyimide-based SEQ ID NO: 143 (DERLERPLTRGFR) polymer (i.e., Full Scramble PLP), and a Cy5.5 labeled polynorbornene dicarboxyimide-based SEQ ID NO: 146 (DELEPLTGFRRRR) polymer (i.e., ScrambleR PLP), as described in Example 21. The cell membranes are shown in green, the nuclei are shown in blue, and the polymers are shown in red.

In addition, the images for the Cy5.5 labeled Full Scramble PLP (i.e., peptide sequence SEQ ID NO: 143 (DERLERPLTRGFR)) and the Cy5.5 labeled ScrambleR PLP (i.e., peptide sequence SEQ ID NO: 146 (DELEPLTGFRRRR)) treated HepG2 cells are set forth in FIGS. 31 and 32, respectively. In addition, a comparative of the protein-like polymers (i.e., Cy5.5 labeled PPR Low PLP, Cy5.5 labeled PPR High PLP, Cy5.5 labeled Full Scramble PLP, and Cy5.5 labeled ScrambleR PLP) at a concentration of 10 μM is provided at FIG. 33.

These results show that the Full Scramble PLP and the ScrambleR PLP have the ability to penetrate the cell membrane. Thus, while the Full Scramble PLP and the ScrambleR PLP are able to get into cells due to being cationic, they are not active in inhibiting Keap1/Nrf2, as described in other examples.

Example 22

This example shows the ability of a protein-like polymer described herein to permeate the cell. To demonstrate the cell permeability, the cellular uptake of Cy5.5-labeled PLPs was quantified in HepG2 cells via flow cytometry.

Cellular uptake was quantified using flow cytometry in HepG2 cells treated with Cy5.5 labeled PLPs including: OrigPep PLP (SEQ ID NO: 1 (LDEETGEFL)), ProPep PLP (SEQ ID NO: 2 (LDPETGEFL)), ProPepR$_{low}$ PLP (SEQ ID NO: 72 (LDPETGEFLRRRR); DP=average of about 11.6), ProPepR$_{high}$ PLP (SEQ ID NO: 72 (LDPETGEFLRRRR); DP=average of about 22.5), ScrambleR PLP (SEQ ID NO: 146 (DELEPLTGFRRRR)), and Full Scramble PLP (SEQ ID NO: 143 (DERLERPLTRGFR)), as well as Cy5.5 monomer and untreated controls. Briefly, HepG2 cells were cultured using EMEM media and plated into 12-well plates at a cell seeding density of 100,000 cells/well in 1 mL media per well and incubated for 24 hours at 37° C. and 5% $CO_2$. Cells were treated with concentrations from 0.5 μM to 3 μM with respect to dye and incubated for 24 hours at 37° C. After incubation, media was removed, and cells were washed twice with DPBS. Cells were incubated with heparin (0.5 mg/mL in DPBS) for 5 minutes, three times, followed by a final rinse with DPBS. The DPBS was removed and 100 μL of trypsin with 0.25% EDTA was added to each well and allowed to incubate for 5 minutes at 37° C. Cells were transferred to Eppendorf tubes and centrifuged at 1300 rpm for 5 minutes. The supernatant was removed and cells were resuspended in 200 μL of fresh DPBS. Cellular uptake was analyzed via flow cytometry using a BD FacsAria IIu 4-Laser flow cytometer (Becton Dickinson Inc., USA). Mean fluorescence intensity and histogram data were prepared for presentation using FlowJo v10. The results are set forth in FIGS. 34A-B and 35A-B.

Figure 34A:
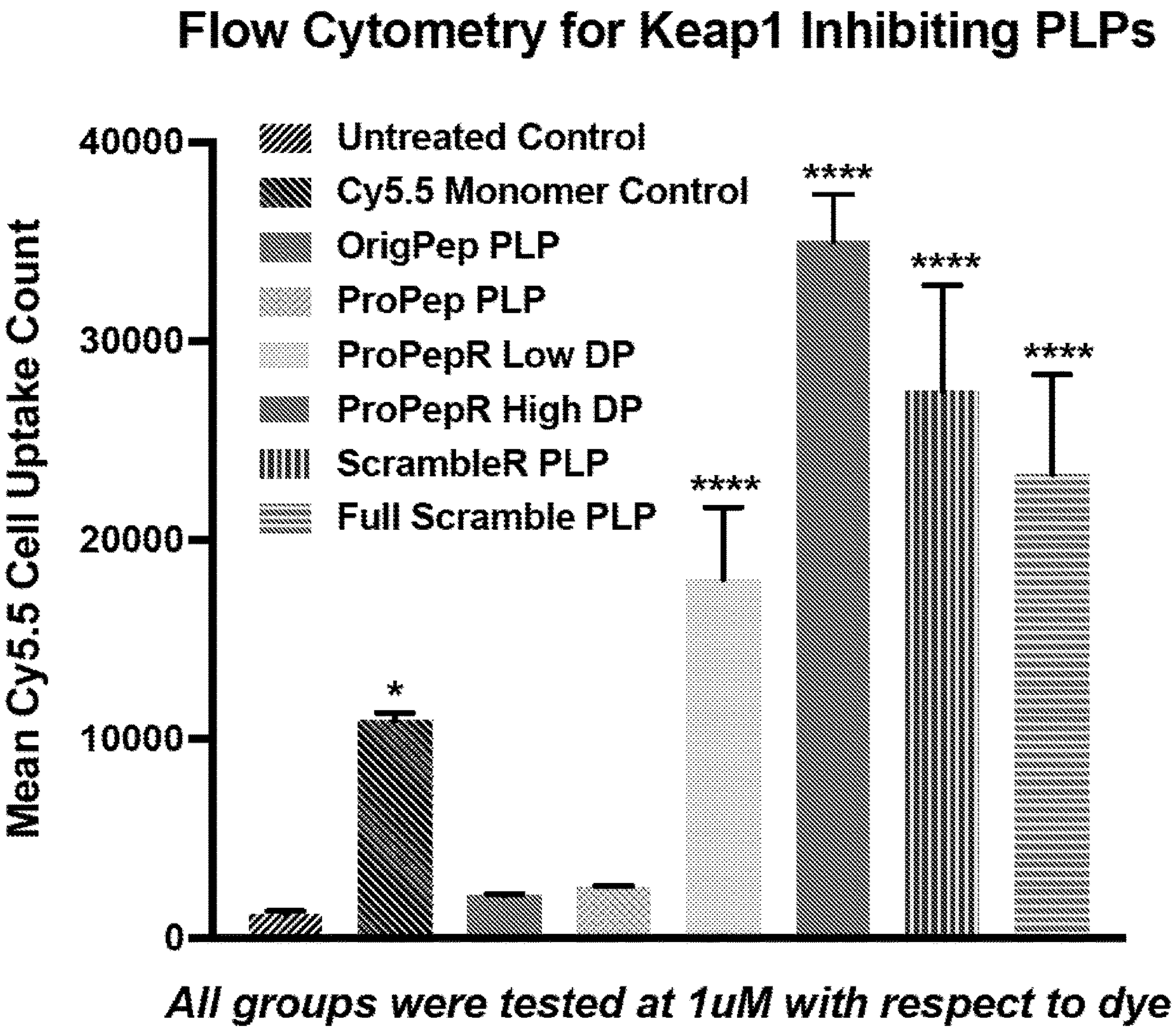
FIG. 34A shows cellular uptake via flow cytometry data (1 μM with respect to the dye) exhibited by (a) an untreated control, (b) a Cy5.5 labeled monomer control (c) a Cy5.5 labeled polynorbornene dicarboxyimide-based SEQ ID NO: 1 (LDEETGEFL) polymer (i.e., OrigPep PLP), (d) a Cy5.5 labeled polynorbornene dicarboxyimide-based SEQ ID NO: 2 (LDPETGEFL) polymer (i.e., ProPep PLP), (e) a Cy5.5 labeled low degree of polymerization (DP=average of about 11.6) polynorbornene dicarboxyimide-based SEQ ID NO: 72 (LDPETGEFLRRRR) polymer (i.e., ProPepR Low DP), (f) a Cy5.5 labeled high degree of polymerization (DP=average of about 22.5) polynorbornene dicarboxyimide-based SEQ ID NO: 72 (LDPETGEFLRRRR) polymer (i.e., ProPepR High DP), (g) a Cy5.5 labeled polynorbornene dicarboxyimide-based SEQ ID NO: 146 (DELEPLTGFRRRR) polymer (i.e., ScrambleR PLP), and (h) a Cy5.5 labeled polynorbornene dicarboxyimide-based SEQ ID NO: 143 (DERLERPLTRGFR) polymer (i.e., Full Scramble PLP), as described in Example 22.
Figure 34B:
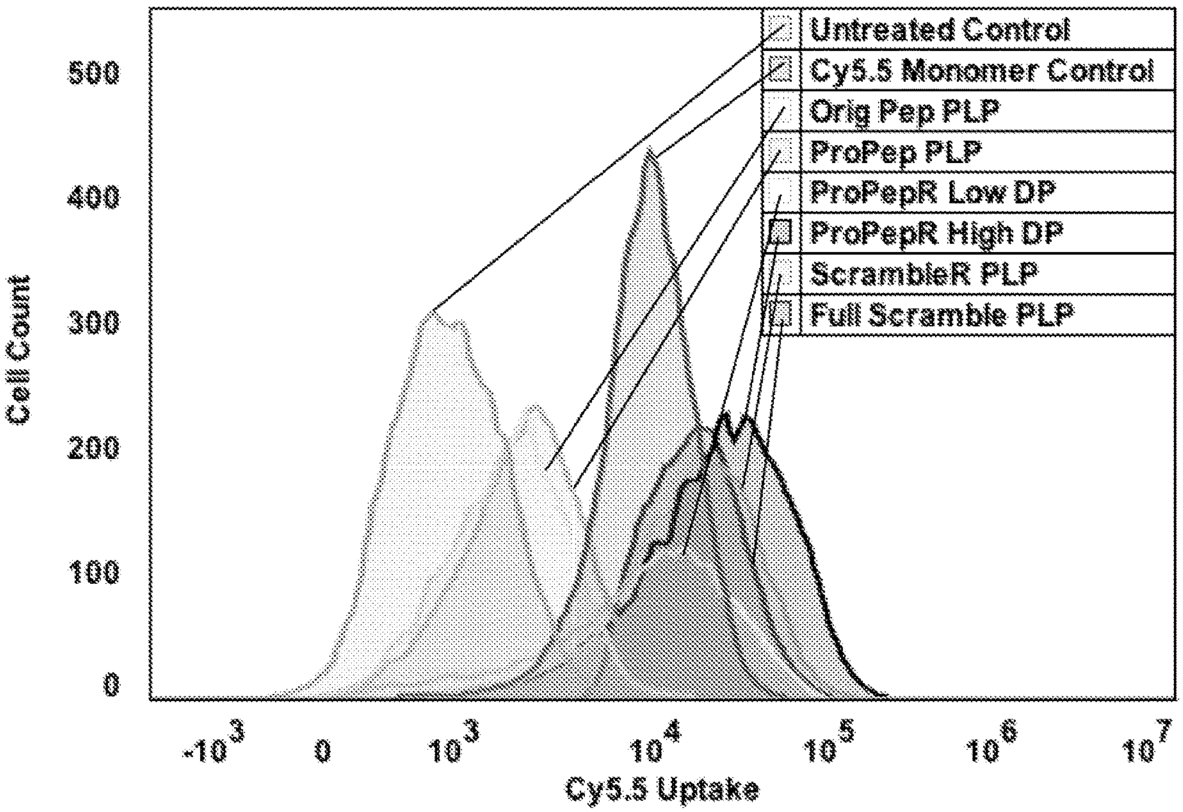
FIG. 34B shows the histogram associated with the flow cytometry data of FIG. 34A, as described in Example 22.

As shown in FIGS. 34A and 34B, which shows cellular uptake via flow cytometry data (1 μM with respect to the dye), the PLPs comprising OrigPep PLP (SEQ ID NO: 1 (LDEETGEFL)) and ProPep PLP (SEQ ID NO: 2 (LDPETGEFL)) exhibit limited cellular uptake, whereas PLPs comprising ProPepR$_{low}$ PLP (SEQ ID NO: 72 (LDPETGEFLRRRR); DP=average of about 11.6), ProPepR$_{high}$ PLP (SEQ ID NO: 72 (LDPETGEFLRRRR); DP=average of about 22.5), ScrambleR PLP (SEQ ID NO: 146 (DELEPLTGFRRRR)), and Full Scramble PLP (SEQ ID NO: 143 (DERLERPLTRGFR)) exhibited high cellular uptake. See also FIGS. 26-33. These results, when taken into consideration with FIGS. 26-33, show that PLPs comprising ProPepR$_{low}$ PLP (SEQ ID NO: 72 (LDPETGEFLRRRR); DP=average of about 11.6), ProPepR$_{high}$ PLP (SEQ ID NO: 72 (LDPETGEFLRRRR); DP=average of about 22.5), ScrambleR PLP (SEQ ID NO: 146 (DELEPLTGFRRRR)), and Full Scramble PLP (SEQ ID NO: 143 (DERLERPLTRGFR)) were able to penetrate the cell membrane, escape endosomes, and access the Keap1 cytosolic target.

Figure 35A:
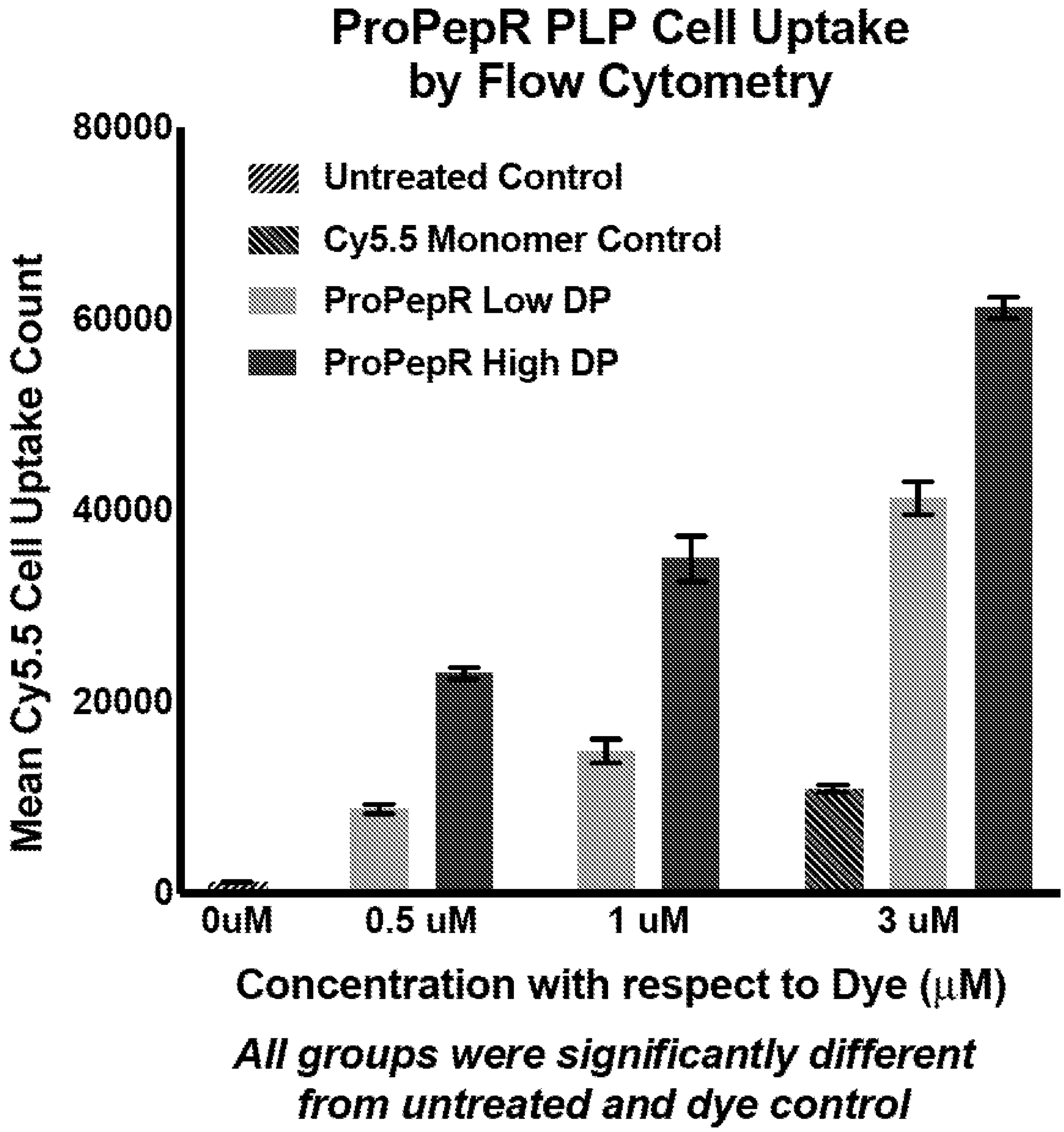
FIG. 35A shows the dose dependent (i.e., 0 μM, 0.5 μM, 1 μM, and 3 μM with respect to the dye) cellular uptake flow cytometry data exhibited by (a) an untreated control, (b) a Cy5.5 labeled monomer control (c) a Cy5.5 labeled low degree of polymerization (DP=average of about 11.6) polynorbornene dicarboxyimide-based SEQ ID NO: 72 (LDPETGEFLRRRR) polymer (i.e., ProPepR Low DP), and (d) a Cy5.5 labeled high degree of polymerization (DP=average of about 22.5) polynorbornene dicarboxyimide-based SEQ ID NO: 72 (LDPETGEFLRRRR) polymer (i.e., ProPepR High DP), as described in Example 22.
Figure 35B:
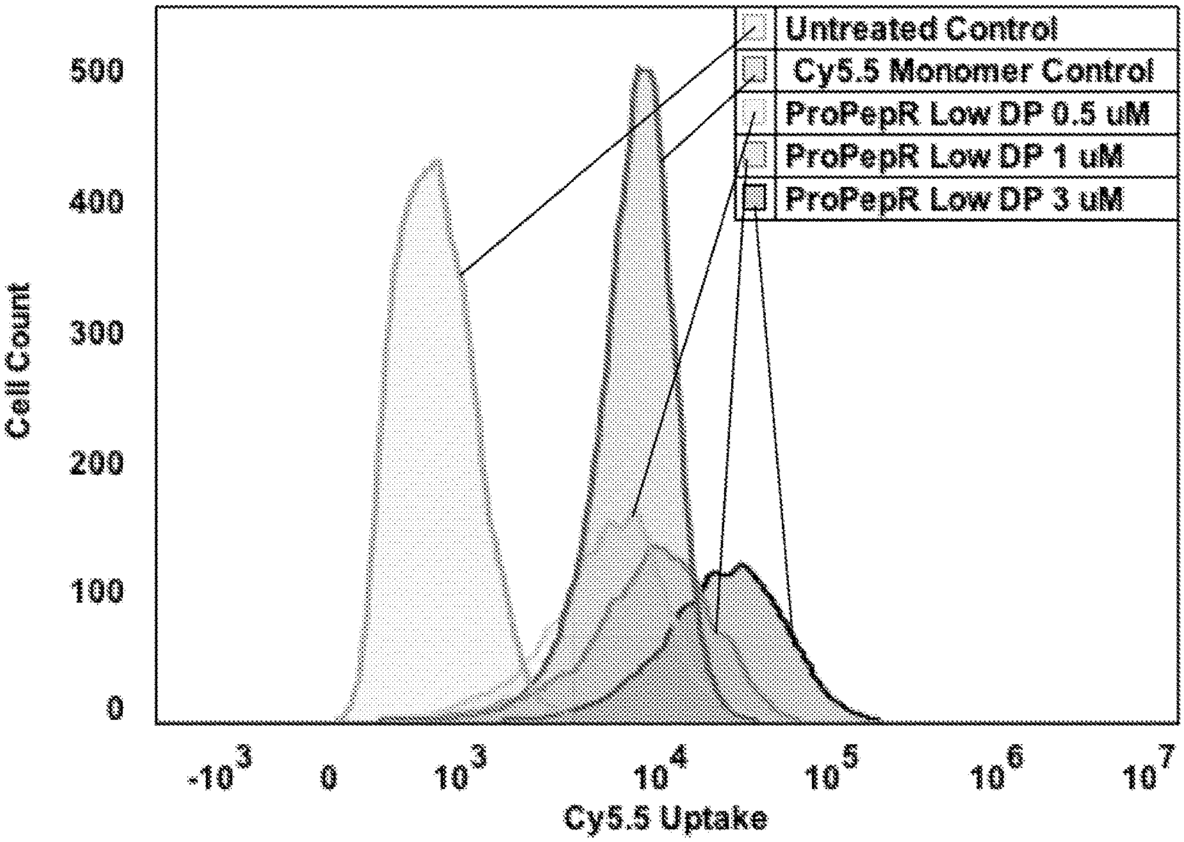
FIG. 35B shows the histogram associated with the flow cytometry data of the Cy5.5 labeled low degree of polymerization (DP=average of about 11.6) polynorbornene dicarboxyimide-based SEQ ID NO: 72 (LDPETGEFLRRRR) polymer (i.e., ProPepR Low DP) of FIG. 35A, as described in Example 22.
Figure 35C:
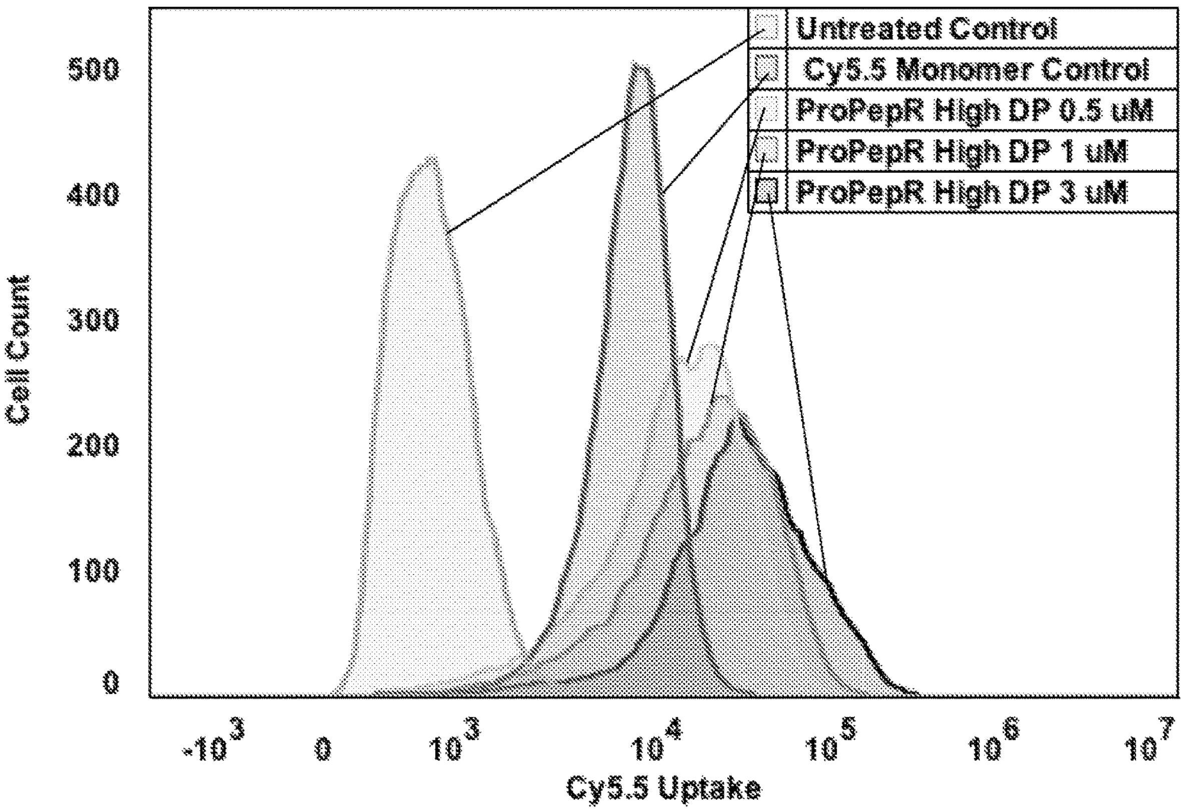
FIG. 35C shows the histogram associated with the flow cytometry data of the Cy5.5 labeled high degree of polymerization (DP=average of about 22.5) polynorbornene dicarboxyimide-based SEQ ID NO: 72 (LDPETGEFLRRRR) polymer (i.e., ProPepR High DP) of FIG. 35A, as described in Example 22.

As shown in FIGS. 35A-35C, cellular uptake for the both the PLP comprising ProPepR$_{low}$ PLP (SEQ ID NO: 72 (LDPETGEFLRRRR); DP=average of about 11.6) and the PLP comprising ProPepR$_{high}$ PLP (SEQ ID NO: 72 (LDPETGEFLRRRR) occurred in a dose-dependent manner. In addition, the PLP comprising ProPepR$_{high}$ PLP (SEQ ID NO: 72 (LDPETGEFLRRRR) exhibited enhanced cellular uptake compared to the PLP comprising ProPepR$_{low}$ PLP (SEQ ID NO: 72 (LDPETGEFLRRRR); DP=average of about 11.6). Without wishing to be bound by any particular theory, it is believed that the increased number of cationic residues displayed on the larger polymer results enhances the cellular permeability.

Example 23

This example shows the ability of a protein-like polymer described herein to cross the blood brain barrier (BBB) to reach targets for treating diseases of the central nervous system such as neurodegenerative disease. To assess the potential of the Keap1-inhibiting PLPs to reach the CNS, human brain microvascular endothelial cells (HBEC-5i) were used in an in vitro assay to mimic the BBB in a transwell culture set-up.

Human cerebral microvascular endothelial cells (HBEC-5i, ATCC® CRL-3245) were purchased from American Type Culture Collection (ATCC). HBEC-5i cells were cultured according to manufacturer's instructions (monolayer of cells on 0.1% gelatin coated T-flasks in DMEM:F12 medium supplemented with 10% FBS, 1% penicillin/streptomycin antibiotic solution, and 40 μg/mL endothelial growth supplement (ECGS)). Cells were grown in an atmosphere of 5% $CO_2$ at 37° C., with the medium changed every other day. Once the cells reached confluency, they were detached with trypsin-EDTA and plated at a seeding density of 8,000 cells/well into 0.1% gelatin solution coated tissue culture inserts [transparent polyester (PET) membrane with 1.0 μm pores] for 24-well plates (BD Falcon, United States). The cells were allowed to grow for 8 days, with media changes every 2 days. On day 8, the cells were washed twice with PBS and once with DMEM:F12 medium without phenol red. The PLP comprising ProPepR$_{low}$ PLP (SEQ ID NO: 72 (LDPETGEFLRRRR); DP=average of about 11.6) and the PLP comprising ProPepR$_{high}$ PLP (SEQ ID NO: 72 (LDPETGEFLRRRR) were added to the apical side of cell monolayer in the in vitro BBB model to final concentrations of 1, 2.5, 5, and 10 μM with respect to dye along with controls (untreated, NaF, and Cy5.5 monomer). Cells were allowed to incubate for 24 hours at 37° C. in 5% $CO_2$. Media was collected from the apical and basolateral chambers of each well. Translocation was assessed using a Perkin Elmer EnSpire multimode Plate Reader to measure the presence of Cy5.5 in the basolateral media from the outer well, and calculated as % Translocation=(fluorescence outer well−fluorescence from cell media)/(fluorescence control−fluorescence media). The results are set forth in FIG. 36.

Figure 36:
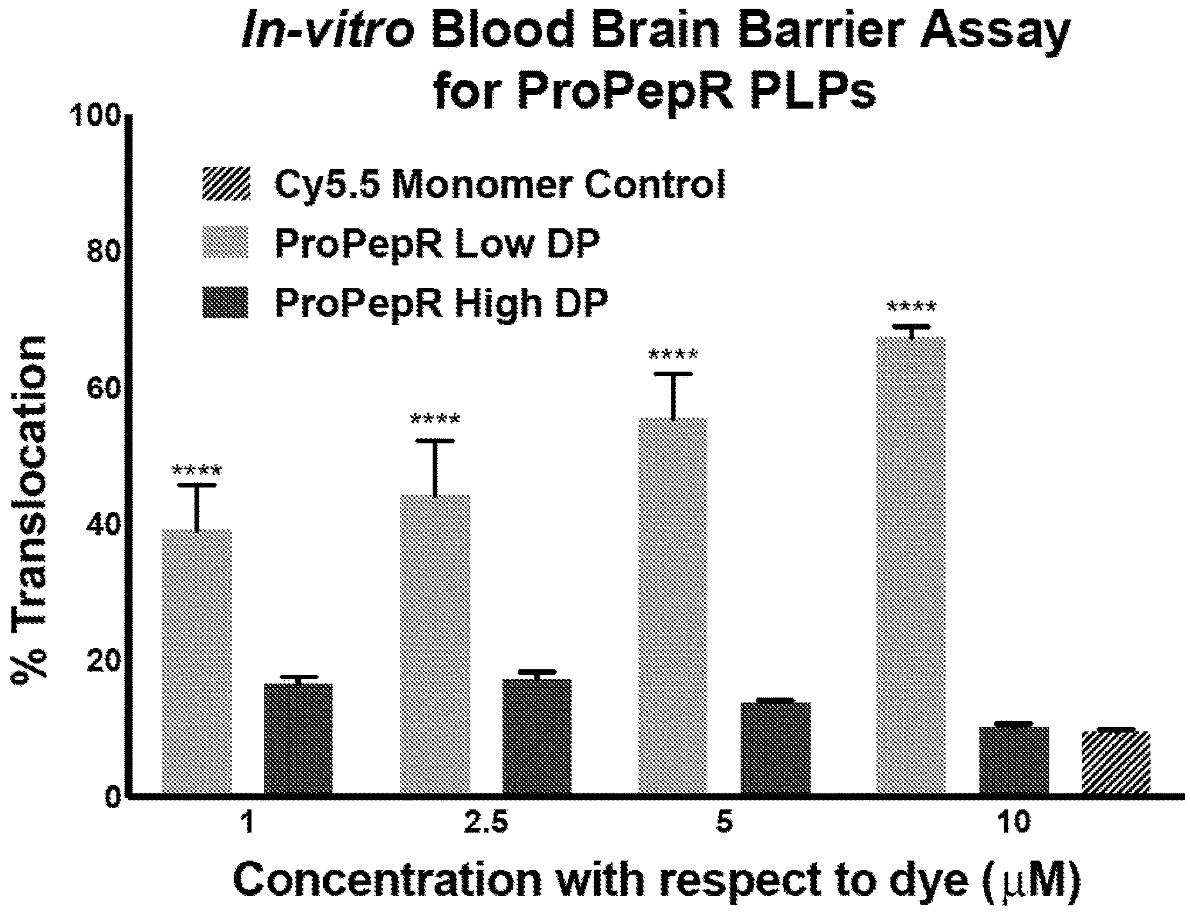
FIG. 36 shows the translocation percentage in an in vitro blood brain barrier assay exhibited by (a) a Cy5.5 labeled monomer control (b) a Cy5.5 labeled low degree of polymerization (DP=average of about 11.6) polynorbornene dicarboxyimide-based SEQ ID NO: 72 (LDPETGEFLRRRR) polymer (i.e., ProPepR Low DP), and (c) a Cy5.5 labeled high degree of polymerization (DP=average of about 22.5) polynorbornene dicarboxyimide-based SEQ ID NO: 72 (LDPETGEFLRRRR) polymer (i.e., ProPepR High DP), as described in Example 23.

As shown in FIG. 36, compared to the Cy5.5 monomer control, the PLP comprising ProPepR$_{low}$ PLP (SEQ ID NO: 72 (LDPETGEFLRRRR); DP=average of about 11.6) exhibited significant and dose dependent translocation across the in vitro BBB cell layer. However, relative to the PLP comprising ProPepR$_{low}$ PLP (SEQ ID NO: 72 (LDPETGEFLRRRR); DP=average of about 11.6), the PLP comprising ProPepR$_{high}$ PLP (SEQ ID NO: 72 (LDPETGEFLRRRR) exhibited reduced translocation across the in vitro BBB cell layer at all concentrations tested. Without wishing to be bound by any particular theory, it is believed that larger size of the ProPepR$_{high}$ PLP (SEQ ID NO: 72 (LDPETGEFLRRRR) limited its translocation through in vitro BBB membrane.

Example 24

This example shows the biocompatibility of a protein-like polymer described herein, as determined by the cell viability of IMR32 (neuroblastoma) cells treated with the protein-like polymer.

IMR32 (neuroblastoma) cells from ATCC were grown in Eagle's Minimum Essential Medium (EMEM) supplemented with 10% fetal bovine serum (FBS), and 1% penicillin-streptomycin. Cells were maintained at 37° C. and 5% $CO_2$ and cultured according to manufacturer's recommendations. IMR32 cells were plated in 96-well plates at a density of 10,000 cells/well in 200 uL of media and incubated for 24 hours. Cells were treated with test (PLPs comprising ProPepR$_{low}$ PLP (SEQ ID NO: 72 (LDPETGEFLRRRR); DP=average of about 11.6), ProPepR$_{high}$ PLP (SEQ ID NO: 72 (LDPETGEFLRRRR); DP=average of about 22.5), ScrambleR PLP (SEQ ID NO: 146 (DELEPLTGFRRRR)), and Full Scramble PLP (SEQ ID NO: 143 (DERLERPLTRGFR)) and control (untreated control) groups at concentrations of 0 μM, 0.1 μM, 1 μM, 5 μM, 7.5 μM, 10 μM, 20 μM, 30 μM, 40 μM, and 50 μM with respect to peptide in triplicate. Forty-eight hours after treatment, cells were treated with 20 μL of MTS assay reagent and allowed to develop. Absorbance was measured at 490 nm using a Perkin Elmer EnSpire plate reader every hour after MTS addition. Viability was assessed after background subtraction from cell free control wells and calculated as relative viability based on the average of untreated control wells. Viability is reported as a percentage of untreated cells and prepared for presentation using Prism9. The results are set forth in FIG. 37.

Figure 37:
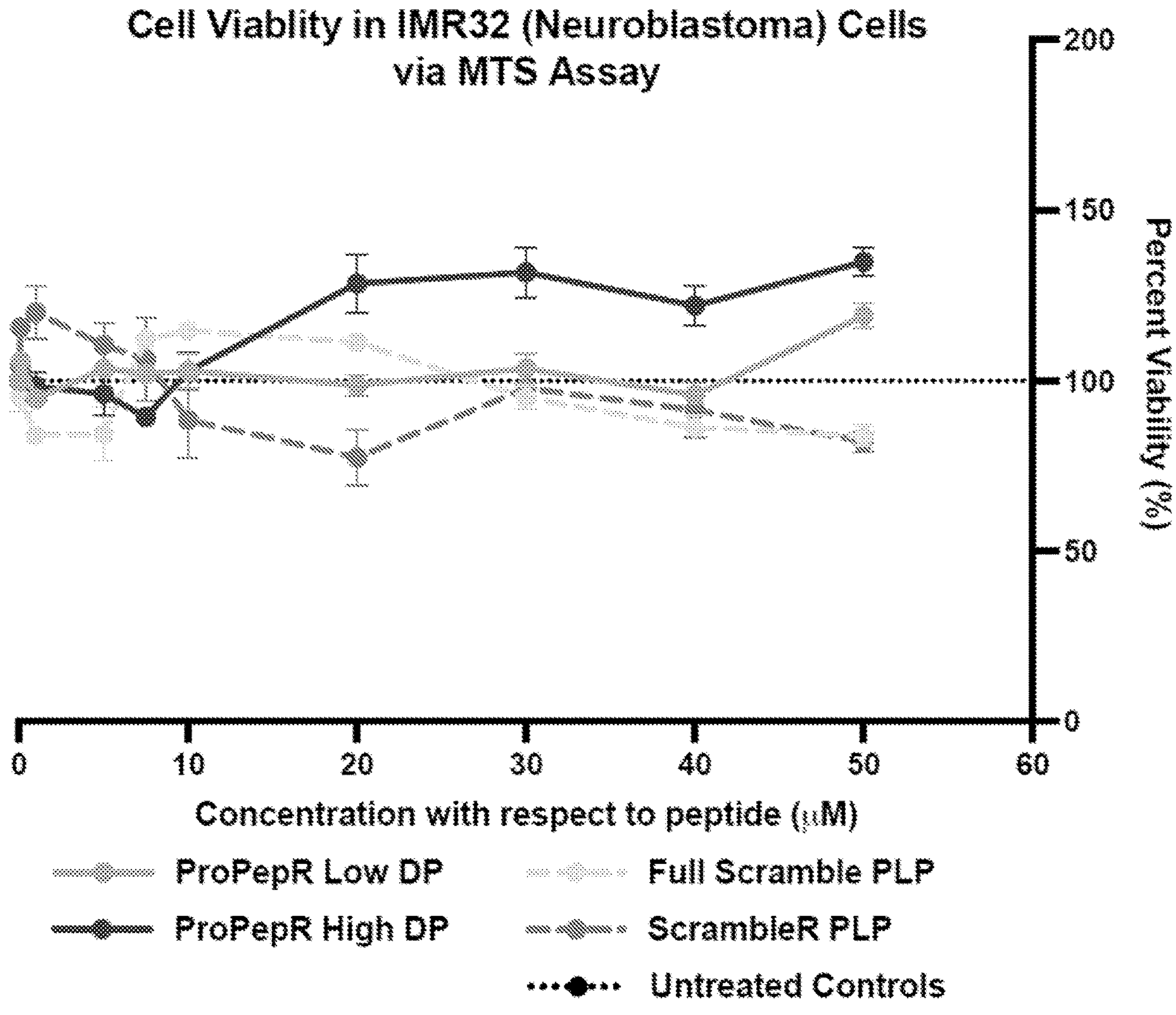
FIG. 37 shows the cell viability (%) of IMR32 (neuroblastoma) cells via an MTS assay exhibited by (a) an untreated control, (b) a low degree of polymerization (DP=average of about 11.6) polynorbornene dicarboxyimide-based SEQ ID NO: 72 (LDPETGEFLRRRR) polymer (i.e., ProPepR Low DP), (c) a high degree of polymerization (DP=average of about 22.5) polynorbornene dicarboxyimide-based SEQ ID NO: 72 (LDPETGEFLRRRR) polymer (i.e., ProPepR High DP), (d) a polynorbornene dicarboxyimide-based SEQ ID NO: 143 (DERLERPLTRGFR) polymer (i.e., Full Scramble PLP), and (e) a polynorbornene dicarboxyimide-based SEQ ID NO: 146 (DELEPLTGFRRRR) polymer (i.e., ScrambleR PLP), as described in Example 24.

As shown in FIG. 37, no significant decrease in cell viability was observed for any of the PLPs. These results show that PLPs comprising ProPepR$_{low}$ PLP (SEQ ID NO: 72 (LDPETGEFLRRRR); DP=average of about 11.6), ProPepR$_{high}$ PLP (SEQ ID NO: 72 (LDPETGEFLRRRR); DP=average of about 22.5), ScrambleR PLP (SEQ ID NO: 146 (DELEPLTGFRRRR)), and Full Scramble PLP (SEQ ID NO: 143 (DERLERPLTRGFR) are well-tolerated by the IMR32 (neuroblastoma) cells.

Example 25

This example shows the results of an Antioxidant Response Element (ARE) reporter assay for an ARE reporter HepG2 cell line treated with an untreated control, a tBHQ positive control, a low degree of polymerization (DP=average of about 11.6) polynorbornene dicarboxyimide-based SEQ ID NO: 72 (LDPETGEFLRRRR) polymer (i.e., ProPepR Low DP), (d) a SEQ ID NO: 72 (LDPETGEFLRRRR) peptide (i.e., ProPepR Free Peptide), a high degree of polymerization (DP=average of about 22.5) polynorbornene dicarboxyimide-based SEQ ID NO: 72 (LDPETGEFLRRRR) polymer (i.e., ProPepR High DP), a polynorbornene dicarboxyimide-based SEQ ID NO: 143 (DERLERPLTRGFR) polymer (i.e., Full Scramble PLP), and a polynorbornene dicarboxyimide-based SEQ ID NO: 146 (DELEPLTGFRRRR) polymer (i.e., ScrambleR PLP).

The Antioxidant Response Element (ARE) Luciferase Reporter HepG2 Cell line was used to probe Nrf2 antioxidant pathway activation. ARE-HepG2 cells were cultured in growth media (BPS bioscience) according to manufacturer's recommendations. Cells were plated at a seeding density of 25 k cells/well into white opaque 96 well plates. PLPs and peptides were tested at concentrations ranging from 0 μM to 50 μM with respect to peptide along with controls (untreated and tBHQ positive control at 100 μM) in triplicate. Cells were incubated for 24 hours post-treatment. ONE-step luciferase assay reagent was added at 100 μL/well, followed by rocking at room temperature for 15 min. Luminescence was assessed using a Biotek SynergyNeo2 plate reader. Background luminescence of cell free controls wells was subtracted from test wells. ARE activation was reported as luminescence relative to the average of the untreated controls wells.

Figure 38A:
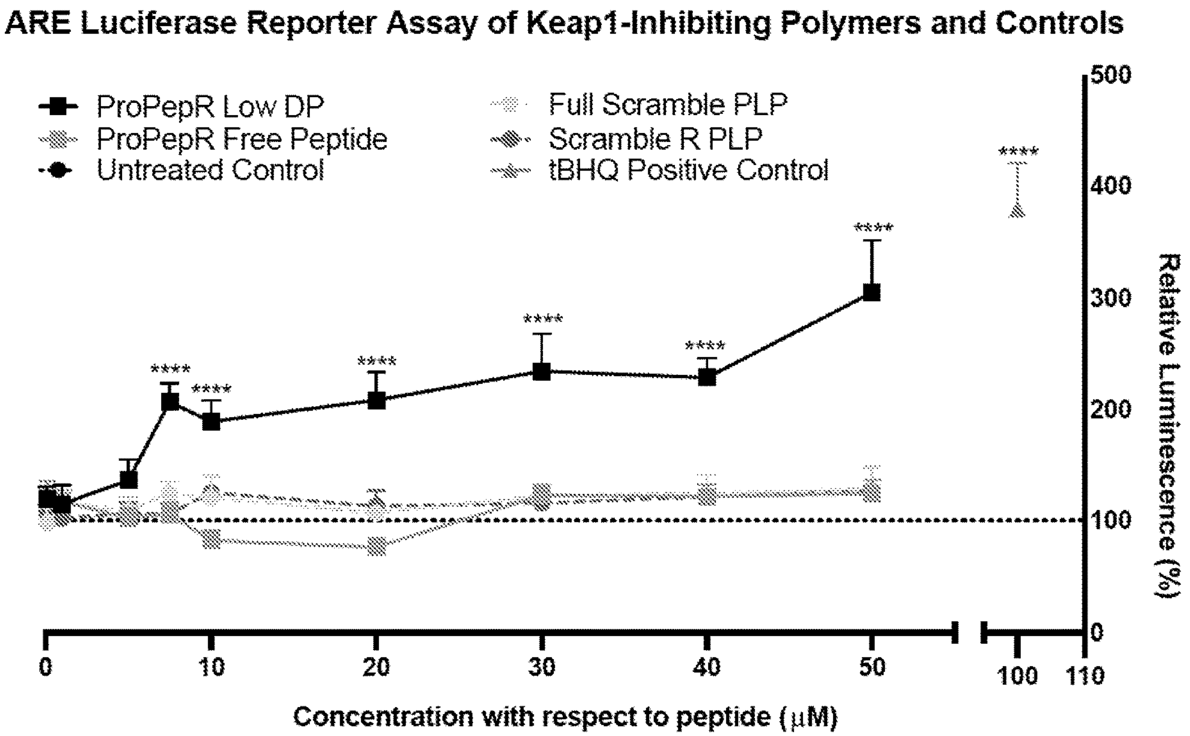
FIG. 38A shows the results of an Antioxidant Response Element (ARE) luciferase reporter assay for a HepG2 cell line treated with (a) an untreated control, (b) a tert-Butylhydroquinone (tBHQ) positive control, (c) a low degree of polymerization (DP=average of about 11.6) polynorbornene dicarboxyimide-based SEQ ID NO: 72 (LDPETGEFLRRRR) polymer (i.e., ProPepR Low DP), (d) a SEQ ID NO: 72 (LDPETGEFLRRRR) peptide (i.e., ProPepR Free Peptide), (e) a polynorbornene dicarboxyimide-based SEQ ID NO: 143 (DERLERPLTRGFR) polymer (i.e., Full Scramble PLP), and (f) a polynorbornene dicarboxyimide-based SEQ ID NO: 146 (DELEPLTGFRRRR) polymer (i.e., ScrambleR PLP), as described in Example 25.

The results for a HepG2 cell line treated with (a) an untreated control, (b) a tBHQ positive control, (c) a low degree of polymerization (DP=average of about 11.6) polynorbornene dicarboxyimide-based SEQ ID NO: 72 (LDPETGEFLRRRR) polymer (i.e., ProPepR Low DP), (d) a SEQ ID NO: 72 (LDPETGEFLRRRR) peptide (i.e., ProPepR Free Peptide), (e) a polynorbornene dicarboxyimide-based SEQ ID NO: 143 (DERLERPLTRGFR) polymer (i.e., Full Scramble PLP), and (f) a polynorbornene dicarboxyimide-based SEQ ID NO: 146 (DELEPLTGFRRRR) polymer (i.e., ScrambleR PLP) are set forth in FIG. 38A.

As shown in FIG. 38A, only low degree of polymerization (DP=average of about 11.6) polynorbornene dicarboxyimide-based SEQ ID NO: 72 (LDPETGEFLRRRR) polymer (i.e., ProPepR Low DP) resulted in ARE activation. These results show that ProPepR Low DP enters the cells and activates ARE. In contrast, Full Scramble PLP and ScrambleR PLP did not activate ARE, demonstrating that while the scrambled PLPs are able to get into the cell, they do not activate ARE. Similarly, ProPepR Free Peptide did not activate ARE, demonstrating that ProPepR Free Peptide was not able to enter the cell.

Figure 38B:
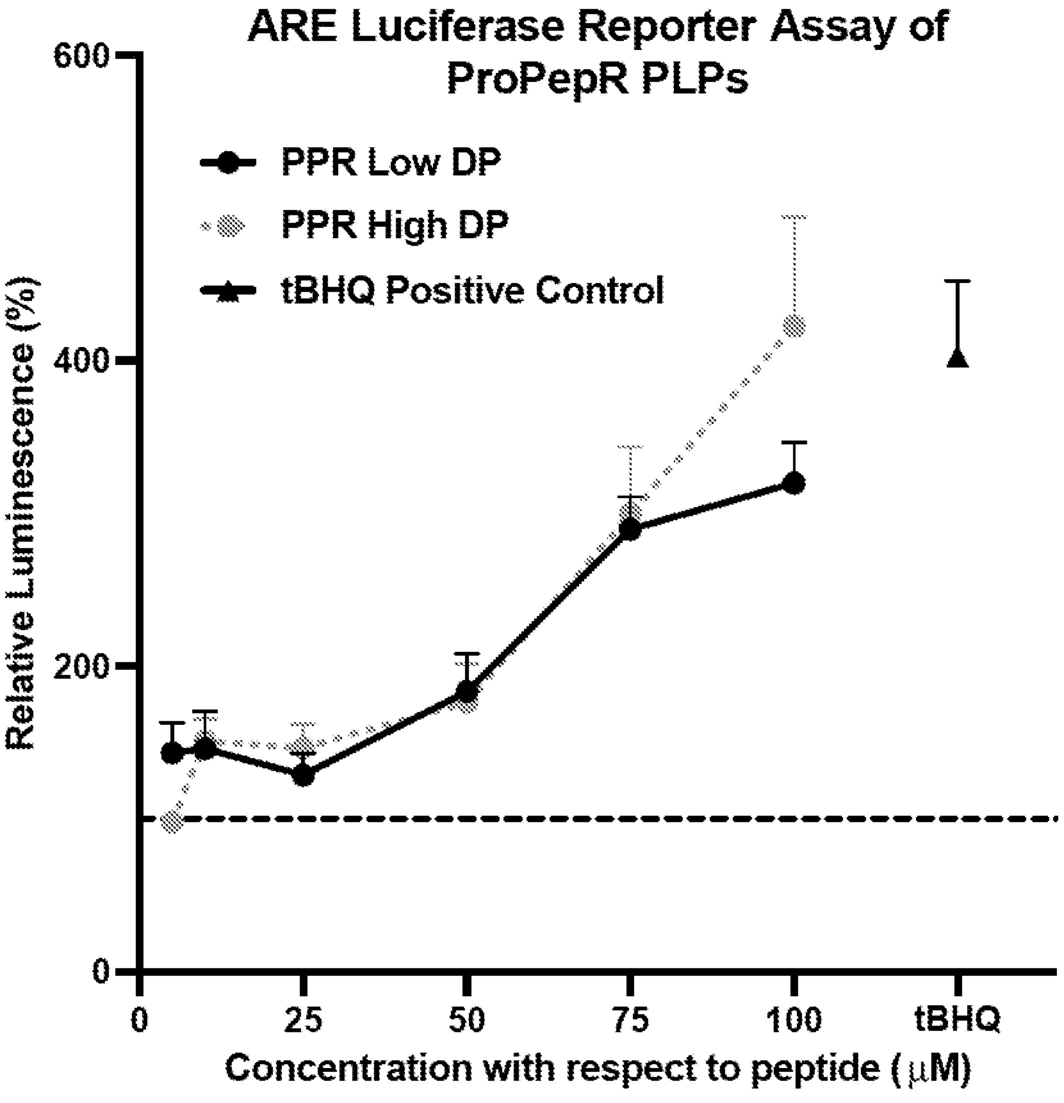
FIG. 38B shows the results of an Antioxidant Response Element (ARE) luciferase reporter assay for a HepG2 cell line treated with (a) a tBHQ positive control, (b) a low degree of polymerization (DP=average of about 11.6) polynorbornene dicarboxyimide-based SEQ ID NO: 72 (LDPETGEFLRRRR) polymer (i.e., ProPepR Low DP), and (c) a high degree of polymerization (DP=average of about 22.5) polynorbornene dicarboxyimide-based SEQ ID NO: 72 (LDPETGEFLRRRR) polymer (i.e., ProPepR High DP), as described in Example 25.

The results for a HepG2 cell line treated with (a) a tBHQ positive control, (b) a low degree of polymerization (DP=average of about 11.6) polynorbornene dicarboxyimide-based SEQ ID NO: 72 (LDPETGEFLRRRR) polymer (i.e., ProPepR Low DP), and (c) a high degree of polymerization (DP=average of about 22.5) polynorbornene dicarboxyimide-based SEQ ID NO: 72 (LDPETGEFLRRRR) polymer (i.e., ProPepR High DP) are set forth in FIG. 38B.

As shown in FIG. 38B, both the low degree of polymerization (DP=average of about 11.6) polynorbornene dicarboxyimide-based SEQ ID NO: 72 (LDPETGEFLRRRR) polymer (i.e., ProPepR Low DP) and the high degree of polymerization (DP=average of about 22.5) polynorbornene dicarboxyimide-based SEQ ID NO: 72 (LDPETGEFLRRRR) polymer (i.e., ProPepR High DP) resulted in ARE activation.

Example 26

This example shows that the activation seen in the Antioxidant Response Element (ARE) luciferase reporter assay for a HepG2 cell line was not due to stress-induced activation.

To demonstrate that the activation seen in the Antioxidant Response Element (ARE) luciferase reporter assay for a HepG2 cell line was not due to stress-induced activation, an Antioxidant Response Element (ARE) luciferase reporter assay for a HepG2 cell line, which was pretreated with N-acetylcysteine to rule out stress-induced activation, was subsequently treated with (a) an untreated control, (b) a tBHQ positive control, and (c) a low degree of polymerization (DP=average of about 11.6) polynorbornene dicarboxyimide-based SEQ ID NO: 72 (LDPETGEFLRRRR) polymer (i.e., ProPepR Low DP).

The Antioxidant Response Element (ARE) Reporter HepG2 Cell line was used to probe Nrf2 antioxidant pathway activation. ARE-HepG2 cells were cultured in growth media (BPS bioscience) according to manufacturer's recommendations. Pretreatment with N-acetylcysteine was performed to determine stress induced activation vs. targeted Keap1 inhibition. Cells were plated at a seeding density of 25 k cells/well into opaque 96 well plates in cell growth media dosed with 100 μg/mL of NAC. ProPepR Low DP was tested at concentrations ranging from 0 μM to 50 μM with respect to peptide along with controls (untreated and tBHQ positive control at 100 μM) in triplicate. Cells were incubated for 24 hours post-treatment. ONE-step luciferase assay reagent was added at 100 μL/well, followed by rocking at room temperature for 15 min. Luminescence was assessed using a Biotek SynergyNeo2 plate reader. Background luminescence of cell free controls wells was subtracted from test wells. ARE activation was reported as luminescence relative to the average of the untreated controls wells. The results are set forth in FIG. 39A.

Figure 39A:
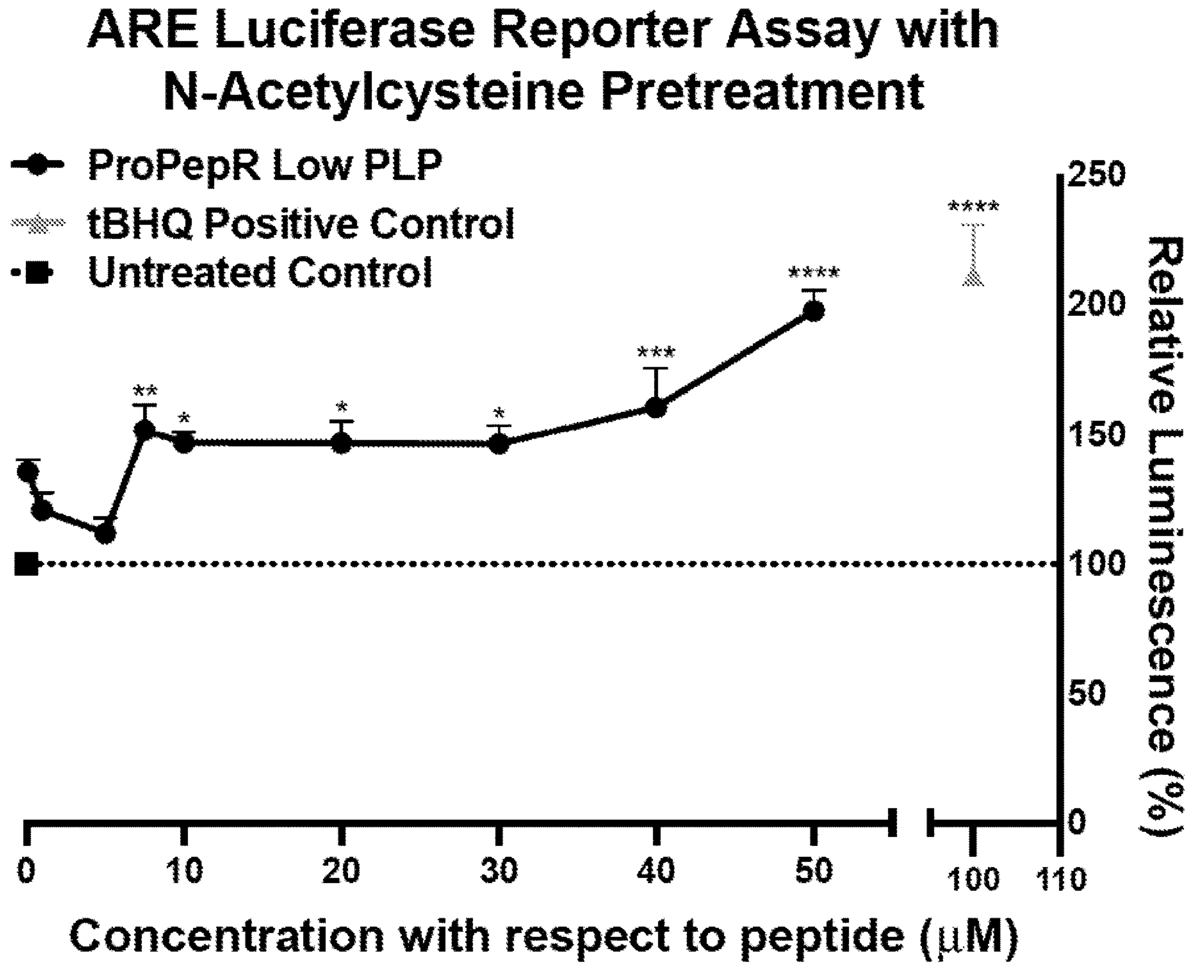
FIG. 39A shows the results of an Antioxidant Response Element (ARE) luciferase reporter assay for a HepG2 cell line, which has been pretreated with N-acetylcysteine to rule out stress-induced activation, treated with (a) an untreated control, (b) a tBHQ positive control, and (c) a low degree of polymerization (DP=average of about 11.6) polynorbornene dicarboxyimide-based SEQ ID NO: 72 (LDPETGE-FLRRRR) polymer (i.e., ProPepR Low DP), as described in Example 26.

As shown in FIG. 39A, low degree of polymerization (DP=average of about 11.6) polynorbornene dicarboxyimide-based SEQ ID NO: 72 (LDPETGEFLRRRR) polymer (i.e., ProPepR Low DP) maintains ARE activation after pretreatment with N-acetylcysteine. These results show that ARE activation with ProPepR Low DP is not stress-induced.

To further demonstrate that the activation seen in the Antioxidant Response Element (ARE) luciferase reporter assay for a HepG2 cell line was not due to stress-induced activation, an MTS cell viability assay was performed over a concentration range of 0 μM to 100 μM for a low degree of polymerization (DP=average of about 11.6) polynorbornene dicarboxyimide-based SEQ ID NO: 72 (LDPETGEFLRRRR) polymer (i.e., ProPepR Low DP), a high degree of polymerization (DP=average of about 22.5) polynorbornene dicarboxyimide-based SEQ ID NO: 72 (LDPETGEFLRRRR) polymer (i.e., ProPepR High DP), a SEQ ID NO: 72 (LDPETGEFLRRRR) peptide (i.e., ProPepR Free Peptide), a polynorbornene dicarboxyimide-based SEQ ID NO: 143 (DERLERPLTRGFR) polymer (i.e., Full Scramble PLP), and a polynorbornene dicarboxyimide-based SEQ ID NO: 146 (DELEPLTGFRRRR) polymer (i.e., ScrambleR PLP), as well as untreated, vehicle and tBHQ positive controls.

Cells were plated at a seeding density of 25 k cells/well into 96 well plates in cell growth media and allowed to incubate for 24 hours. Cells were treated with peptide or PLPs over a range of concentrations (i.e., 0 μM to 100 μM with respect to peptide) at n=3. After 24 hours, 10 μL of MTS reagent was added to each well, and the cells incubated for four hours at 37° C. Absorbance was measured at 490 nm using a Perkin Elmer EnSpire plate reader every hour after MTS addition. Viability was assessed after background subtraction from cell free control wells and calculated as relative viability based on the average of untreated control wells. Viability is reported as a percentage of untreated cells and prepared for presentation using Prism9. The results are set forth in FIG. 39B.

Figure 39B:
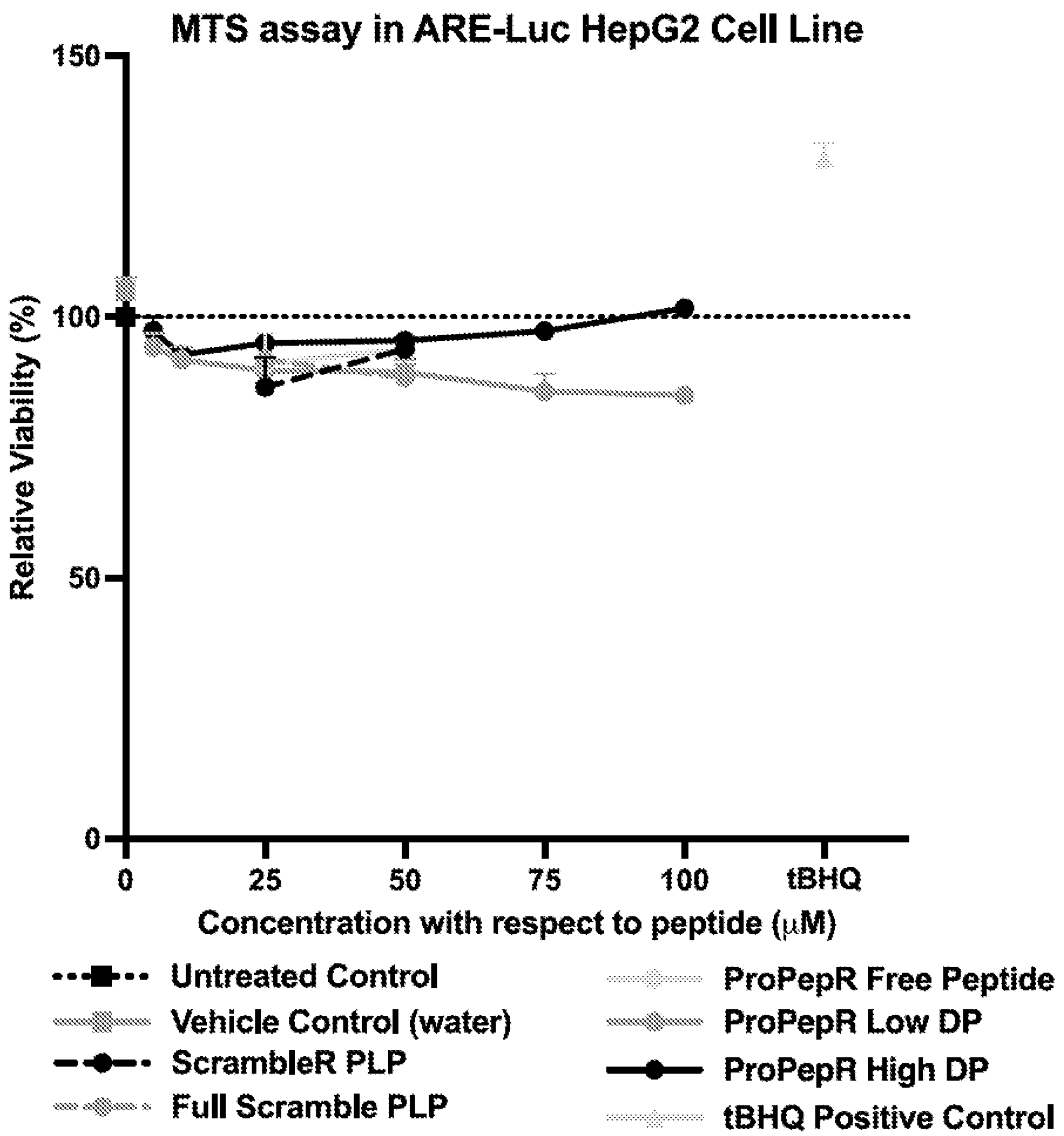
FIG. 39B shows the results of an MTS cell viability assay for an ARE-Luc HepG2 cell line treated with (a) an untreated control, (b) a vehicle control (water), (c) a tBHQ positive control, (d) a low degree of polymerization (DP=average of about 11.6) polynorbornene dicarboxyimide-based SEQ ID NO: 72 (LDPETGEFLRRRR) polymer (i.e., ProPepR Low DP), (e) a high degree of polymerization (DP=average of about 22.5) polynorbornene dicarboxyimide-based SEQ ID NO: 72 (LDPETGEFLRRRR) polymer (i.e., ProPepR High DP), (f) a SEQ ID NO: 72 (LDPETGEFLRRRR) peptide (i.e., ProPepR Free Peptide), (g) a polynorbornene dicarboxyimide-based SEQ ID NO: 143 (DERLERPLTRGFR) polymer (i.e., Full Scramble PLP), and (h) a polynorbornene dicarboxyimide-based SEQ ID NO: 146 (DELEPLTGFRRRR) polymer (i.e., ScrambleR PLP), as described in Example 26.

As shown in FIG. 39B, the MTS assay for each of a low degree of polymerization (DP=average of about 11.6) polynorbornene dicarboxyimide-based SEQ ID NO: 72 (LDPETGEFLRRRR) polymer (i.e., ProPepR Low DP), a high degree of polymerization (DP=average of about 22.5) polynorbornene dicarboxyimide-based SEQ ID NO: 72 (LDPETGEFLRRRR) polymer (i.e., ProPepR High DP), a SEQ ID NO: 72 (LDPETGEFLRRRR) peptide (i.e., ProPepR Free Peptide), a polynorbornene dicarboxyimide-based SEQ ID NO: 143 (DERLERPLTRGFR) polymer (i.e., Full Scramble PLP), and a polynorbornene dicarboxyimide-based SEQ ID NO: 146 (DELEPLTGFRRRR) polymer (i.e., ScrambleR PLP) maintained approximately 100% relative viability. These results further show that the activation shown in the reporter assay is not stress-induced as the tested compounds were well tolerated.

Example 27

This example shows that that displaying peptides on a different backbone does not impact cell viability in the Antioxidant Response Element (ARE)-Luciferase Reporter HepG2 cell line.

To demonstrate that the PLPs are well-tolerated in the ARE-Luc Reporter HepG2 cell line, an MTS cell viability assay was performed over a concentration range of 0 μM to 100 μM for a (meth)acrylamide-based brush polymer ("RAFT PLP") comprising (meth)acrylamide-based SEQ ID NO: 72 (LDPETGEFLRRRR) peptide monomer, as well as untreated, vehicle and tBHQ positive controls.

Cells were plated at a seeding density of 25 k cells/well into 96 well plates in cell growth media and allowed to incubate for 24 hours. Cells were treated with peptide or PLPs over a range of concentrations (i.e., 0 μM to 100 μM with respect to peptide) at n=3. After 24 hours, 10 μL of MTS reagent was added to each well, and the cells incubated for four hours at 37° C. Absorbance was measured at 490 nm using a Perkin Elmer EnSpire plate reader every hour after MTS addition. Viability was assessed after background subtraction from cell free control wells and calculated as relative viability based on the average of untreated control wells. Viability is reported as a percentage of untreated cells and prepared for presentation using Prism9. The results are set forth in FIG. 40.

Figure 40:
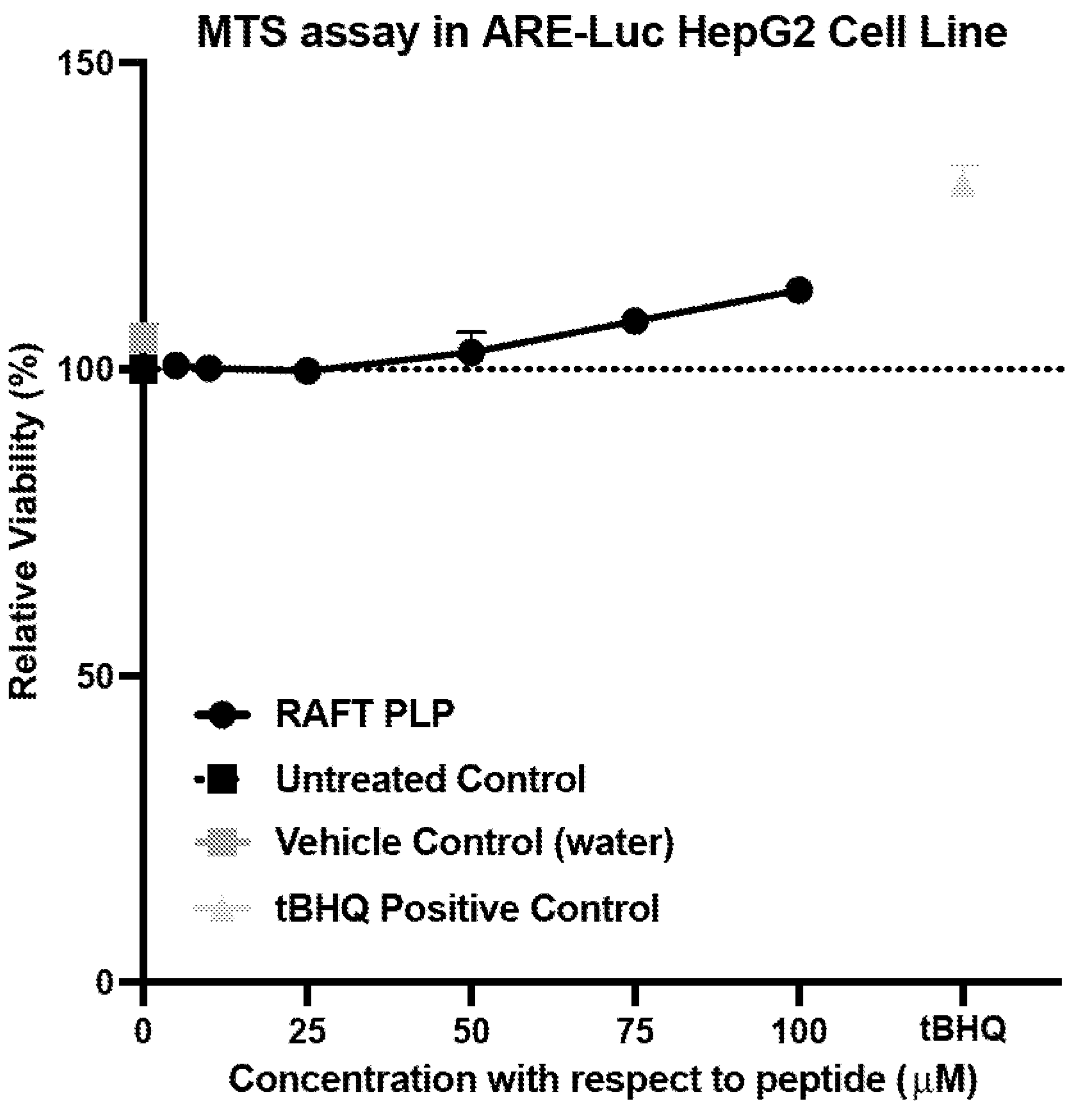
FIG. 40 shows the results of an MTS cell viability assay for an ARE-Luc HepG2 cell line treated with (a) an untreated control, (b) a vehicle control (water), (c) a tBHQ positive control, and (d) a (meth)acrylamide-based brush polymer ("RAFT PLP") comprising (meth)acrylamide-based SEQ ID NO: 72 (LDPETGEFLRRRR) peptide monomer, as described in Example 27.

As shown in FIG. 40, the MTS assay for the (meth) acrylamide-based brush polymer ("RAFT PLP") comprising (meth)acrylamide-based SEQ ID NO: 72 (LDPETGEFLRRRR) peptide monomer maintained approximately 100% relative viability, and are well-tolerated.

Example 28

This example shows the MARTINI binding energies for the complex between the Kelch domain and a polynorbornene dicarboxyimide-based protein-like polymer (PLP) comprising peptides: SEQ ID NO: 1 (LDEETGEFL), SEQ ID NO: 2 (LDPETGEFL), SEQ ID NO: 70 (LDPETGEFLRR), or SEQ ID NO: 72 (LDPETGEFLRRRR).

MARTINI coarse-grained simulations were carried out for polynorbornene dicarboxyimide-based PLPs comprising SEQ ID NO: 1 (LDEETGEFL), SEQ ID NO: 2 (LDPETGEFL), SEQ ID NO: 70 (LDPETGEFLRR), or SEQ ID NO: 72 (LDPETGEFLRRRR), having a degree of polymerization of 15, according to the method provided in Example 9. The $8^{th}$ peptide on the PLP backbone was aligned with the All-Atom simulation structures provided in Example 8 to ensure that the PLPs were initially docked into the Kelch binding pocket. Each production run was performed for 3 μs with a time step of 15 fs, and the results are set forth in FIG. 41.

Figure 41:
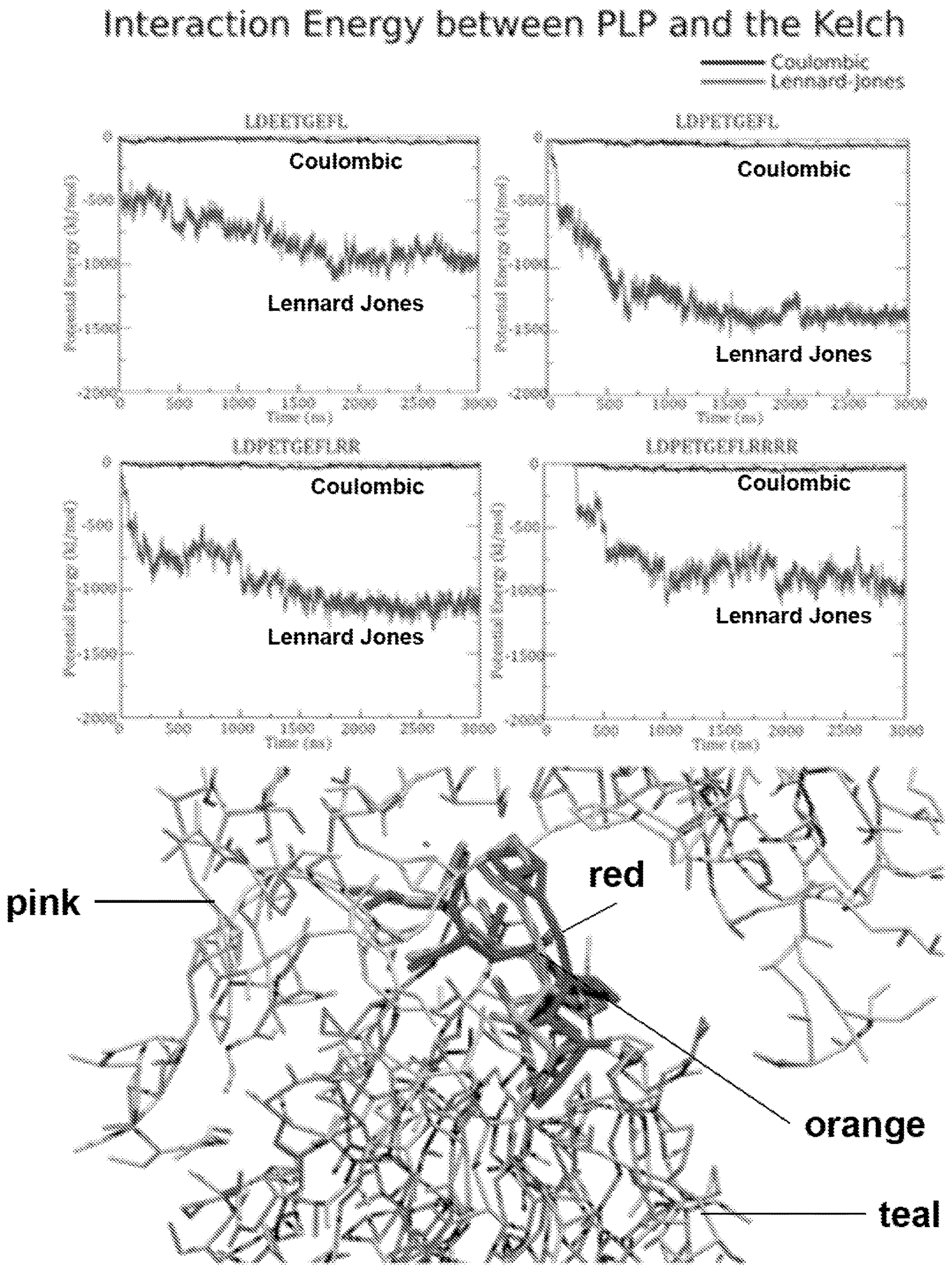
FIG. 41 (Top) shows the MARTINI interaction energy simulations between the Kelch domain and polynorbornene dicarboxyimide-based PLPs comprising peptides: SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR).

As is apparent from the results set forth at the top of FIG. 41, the MARTINI binding energies for the complex between the Kelch domain and a polynorbornene dicarboxyimide-based protein-like polymer (PLP) comprising peptides: SEQ ID NO: 1 (LDEETGEFL), SEQ ID NO: 2 (LDPETGEFL), SEQ ID NO: 70 (LDPETGEFLRR), and SEQ ID NO: 72 (LDPETGEFLRRRR) all converged after approximately 1.5 μs and were highly negative. These results demonstrate a stable binding behavior and indicate that the interaction between these four PLPs and the Kelch domain is favorable.

In addition, a simulation snapshot of the complex between the Kelch domain and a polynorbornene dicarboxyimide-based protein-like polymer (PLP) comprising SEQ ID NO: 72 (LDPETGEFLRRRR) was taken at 0 μs and 3 μs, and the results are set forth at the bottom of FIG. 41. The results show that the $8^{th}$ peptide of the polynorbornene dicarboxyimide-based PLP comprising SEQ ID NO: 72 (LDPETGEFLRRRR) was initially docketed into the Kelch active site, and after a long simulation (i.e., 3 μs), the peptide had barely moved. These results show that the PLP comprising SEQ ID NO: 72 (LDPETGEFLRRRR) forms a stable complex with the Kelch domain.

Example 29

This example shows the MARTINI binding energies for the complex between the Kelch domain and a polynorbornene dicarboxyimide-based protein-like polymer (PLP) comprising peptide SEQ ID NO: 72 (LDPETGEFLRRRR) and having a degree of polymerization of 5, 10, or 15.

MARTINI coarse-grained simulations were carried out for a polynorbornene dicarboxyimide-based PLP comprising SEQ ID NO: 72 (LDPETGEFLRRRR), having a degree of polymerization of 5, 10, or 15, according to the method provided in Example 9. The middle peptide on the PLP backbone was aligned with the All-Atom simulation structures provided in Example 8 to ensure that the PLPs were initially docked into the Kelch binding pocket. Each production run was performed for 3 μs with a time step of 15 fs, and the results are set forth in FIG. 42.

Figure 42:
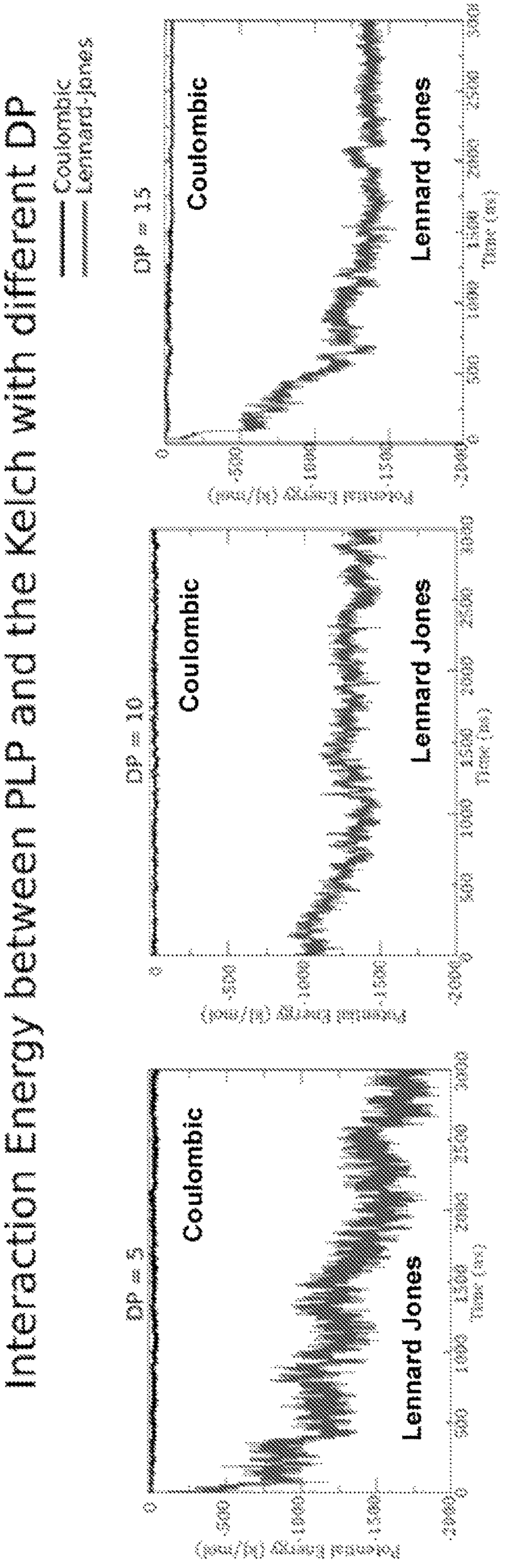
FIG. 42 shows the MARTINI interaction energy simulations between the Kelch domain and polynorbornene dicarboxyimide-based PLPs comprising SEQ ID NO: 72 (LDPETGEFLRRRR) with DP=5, 10, and 15.

As is apparent from the results set forth at the top of FIG. 42, the MARTINI binding energies for the complex between the Kelch domain and a polynorbornene dicarboxyimide-based protein-like polymer (PLP) comprising peptide SEQ ID NO: 72 (LDPETGEFLRRRR) and having a degree of polymerization of 5, 10, or 15 all converged after approximately 2 μs and were highly negative. These results demonstrate a stable binding behavior and indicate that the interaction between these three PLPs and the Kelch domain is favorable.

In addition, FIG. 42 shows that the MARTINI binding energies for the complex between the Kelch domain and a polynorbornene dicarboxyimide-based protein-like polymer (PLP) comprising peptide SEQ ID NO: 72 (LDPETGEFLRRRR) were approximately the same magnitude for degrees of polymerization of 5, 10, and 15. These results show that the degree of polymerization has minimal effect on the binding affinity between the PLP and a single Kelch domain.

Example 30

To further probe the binding between the Keap1 Kelch domain and ProPepR peptide SEQ ID NO: 72 (LDPETGEFLRRRR), in silico modeling between a Keap1 dimer and a polynorbornene dicarboxyimide-based PLP comprising the ProPepR peptide SEQ ID NO: 72 (LDPETGEFLRRRR) was performed.

Keap1 interacts with Nrf2 in a dimerized structure, wherein the DLG and ETGE regions of Nrf2 bind two identical Kelch domains. To determine the degree of polymerization necessary for a polynorbornene dicarboxyimide-based PLP comprising the ProPepR peptide SEQ ID NO: 72 (LDPETGEFLRRRR) to bind and bridge both Kelch domains of a Keap1 homodimer simultaneously, MARTINI coarse-grained simulations were carried out using two Kelch domains, spaced 80 Å apart to represent the natural structure of the Keap-1 homodimer.

Figure 43A:
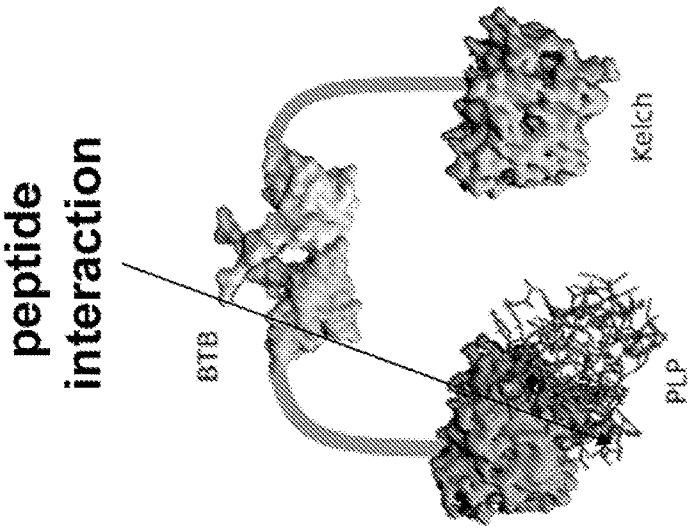
FIGS. 43A-43C show the binding of double Kelch domains with polynorbornene dicarboxyimide-based PLPs comprising SEQ ID NO: 72 (LDPETGEFLRRRR) (ProPepR PLP) (grey) of DP=15, 20, 25 (from left to right) from MARTINI coarse-grained simulations where peptides that bind to the active site of Kelch domains are highlighted. The BTB domains are added to the illustration to reflect the complete Keap1 structure. In particular.
Figure 43B:
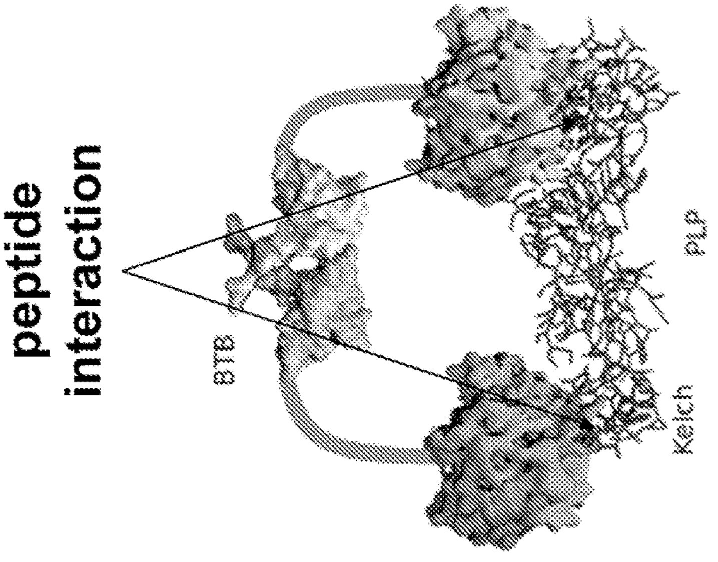
Figure 43C:
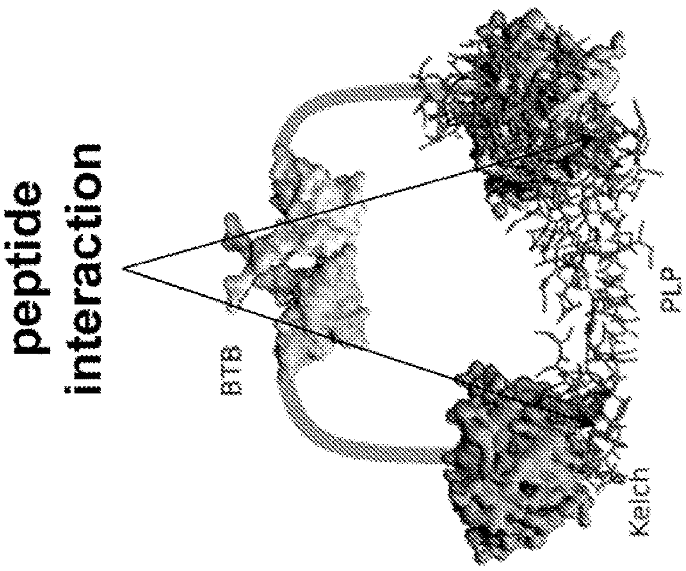

The results of the simulations with a polynorbornene dicarboxyimide-based PLP comprising the ProPepR peptide, having a degree of polymerization (DP)=15, 20, and 25 are set forth in FIGS. 43A-43C, respectively. As shown in FIG. 43A, which depicts the binding of the Keap1 dimer and the polynorbornene dicarboxyimide-based PLP comprising the ProPepR peptide with a DP=15, the first peptide side-chain was able to stably bind to one Kelch domain, but the PLP did not reach the other Kelch domain for dual-binding. However, as shown in FIGS. 43B and 43C, which depict the binding of the Keap1 dimer and the polynorbornene dicarboxyimide-based PLP comprising the ProPepR peptide with a DP=20 and 25, respectively, the PLP was able to span the gap to the other Kelch domain, indicating the potential to bind and bridge both Kelch domains of a Keap1 homodimer at the same time. Further simulations confirmed that simultaneous binding between the Keap1 dimer and the polynorbornene dicarboxyimide-based PLP comprising the ProPepR peptide with a DP=20 and 25 is stable for binding of both Kelch domains simultaneously.

These results show that (i) the binding between the Keap1 Kelch domain and ProPepR peptide SEQ ID NO: 72 (LDPETGEFLRRRR) is favorable and (ii) polynorbornene dicarboxyimide-based PLPs with a DP of about 20 or more are capable of binding both Kelch domains of a Keap1 dimer simultaneously.

STATEMENTS REGARDING INCORPORATION BY REFERENCE AND VARIATIONS (1) All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

(2) The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

(3) When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

(4) It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

(5) Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

(6) Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

(7) As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

(8) One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

(9) All references, including publications, patent applications, and patents, cited herein are hereby incorporated by reference to the same extent as if each reference were individually and specifically indicated to be incorporated by reference and were set forth in its entirety herein.

(10) The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

(11) Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide comprising:

an amino acid sequence having 85% or greater sequence identity to the amino acid sequence LDEETGEFL (SEQ ID NO: 1); and a charge modulating domain consisting of 2 to 7 amino residues, wherein the charge modulating domain is a cationic residue domain or a combination of a glycine-serine domain and a cationic residue domain;

wherein the total length of the peptide is 11 to 16 amino acid residues.

2. The peptide of claim 1, wherein the amino acid sequence having 85% or greater sequence identity to the amino acid sequence LDEETGEFL (SEQ ID NO: 1) is LDEETGEFL (SEQ ID NO: 1) or LDPETGEFL (SEQ ID NO: 2).

3. The peptide of claim 1, wherein the peptide has a net positive charge.

4. The peptide of claim 1, wherein the total length of the peptide is 11 to 15 amino acid residues.

5. The peptide of claim 1, wherein the peptide is

| | |
|---|---|
| (LDEETGEFLRR) | SEQ ID NO: 3 |
| (LDEETGEFLRRR) | SEQ ID NO: 4 |
| (LDEETGEFLRRRR) | SEQ ID NO: 5 |
| (LDEETGEFLRRRRR) | SEQ ID NO: 6 |
| (RRLDEETGEFL) | SEQ ID NO: 7 |

-continued

SEQ ID NO: 8
(RRRLDEETGEFL)

SEQ ID NO: 9
(RRRRLDEETGEFL)

SEQ ID NO: 10
(RRRRRLDEETGEFL)

SEQ ID NO: 11
(RRLDEETGEFLRR)

SEQ ID NO: 12
(RRRLDEETGEFLRRR)

SEQ ID NO: 13
(RLDEETGEFLR)

SEQ ID NO: 14
(RLDEETGEFLRR)

SEQ ID NO: 15
(RRLDEETGEFLR)

SEQ ID NO: 16
(RLDEETGEFLRRR)

SEQ ID NO: 17
(RRRLDEETGEFLR)

SEQ ID NO: 18
(RLDEETGEFLRRRR)

SEQ ID NO: 19
(RRLDEETGEFLRRR)

SEQ ID NO: 20
(RRRLDEETGEFLRR)

SEQ ID NO: 21
(RRRRLDEETGEFLR)

SEQ ID NO: 22
(RLDEETGEFLRRRRR)

SEQ ID NO: 23
(RRLDEETGEFLRRRR)

SEQ ID NO: 24
(RRRRLDEETGEFLRR)

SEQ ID NO: 25
(RRRRRLDEETGEFLR)

SEQ ID NO: 26
(LDEETGEFLKK)

SEQ ID NO: 27
(LDEETGEFLKKK)

SEQ ID NO: 28
(LDEETGEFLKKKK)

SEQ ID NO: 29
(LDEETGEFLKKKKK)

SEQ ID NO: 30
(KKLDEETGEFL)

SEQ ID NO: 31
(KKKLDEETGEFL)

SEQ ID NO: 32
(KKKKLDEETGEFL)

SEQ ID NO: 33
(KKKKKLDEETGEFL)

SEQ ID NO: 34
(KKLDEETGEFLKK)

-continued

SEQ ID NO: 35
(KKKLDEETGEFLKKK)

SEQ ID NO: 36
(KLDEETGEFLK)

SEQ ID NO: 37
(KLDEETGEFLKK)

SEQ ID NO: 38
(KKLDEETGEFLK)

SEQ ID NO: 39
(KLDEETGEFLKKK)

SEQ ID NO: 40
(KKKLDEETGEFLK)

SEQ ID NO: 41
(KLDEETGEFLKKKK)

SEQ ID NO: 42
(KKLDEETGEFLKKK)

SEQ ID NO: 43
(KKKLDEETGEFLKK)

SEQ ID NO: 44
(KKKKLDEETGEFLK)

SEQ ID NO: 45
(KLDEETGEFLKKKKK)

SEQ ID NO: 46
(KKLDEETGEFLKKKK)

SEQ ID NO: 47
(KKKKLDEETGEFLKK)

SEQ ID NO: 48
(KKKKKLDEETGEFLK)

SEQ ID NO: 49
(LDEETGEFLKRKR)

SEQ ID NO: 50
(KRKRLDEETGEFL)

SEQ ID NO: 51
(RKRKLDEETGEFL)

SEQ ID NO: 52
(LDEETGEFLRKRK)

SEQ ID NO: 53
(KKLDEETGEFLRR)

SEQ ID NO: 54
(RRLDEETGEFLKK)

SEQ ID NO: 55
(KLDEETGEFLRRR)

SEQ ID NO: 56
(KKKLDEETGEFLR)

SEQ ID NO: 57
(RRRLDEETGEFLK)

SEQ ID NO: 58
(KRLDEETGEFLKR)

SEQ ID NO: 59
(RKLDEETGEFLRK)

SEQ ID NO: 60
(RKLDEETGEFLKR)

SEQ ID NO: 61
(KRLDEETGEFLRK)

-continued

SEQ ID NO: 62
(LDEETGEFLKKRR)

SEQ ID NO: 63
(LDEETGEFLRRKK)

SEQ ID NO: 64
(KKRRLDEETGEFL)

SEQ ID NO: 65
(RRKKLDEETGEFL)

SEQ ID NO: 66
(LDEETGEFLGSGSGRR)

SEQ ID NO: 67
(GSGSGRRLDEETGEFL)

SEQ ID NO: 68
(LDEETGEFLGSGSGKK)

SEQ ID NO: 69
(GSGSGKKLDEETGEFL)

SEQ ID NO: 70
(LDPETGEFLRR)

SEQ ID NO: 71
(LDPETGEFLRRR)

SEQ ID NO: 72
(LDPETGEFLRRRR)

SEQ ID NO: 73
(LDPETGEFLRRRRR)

SEQ ID NO: 74
(RRLDPETGEFL)

SEQ ID NO: 75
(RRRLDPETGEFL)

SEQ ID NO: 76
(RRRRLDPETGEFL)

SEQ ID NO: 77
(RRRRRLDPETGEFL)

SEQ ID NO: 78
(RRLDPETGEFLRR)

SEQ ID NO: 79
(RRRLDPETGEFLRRR)

SEQ ID NO: 80
(RLDPETGEFLR)

SEQ ID NO: 81
(RLDPETGEFLRR)

SEQ ID NO: 82
(RRLDPETGEFLR)

SEQ ID NO: 83
(RLDPETGEFLRRR)

SEQ ID NO: 84
(RRRLDPETGEFLR)

SEQ ID NO: 85
(RLDPETGEFLRRRR)

SEQ ID NO: 86
(RRLDPETGEFLRRR)

SEQ ID NO: 87
(RRRLDPETGEFLRR)

SEQ ID NO: 88
(RRRRLDPETGEFLR)

-continued

SEQ ID NO: 89
(RLDPETGEFLRRRRR)

SEQ ID NO: 90
(RRLDPETGEFLRRRR)

SEQ ID NO: 91
(RRRRLDPETGEFLRR)

SEQ ID NO: 92
(RRRRRLDPETGEFLR)

SEQ ID NO: 93
(LDPETGEFLKK)

SEQ ID NO: 94
(LDPETGEFLKKK)

SEQ ID NO: 95
(LDPETGEFLKKKK)

SEQ ID NO: 96
(LDPETGEFLKKKKK)

SEQ ID NO: 97
(KKLDPETGEFL)

SEQ ID NO: 98
(KKKLDPETGEFL)

SEQ ID NO: 99
(KKKKLDPETGEFL)

SEQ ID NO: 100
(KKKKKLDPETGEFL)

SEQ ID NO: 101
(KKLDPETGEFLKK)

SEQ ID NO: 102
(KKKLDPETGEFLKKK)

SEQ ID NO: 103
(KLDPETGEFLK)

SEQ ID NO: 104
(KLDPETGEFLKK)

SEQ ID NO: 105
(KKLDPETGEFLK)

SEQ ID NO: 106
(KLDPETGEFLKKK)

SEQ ID NO: 107
(KKKLDPETGEFLK)

SEQ ID NO: 108
(KLDPETGEFLKKKK)

SEQ ID NO: 109
(KKLDPETGEFLKKK)

SEQ ID NO: 110
(KKKLDPETGEFLKK)

SEQ ID NO: 111
(KKKKLDPETGEFLK)

SEQ ID NO: 112
(KLDPETGEFLKKKKK)

SEQ ID NO: 113
(KKLDPETGEFLKKKK)

SEQ ID NO: 114
(KKKKLDPETGEFLKK)

SEQ ID NO: 115
(KKKKKLDPETGEFLK)

-continued

SEQ ID NO: 116
(LDPETGEFLKRKR)

SEQ ID NO: 117
(KRKRLDPETGEFL)

SEQ ID NO: 118
(RKRKLDPETGEFL)

SEQ ID NO: 119
(LDPETGEFLRKRK)

SEQ ID NO: 120
(KKLDPETGEFLRR)

SEQ ID NO: 121
(RRLDPETGEFLKK)

SEQ ID NO: 122
(KLDPETGEFLRRR)

SEQ ID NO: 123
(KKKLDPETGEFLR)

SEQ ID NO: 124
(RRRLDPETGEFLK)

SEQ ID NO: 125
(KRLDPETGEFLKR)

SEQ ID NO: 126
(RKLDPETGEFLRK)

SEQ ID NO: 127
(RKLDPETGEFLKR)

SEQ ID NO: 128
(KRLDPETGEFLRK)

SEQ ID NO: 129
(LDPETGEFLKKRR)

SEQ ID NO: 130
(LDPETGEFLRRKK)

SEQ ID NO: 131
(KKRRLDPETGEFL)

SEQ ID NO: 132
(RRKKLDPETGEFL)

SEQ ID NO: 133
(LDPETGEFLGSGSGRR)

SEQ ID NO: 134
(GSGSGRRLDPETGEFL)

SEQ ID NO: 135
(LDPETGEFLGSGSGKK)

SEQ ID NO: 136
(GSGSGKKLDPETGEFL)

SEQ ID NO: 140
(YGRKKRRLDPETGEFL)
or

SEQ ID NO: 141
(LDPETGEFLYGRKKRR).

6. A polymer comprising:

a first polymer segment comprising at least 2 first repeating units; wherein each of the first repeating units of the first polymer segment comprises a first polymer backbone group directly or indirectly covalently linked to a first polymer side chain group comprising a peptide;

wherein the peptide comprises:

an amino acid sequence having 85% or greater sequence identity to the amino acid sequence LDEETGEFL (SEQ ID NO: 1); and a charge modulating domain consisting of 2 to 7 amino residues, wherein the charge modulating domain is a cationic residue domain or a combination of a glycine-serine domain and a cationic residue domain;

wherein the total length of the peptide is 11 to 16 amino acids.

7. The polymer of claim 6, wherein the amino acid sequence having 85% or greater sequence identity to the amino acid sequence LDEETGEFL (SEQ ID NO: 1) is LDEETGEFL (SEQ ID NO: 1) or LDPETGEFL (SEQ ID NO: 2).

8. The polymer of claim 6, wherein the peptide is

SEQ ID NO: 3
(LDEETGEFLRR)

SEQ ID NO: 4
(LDEETGEFLRRR)

SEQ ID NO: 5
(LDEETGEFLRRRR)

SEQ ID NO: 6
(LDEETGEFLRRRRR)

SEQ ID NO: 7
(RRLDEETGEFL)

SEQ ID NO: 8
(RRRLDEETGEFL)

SEQ ID NO: 9
(RRRRLDEETGEFL)

SEQ ID NO: 10
(RRRRRLDEETGEFL)

SEQ ID NO: 11
(RRLDEETGEFLRR)

SEQ ID NO: 12
(RRRLDEETGEFLRRR)

SEQ ID NO: 13
(RLDEETGEFLR)

SEQ ID NO: 14
(RLDEETGEFLRR)

SEQ ID NO: 15
(RRLDEETGEFLR)

SEQ ID NO: 16
(RLDEETGEFLRRR)

SEQ ID NO: 17
(RRRLDEETGEFLR)

SEQ ID NO: 18
(RLDEETGEFLRRRR)

SEQ ID NO: 19
(RRLDEETGEFLRRR)

SEQ ID NO: 20
(RRRLDEETGEFLRR)

SEQ ID NO: 21
(RRRRLDEETGEFLR)

SEQ ID NO: 22
(RLDEETGEFLRRRRR)

SEQ ID NO: 23
(RRLDEETGEFLRRRR)

SEQ ID NO: 24
(RRRRLDEETGEFLRR)

-continued

SEQ ID NO: 25
(RRRRRLDEETGEFLR)

SEQ ID NO: 26
(LDEETGEFLKK)

SEQ ID NO: 27
(LDEETGEFLKKK)

SEQ ID NO: 28
(LDEETGEFLKKKK)

SEQ ID NO: 29
(LDEETGEFLKKKKK)

SEQ ID NO: 30
(KKLDEETGEFL)

SEQ ID NO: 31
(KKKLDEETGEFL)

SEQ ID NO: 32
(KKKKLDEETGEFL)

SEQ ID NO: 33
(KKKKKLDEETGEFL)

SEQ ID NO: 34
(KKLDEETGEFLKK)

SEQ ID NO: 35
(KKKLDEETGEFLKKK)

SEQ ID NO: 36
(KLDEETGEFLK)

SEQ ID NO: 37
(KLDEETGEFLKK)

SEQ ID NO: 38
(KKLDEETGEFLK)

SEQ ID NO: 39
(KLDEETGEFLKKK)

SEQ ID NO: 40
(KKKLDEETGEFLK)

SEQ ID NO: 41
(KLDEETGEFLKKKK)

SEQ ID NO: 42
(KKLDEETGEFLKKK)

SEQ ID NO: 43
(KKKLDEETGEFLKK)

SEQ ID NO: 44
(KKKKLDEETGEFLK)

SEQ ID NO: 45
(KLDEETGEFLKKKKK)

SEQ ID NO: 46
(KKLDEETGEFLKKKK)

SEQ ID NO: 47
(KKKKLDEETGEFLKK)

SEQ ID NO: 48
(KKKKKLDEETGEFLK)

SEQ ID NO: 49
(LDEETGEFLKRKR)

SEQ ID NO: 50
(KRKRLDEETGEFL)

SEQ ID NO: 51
(RKRKLDEETGEFL)

-continued

SEQ ID NO: 52
(LDEETGEFLRKRK)

SEQ ID NO: 53
(KKLDEETGEFLRR)

SEQ ID NO: 54
(RRLDEETGEFLKK)

SEQ ID NO: 55
(KLDEETGEFLRRR)

SEQ ID NO: 56
(KKKLDEETGEFLR)

SEQ ID NO: 57
(RRRLDEETGEFLK)

SEQ ID NO: 58
(KRLDEETGEFLKR)

SEQ ID NO: 59
(RKLDEETGEFLRK)

SEQ ID NO: 60
(RKLDEETGEFLKR)

SEQ ID NO: 61
(KRLDEETGEFLRK)

SEQ ID NO: 62
(LDEETGEFLKKRR)

SEQ ID NO: 63
(LDEETGEFLRRKK)

SEQ ID NO: 64
(KKRRLDEETGEFL)

SEQ ID NO: 65
(RRKKLDEETGEFL)

SEQ ID NO: 66
(LDEETGEFLGSGSGRR)

SEQ ID NO: 67
(GSGSGRRLDEETGEFL)

SEQ ID NO: 68
(LDEETGEFLGSGSGKK)

SEQ ID NO: 69
(GSGSGKKLDEETGEFL)

SEQ ID NO: 70
(LDPETGEFLRR)

SEQ ID NO: 71
(LDPETGEFLRRR)

SEQ ID NO: 72
(LDPETGEFLRRRR)

SEQ ID NO: 73
(LDPETGEFLRRRRR)

SEQ ID NO: 74
(RRLDPETGEFL)

SEQ ID NO: 75
(RRRLDPETGEFL)

SEQ ID NO: 76
(RRRRLDPETGEFL)

SEQ ID NO: 77
(RRRRRLDPETGEFL)

SEQ ID NO: 78
(RRLDPETGEFLRR)

-continued

SEQ ID NO: 79
(RRRLDPETGEFLRRR)

SEQ ID NO: 80
(RLDPETGEFLR)

SEQ ID NO: 81
(RLDPETGEFLRR)

SEQ ID NO: 82
(RRLDPETGEFLR)

SEQ ID NO: 83
(RLDPETGEFLRRR)

SEQ ID NO: 84
(RRRLDPETGEFLR)

SEQ ID NO: 85
(RLDPETGEFLRRRR)

SEQ ID NO: 86
(RRLDPETGEFLRRR)

SEQ ID NO: 87
(RRRLDPETGEFLRR)

SEQ ID NO: 88
(RRRRLDPETGEFLR)

SEQ ID NO: 89
(RLDPETGEFLRRRRR)

SEQ ID NO: 90
(RRLDPETGEFLRRRR)

SEQ ID NO: 91
(RRRRLDPETGEFLRR)

SEQ ID NO: 92
(RRRRRLDPETGEFLR)

SEQ ID NO: 93
(LDPETGEFLKK)

SEQ ID NO: 94
(LDPETGEFLKKK)

SEQ ID NO: 95
(LDPETGEFLKKKK)

SEQ ID NO: 96
(LDPETGEFLKKKKK)

SEQ ID NO: 97
(KKLDPETGEFL)

SEQ ID NO: 98
(KKKLDPETGEFL)

SEQ ID NO: 99
(KKKKLDPETGEFL)

SEQ ID NO: 100
(KKKKKLDPETGEFL)

SEQ ID NO: 101
(KKLDPETGEFLKK)

SEQ ID NO: 102
(KKKLDPETGEFLKKK)

SEQ ID NO: 103
(KLDPETGEFLK)

SEQ ID NO: 104
(KLDPETGEFLKK)

SEQ ID NO: 105
(KKLDPETGEFLK)

-continued

SEQ ID NO: 106
(KLDPETGEFLKKK)

SEQ ID NO: 107
(KKKLDPETGEFLK)

SEQ ID NO: 108
(KLDPETGEFLKKKK)

SEQ ID NO: 109
(KKLDPETGEFLKKK)

SEQ ID NO: 110
(KKKLDPETGEFLKK)

SEQ ID NO: 111
(KKKKLDPETGEFLK)

SEQ ID NO: 112
(KLDPETGEFLKKKKK)

SEQ ID NO: 113
(KKLDPETGEFLKKKK)

SEQ ID NO: 114
(KKKKLDPETGEFLKK)

SEQ ID NO: 115
(KKKKKLDPETGEFLK)

SEQ ID NO: 116
(LDPETGEFLKRKR)

SEQ ID NO: 117
(KRKRLDPETGEFL)

SEQ ID NO: 118
(RKRKLDPETGEFL)

SEQ ID NO: 119
(LDPETGEFLRKRK)

SEQ ID NO: 120
(KKLDPETGEFLRR)

SEQ ID NO: 121
(RRLDPETGEFLKK)

SEQ ID NO: 122
(KLDPETGEFLRRR)

SEQ ID NO: 123
(KKKLDPETGEFLR)

SEQ ID NO: 124
(RRRLDPETGEFLK)

SEQ ID NO: 125
(KRLDPETGEFLKR)

SEQ ID NO: 126
(RKLDPETGEFLRK)

SEQ ID NO: 127
(RKLDPETGEFLKR)

SEQ ID NO: 128
(KRLDPETGEFLRK)

SEQ ID NO: 129
(LDPETGEFLKKRR)

SEQ ID NO: 130
(LDPETGEFLRRKK)

SEQ ID NO: 131
(KKRRLDPETGEFL)

SEQ ID NO: 132
(RRKKLDPETGEFL)

-continued

SEQ ID NO: 133
(LDPETGEFLGSGSGRR)

SEQ ID NO: 134
(GSGSGRRLDPETGEFL)

SEQ ID NO: 135
(LDPETGEFLGSGSGKK)

SEQ ID NO: 136
(GSGSGKKLDPETGEFL)

SEQ ID NO: 140
(YGRKKRRLDPETGEFL)
or

SEQ ID NO: 141
(LDPETGEFLYGRKKRR).

9. The polymer of claim 6, wherein the polymer is a brush polymer, wherein the brush polymer is a high-density brush polymer characterized by a brush density greater than or equal to 50%.

10. The polymer of claim 6, wherein the first polymer segment comprises at least 5 first repeating units.

11. The polymer of claim 6, wherein at least a portion of the peptide side-chain is linked to the polymer backbone or consists of a degradable or triggerable linker.

12. The polymer of claim 6 characterized by the formula (FX1a), (FX1b), (FX1c), (FX1d); (FX1e); (FX1f); or (FX1g):

$Q^1$-T-$Q^2$ (FX1a);

$Q^1$-T-$[S]_h$-$Q^2$ (FX1b);

$Q^1$-$[S]_h$-T-$Q^2$ (FX1c);

$Q^1$-$[S]_i$-T-$[S]_h$-$Q^2$ (FX1d);

$Q^1$-$[S]_i$-T-$[S]_h$-T-$Q^2$ (FX1e);

$Q^1$-T-$[S]_i$-T-$[S]_h$-$Q^2$ (FX1f); or $Q^1$-T-$[S]_i$-T-$[S]_h$-T-$Q^2$ (FX1g);

wherein each T is independently the first polymer segment comprising the first repeating units and each S is independently an additional polymer segment; $Q^1$ is a first backbone terminating group; $Q^2$ is a second backbone terminating group; and wherein h is zero or an integer selected over the range of 1 to 1000 and i is zero or an integer selected over the range of 1 to 1000; and wherein each -T- is independently-$[Y^1]_m$—; wherein each $Y^1$ is independently the first repeating unit of the first polymer segment; and each m is independently an integer selected from the range 0 to 1000, provided that at least one m is an integer selected from the range 1 to 1000.

13. The polymer of claim 6 characterized by the formula (FX2a), (FX2b), or (FX2c):

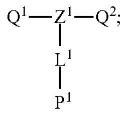
(FX2a)

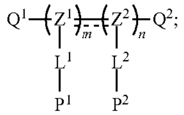 or
(FX2b)

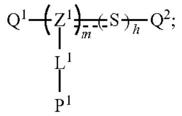
(FX2c)

wherein each $Z^1$ is independently a first polymer backbone group and each $Z^2$ is independently a second polymer backbone group;

each S is independently a repeating unit having a composition different from the first repeating unit;

$Q^1$ is a first backbone terminating group and $Q^2$ is a second backbone terminating group;

each $L^1$ is independently a first linking group, each $L^2$ is independently a second linking group;

each $P^1$ is the peptide; wherein each $P^2$ is a polymer side chain having a composition different from that of $P^1$;

each m is independently an integer selected from the range of 2 to 1000;

each n is independently an integer selected from the range of 0 to 1000; and each h is independently an integer selected from the range of 0 to 1000.

14. The polymer of claim 6, wherein each of the first polymer backbone group and/or the second polymer backbone group is a substituted or unsubstituted polymerized norbornene, olefin, cyclic olefin, norbornene anhydride, cyclooctene, cyclopentadiene, styrene, acrylamide, or acrylate.

15. A composition comprising the peptide of claim 1 and a pharmaceutically acceptable excipient.

* * * * *

```
                    SEQUENCE LISTING


<160> NUMBER OF SEQ ID NOS: 146

<210> SEQ ID NO 1
<211> LENGTH: 9
<212> TYPE: PRT
<213> ORGANISM: Artificial
<220> FEATURE:
<223> OTHER INFORMATION: Synthetic construct

<400> SEQUENCE: 1

Leu Asp Glu Glu Thr Gly Glu Phe Leu
1               5


<210> SEQ ID NO 2
<211> LENGTH: 9
<212> TYPE: PRT
<213> ORGANISM: Artificial
<220> FEATURE:
<223> OTHER INFORMATION: Synthetic construct

<400> SEQUENCE: 2

Leu Asp Pro Glu Thr Gly Glu Phe Leu
1               5


<210> SEQ ID NO 3
<211> LENGTH: 11
<212> TYPE: PRT
<213> ORGANISM: Artificial
<220> FEATURE:
<223> OTHER INFORMATION: Synthetic construct

<400> SEQUENCE: 3
```

```
Leu Asp Glu Glu Thr Gly Glu Phe Leu Arg Arg
1               5                   10


<210> SEQ ID NO 4
<211> LENGTH: 12
<212> TYPE: PRT
<213> ORGANISM: Artificial
<220> FEATURE:
<223> OTHER INFORMATION: Synthetic construct

<400> SEQUENCE: 4

Leu Asp Glu Glu Thr Gly Glu Phe Leu Arg Arg Arg
1               5                   10


<210> SEQ ID NO 5
<211> LENGTH: 13
<212> TYPE: PRT
<213> ORGANISM: Artificial
<220> FEATURE:
<223> OTHER INFORMATION: Synthetic construct

<400> SEQUENCE: 5

Leu Asp Glu Glu Thr Gly Glu Phe Leu Arg Arg Arg Arg
1               5                   10


<210> SEQ ID NO 6
<211> LENGTH: 14
<212> TYPE: PRT
<213> ORGANISM: Artificial
<220> FEATURE:
<223> OTHER INFORMATION: Synthetic construct

<400> SEQUENCE: 6

Leu Asp Glu Glu Thr Gly Glu Phe Leu Arg Arg Arg Arg Arg
1               5                   10


<210> SEQ ID NO 7
<211> LENGTH: 11
<212> TYPE: PRT
<213> ORGANISM: Artificial
<220> FEATURE:
<223> OTHER INFORMATION: Synthetic construct

<400> SEQUENCE: 7

Arg Arg Leu Asp Glu Glu Thr Gly Glu Phe Leu
1               5                   10


<210> SEQ ID NO 8
<211> LENGTH: 12
<212> TYPE: PRT
<213> ORGANISM: Artificial
<220> FEATURE:
<223> OTHER INFORMATION: Synthetic construct

<400> SEQUENCE: 8

Arg Arg Arg Leu Asp Glu Glu Thr Gly Glu Phe Leu
1               5                   10


<210> SEQ ID NO 9
<211> LENGTH: 13
<212> TYPE: PRT
<213> ORGANISM: Artificial
<220> FEATURE:
<223> OTHER INFORMATION: Synthetic construct

<400> SEQUENCE: 9

Arg Arg Arg Arg Leu Asp Glu Glu Thr Gly Glu Phe Leu
```

1 5 10

<210> SEQ ID NO 10
<211> LENGTH: 14
<212> TYPE: PRT
<213> ORGANISM: Artificial
<220> FEATURE:
<223> OTHER INFORMATION: Synthetic construct

<400> SEQUENCE: 10

Arg Arg Arg Arg Arg Leu Asp Glu Glu Thr Gly Glu Phe Leu
1 5 10

<210> SEQ ID NO 11
<211> LENGTH: 13
<212> TYPE: PRT
<213> ORGANISM: Artificial
<220> FEATURE:
<223> OTHER INFORMATION: Synthetic construct

<400> SEQUENCE: 11

Arg Arg Leu Asp Glu Glu Thr Gly Glu Phe Leu Arg Arg
1 5 10

<210> SEQ ID NO 12
<211> LENGTH: 15
<212> TYPE: PRT
<213> ORGANISM: Artificial
<220> FEATURE:
<223> OTHER INFORMATION: Synthetic construct

<400> SEQUENCE: 12

Arg Arg Arg Leu Asp Glu Glu Thr Gly Glu Phe Leu Arg Arg Arg
1 5 10 15

<210> SEQ ID NO 13
<211> LENGTH: 11
<212> TYPE: PRT
<213> ORGANISM: Artificial
<220> FEATURE:
<223> OTHER INFORMATION: Synthetic construct

<400> SEQUENCE: 13

Arg Leu Asp Glu Glu Thr Gly Glu Phe Leu Arg
1 5 10

<210> SEQ ID NO 14
<211> LENGTH: 12
<212> TYPE: PRT
<213> ORGANISM: Artificial
<220> FEATURE:
<223> OTHER INFORMATION: Synthetic construct

<400> SEQUENCE: 14

Arg Leu Asp Glu Glu Thr Gly Glu Phe Leu Arg Arg
1 5 10

<210> SEQ ID NO 15
<211> LENGTH: 12
<212> TYPE: PRT
<213> ORGANISM: Artificial
<220> FEATURE:
<223> OTHER INFORMATION: Synthetic construct

<400> SEQUENCE: 15

Arg Arg Leu Asp Glu Glu Thr Gly Glu Phe Leu Arg
1 5 10

<210> SEQ ID NO 16
<211> LENGTH: 13
<212> TYPE: PRT
<213> ORGANISM: Artificial
<220> FEATURE:
<223> OTHER INFORMATION: Synthetic construct

<400> SEQUENCE: 16

```
Arg Leu Asp Glu Glu Thr Gly Glu Phe Leu Arg Arg Arg
1               5                   10
```

<210> SEQ ID NO 17
<211> LENGTH: 13
<212> TYPE: PRT
<213> ORGANISM: Artificial
<220> FEATURE:
<223> OTHER INFORMATION: Synthetic construct

<400> SEQUENCE: 17

```
Arg Arg Arg Leu Asp Glu Glu Thr Gly Glu Phe Leu Arg
1               5                   10
```

<210> SEQ ID NO 18
<211> LENGTH: 14
<212> TYPE: PRT
<213> ORGANISM: Artificial
<220> FEATURE:
<223> OTHER INFORMATION: Synthetic construct

<400> SEQUENCE: 18

```
Arg Leu Asp Glu Glu Thr Gly Glu Phe Leu Arg Arg Arg Arg
1               5                   10
```

<210> SEQ ID NO 19
<211> LENGTH: 14
<212> TYPE: PRT
<213> ORGANISM: Artificial
<220> FEATURE:
<223> OTHER INFORMATION: Synthetic construct

<400> SEQUENCE: 19

```
Arg Arg Leu Asp Glu Glu Thr Gly Glu Phe Leu Arg Arg Arg
1               5                   10
```

<210> SEQ ID NO 20
<211> LENGTH: 14
<212> TYPE: PRT
<213> ORGANISM: Artificial
<220> FEATURE:
<223> OTHER INFORMATION: Synthetic sequence

<400> SEQUENCE: 20

```
Arg Arg Arg Leu Asp Glu Glu Thr Gly Glu Phe Leu Arg Arg
1               5                   10
```

<210> SEQ ID NO 21
<211> LENGTH: 14
<212> TYPE: PRT
<213> ORGANISM: Artificial
<220> FEATURE:
<223> OTHER INFORMATION: Synthetic construct

<400> SEQUENCE: 21

```
Arg Arg Arg Arg Leu Asp Glu Glu Thr Gly Glu Phe Leu Arg
1               5                   10
```

<210> SEQ ID NO 22
<211> LENGTH: 15
<212> TYPE: PRT
<213> ORGANISM: Artificial
<220> FEATURE:
<223> OTHER INFORMATION: Synthetic construct

<400> SEQUENCE: 22

Arg Leu Asp Glu Glu Thr Gly Glu Phe Leu Arg Arg Arg Arg Arg
1 5 10 15

<210> SEQ ID NO 23
<211> LENGTH: 15
<212> TYPE: PRT
<213> ORGANISM: Artificial
<220> FEATURE:
<223> OTHER INFORMATION: Synthetic construct

<400> SEQUENCE: 23

Arg Arg Leu Asp Glu Glu Thr Gly Glu Phe Leu Arg Arg Arg Arg
1 5 10 15

<210> SEQ ID NO 24
<211> LENGTH: 15
<212> TYPE: PRT
<213> ORGANISM: Artificial
<220> FEATURE:
<223> OTHER INFORMATION: Synthetic construct

<400> SEQUENCE: 24

Arg Arg Arg Arg Leu Asp Glu Glu Thr Gly Glu Phe Leu Arg Arg
1 5 10 15

<210> SEQ ID NO 25
<211> LENGTH: 15
<212> TYPE: PRT
<213> ORGANISM: Artificial
<220> FEATURE:
<223> OTHER INFORMATION: Synthetic construct

<400> SEQUENCE: 25

Arg Arg Arg Arg Arg Leu Asp Glu Glu Thr Gly Glu Phe Leu Arg
1 5 10 15

<210> SEQ ID NO 26
<211> LENGTH: 11
<212> TYPE: PRT
<213> ORGANISM: Artificial
<220> FEATURE:
<223> OTHER INFORMATION: Synthetic construct

<400> SEQUENCE: 26

Leu Asp Glu Glu Thr Gly Glu Phe Leu Lys Lys
1 5 10

<210> SEQ ID NO 27
<211> LENGTH: 12
<212> TYPE: PRT
<213> ORGANISM: Artificial
<220> FEATURE:
<223> OTHER INFORMATION: Synthetic construct

<400> SEQUENCE: 27

Leu Asp Glu Glu Thr Gly Glu Phe Leu Lys Lys Lys
1 5 10

<210> SEQ ID NO 28
<211> LENGTH: 13
<212> TYPE: PRT
<213> ORGANISM: Artificial
<220> FEATURE:
<223> OTHER INFORMATION: Synthetic construct

<400> SEQUENCE: 28

```
Leu Asp Glu Glu Thr Gly Glu Phe Leu Lys Lys Lys Lys
1               5                   10
```

<210> SEQ ID NO 29
<211> LENGTH: 14
<212> TYPE: PRT
<213> ORGANISM: Artificial
<220> FEATURE:
<223> OTHER INFORMATION: Synthetic construct

<400> SEQUENCE: 29

```
Leu Asp Glu Glu Thr Gly Glu Phe Leu Lys Lys Lys Lys Lys
1               5                   10
```

<210> SEQ ID NO 30
<211> LENGTH: 11
<212> TYPE: PRT
<213> ORGANISM: Artificial
<220> FEATURE:
<223> OTHER INFORMATION: Synthetic construct

<400> SEQUENCE: 30

```
Lys Lys Leu Asp Glu Glu Thr Gly Glu Phe Leu
1               5                   10
```

<210> SEQ ID NO 31
<211> LENGTH: 12
<212> TYPE: PRT
<213> ORGANISM: Artificial
<220> FEATURE:
<223> OTHER INFORMATION: Synthetic construct

<400> SEQUENCE: 31

```
Lys Lys Lys Leu Asp Glu Glu Thr Gly Glu Phe Leu
1               5                   10
```

<210> SEQ ID NO 32
<211> LENGTH: 13
<212> TYPE: PRT
<213> ORGANISM: Artificial
<220> FEATURE:
<223> OTHER INFORMATION: Synthetic construct

<400> SEQUENCE: 32

```
Lys Lys Lys Lys Leu Asp Glu Glu Thr Gly Glu Phe Leu
1               5                   10
```

<210> SEQ ID NO 33
<211> LENGTH: 14
<212> TYPE: PRT
<213> ORGANISM: Artificial
<220> FEATURE:
<223> OTHER INFORMATION: Synthetic construct

<400> SEQUENCE: 33

```
Lys Lys Lys Lys Lys Leu Asp Glu Glu Thr Gly Glu Phe Leu
1               5                   10
```

<210> SEQ ID NO 34

<211> LENGTH: 13
<212> TYPE: PRT
<213> ORGANISM: Artificial
<220> FEATURE:
<223> OTHER INFORMATION: Synthetic construct

<400> SEQUENCE: 34

Lys Lys Leu Asp Glu Glu Thr Gly Glu Phe Leu Lys Lys
1 5 10

<210> SEQ ID NO 35
<211> LENGTH: 15
<212> TYPE: PRT
<213> ORGANISM: Artificial
<220> FEATURE:
<223> OTHER INFORMATION: Synthetic construct

<400> SEQUENCE: 35

Lys Lys Lys Leu Asp Glu Glu Thr Gly Glu Phe Leu Lys Lys Lys
1 5 10 15

<210> SEQ ID NO 36
<211> LENGTH: 11
<212> TYPE: PRT
<213> ORGANISM: Artificial
<220> FEATURE:
<223> OTHER INFORMATION: Synthetic construct

<400> SEQUENCE: 36

Lys Leu Asp Glu Glu Thr Gly Glu Phe Leu Lys
1 5 10

<210> SEQ ID NO 37
<211> LENGTH: 12
<212> TYPE: PRT
<213> ORGANISM: Artificial
<220> FEATURE:
<223> OTHER INFORMATION: Synthetic construct

<400> SEQUENCE: 37

Lys Leu Asp Glu Glu Thr Gly Glu Phe Leu Lys Lys
1 5 10

<210> SEQ ID NO 38
<211> LENGTH: 12
<212> TYPE: PRT
<213> ORGANISM: Artificial
<220> FEATURE:
<223> OTHER INFORMATION: Synthetic construct

<400> SEQUENCE: 38

Lys Lys Leu Asp Glu Glu Thr Gly Glu Phe Leu Lys
1 5 10

<210> SEQ ID NO 39
<211> LENGTH: 13
<212> TYPE: PRT
<213> ORGANISM: Artificial
<220> FEATURE:
<223> OTHER INFORMATION: Synthetic construct

<400> SEQUENCE: 39

Lys Leu Asp Glu Glu Thr Gly Glu Phe Leu Lys Lys Lys
1 5 10

<210> SEQ ID NO 40
<211> LENGTH: 13

<212> TYPE: PRT
<213> ORGANISM: Artificial
<220> FEATURE:
<223> OTHER INFORMATION: Synthetic construct

<400> SEQUENCE: 40

Lys Lys Lys Leu Asp Glu Glu Thr Gly Glu Phe Leu Lys
1 5 10

<210> SEQ ID NO 41
<211> LENGTH: 14
<212> TYPE: PRT
<213> ORGANISM: Artificial
<220> FEATURE:
<223> OTHER INFORMATION: Synthetic construct

<400> SEQUENCE: 41

Lys Leu Asp Glu Glu Thr Gly Glu Phe Leu Lys Lys Lys Lys
1 5 10

<210> SEQ ID NO 42
<211> LENGTH: 14
<212> TYPE: PRT
<213> ORGANISM: Artificial
<220> FEATURE:
<223> OTHER INFORMATION: Synthetic construct

<400> SEQUENCE: 42

Lys Lys Leu Asp Glu Glu Thr Gly Glu Phe Leu Lys Lys Lys
1 5 10

<210> SEQ ID NO 43
<211> LENGTH: 14
<212> TYPE: PRT
<213> ORGANISM: Artificial
<220> FEATURE:
<223> OTHER INFORMATION: Synthetic construct

<400> SEQUENCE: 43

Lys Lys Lys Leu Asp Glu Glu Thr Gly Glu Phe Leu Lys Lys
1 5 10

<210> SEQ ID NO 44
<211> LENGTH: 14
<212> TYPE: PRT
<213> ORGANISM: Artificial
<220> FEATURE:
<223> OTHER INFORMATION: Synthetic construct

<400> SEQUENCE: 44

Lys Lys Lys Lys Leu Asp Glu Glu Thr Gly Glu Phe Leu Lys
1 5 10

<210> SEQ ID NO 45
<211> LENGTH: 15
<212> TYPE: PRT
<213> ORGANISM: Artificial
<220> FEATURE:
<223> OTHER INFORMATION: Synthetic construct

<400> SEQUENCE: 45

Lys Leu Asp Glu Glu Thr Gly Glu Phe Leu Lys Lys Lys Lys Lys
1 5 10 15

<210> SEQ ID NO 46
<211> LENGTH: 15
<212> TYPE: PRT

<213> ORGANISM: Artificial
<220> FEATURE:
<223> OTHER INFORMATION: Synthetic construct

<400> SEQUENCE: 46

Lys Lys Leu Asp Glu Glu Thr Gly Glu Phe Leu Lys Lys Lys Lys
1 5 10 15

<210> SEQ ID NO 47
<211> LENGTH: 15
<212> TYPE: PRT
<213> ORGANISM: Artificial
<220> FEATURE:
<223> OTHER INFORMATION: Synthetic construct

<400> SEQUENCE: 47

Lys Lys Lys Lys Leu Asp Glu Glu Thr Gly Glu Phe Leu Lys Lys
1 5 10 15

<210> SEQ ID NO 48
<211> LENGTH: 15
<212> TYPE: PRT
<213> ORGANISM: Artificial
<220> FEATURE:
<223> OTHER INFORMATION: Synthetic construct

<400> SEQUENCE: 48

Lys Lys Lys Lys Lys Leu Asp Glu Glu Thr Gly Glu Phe Leu Lys
1 5 10 15

<210> SEQ ID NO 49
<211> LENGTH: 13
<212> TYPE: PRT
<213> ORGANISM: Artificial
<220> FEATURE:
<223> OTHER INFORMATION: Synthetic construct

<400> SEQUENCE: 49

Leu Asp Glu Glu Thr Gly Glu Phe Leu Lys Arg Lys Arg
1 5 10

<210> SEQ ID NO 50
<211> LENGTH: 13
<212> TYPE: PRT
<213> ORGANISM: Artificial
<220> FEATURE:
<223> OTHER INFORMATION: Synthetic construct

<400> SEQUENCE: 50

Lys Arg Lys Arg Leu Asp Glu Glu Thr Gly Glu Phe Leu
1 5 10

<210> SEQ ID NO 51
<211> LENGTH: 13
<212> TYPE: PRT
<213> ORGANISM: Artificial
<220> FEATURE:
<223> OTHER INFORMATION: Synthetic construct

<400> SEQUENCE: 51

Arg Lys Arg Lys Leu Asp Glu Glu Thr Gly Glu Phe Leu
1 5 10

<210> SEQ ID NO 52
<211> LENGTH: 13
<212> TYPE: PRT
<213> ORGANISM: Artificial

<220> FEATURE:
<223> OTHER INFORMATION: Synthetic construct

<400> SEQUENCE: 52

Leu Asp Glu Glu Thr Gly Glu Phe Leu Arg Lys Arg Lys
1 5 10

<210> SEQ ID NO 53
<211> LENGTH: 13
<212> TYPE: PRT
<213> ORGANISM: Artificial
<220> FEATURE:
<223> OTHER INFORMATION: Synthetic construct

<400> SEQUENCE: 53

Lys Lys Leu Asp Glu Glu Thr Gly Glu Phe Leu Arg Arg
1 5 10

<210> SEQ ID NO 54
<211> LENGTH: 13
<212> TYPE: PRT
<213> ORGANISM: Artificial
<220> FEATURE:
<223> OTHER INFORMATION: Synthetic construct

<400> SEQUENCE: 54

Arg Arg Leu Asp Glu Glu Thr Gly Glu Phe Leu Lys Lys
1 5 10

<210> SEQ ID NO 55
<211> LENGTH: 13
<212> TYPE: PRT
<213> ORGANISM: Artificial
<220> FEATURE:
<223> OTHER INFORMATION: Synthetic construct

<400> SEQUENCE: 55

Lys Leu Asp Glu Glu Thr Gly Glu Phe Leu Arg Arg Arg
1 5 10

<210> SEQ ID NO 56
<211> LENGTH: 13
<212> TYPE: PRT
<213> ORGANISM: Artificial
<220> FEATURE:
<223> OTHER INFORMATION: Synthetic construct

<400> SEQUENCE: 56

Lys Lys Lys Leu Asp Glu Glu Thr Gly Glu Phe Leu Arg
1 5 10

<210> SEQ ID NO 57
<211> LENGTH: 13
<212> TYPE: PRT
<213> ORGANISM: Artificial
<220> FEATURE:
<223> OTHER INFORMATION: Synthetic construct

<400> SEQUENCE: 57

Arg Arg Arg Leu Asp Glu Glu Thr Gly Glu Phe Leu Lys
1 5 10

<210> SEQ ID NO 58
<211> LENGTH: 13
<212> TYPE: PRT
<213> ORGANISM: Artificial
<220> FEATURE:

```
<223> OTHER INFORMATION: Synthetic construct

<400> SEQUENCE: 58

Lys Arg Leu Asp Glu Glu Thr Gly Glu Phe Leu Lys Arg
1               5                   10


<210> SEQ ID NO 59
<211> LENGTH: 13
<212> TYPE: PRT
<213> ORGANISM: Artificial
<220> FEATURE:
<223> OTHER INFORMATION: Synthetic construct

<400> SEQUENCE: 59

Arg Lys Leu Asp Glu Glu Thr Gly Glu Phe Leu Arg Lys
1               5                   10


<210> SEQ ID NO 60
<211> LENGTH: 13
<212> TYPE: PRT
<213> ORGANISM: Artificial
<220> FEATURE:
<223> OTHER INFORMATION: Synthetic construct

<400> SEQUENCE: 60

Arg Lys Leu Asp Glu Glu Thr Gly Glu Phe Leu Lys Arg
1               5                   10


<210> SEQ ID NO 61
<211> LENGTH: 13
<212> TYPE: PRT
<213> ORGANISM: Artificial
<220> FEATURE:
<223> OTHER INFORMATION: Synthetic construct

<400> SEQUENCE: 61

Lys Arg Leu Asp Glu Glu Thr Gly Glu Phe Leu Arg Lys
1               5                   10


<210> SEQ ID NO 62
<211> LENGTH: 13
<212> TYPE: PRT
<213> ORGANISM: Artificial
<220> FEATURE:
<223> OTHER INFORMATION: Synthetic construct

<400> SEQUENCE: 62

Leu Asp Glu Glu Thr Gly Glu Phe Leu Lys Lys Arg Arg
1               5                   10


<210> SEQ ID NO 63
<211> LENGTH: 13
<212> TYPE: PRT
<213> ORGANISM: Artificial
<220> FEATURE:
<223> OTHER INFORMATION: Synthetic construct

<400> SEQUENCE: 63

Leu Asp Glu Glu Thr Gly Glu Phe Leu Arg Arg Lys Lys
1               5                   10


<210> SEQ ID NO 64
<211> LENGTH: 13
<212> TYPE: PRT
<213> ORGANISM: Artificial
<220> FEATURE:
<223> OTHER INFORMATION: Synthetic construct
```

-continued

<400> SEQUENCE: 64

Lys Lys Arg Arg Leu Asp Glu Glu Thr Gly Glu Phe Leu
1 5 10

<210> SEQ ID NO 65
<211> LENGTH: 13
<212> TYPE: PRT
<213> ORGANISM: Artificial
<220> FEATURE:
<223> OTHER INFORMATION: Synthetic construct

<400> SEQUENCE: 65

Arg Arg Lys Lys Leu Asp Glu Glu Thr Gly Glu Phe Leu
1 5 10

<210> SEQ ID NO 66
<211> LENGTH: 16
<212> TYPE: PRT
<213> ORGANISM: Artificial
<220> FEATURE:
<223> OTHER INFORMATION: Synthetic construct

<400> SEQUENCE: 66

Leu Asp Glu Glu Thr Gly Glu Phe Leu Gly Ser Gly Ser Gly Arg Arg
1 5 10 15

<210> SEQ ID NO 67
<211> LENGTH: 16
<212> TYPE: PRT
<213> ORGANISM: Artificial
<220> FEATURE:
<223> OTHER INFORMATION: Synthetic construct

<400> SEQUENCE: 67

Gly Ser Gly Ser Gly Arg Arg Leu Asp Glu Glu Thr Gly Glu Phe Leu
1 5 10 15

<210> SEQ ID NO 68
<211> LENGTH: 16
<212> TYPE: PRT
<213> ORGANISM: Artificial
<220> FEATURE:
<223> OTHER INFORMATION: Synthetic construct

<400> SEQUENCE: 68

Leu Asp Glu Glu Thr Gly Glu Phe Leu Gly Ser Gly Ser Gly Lys Lys
1 5 10 15

<210> SEQ ID NO 69
<211> LENGTH: 16
<212> TYPE: PRT
<213> ORGANISM: Artificial
<220> FEATURE:
<223> OTHER INFORMATION: Synthetic construct

<400> SEQUENCE: 69

Gly Ser Gly Ser Gly Lys Lys Leu Asp Glu Glu Thr Gly Glu Phe Leu
1 5 10 15

<210> SEQ ID NO 70
<211> LENGTH: 11
<212> TYPE: PRT
<213> ORGANISM: Artificial
<220> FEATURE:
<223> OTHER INFORMATION: Synthetic construct

<400> SEQUENCE: 70

Leu Asp Pro Glu Thr Gly Glu Phe Leu Arg Arg
1 5 10

<210> SEQ ID NO 71
<211> LENGTH: 12
<212> TYPE: PRT
<213> ORGANISM: Artificial
<220> FEATURE:
<223> OTHER INFORMATION: Synthetic construct

<400> SEQUENCE: 71

Leu Asp Pro Glu Thr Gly Glu Phe Leu Arg Arg Arg
1 5 10

<210> SEQ ID NO 72
<211> LENGTH: 13
<212> TYPE: PRT
<213> ORGANISM: Artificial
<220> FEATURE:
<223> OTHER INFORMATION: Synthetic construct

<400> SEQUENCE: 72

Leu Asp Pro Glu Thr Gly Glu Phe Leu Arg Arg Arg Arg
1 5 10

<210> SEQ ID NO 73
<211> LENGTH: 14
<212> TYPE: PRT
<213> ORGANISM: Artificial
<220> FEATURE:
<223> OTHER INFORMATION: Synthetic construct

<400> SEQUENCE: 73

Leu Asp Pro Glu Thr Gly Glu Phe Leu Arg Arg Arg Arg Arg
1 5 10

<210> SEQ ID NO 74
<211> LENGTH: 11
<212> TYPE: PRT
<213> ORGANISM: Artificial
<220> FEATURE:
<223> OTHER INFORMATION: Synthetic construct

<400> SEQUENCE: 74

Arg Arg Leu Asp Pro Glu Thr Gly Glu Phe Leu
1 5 10

<210> SEQ ID NO 75
<211> LENGTH: 12
<212> TYPE: PRT
<213> ORGANISM: Artificial
<220> FEATURE:
<223> OTHER INFORMATION: Synthetic construct

<400> SEQUENCE: 75

Arg Arg Arg Leu Asp Pro Glu Thr Gly Glu Phe Leu
1 5 10

<210> SEQ ID NO 76
<211> LENGTH: 13
<212> TYPE: PRT
<213> ORGANISM: Artificial
<220> FEATURE:
<223> OTHER INFORMATION: Synthetic construct

<400> SEQUENCE: 76

```
Arg Arg Arg Arg Leu Asp Pro Glu Thr Gly Glu Phe Leu
1               5                   10


<210> SEQ ID NO 77
<211> LENGTH: 14
<212> TYPE: PRT
<213> ORGANISM: Artificial
<220> FEATURE:
<223> OTHER INFORMATION: Synthetic construct

<400> SEQUENCE: 77

Arg Arg Arg Arg Arg Leu Asp Pro Glu Thr Gly Glu Phe Leu
1               5                   10


<210> SEQ ID NO 78
<211> LENGTH: 13
<212> TYPE: PRT
<213> ORGANISM: Artificial
<220> FEATURE:
<223> OTHER INFORMATION: Synthetic construct

<400> SEQUENCE: 78

Arg Arg Leu Asp Pro Glu Thr Gly Glu Phe Leu Arg Arg
1               5                   10


<210> SEQ ID NO 79
<211> LENGTH: 15
<212> TYPE: PRT
<213> ORGANISM: Artificial
<220> FEATURE:
<223> OTHER INFORMATION: Synthetic construct

<400> SEQUENCE: 79

Arg Arg Arg Leu Asp Pro Glu Thr Gly Glu Phe Leu Arg Arg Arg
1               5                   10                  15


<210> SEQ ID NO 80
<211> LENGTH: 11
<212> TYPE: PRT
<213> ORGANISM: Artificial
<220> FEATURE:
<223> OTHER INFORMATION: Synthetic construct

<400> SEQUENCE: 80

Arg Leu Asp Pro Glu Thr Gly Glu Phe Leu Arg
1               5                   10


<210> SEQ ID NO 81
<211> LENGTH: 12
<212> TYPE: PRT
<213> ORGANISM: Artificial
<220> FEATURE:
<223> OTHER INFORMATION: Synthetic construct

<400> SEQUENCE: 81

Arg Leu Asp Pro Glu Thr Gly Glu Phe Leu Arg Arg
1               5                   10


<210> SEQ ID NO 82
<211> LENGTH: 12
<212> TYPE: PRT
<213> ORGANISM: Artificial
<220> FEATURE:
<223> OTHER INFORMATION: Synthetic construct

<400> SEQUENCE: 82
```

Arg Arg Leu Asp Pro Glu Thr Gly Glu Phe Leu Arg
1 5 10

<210> SEQ ID NO 83
<211> LENGTH: 13
<212> TYPE: PRT
<213> ORGANISM: Artificial
<220> FEATURE:
<223> OTHER INFORMATION: Synthetic construct

<400> SEQUENCE: 83

Arg Leu Asp Pro Glu Thr Gly Glu Phe Leu Arg Arg Arg
1 5 10

<210> SEQ ID NO 84
<211> LENGTH: 13
<212> TYPE: PRT
<213> ORGANISM: Artificial
<220> FEATURE:
<223> OTHER INFORMATION: Synthetic construct

<400> SEQUENCE: 84

Arg Arg Arg Leu Asp Pro Glu Thr Gly Glu Phe Leu Arg
1 5 10

<210> SEQ ID NO 85
<211> LENGTH: 14
<212> TYPE: PRT
<213> ORGANISM: Artificial
<220> FEATURE:
<223> OTHER INFORMATION: Synthetic construct

<400> SEQUENCE: 85

Arg Leu Asp Pro Glu Thr Gly Glu Phe Leu Arg Arg Arg Arg
1 5 10

<210> SEQ ID NO 86
<211> LENGTH: 14
<212> TYPE: PRT
<213> ORGANISM: Artificial
<220> FEATURE:
<223> OTHER INFORMATION: Synthetic construct

<400> SEQUENCE: 86

Arg Arg Leu Asp Pro Glu Thr Gly Glu Phe Leu Arg Arg Arg
1 5 10

<210> SEQ ID NO 87
<211> LENGTH: 14
<212> TYPE: PRT
<213> ORGANISM: Artificial
<220> FEATURE:
<223> OTHER INFORMATION: Synthetic construct

<400> SEQUENCE: 87

Arg Arg Arg Leu Asp Pro Glu Thr Gly Glu Phe Leu Arg Arg
1 5 10

<210> SEQ ID NO 88
<211> LENGTH: 14
<212> TYPE: PRT
<213> ORGANISM: Artificial
<220> FEATURE:
<223> OTHER INFORMATION: Synthetic construct

<400> SEQUENCE: 88

Arg Arg Arg Arg Leu Asp Pro Glu Thr Gly Glu Phe Leu Arg 1 5 10

<210> SEQ ID NO 89
<211> LENGTH: 15
<212> TYPE: PRT
<213> ORGANISM: Artificial
<220> FEATURE:
<223> OTHER INFORMATION: Synthetic construct

<400> SEQUENCE: 89

Arg Leu Asp Pro Glu Thr Gly Glu Phe Leu Arg Arg Arg Arg Arg
1 5 10 15

<210> SEQ ID NO 90
<211> LENGTH: 15
<212> TYPE: PRT
<213> ORGANISM: Artificial
<220> FEATURE:
<223> OTHER INFORMATION: Synthetic construct

<400> SEQUENCE: 90

Arg Arg Leu Asp Pro Glu Thr Gly Glu Phe Leu Arg Arg Arg Arg
1 5 10 15

<210> SEQ ID NO 91
<211> LENGTH: 15
<212> TYPE: PRT
<213> ORGANISM: Artificial
<220> FEATURE:
<223> OTHER INFORMATION: Synthetic construct

<400> SEQUENCE: 91

Arg Arg Arg Arg Leu Asp Pro Glu Thr Gly Glu Phe Leu Arg Arg
1 5 10 15

<210> SEQ ID NO 92
<211> LENGTH: 15
<212> TYPE: PRT
<213> ORGANISM: Artificial
<220> FEATURE:
<223> OTHER INFORMATION: Synthetic construct

<400> SEQUENCE: 92

Arg Arg Arg Arg Arg Leu Asp Pro Glu Thr Gly Glu Phe Leu Arg
1 5 10 15

<210> SEQ ID NO 93
<211> LENGTH: 11
<212> TYPE: PRT
<213> ORGANISM: Artificial
<220> FEATURE:
<223> OTHER INFORMATION: Synthetic construct

<400> SEQUENCE: 93

Leu Asp Pro Glu Thr Gly Glu Phe Leu Lys Lys
1 5 10

<210> SEQ ID NO 94
<211> LENGTH: 12
<212> TYPE: PRT
<213> ORGANISM: Artificial
<220> FEATURE:
<223> OTHER INFORMATION: Synthetic construct

<400> SEQUENCE: 94

Leu Asp Pro Glu Thr Gly Glu Phe Leu Lys Lys Lys
1 5 10

-continued

<210> SEQ ID NO 95
<211> LENGTH: 13
<212> TYPE: PRT
<213> ORGANISM: Artificial
<220> FEATURE:
<223> OTHER INFORMATION: Synthetic construct

<400> SEQUENCE: 95

Leu Asp Pro Glu Thr Gly Glu Phe Leu Lys Lys Lys Lys
1 5 10

<210> SEQ ID NO 96
<211> LENGTH: 14
<212> TYPE: PRT
<213> ORGANISM: Artificial
<220> FEATURE:
<223> OTHER INFORMATION: Synthetic construct

<400> SEQUENCE: 96

Leu Asp Pro Glu Thr Gly Glu Phe Leu Lys Lys Lys Lys Lys
1 5 10

<210> SEQ ID NO 97
<211> LENGTH: 11
<212> TYPE: PRT
<213> ORGANISM: Artificial
<220> FEATURE:
<223> OTHER INFORMATION: Synthetic construct

<400> SEQUENCE: 97

Lys Lys Leu Asp Pro Glu Thr Gly Glu Phe Leu
1 5 10

<210> SEQ ID NO 98
<211> LENGTH: 12
<212> TYPE: PRT
<213> ORGANISM: Artificial
<220> FEATURE:
<223> OTHER INFORMATION: Synthetic construct

<400> SEQUENCE: 98

Lys Lys Lys Leu Asp Pro Glu Thr Gly Glu Phe Leu
1 5 10

<210> SEQ ID NO 99
<211> LENGTH: 13
<212> TYPE: PRT
<213> ORGANISM: Artificial
<220> FEATURE:
<223> OTHER INFORMATION: Synthetic construct

<400> SEQUENCE: 99

Lys Lys Lys Lys Leu Asp Pro Glu Thr Gly Glu Phe Leu
1 5 10

<210> SEQ ID NO 100
<211> LENGTH: 14
<212> TYPE: PRT
<213> ORGANISM: Artificial
<220> FEATURE:
<223> OTHER INFORMATION: Synthetic construct

<400> SEQUENCE: 100

Lys Lys Lys Lys Lys Leu Asp Pro Glu Thr Gly Glu Phe Leu
1 5 10

<210> SEQ ID NO 101
<211> LENGTH: 13
<212> TYPE: PRT
<213> ORGANISM: Artificial
<220> FEATURE:
<223> OTHER INFORMATION: Synthetic construct

<400> SEQUENCE: 101

Lys Lys Leu Asp Pro Glu Thr Gly Glu Phe Leu Lys Lys
1 5 10

<210> SEQ ID NO 102
<211> LENGTH: 15
<212> TYPE: PRT
<213> ORGANISM: Artificial
<220> FEATURE:
<223> OTHER INFORMATION: Synthetic construct

<400> SEQUENCE: 102

Lys Lys Lys Leu Asp Pro Glu Thr Gly Glu Phe Leu Lys Lys Lys
1 5 10 15

<210> SEQ ID NO 103
<211> LENGTH: 11
<212> TYPE: PRT
<213> ORGANISM: Artificial
<220> FEATURE:
<223> OTHER INFORMATION: Synthetic construct

<400> SEQUENCE: 103

Lys Leu Asp Pro Glu Thr Gly Glu Phe Leu Lys
1 5 10

<210> SEQ ID NO 104
<211> LENGTH: 12
<212> TYPE: PRT
<213> ORGANISM: Artificial
<220> FEATURE:
<223> OTHER INFORMATION: Synthetic construct

<400> SEQUENCE: 104

Lys Leu Asp Pro Glu Thr Gly Glu Phe Leu Lys Lys
1 5 10

<210> SEQ ID NO 105
<211> LENGTH: 12
<212> TYPE: PRT
<213> ORGANISM: Artificial
<220> FEATURE:
<223> OTHER INFORMATION: Synthetic construct

<400> SEQUENCE: 105

Lys Lys Leu Asp Pro Glu Thr Gly Glu Phe Leu Lys
1 5 10

<210> SEQ ID NO 106
<211> LENGTH: 13
<212> TYPE: PRT
<213> ORGANISM: Artificial
<220> FEATURE:
<223> OTHER INFORMATION: Synthetic construct

<400> SEQUENCE: 106

Lys Leu Asp Pro Glu Thr Gly Glu Phe Leu Lys Lys Lys
1 5 10

<210> SEQ ID NO 107
<211> LENGTH: 13
<212> TYPE: PRT
<213> ORGANISM: Artificial
<220> FEATURE:
<223> OTHER INFORMATION: Synthetic construct

<400> SEQUENCE: 107

Lys Lys Lys Leu Asp Pro Glu Thr Gly Glu Phe Leu Lys
1 5 10

<210> SEQ ID NO 108
<211> LENGTH: 14
<212> TYPE: PRT
<213> ORGANISM: Artificial
<220> FEATURE:
<223> OTHER INFORMATION: Synthetic construct

<400> SEQUENCE: 108

Lys Leu Asp Pro Glu Thr Gly Glu Phe Leu Lys Lys Lys Lys
1 5 10

<210> SEQ ID NO 109
<211> LENGTH: 14
<212> TYPE: PRT
<213> ORGANISM: Artificial
<220> FEATURE:
<223> OTHER INFORMATION: Synthetic construct

<400> SEQUENCE: 109

Lys Lys Leu Asp Pro Glu Thr Gly Glu Phe Leu Lys Lys Lys
1 5 10

<210> SEQ ID NO 110
<211> LENGTH: 14
<212> TYPE: PRT
<213> ORGANISM: Artificial
<220> FEATURE:
<223> OTHER INFORMATION: Synthetic construct

<400> SEQUENCE: 110

Lys Lys Lys Leu Asp Pro Glu Thr Gly Glu Phe Leu Lys Lys
1 5 10

<210> SEQ ID NO 111
<211> LENGTH: 14
<212> TYPE: PRT
<213> ORGANISM: Artificial
<220> FEATURE:
<223> OTHER INFORMATION: Synthetic construct

<400> SEQUENCE: 111

Lys Lys Lys Lys Leu Asp Pro Glu Thr Gly Glu Phe Leu Lys
1 5 10

<210> SEQ ID NO 112
<211> LENGTH: 15
<212> TYPE: PRT
<213> ORGANISM: Artificial
<220> FEATURE:
<223> OTHER INFORMATION: Synthetic construct

<400> SEQUENCE: 112

Lys Leu Asp Pro Glu Thr Gly Glu Phe Leu Lys Lys Lys Lys Lys
1 5 10 15

<210> SEQ ID NO 113

<211> LENGTH: 15
<212> TYPE: PRT
<213> ORGANISM: Artificial
<220> FEATURE:
<223> OTHER INFORMATION: Synthetic construct

<400> SEQUENCE: 113

Lys Lys Leu Asp Pro Glu Thr Gly Glu Phe Leu Lys Lys Lys Lys
1 5 10 15

<210> SEQ ID NO 114
<211> LENGTH: 15
<212> TYPE: PRT
<213> ORGANISM: Artificial
<220> FEATURE:
<223> OTHER INFORMATION: Synthetic construct

<400> SEQUENCE: 114

Lys Lys Lys Lys Leu Asp Pro Glu Thr Gly Glu Phe Leu Lys Lys
1 5 10 15

<210> SEQ ID NO 115
<211> LENGTH: 15
<212> TYPE: PRT
<213> ORGANISM: Artificial
<220> FEATURE:
<223> OTHER INFORMATION: Synthetic construct

<400> SEQUENCE: 115

Lys Lys Lys Lys Lys Leu Asp Pro Glu Thr Gly Glu Phe Leu Lys
1 5 10 15

<210> SEQ ID NO 116
<211> LENGTH: 13
<212> TYPE: PRT
<213> ORGANISM: Artificial
<220> FEATURE:
<223> OTHER INFORMATION: Synthetic construct

<400> SEQUENCE: 116

Leu Asp Pro Glu Thr Gly Glu Phe Leu Lys Arg Lys Arg
1 5 10

<210> SEQ ID NO 117
<211> LENGTH: 13
<212> TYPE: PRT
<213> ORGANISM: Artificial
<220> FEATURE:
<223> OTHER INFORMATION: Synthetic construct

<400> SEQUENCE: 117

Lys Arg Lys Arg Leu Asp Pro Glu Thr Gly Glu Phe Leu
1 5 10

<210> SEQ ID NO 118
<211> LENGTH: 13
<212> TYPE: PRT
<213> ORGANISM: Artificial
<220> FEATURE:
<223> OTHER INFORMATION: Synthetic construct

<400> SEQUENCE: 118

Arg Lys Arg Lys Leu Asp Pro Glu Thr Gly Glu Phe Leu
1 5 10

<210> SEQ ID NO 119
<211> LENGTH: 13

<212> TYPE: PRT
<213> ORGANISM: Artificial
<220> FEATURE:
<223> OTHER INFORMATION: Synthetic construct

<400> SEQUENCE: 119

Leu Asp Pro Glu Thr Gly Glu Phe Leu Arg Lys Arg Lys
1 5 10

<210> SEQ ID NO 120
<211> LENGTH: 13
<212> TYPE: PRT
<213> ORGANISM: Artificial
<220> FEATURE:
<223> OTHER INFORMATION: Synthetic construct

<400> SEQUENCE: 120

Lys Lys Leu Asp Pro Glu Thr Gly Glu Phe Leu Arg Arg
1 5 10

<210> SEQ ID NO 121
<211> LENGTH: 13
<212> TYPE: PRT
<213> ORGANISM: Artificial
<220> FEATURE:
<223> OTHER INFORMATION: Synthetic construct

<400> SEQUENCE: 121

Arg Arg Leu Asp Pro Glu Thr Gly Glu Phe Leu Lys Lys
1 5 10

<210> SEQ ID NO 122
<211> LENGTH: 13
<212> TYPE: PRT
<213> ORGANISM: Artificial
<220> FEATURE:
<223> OTHER INFORMATION: Synthetic construct

<400> SEQUENCE: 122

Lys Leu Asp Pro Glu Thr Gly Glu Phe Leu Arg Arg Arg
1 5 10

<210> SEQ ID NO 123
<211> LENGTH: 13
<212> TYPE: PRT
<213> ORGANISM: Artificial
<220> FEATURE:
<223> OTHER INFORMATION: Synthetic construct

<400> SEQUENCE: 123

Lys Lys Lys Leu Asp Pro Glu Thr Gly Glu Phe Leu Arg
1 5 10

<210> SEQ ID NO 124
<211> LENGTH: 13
<212> TYPE: PRT
<213> ORGANISM: Artificial
<220> FEATURE:
<223> OTHER INFORMATION: Synthetic construct

<400> SEQUENCE: 124

Arg Arg Arg Leu Asp Pro Glu Thr Gly Glu Phe Leu Lys
1 5 10

<210> SEQ ID NO 125
<211> LENGTH: 13
<212> TYPE: PRT

<213> ORGANISM: Artificial
<220> FEATURE:
<223> OTHER INFORMATION: Synthetic construct

<400> SEQUENCE: 125

Lys Arg Leu Asp Pro Glu Thr Gly Glu Phe Leu Lys Arg
1 5 10

<210> SEQ ID NO 126
<211> LENGTH: 13
<212> TYPE: PRT
<213> ORGANISM: Artificial
<220> FEATURE:
<223> OTHER INFORMATION: Synthetic construct

<400> SEQUENCE: 126

Arg Lys Leu Asp Pro Glu Thr Gly Glu Phe Leu Arg Lys
1 5 10

<210> SEQ ID NO 127
<211> LENGTH: 13
<212> TYPE: PRT
<213> ORGANISM: Artificial
<220> FEATURE:
<223> OTHER INFORMATION: Synthetic construct

<400> SEQUENCE: 127

Arg Lys Leu Asp Pro Glu Thr Gly Glu Phe Leu Lys Arg
1 5 10

<210> SEQ ID NO 128
<211> LENGTH: 13
<212> TYPE: PRT
<213> ORGANISM: Artificial
<220> FEATURE:
<223> OTHER INFORMATION: Synthetic construct

<400> SEQUENCE: 128

Lys Arg Leu Asp Pro Glu Thr Gly Glu Phe Leu Arg Lys
1 5 10

<210> SEQ ID NO 129
<211> LENGTH: 13
<212> TYPE: PRT
<213> ORGANISM: Artificial
<220> FEATURE:
<223> OTHER INFORMATION: Synthetic construct

<400> SEQUENCE: 129

Leu Asp Pro Glu Thr Gly Glu Phe Leu Lys Lys Arg Arg
1 5 10

<210> SEQ ID NO 130
<211> LENGTH: 13
<212> TYPE: PRT
<213> ORGANISM: Artificial
<220> FEATURE:
<223> OTHER INFORMATION: Synthetic construct

<400> SEQUENCE: 130

Leu Asp Pro Glu Thr Gly Glu Phe Leu Arg Arg Lys Lys
1 5 10

<210> SEQ ID NO 131
<211> LENGTH: 13
<212> TYPE: PRT
<213> ORGANISM: Artificial

<220> FEATURE:
<223> OTHER INFORMATION: Synthetic construct

<400> SEQUENCE: 131

Lys Lys Arg Arg Leu Asp Pro Glu Thr Gly Glu Phe Leu
1               5                   10

<210> SEQ ID NO 132
<211> LENGTH: 13
<212> TYPE: PRT
<213> ORGANISM: Artificial
<220> FEATURE:
<223> OTHER INFORMATION: Synthetic construct

<400> SEQUENCE: 132

Arg Arg Lys Lys Leu Asp Pro Glu Thr Gly Glu Phe Leu
1               5                   10

<210> SEQ ID NO 133
<211> LENGTH: 16
<212> TYPE: PRT
<213> ORGANISM: Artificial
<220> FEATURE:
<223> OTHER INFORMATION: Synthetic construct

<400> SEQUENCE: 133

Leu Asp Pro Glu Thr Gly Glu Phe Leu Gly Ser Gly Ser Gly Arg Arg
1               5                   10                  15

<210> SEQ ID NO 134
<211> LENGTH: 16
<212> TYPE: PRT
<213> ORGANISM: Artificial
<220> FEATURE:
<223> OTHER INFORMATION: Synthetic construct

<400> SEQUENCE: 134

Gly Ser Gly Ser Gly Arg Arg Leu Asp Pro Glu Thr Gly Glu Phe Leu
1               5                   10                  15

<210> SEQ ID NO 135
<211> LENGTH: 16
<212> TYPE: PRT
<213> ORGANISM: Artificial
<220> FEATURE:
<223> OTHER INFORMATION: Synthetic construct

<400> SEQUENCE: 135

Leu Asp Pro Glu Thr Gly Glu Phe Leu Gly Ser Gly Ser Gly Lys Lys
1               5                   10                  15

<210> SEQ ID NO 136
<211> LENGTH: 16
<212> TYPE: PRT
<213> ORGANISM: Artificial
<220> FEATURE:
<223> OTHER INFORMATION: Synthetic construct -continued

<400> SEQUENCE: 136

Gly Ser Gly Ser Gly Lys Lys Leu Asp Pro Glu Thr Gly Glu Phe Leu
1 5 10 15

<210> SEQ ID NO 137
<211> LENGTH: 8
<212> TYPE: PRT
<213> ORGANISM: Artificial
<220> FEATURE:
<223> OTHER INFORMATION: Synthetic construct

<400> SEQUENCE: 137

Leu Asp Pro Thr Gly Glu Phe Leu
1 5

<210> SEQ ID NO 138
<211> LENGTH: 8
<212> TYPE: PRT
<213> ORGANISM: Artificial
<220> FEATURE:
<223> OTHER INFORMATION: Synthetic construct

<400> SEQUENCE: 138

Leu Asp Pro Glu Thr Gly Phe Leu
1 5

<210> SEQ ID NO 139
<211> LENGTH: 13
<212> TYPE: PRT
<213> ORGANISM: Artificial
<220> FEATURE:
<223> OTHER INFORMATION: Synthetic construct

<400> SEQUENCE: 139

Asp Glu Arg Leu Arg Glu Arg Pro Leu Thr Gly Phe Arg
1 5 10

<210> SEQ ID NO 140
<211> LENGTH: 16
<212> TYPE: PRT
<213> ORGANISM: Artificial
<220> FEATURE:
<223> OTHER INFORMATION: Synthetic construct

<400> SEQUENCE: 140

Tyr Gly Arg Lys Lys Arg Arg Leu Asp Pro Glu Thr Gly Glu Phe Leu
1 5 10 15

<210> SEQ ID NO 141
<211> LENGTH: 16
<212> TYPE: PRT
<213> ORGANISM: Artificial
<220> FEATURE:
<223> OTHER INFORMATION: Synthetic construct

<400> SEQUENCE: 141

Leu Asp Pro Glu Thr Gly Glu Phe Leu Tyr Gly Arg Lys Lys Arg Arg
1 5 10 15

<210> SEQ ID NO 142
<211> LENGTH: 11
<212> TYPE: PRT
<213> ORGANISM: Artificial
<220> FEATURE:
<223> OTHER INFORMATION: Synthetic construct

<400> SEQUENCE: 142

-continued

```
Tyr Gly Arg Lys Lys Arg Arg Gln Arg Arg Arg
1               5                   10


<210> SEQ ID NO 143
<211> LENGTH: 13
<212> TYPE: PRT
<213> ORGANISM: Artificial
<220> FEATURE:
<223> OTHER INFORMATION: Synthetic construct

<400> SEQUENCE: 143

Asp Glu Arg Leu Glu Arg Pro Leu Thr Arg Gly Phe Arg
1               5                   10


<210> SEQ ID NO 144
<211> LENGTH: 9
<212> TYPE: PRT
<213> ORGANISM: Artificial
<220> FEATURE:
<223> OTHER INFORMATION: Synthetic construct

<400> SEQUENCE: 144

Leu Glu Leu Glu Asp Glu Phe Thr Gly
1               5


<210> SEQ ID NO 145
<211> LENGTH: 9
<212> TYPE: PRT
<213> ORGANISM: Artificial
<220> FEATURE:
<223> OTHER INFORMATION: Synthetic construct

<400> SEQUENCE: 145

Asp Glu Leu Glu Pro Leu Thr Gly Phe
1               5


<210> SEQ ID NO 146
<211> LENGTH: 13
<212> TYPE: PRT
<213> ORGANISM: Artificial
<220> FEATURE:
<223> OTHER INFORMATION: Synthetic construct

<400> SEQUENCE: 146

Asp Glu Leu Glu Pro Leu Thr Gly Phe Arg Arg Arg Arg
1               5                   10
```